US010040858B2

(12) United States Patent
Sikorski et al.

(10) Patent No.: US 10,040,858 B2
(45) Date of Patent: Aug. 7, 2018

(54) ANTI-CSF1R ANTIBODIES FOR TREATING PVNS

(71) Applicant: FIVE PRIME THERAPEUTICS, INC., South San Francisco, CA (US)

(72) Inventors: Robert Sikorski, South San Francisco, CA (US); Julie Hambleton, South San Francisco, CA (US); Nilacantan Sankar, South San Francisco, CA (US)

(73) Assignee: Five Prime Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 14/976,346

(22) Filed: Dec. 21, 2015

(65) Prior Publication Data
US 2016/0185869 A1 Jun. 30, 2016

Related U.S. Application Data

(60) Provisional application No. 62/095,297, filed on Dec. 22, 2014, provisional application No. 62/163,251, filed on May 18, 2015.

(51) Int. Cl.
*C07K 16/28* (2006.01)
*A61K 39/395* (2006.01)
*A61K 39/00* (2006.01)

(52) U.S. Cl.
CPC .... *C07K 16/2866* (2013.01); *A61K 2039/505* (2013.01); *A61K 2039/545* (2013.01); *C07K 2317/24* (2013.01); *C07K 2317/34* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,866,114 A | 2/1999 | Pandit et al. | |
| 6,184,354 B1 | 2/2001 | Koths et al. | |
| 7,108,852 B2 | 9/2006 | Devalaraja et al. | |
| 7,247,618 B2 | 7/2007 | Rajavashisth | |
| 7,455,836 B2 | 11/2008 | Hamilton et al. | |
| 7,553,854 B2 | 6/2009 | Sutton et al. | |
| 7,807,389 B2 | 10/2010 | Ritchlin et al. | |
| 7,919,594 B2 | 4/2011 | Smith et al. | |
| 8,119,637 B2 | 2/2012 | Ibrahim et al. | |
| 8,158,636 B2 | 4/2012 | Ibrahim et al. | |
| 8,173,689 B2 | 5/2012 | Sutton et al. | |
| 8,206,715 B2 * | 6/2012 | Wong | C07K 16/2866 424/130.1 |
| 8,293,769 B2 | 10/2012 | Ng et al. | |
| 8,513,199 B2 | 8/2013 | Brasel et al. | |
| 8,710,048 B2 | 4/2014 | Sutton et al. | |
| 8,747,845 B2 | 6/2014 | Wong et al. | |
| 9,221,910 B2 * | 12/2015 | Fertig | C07K 16/2866 |

| | | |
|---|---|---|
| 2002/0119494 A1 | 8/2002 | Jung et al. |
| 2002/0193575 A1 | 12/2002 | Holmes et al. |
| 2003/0103976 A1 | 6/2003 | Serizawa et al. |
| 2006/0286102 A1 | 12/2006 | Jin et al. |
| 2007/0072797 A1 | 3/2007 | Robinson et al. |
| 2007/0148172 A1 | 6/2007 | Lawson et al. |
| 2007/0166788 A1 | 7/2007 | Jin et al. |
| 2008/0219971 A1 | 9/2008 | Smith et al. |
| 2009/0148883 A1 | 6/2009 | Manthey |
| 2009/0155164 A1 | 6/2009 | Brasel et al. |
| 2010/0136006 A1 | 6/2010 | Lin et al. |
| 2010/0136007 A1 | 6/2010 | Lin et al. |
| 2010/0261679 A1 | 10/2010 | Sutton et al. |
| 2011/0165156 A1 | 7/2011 | Dimoudis et al. |
| 2011/0243947 A1 | 10/2011 | Doody et al. |
| 2012/0258952 A1 | 10/2012 | Boys et al. |
| 2012/0329997 A1 | 12/2012 | Fertig et al. |
| 2013/0005949 A1 | 1/2013 | Fertig et al. |
| 2013/0302322 A1 | 11/2013 | Wong et al. |
| 2014/0045840 A1 | 2/2014 | Zhang et al. |
| 2014/0079699 A1 | 3/2014 | Wong et al. |
| 2014/0079706 A1 | 3/2014 | Cannarile et al. |

FOREIGN PATENT DOCUMENTS

| | | |
|---|---|---|
| CA | 2388298 | 5/2001 |
| EP | 2241333 A1 | 10/2010 |
| WO | WO 89/03687 | 5/1989 |
| WO | WO 99/29345 | 6/1999 |
| WO | WO 01/34177 | 5/2001 |
| WO | WO 2002/102972 | 12/2002 |
| WO | WO 2004/045532 | 6/2004 |
| WO | WO 2005/070447 | 8/2005 |
| WO | WO 2006/012451 | 2/2006 |
| WO | WO 2007/075933 | 7/2007 |
| WO | WO 2007/081879 | 7/2007 |

(Continued)

OTHER PUBLICATIONS

Tap et al., A pilot study of PLX3397, a selective colony stimulating factor 1 receptor (CSF1R) kinase inhibitor, in pigmented villonodular synovitis (PVNS), J. Clin. Oncol. vol. 32, No. 15, Supp. 1. Abstract Number: 10503, 2014.*

Cassier, et al., "CSF1R Inhibition with Emactuzumab in Locally Advanced Diffuse-Type Tenosynovial Giant Cell Tumours of the Soft Tissue: a Dose-Escalation and Dose-Expansion Phase 1 Study," The Lancet. Oncology, Aug. 1, 2014, pp. 949-956.

Ries, et al., "Targeting Tumor-Associated Macrophages with Anti-CSF-1R Antibody Reveals a Strategy for Cancer Therapy," , Jun. 16, 2014, pp. 846-859.

International Search Report in PCT/US2015/067012, dated Apr. 11, 2016.

Aharinejad et al., Colony-stimulating Factor-1 Blockade by Antisense Oligonucleotides and Small Interfering RNAs Suppresses Growth of Human Mammary Tumor Xenografts in Mice, Cancer Research, vol. 64, Aug. 2004, pp. 5378-5384.

(Continued)

*Primary Examiner* — Elly-Gerald Stoica

(74) *Attorney, Agent, or Firm* — McNeill Baur PLLC

(57) ABSTRACT

Methods of treating pigmented villonodular synovitis (PVNS) with antibodies that bind colony stimulating factor 1 receptor (CSF1R) are provided.

56 Claims, 7 Drawing Sheets

(56) References Cited

FOREIGN PATENT DOCUMENTS

| | | |
|---|---|---|
| WO | WO 2007/120252 | 10/2007 |
| WO | WO 2008/060610 | 5/2008 |
| WO | WO 2008/061013 | 5/2008 |
| WO | WO 2008/124858 | 10/2008 |
| WO | WO 2008/150383 | 12/2008 |
| WO | WO 2009/026303 | 2/2009 |
| WO | WO 2009/058968 | 5/2009 |
| WO | WO 2009/075344 | 6/2009 |
| WO | WO 2009/112245 | 9/2009 |
| WO | WO 2010/062399 | 6/2010 |
| WO | WO 2010/062401 | 6/2010 |
| WO | WO 2011/070024 | 6/2011 |
| WO | WO 2011/107553 | 9/2011 |
| WO | WO 2011/131407 | 10/2011 |
| WO | WO 2011/140249 | 11/2011 |
| WO | WO 2012/082573 | 6/2012 |
| WO | WO 2012/110360 | 8/2012 |
| WO | WO 2013057281 | 4/2013 |
| WO | WO 2013057290 | 4/2013 |
| WO | WO 2013169264 | 11/2013 |
| WO | WO 2014036357 | 6/2014 |

OTHER PUBLICATIONS

Aharinejad et al., Colony-stimulating Factor-1 Antisense Treatment Suppresses Growth of Human Tumor Xenografts in Mice, Cancer Research, vol. 62, Sep. 2002, pp. 5317-5324.

Ando et al., Imatinib Mesylate Inhibits Osteoclastogenesis and Joint Destruction in Rats with Collagen-induced Arthritis, J. Bone Miner. Metab., vol. 24, Jan. 2006, pp. 274-282.

Apollo Cytokine Research, Human hcx™ M-CSF R, Fc Chimera, Product Information Sheet from http://www.biocompare.com/itemdetails.asp?itemid=831066, Feb. 4, 2008.

Birchenall-Roberts, Inhibition of Murine Monocyte Proliferation by a Colony-stimulating Factor-1 Antisense Oligodeoxynucleotide, J. Immunol., vol. 15, Nov. 1990, pp. 3290-3296.

Bischof et al., Exacerbation of Acute Inflammatory Arthritis by the Colony-stimulating Factors CSF-1 and Granulocyte Macrophage (GM)-CSF: Evidence of Macrophage Infiltration and Local Proliferation, Clin. Exp. Immunol., vol. 119, 2000, pp. 361-367.

Campbell et al., The Colony-stimulating Factors and Collagen-induced Arthritis: Exacerbation of Disease by M-CSF and G-CSF and Requirement for Endogenous M-CSF, Journal of Leukocyte Biology, vol. 68, Jul. 2000.

Chaika et al., CSF-1 Receptor/Insulin Chimera Permits CSF-1-dependent Differentiation of 3T3-L1 Preadipocytes, J. Biol. Chem., vol. 272, No. 18, May 1997, pp. 11968-11974.

Chitu et al, Colony-stimulating Factor-1 in Immunity and Inflammation, Current Opinion in Immunology, vol. 18, No. 1, Feb. 2006, pp. 39-48.

Conway et al., Inhibition of Colony-stimulating-factor-1 Signaling in Vivo with the Orally Bioavailable cFMS Kinase Inhibitor GW2580, PNAS, vol. 102, Nov. 2005, pp. 16078.

Conway et al., Effects of the cFMS Kinase Inhibitor 5-(3-Methoxy-4-((4-methoxybenzyl)oxy)benzyl)pyrimidine-2,4-diamine (GW2580) in Normal and Arthritic Rats, J. Pharmacology and Experimental Therapeutics, vol. 326, No. 1, Apr. 2008, pp. 41-50.

Dandekar et al., Comparison of the Signaling Abilities of the Cytoplasmic Domains of the Insulin Receptor and the Insulin Receptor-related Receptor in 3T3-L1 Adipocytes, Endocrinology, vol. 139, No. 8, Jan. 2008, pp. 3578-3584.

Dewar et al., Imatinib as a Potential Antiresorptive Therapy for Bone Disease, Blood, vol. 107, No. 11, Jun. 2006, pp. 4334-4337.

Garceau, V. et al., "Pivotal Advance: Avian Colony-Stimulating Factor 1 (CSF-1), Interlukin-34 (IL-34), and CSF-1 Receptor Genes and Gene Products," Journal of Leukocyte Biology, 2010, vol. 87, pp. 753-764.

Goswami et al., Macrophages Promote the Invasion of Breast Carcinoma Cells via a Colony-stimulating Factor-1/Epidermal Growth Factor . . . , Cancer Research., vol. 65, Jun. 2005.

Haegel, et al., "A Unique Anti-CD115 Monoclonal Antibody Which Inhibits Osteolysis and Skews Human Monocyte Differentiation from M2-Polarized Macrophages Toward Dendritic Cells," mAbs, 2013, 5:5, pp. 736-747.

Haegel, et al., "A Unique Anti-CD115 Monoclonal Antibody Which Inhibits Osteolysis and Skews Human Monocyte Differentiation from M2-Polarized Macrophages Toward Dendritic Cells," mAbs, 5:5, 2013, Suppl., 12 pages.

Hamilton, CSF-1 Signal Transduction, Journal of Leukocyte Biology, vol. 62, Aug. 1997, pp. 145-155.

Hamilton, Colony-stimulating Factors in Inflammation and Autoimmunity, Nature Reviews, vol. 8, Jul. 2008, pp. 533-544.

Hegen et al., Utility of Animal Models for Identification of Potential Therapeutics for Rheumatoid Arthritis, Ann. Rheum. Dis., vol. 67, published online Nov. 2007, pp. 1505-1515.

Ide et al., Expression of Colony-stimulating Factor 1 Receptor During Prostate Development and Prostate Cancer Progression, PNAS, vol. 99, No. 22, Oct. 2002, pp. 14404-14409.

Ide et al., Serum Level of Macrophage Colony-stimulating Factor is Increased in Prostate Cancer Patients with Bone Metastasis, Human Cell, vol. 21, No. 1, Feb. 2008, pp. 1-6.

Irvine et al., A CSF-1 Receptor Kinase Inhibitor Targets Effector Functions and Inhibits Pro-inflammatory Cytokine Production . . . , FASEB, vol. 20, Sep. 2006, pp. E1315-E1326.

Kingsley et al., Molecular Biology of Bone Metastasis, Mol. Cancer Ther., vol. 6, No. 10, Oct. 2007, pp. 2609-2617.

Kitaura et al., M-CSF Mediates TNF-induced Inflammatory Osteolysis, The Journal of Clinical Investigation, vol. 115, No. 12, Dec. 2005, pp. 3418-3427.

Kitaura et al., An M-CSF Receptor c-Fms Antibody Inhibits Mechanical Stress-Induced Root Resorption during Orthodontic Tooth Movement in Mice, Angle Orthodontist, vol. 79, No. 5, 2009, pp. 835-841.

Kluger et al., Macrophage Colony-stimulating Factor-1 Receptor Expression is Associated with Poor Outcome in Breast Cancer by Large Cohort Tissue Microarray Analysis, Clinical Cancer Res, vol. 10, Jan. 2004, pp. 173.

Kubota et al., M-CSF Inhibition Selectively Targets Pathological Angiogenesis and Lymphangiogenesis, J. Exp. Med., vol. 206, No. 5, Apr. 2009, pp. 1089-1102.

Kutza et al., Macrophage Colony-stimulating Factor Antagonists Inhibit Replication of HIV-1 in Human Macrophages, The Journal of Immunology, 2000, vol. 164, pp. 4955-4960.

Lee et al., Functional Dissection of Structural Domains in the Receptor for Colony-stimulating Factor-1, J. Biol. Chem., vol. 267, Aug. 1992, pp. 16472-16483.

Li et al., Conditional Deletion of the Colony Stimulating Factor-1 Receptor (c-fms Proto-Oncogene) in Mice, Genesis, vol. 44, May 2006, pp. 328-335.

Li et al., Role of Dimerization and Modification of the CSF-1 Receptor in its Activation and Internalization During the CSF-1 Response, The EMBO Journal, 1991, pp. 277-288.

Lim et al., Antibody blockade of c-fms suppresses the progression of inflammation and injury in early diabetic nephropathy in obese db/db mice, Diabetologia, vol. 52, 2009, pp. 1669-1679.

Lin et al., Colony-stimulating Factor 1 Promotes Progression of Mammary Tumors to Malignancy, J. Exp. Med., vol. 193, No. 6, Mar. 2001, pp. 727-739.

Lin et al., The Macrophage Growth Factor CSF-1 in Mammary Gland Development and Tumor Progression, J. Mammary Gland Biology and Neoplasia, vol. 7, Apr. 2002, pp. 147-162.

Lin et al., Discovery of a Cytokine and Its Receptor by Functional Screening of the Extracellular Proteome, Science, vol. 320, May 2008, pp. 807-811.

Lin et al. Regulation of Myeloid Growth and Differentiation by a Novel Cytokine, Interleukin-34 (IL-34), via the CSF-1 Receptor, poster presented at Cytokines in Health & Disease, Fifteenth Annual Conference of the International Cytokine Society (San Francisco, CA, Oct. 26-30, 2007, 1 page.

Lipton, Future Treatment of Bone Metastases, Clin. Cancer Res., vol. 12, 20 Suppl., Oct. 2006, pp. 6305s-6308s.

(56) References Cited

OTHER PUBLICATIONS

Lopez-Diego et al., Novel Therapeutic Strategies for Multiple Sclerosis—A Multifaceted Adversary, Nature Reviews Drug Discovery, vol. 7, Nov. 2008, pp. 909-925.
MacDonald et al., An Antibody Against the Colony-stimulating Factor 1 Receptor Depletes the Resident Subset of Monocytes and Tissue- and Tumor-associated Macrophages But Does Not Inhibit Inflammation, Blood, vol. 116, Aug. 2010, pp. 3955-3963.
Mancino et al., Breast Cancer Increases Osteoclastogenesis by Secreting M-CSF and Upregulating RANKL in Stromal Cells, J. Surgical Research, vol. 100, Jul. 2001, pp. 18-24.
Mroczko et al., Serum Macrophage-colony Stimulating Factor Levels in Colorectal Cancer Patients Correlate with Lymph Node Metastasis and Poor Prognosis, Clinica Chimica Acta., vol. 380, Feb. 2007, pp. 208-212.
Montell, Metastasis Movies, Macrophages, Molecules and More, EMBO Reports, vol. 4, No. 5, Apr. 2003, pp. 458-462.
Murray et al., SU11248 Inhibits Tumor Growth and CSF-1R-dependent Osteolysis in an Experimental Breast Cancer Bone Metastasis Model, Clinical & Experimental Metastasis, vol. 2, Aug. 2003, pp. 757-766.
Ohno et al., A c-FMS Tyrosine Kinase Inhibitor, Ki20227, Suppresses Osteoclast Differentiation and Osteolytic Bone Destruction in a Bone Metastasis, Mol. Cancer Ther., vol. 5, Nov. 2006, pp. 2634.
Ohno et al., The Orally-active and Selective c-FMS tyrosine Kinase Inhibitor Ki20227 Inhibits Disease Progression in a Collagen-induced Arthritis Mouse Model, Eur. J. Immunol., 2008, vol. 38:283-291.
Paniagua et al., c-Fms-mediated Differentiation and Priming of Monocyte Lineage Cells Plays a Central Role in Autoimmune Arthritis, Arthritis Research & Therapy, vol. 12, No. R32, Feb. 2010, pp. 1-45.
Paulus et al., Colony-stimulating Factor-1 Antibody Reverses Chemoresistance in Human MCF-7 Breast Cancer Xenografts, Cancer Res., vol. 66, No. 8, Apr. 2006, pp. 4349-4356.
Pederson et al., Identification of Breast Cancer Cell Line-derived Paracrine Factors That Stimulate Osteoclast Activity, Cancer Research, vol. 59, Nov. 1999, pp. 5849-5855.
Pixley et al., CSF-1 Regulation of the Wandering Macrophage: Complexity in Action, Trends in Cell Biology, vol. 14, No. 11, Nov. 2004, pp. 628-638.
Prince et al., 8: Disorders of Bone and Mineral Other Than Osteoporosis, MJA, vol. 180, Apr. 2004, pp. 354-359.
Qiu et al., Primary Structure of c-kit: Relationship with the CSF-1/PDGF Receptor Kinase Family—Oncogenic Activation of v-kit Involves Deletion of Extracellular Domain and C Terminus, The EMBO Journal, vol. 7, No. 4, Jan. 1988, pp. 1003-1011.
R&D Systems, Inc., Recombinant Human M-CSF R/Fc Chimera, Specifications and Use, Catalog No. 329-MR, Nov. 2007, 2 pages.
Rahimi et al., Receptor Chimeras Indicate that the Vascular Endothelial Growth Factor Receptor-1 (VEGFR-1) Modulates Mitogenic Activity of VEGFR-2 in Endothelial Cells, J. Biol. Chem., vol. 275, No. 22, Jun. 2000, pp. 16986-16992.
Ross, M-CSF, c-Fms, and Signaling in Osteoclasts and Their Precursors, Annals NY Acad. Sci., vol. 1068, 2006, pp. 110-116.
Roussel et al., Colony-stimulating Factor 1-mediated Regulation of a Chimeric c-fms / v-fms Receptor Containing the v-fms-encoded Tyrosine Kinase Domain, PNAS, vol. 85, Aug. 1988, pp. 5903-5907.
Sapi, The Role of CSF-1 in Normal Physiology of Mammary Gland and Breast Cancer: An Update, Exp. Biol. Med., vol. 229, 2004, pp. 1-11.
Sarma et al., Macrophage Colony-stimulating Factor Induces Substantial Osteoclast Generation and Bone Resorption in Human Bone Marrow Cultures, Blood, vol. 88, No. 7, Oct. 1996, pp. 2531-2540.
Shaposhink et al., Arterial Colony Stimulating Factor-1 Influences Atherosclerotic Lesions by Regulating Monocyte Migration and Apoptosis, J. Lipid Research, vol. 51, 2010, pp. 1962-1970.

Sherr et al., Inhibition of Colony-Stimulating Factor-1 Activity by Monoclonal Antibodies to the Human CSF-1 Receptor, Blood, vol. 73, No. 7, May 1989, pp. 1786-1793.
Sherr, Colony-Stimulating Factor-1 Receptor, Blood, vol. 75, No. 1, Jan. 1990, pp. 1-12.
Sigma Product Information, "Macrophage Cologny Stimulating Factor Receptor/Fc Chimera (M-CSF R, CD115) Human, Recombinant, Expressed in mouse NSO cells," Product No. M 7559, no date available.
Steinman et al., Virtues and Pitfalls of EAE for the Development of Therapies for Multiple Sclerosis, Trends in Immunology, 2005, 26(11):565-571.
Suzuki et al., Differences in Bone Responses to Recombinant Human Granulocyte Colony-stimulating Factor Between Mice and Rats, J. Toxicol. Sci., vol. 33, No. 2, 2008, pp. 245-249.
Sweet et al., CSF-1 as a Regulator of Macrophage Activation and Immune Response, AI&TE, vol. 51, 2003, pp. 169-177.
Tamura et al., Tyrosine Kinase as Targets for Anti-inflammatory Therapy, Anti-Inflammatory & Anti-Allergy Agents in Medicinal Chemistry, vol. 6, No. 1, 2007, pp. 47-60.
Tanaka et al., Macrophage Colony-stimulating Factor is Indispensable for Both Proliferation and Differentiation of Osteoclast Progenitors, J. Clin. Invest., vol. 91, Jan. 1993, pp. 257-263.
Teitelbaum, Osteoclasts: What Do They Do and How Do They Do It? Am. J. Pathol., vol. 170, No. 2, Feb. 2007, pp. 427-435.
Uemura et al., The Selective M-CSF Receptor Tyrosine Kinase Inhibitor Ki20227 Suppresses Experimental Autoimmune Encephalomyelitis, J. Neuroimmunology, vol. 195, Jan. 2008, pp. 73-80.
Usbiological, CD115, Recombinant, Human, Fc Chimera (BSA Free) (c-fms, Fms, CSF-1 R, M-CSFR), from Google's cache of http://usbio.net/Product.spx?ProdSku+C2447-52E1, as retrieved on Jan. 16, 2008 (1 page).
Van Daalen Wetters et al., Random Mutagenesis of CSF-1 Receptor (FMS) Reveals Multiple Sites for Activating Mutations within the Extracellular Domain, The EMBO Journal, 1992, 11:551-557.
Virk et al., Tumor Metastasis to Bone, Arthritis Research & Therapy, vol. 9, Suppl. 1, 2007, S5, pp. 1-10.
Walsh et al., Post-translational Modifications in the Context of Therapeutic Proteins, Nature Biotechnology, vol. 24, No. 10, Oct. 2006, pp. 1241-1252.
Wang et al., Identification of the Ligand-binding Regions in the Macrophage Colony-stimulating Factor Receptor Extracellular Domain, Mol. Cell Biol., Sep. 1993, pp. 5348-5359.
Weihofen et al., Release of Signal Peptide Fragments Into the Cytosol Requires Cleavage in the Transmembrane Region by a Protease Activity That is Specifically Blocked by a Novel Systeine Protease Inhibitor, J. Biol. Chem., vol. 275, No. 40, Oct. 2000, pp. 30951-30956.
Wu et al., Enhancement of J6-1 Human Leukemic Cell Proliferation by Membrane-bound M-CSF Through a Cell-Cell Contact Mechanism II. Role of an M-CSF Receptor-like Membrane Protein, Leukemia Research, vol. 22, 1998, pp. 55-60.
Wyckoff et al., A Paracrine Loop Between Tumor Cells and Macrophages is Required for Tumor Cell Migration in Mammary Tumors, Cancer Research, vol. 64, Oct. 2004, pp. 7022-7029.
Yano et al., Macrophage Colony-stimulating Factor Gene Transduction into Human Lung Cancer Cells Differentially Regulates Metastasis . . . , Cancer Research, Feb. 1997, pp. 784.
Yao et al., Tumor Necrosis Factor-α Increases Circulating Osteoclast Precursor Numbers by Promoting Their Proliferation and Differentiation in the Bone Marrow Through Up-regulation of c-Fms Expression, J. Biol Chem., vol. 281, Apr. 2006, pp. 11846.
Yoshimoto et al., Elevated levels of Fractalkine Expression and Accumulation of CD16+ Monocytes in Glomeruli of Active Lupus Nephritis, Am. J. Kidney Disease, vol. 50, No. 1, Jul. 2007, pp. 47-58.
Zheng et al., Expression of Bioactive Human M-CSF Soluble Receptor in Transgenic Tobacco Products, Protein Expression and Purification, 2006, 46:367-373; available online Aug. 15, 2005.
International Search Report and the Written Opinion dated Jan. 31, 2012 for International Patent Application PCT/US2011/035231, filed May 4, 2011.

(56) References Cited

OTHER PUBLICATIONS

International Search Report and Written Opinion dated May 24, 2010 for Application No. PCT/US2009/006301, filed Nov. 25, 2009.
International Search Report and Written Opinion dated Jun. 9, 2010 for Application No. PCT/US2009/006299, filed Nov. 25, 2009.
Response to Restriction Election Requirement filed May 3, 2011, for U.S. Appl. No. 12/626,583 (3 pages).
Office Action dated Jun. 21, 2011, for U.S. Appl. No. 12/626,583 (14 pages).
Reply to Office Action filed Aug. 1, 2011, for U.S. Appl. No. 12/626,583 (15 pages).
Notice of Allowance and Fees Due and Examiner initiated interview summary dated Dec. 8, 2011, for U.S. Appl. No. 12/626,583 (9 pages).
Office Action dated Nov. 16, 2010, for U.S. Appl. No. 12/626,598 (7 pages).
Amendment and Response to Restriction Requirement filed Feb. 16, 2011, for U.S. Appl. No. 12/626,598 (7 pages).
Office Action dated Mar. 16, 2001, for U.S. Appl. No. 12/626,598 (12 pages).
Reply to Office Action filed Jun. 16, 2011 for U.S. Appl. No. 12/626,598 (7 pages).
Final Office Action dated Aug. 3, 2011, for U.S. Appl. No. 12/626,598 (6 pages).
Amendment After Final filed Aug. 16, 2011, for U.S. Appl. No. 12/626,598 (8 pages).
Notice of Allowance and Fees Due dated Oct. 13, 2011, for U.S. Appl. No. 12/626,598 (6 pages).
Burns & Wilks, c-FMS inhibitors: a patent review, Expert Opin Ther Pat., 2011, 21(2):147-165.
File History of U.S. Appl. No. 13/891,455, filed May 10, 2013.
File History of U.S. App. No. 14/014,446, filed Aug. 30, 2013.
Priceman et al., Targeting distinct tumor-infiltrating myeloid cells by inhibiting CSF-1 receptor: combating tumor evasion of antiangiogenic therapy, Blood, 2010 115(7):1461-1471.
Sasmono et al., Mouse neutrophilic granulocytes express mRNA encoding the macrophage colony-stimulating factor receptor (CSF-1R) as well as many other macrophage-specific transcripts and can transdifferentiate into macrophages in vitro in response to CSF-1, J Leukoc Biol, 2007, 82(1):111-123.
Sigma Product Information, "Macrophage Cologny Stimulating Factor Receptor/Fc Chimera (M-CSF R, CD115) Human, Recombinant, Expressed in mouse NSO cells," Product Number M 7559, 2011, 2 pages.
Aikawa et al., PU.1-mediated upregulation of CSF1R is crucial for leukemia stem cell potential induced by MOZ-TIF2, Nature Medicine, vol. 16, May 2010, pp. 580-585.
Pasternak et al., ACC/AHA/NHLBI Clinical Advisory on the Use and Safety of Statins, J Am College Cardiology, 2002, 40(3):567-572.
Seeff, Should There Be a Standard of Care (SOC) for Drug-Induced Liver Injury (DILI)?, Presentation, Drug-Induced Liver Injury: Are We Ready to Look, Mar. 23-24, 2011, AASLD, FDA/CDER, PhRMA, 20 pages.
International Search Report and Written Opinion dated Jan. 7, 2014, for Application No. PCT/US2013/057442, filed Aug. 30, 2013, 15 pages.
Paul, WE, Fundamental Immunology, 3rd Ed., Raven Press, NY, Chapter 9, pp. 292-295 (1993).
Rudikoff et al., "Single amino acid substitution altering antigen-binding specificity," Proc. Natl. Acad. Sci. USA, 79: 1979-1983 (1982).
Colman, "Effects of amino acid sequence changes on antibody-antigen interactions," Research in Immunology, Elsevier, NY, 145(1): 33-36 (1994).
Bloom et al., Colony stimulating factor-1 in the induction of lupus nephritis, Kidney International, 1993, 43:1000-1009.
Carayannopoulos & Capra, Immunoglobulins: Structure and Function, Fundamental Immunology, 3rd Edition, Paul ed., Raven Press, NY, 1993, 292-295.
Chara et al., Monocyte populations as markers of response to adalimumab plus MTX in rheumatoid arthritis, Arthritis Research & Therapy, 2012, 14:R175 including supplemental data, 13 pages.
Chemel et al., Interleukin 34 expression is associated with synovitis severity in rheumatoid arthritis patients, Ann Rheum Dis, 2012, 71(1)150-154.
Cooper et al., FccRIIIa Expression on Monocytes in Rheumatoid Arthritis: Role in Immune-Complex Stimulated TNF Production and Non-Response to Methotrexate Therapy, PLoS One, 2012, 7(1):e28918, 10 pages.
Cros et al., Human CD14dim Monocytes Patrol and Sense Nucleic Acids and Viruses via TLR7 and TLR8 Receptors, Immunity, 2010, 33:375-386.
Garcia et al., Colony-Stimulating Factor (CSF)-1 Receptor Blockade Overcomes Overlapping Effects of M-CSF and IL-34 on Myeloid Differentiation and Gene Expression to Reduce Inflammation in Human and Murine Models of Rheumatoid Arthritis, ACR Poster, Nov. 2012, 1 page.
Garnero et al., Biochemical markers of joint tissue turnover in early rheumatoid arthritis, Clin Exp Rheumatol, 2003, 21(Suppl. 31):S54-S58.
Kawanaka et al., CD14+, CD16+ Blood Monocytes and Joint Inflammation in Rheumatoid Arthritis, Arthritis & Rheumatism, 2002, 46(10):2578-2586.
Kelley, Leukocyte—Renal Epithelial Cell Interactions Regulate Lupus Nephritis, Semin Nephrol, 27:59-68 Jan. 2007.
Koch et al., Investigating the role of proinflammatory CD16+ monocytes in the pathogenesis of inflammatory bowel disease, Clin Exper Immunol, 2010, 161:332-341.
Kutzelnigg et al., Cortical demyelination and diffuse white matter injury in multiple sclerosis, Brain, 2005, 128:2705-2712.
Le Meur et al., Macrophage accumulation at a site of renal inflammation is dependent on the M-CSF/c-fms pathway, J Leukoc Biol, 2002, 72(3):530-537.
Lenda et al., Negative role of colony-stimulating factor-1 in macrophage, T cell, and B cell mediated autoimmune disease in MRL-Fas(lpr) mice, J Immunol, 2004, 173(7):4744-4754.
Liu et al., The mechanism of shared but distinct CSF-1R signaling by the non-homologous cytokines IL-34 and CSF-1, Biochimica et Biophysica Acta, 2012, 1824:938-945.
Menke et al., Circulating CSF-1 Promotes Monocyte and Macrophage Phenotypes that Enhance Lupus Nephritis, j Am Soc Nephrol, 2009, 20:2581-2592.
Menke et al., CSF-1 signals directly to renal tubular epithelial cells to mediate repair in mice, J Clin Invest, 2009, 119(8):2330-2342.
Patel & Player, Colony-Stimulating Factor-1 Receptor Inhibitors for the Treatment of Cancer and Inflammatory Disease, Curr Topics Med Chem, 2009, 9:599-610.
Rauen & Mertens, Unravelling the pathogenesis of lupus nephritis: novel genetic study confirms decisive contribution of circulating colony-stimulating factor-1 (CSF-1), Int Urol Nephrol, 2010, 42:419-521.
Rossol et al., The CD14-bright CD16+ Monocyte Subset Is Expanded in Rheumatoid Arthritis and Promotes Expansion of the Th17 Cell Population, Arthritis & Rheumatism, 2012, 64(3):671-677.
Seshan & Jennette, Renal Disease in Systemic Lupus Erythematosus With Emphasis on Classification of Lupus Glomerulonephritis, Arch Pathol Lab Med, 2009, 133:233-248.
Subimerb et al., Circulating CD14+CD16+monocyte levels predict tissue invasive character of cholangiocarcinoma, Clinical and Experimental Immunology, 2010, 161:471-479.
TECOmedical Group, TRAP5b Tartrate-Resistant Acid Phosphatase active isoform 5b, A biomarker for osteoclastic bone-resporption activity, Bone-resporption in renal insufficiency, Catalog, Jul. 2011, 20 pages.
Toh et al., Colony Stimulating Factor 1 Receptor Inhibition Has Anti-Inflammatory and Potent Early Onset Bone and Cartilage Protective Effects, Abstract, ACR/ARHP Scientific Meeting, Nov. 7, 2011, 1 page.

(56) References Cited

OTHER PUBLICATIONS

Wada et al., Systemic autoimmune nephritogenic components induce CSF-1 and TNF-alpha in MRL kidneys, Kidney International, 1997, 52:934-941.
Wei et al., Functional overlap but differential expression of CSF-1 and IL-34 in their CSF-1 receptor-mediated regulation of myeloid cells, J Leukoc Biol, 2010, 88(3):495-505.
Wentworth & Davis, Systemic lupus erythematosus, Nature Rev, 2009, 8:103-104.
Wijngaarden et al., Fc-gamma receptor expression levels on monocytes are elevated in rheumatoid arthritis patients with high erythrocyte sedimentation rate who do not use anti-rheumatic drugs, Rheumatology, 2003, 42:681-688.
Yang et al., Increase in the level of macrophage colony-stimulating factor in patients with systemic lupus erythematosus, Ann Rheum Dis, 2008, 67:429-430.
Zhang et al., Hyper-Activated Pro-Inflammatory CD16+ Monocytes Correlate with the Severity of Liver Injury and Fibrosis in Patients with Chronic Hepatitis B, PLoS One, 2011, 6:(3):e17484, 10 pages.
Ziegler-Heitbrock, The CD14 CD16 blood monocytes: their role in infection and inflammation, J Leuko Biol, 2007, 81:584-592.
International Search Report and Written Opinion dated Sep. 7, 2012 for Application No. PCT/US2012/037520, filed May 11, 2012, 13 pages.
File History of U.S. Appl. No. 13/100,990, filed May 4, 2011.
Extended European Search Report, European Patent Appl. No. 11778283.9, dated Apr. 22, 2015.
T Tsuboi et al., Leukemia 14: 1460-66 (2000).
File History of U.S. Appl. No. 14/266,209, filed Apr. 30, 2014.
File History of U.S. Appl. No. 13/464,503, filed May 4, 2012.
File History of U.S. Appl. No. 14/924,568, filed Oct. 27, 2015.
Cassier et al., "CSF1R Inhibition with Emactuzumab in Locally Advanced Diffuse-Type Tenosynovial Giant Cell Tumors of the Soft Tissue: a Dose-Escalation and Dose-Expansion Phase 1 Study," Lancet Oncol., 2015, 16:949-56.
Sankhala et al, "A Phase ½ Dose Escalation and Expansion Study of Cabiralizumab (FPA008), an Anti-CSF1R Antibody, in Tenosynovial Giant Cell Tumor (TGCT, Diffuse Pigmented Villonodular Synovitis D-PVNS)," Five Prime Therapeutics, Poster, Jun. 2017, 1 page.
Tap et al., "Structure-Guided Blockade of CSF1R Kinase in Tenosynovial Giant-Cell Tumor," N Engl J Med, 2015, 373:428-37.
Tap et al., "Structure-Guided Blockade of CSF1R Kinase in Tenosynovial Giant-Cell Tumor," N Engl J Med, Supplementary Appendix, 2015, 40 pages.
Cassier et al., "Efficacy of Imatinib Mesylate for the Treatment of Locally Advanced and/or Metastatic Tenosynovial Giant Cell Tumor/Pigmented Villonodular Synovitis," Cancer, 2012, 118:1649-55.
Cassier et al., "Phase 1 Study of RG7155, a Novel anti-CSF1R Antibody, in Patients with Locally Advanced Pigmented Villonodular Synovitis (PVNS)," J. Clin. Oncol., 2014, 32:5s: Suppl. Abstr 10504.
Eisenhauer et al., "New Response Evaluation Criteria in Solid Tumours: revised RECIST Guideline (version 1.1)," Eur. J. Cancer, 2009, 45:228-247.
Radi et al., "Increased Serum Enzyme Levels Associated with Kupffer Cell Reduction with No Signs of Hepatic or Skeletal Muscle Injury," Amer. Jour. Pathology, 2011, 179:240-247.
Ravi et al., "Treatment of Tenosynovial Giant Cell Tumor and Pigmented Villonodular Synovitis," Curr Opin Oncol, 2011, 23:361-6.
Tap et al., "A Pilot Study of PLX3397, a Selective Colony-Stimulating Factor 1 Receptor (CSF1R) Kinase Inhibitor, in Pigmented Villonodular Synovitis (PVNS)," J. Clin Oncol, 2014, 32:5s: Suppl Abstr 10503.
West et al., "A Landscape Effect in Tenosynovial Giant-Cell Tumor from Activation of CSF1 Expression by a Translocation in a Minority of Tumor Cells," Proc Natl Acad Sci USA, 2006, 103:690-5.

* cited by examiner

SEQUENCE LISTING

<160> NUMBER OF SEQ ID NOS: 95

<210> SEQ ID NO 1
<211> LENGTH: 953
<212> TYPE: PRT
<213> ORGANISM: Artificial sequence
<220> FEATURE:
<223> OTHER INFORMATION: hCSF1R (full-length, no leader sequence)

<400> SEQUENCE: 1

```
Ile Pro Val Ile Glu Pro Ser Val Pro Glu Leu Val Val Lys Pro Gly
1               5                   10                  15

Ala Thr Val Thr Leu Arg Cys Val Gly Asn Gly Ser Val Glu Trp Asp
            20                  25                  30

Gly Pro Pro Ser Pro His Trp Thr Leu Tyr Ser Asp Gly Ser Ser Ser
        35                  40                  45

Ile Leu Ser Thr Asn Asn Ala Thr Phe Gln Asn Thr Gly Thr Tyr Arg
    50                  55                  60

Cys Thr Glu Pro Gly Asp Pro Leu Gly Gly Ser Ala Ala Ile His Leu
65                  70                  75                  80

Tyr Val Lys Asp Pro Ala Arg Pro Trp Asn Val Leu Ala Gln Glu Val
                85                  90                  95

Val Val Phe Glu Asp Gln Asp Ala Leu Leu Pro Cys Leu Leu Thr Asp
            100                 105                 110

Pro Val Leu Glu Ala Gly Val Ser Leu Val Arg Val Arg Gly Arg Pro
        115                 120                 125

Leu Met Arg His Thr Asn Tyr Ser Phe Ser Pro Trp His Gly Phe Thr
    130                 135                 140

Ile His Arg Ala Lys Phe Ile Gln Ser Gln Asp Tyr Gln Cys Ser Ala
145                 150                 155                 160

Leu Met Gly Gly Arg Lys Val Met Ser Ile Ser Ile Arg Leu Lys Val
                165                 170                 175
```

```
Gln Lys Val Ile Pro Gly Pro Pro Ala Leu Thr Leu Val Pro Ala Glu
            180                 185                 190

Leu Val Arg Ile Arg Gly Glu Ala Ala Gln Ile Val Cys Ser Ala Ser
        195                 200                 205

Ser Val Asp Val Asn Phe Asp Val Phe Leu Gln His Asn Asn Thr Lys
    210                 215                 220

Leu Ala Ile Pro Gln Gln Ser Asp Phe His Asn Asn Arg Tyr Gln Lys
225                 230                 235                 240

Val Leu Thr Leu Asn Leu Asp Gln Val Asp Phe Gln His Ala Gly Asn
                245                 250                 255

Tyr Ser Cys Val Ala Ser Asn Val Gln Gly Lys His Ser Thr Ser Met
            260                 265                 270

Phe Phe Arg Val Val Glu Ser Ala Tyr Leu Asn Leu Ser Ser Glu Gln
        275                 280                 285

Asn Leu Ile Gln Glu Val Thr Val Gly Glu Gly Leu Asn Leu Lys Val
    290                 295                 300

Met Val Glu Ala Tyr Pro Gly Leu Gln Gly Phe Asn Trp Thr Tyr Leu
305                 310                 315                 320

Gly Pro Phe Ser Asp His Gln Pro Glu Pro Lys Leu Ala Asn Ala Thr
                325                 330                 335

Thr Lys Asp Thr Tyr Arg His Thr Phe Thr Leu Ser Leu Pro Arg Leu
            340                 345                 350

Lys Pro Ser Glu Ala Gly Arg Tyr Ser Phe Leu Ala Arg Asn Pro Gly
        355                 360                 365

Gly Trp Arg Ala Leu Thr Phe Glu Leu Thr Leu Arg Tyr Pro Pro Glu
    370                 375                 380

Val Ser Val Ile Trp Thr Phe Ile Asn Gly Ser Gly Thr Leu Leu Cys
385                 390                 395                 400

Ala Ala Ser Gly Tyr Pro Gln Pro Asn Val Thr Trp Leu Gln Cys Ser
                405                 410                 415

Gly His Thr Asp Arg Cys Asp Glu Ala Gln Val Leu Gln Val Trp Asp
            420                 425                 430

Asp Pro Tyr Pro Glu Val Leu Ser Gln Glu Pro Phe His Lys Val Thr
        435                 440                 445

Val Gln Ser Leu Leu Thr Val Glu Thr Leu Glu His Asn Gln Thr Tyr
    450                 455                 460

Glu Cys Arg Ala His Asn Ser Val Gly Ser Gly Ser Trp Ala Phe Ile
465                 470                 475                 480

Pro Ile Ser Ala Gly Ala His Thr His Pro Pro Asp Glu Phe Leu Phe
                485                 490                 495

Thr Pro Val Val Ala Cys Met Ser Ile Met Ala Leu Leu Leu Leu
            500                 505                 510

Leu Leu Leu Leu Leu Leu Tyr Lys Tyr Lys Gln Lys Pro Lys Tyr Gln
        515                 520                 525

Val Arg Trp Lys Ile Ile Glu Ser Tyr Glu Gly Asn Ser Tyr Thr Phe
    530                 535                 540

Ile Asp Pro Thr Gln Leu Pro Tyr Asn Glu Lys Trp Glu Phe Pro Arg
545                 550                 555                 560

Asn Asn Leu Gln Phe Gly Lys Thr Leu Gly Ala Gly Ala Phe Gly Lys
                565                 570                 575

Val Val Glu Ala Thr Ala Phe Gly Leu Gly Lys Glu Asp Ala Val Leu
            580                 585                 590

Lys Val Ala Val Lys Met Leu Lys Ser Thr Ala His Ala Asp Glu Lys
```

Glu Ala Leu Met Ser Glu Leu Lys Ile Met Ser His Leu Gly Gln His
                595                 600                 605
Glu Asn Ile Val Asn Leu Leu Gly Ala Cys Thr His Gly Gly Pro Val
610                 615                 620
Leu Val Ile Thr Glu Tyr Cys Cys Tyr Gly Asp Leu Leu Asn Phe Leu
625                 630                 635                 640
Arg Arg Lys Ala Glu Ala Met Leu Gly Pro Ser Leu Ser Pro Gly Gln
            645                 650                 655
Asp Pro Glu Gly Gly Val Asp Tyr Lys Asn Ile His Leu Glu Lys Lys
660                 665                 670
Tyr Val Arg Arg Asp Ser Gly Phe Ser Ser Gln Gly Val Asp Thr Tyr
            675                 680                 685
Val Glu Met Arg Pro Val Ser Thr Ser Ser Asn Asp Ser Phe Ser Glu
690                 695                 700
Gln Asp Leu Asp Lys Glu Asp Gly Arg Pro Leu Glu Leu Arg Asp Leu
705                 710                 715                 720
Leu His Phe Ser Ser Gln Val Ala Gln Gly Met Ala Phe Leu Ala Ser
            725                 730                 735
Lys Asn Cys Ile His Arg Asp Val Ala Ala Arg Asn Val Leu Leu Thr
740                 745                 750
Asn Gly His Val Ala Lys Ile Gly Asp Phe Gly Leu Ala Arg Asp Ile
            755                 760                 765
Met Asn Asp Ser Asn Tyr Ile Val Lys Gly Asn Ala Arg Leu Pro Val
770                 775                 780
Lys Trp Met Ala Pro Glu Ser Ile Phe Asp Cys Val Tyr Thr Val Gln
785                 790                 795                 800
Ser Asp Val Trp Ser Tyr Gly Ile Leu Leu Trp Glu Ile Phe Ser Leu
            805                 810                 815
Gly Leu Asn Pro Tyr Pro Gly Ile Leu Val Asn Ser Lys Phe Tyr Lys
820                 825                 830
Leu Val Lys Asp Gly Tyr Gln Met Ala Gln Pro Ala Phe Ala Pro Lys
            835                 840                 845
Asn Ile Tyr Ser Ile Met Gln Ala Cys Trp Ala Leu Glu Pro Thr His
850                 855                 860
Arg Pro Thr Phe Gln Gln Ile Cys Ser Phe Leu Gln Glu Gln Ala Gln
            865                 870                 875                 880
Glu Asp Arg Arg Glu Arg Asp Tyr Thr Asn Leu Pro Ser Ser Ser Arg
            885                 890                 895
Ser Gly Gly Ser Gly Ser Ser Ser Glu Leu Glu Glu Glu Ser Ser
            900                 905                 910
Ser Glu His Leu Thr Cys Cys Glu Gln Gly Asp Ile Ala Gln Pro Leu
            915                 920                 925
Leu Gln Pro Asn Asn Tyr Gln Phe Cys
930                 935                 940
945                 950

<210> SEQ ID NO 2
<211> LENGTH: 972
<212> TYPE: PRT
<213> ORGANISM: Homo sapiens
<220> FEATURE:
<221> NAME/KEY: MISC_FEATURE
<222> LOCATION: (1)..(972)
<223> OTHER INFORMATION: hCSF1R (full-length, + leader sequence)

<400> SEQUENCE: 2

```
Met Gly Pro Gly Val Leu Leu Leu Leu Ala Thr Ala Trp His
1               5                   10                  15

Gly Gln Gly Ile Pro Val Ile Glu Pro Ser Val Pro Glu Leu Val Val
                20                  25                  30

Lys Pro Gly Ala Thr Val Thr Leu Arg Cys Val Gly Asn Gly Ser Val
                35                  40                  45

Glu Trp Asp Gly Pro Pro Ser Pro His Trp Thr Leu Tyr Ser Asp Gly
50                  55                  60

Ser Ser Ser Ile Leu Ser Thr Asn Asn Ala Thr Phe Gln Asn Thr Gly
65                  70                  75                  80

Thr Tyr Arg Cys Thr Glu Pro Gly Asp Pro Leu Gly Ser Ala Ala
                85                  90                  95

Ile His Leu Tyr Val Lys Asp Pro Ala Arg Pro Trp Asn Val Leu Ala
                100                 105                 110

Gln Glu Val Val Val Phe Glu Asp Gln Asp Ala Leu Leu Pro Cys Leu
                115                 120                 125

Leu Thr Asp Pro Val Leu Glu Ala Gly Val Ser Leu Val Arg Val Arg
    130                 135                 140

Gly Arg Pro Leu Met Arg His Thr Asn Tyr Ser Phe Ser Pro Trp His
145                 150                 155                 160

Gly Phe Thr Ile His Arg Ala Lys Phe Ile Gln Ser Gln Asp Tyr Gln
                165                 170                 175

Cys Ser Ala Leu Met Gly Gly Arg Lys Val Met Ser Ile Ser Ile Arg
                180                 185                 190

Leu Lys Val Gln Lys Val Ile Pro Gly Pro Pro Ala Leu Thr Leu Val
                195                 200                 205

Pro Ala Glu Leu Val Arg Ile Arg Gly Glu Ala Ala Gln Ile Val Cys
    210                 215                 220

Ser Ala Ser Ser Val Asp Val Asn Phe Asp Val Phe Leu Gln His Asn
225                 230                 235                 240

Asn Thr Lys Leu Ala Ile Pro Gln Gln Ser Asp Phe His Asn Asn Arg
                245                 250                 255

Tyr Gln Lys Val Leu Thr Leu Asn Leu Asp Gln Val Asp Phe Gln His
                260                 265                 270

Ala Gly Asn Tyr Ser Cys Val Ala Ser Asn Val Gln Gly Lys His Ser
                275                 280                 285

Thr Ser Met Phe Phe Arg Val Val Glu Ser Ala Tyr Leu Asn Leu Ser
    290                 295                 300

Ser Glu Gln Asn Leu Ile Gln Glu Val Thr Val Gly Glu Gly Leu Asn
305                 310                 315                 320

Leu Lys Val Met Val Glu Ala Tyr Pro Gly Leu Gln Gly Phe Asn Trp
                325                 330                 335

Thr Tyr Leu Gly Pro Phe Ser Asp His Gln Pro Glu Pro Lys Leu Ala
                340                 345                 350

Asn Ala Thr Thr Lys Asp Thr Tyr Arg His Thr Phe Thr Leu Ser Leu
                355                 360                 365

Pro Arg Leu Lys Pro Ser Glu Ala Gly Arg Tyr Ser Phe Leu Ala Arg
    370                 375                 380

Asn Pro Gly Gly Trp Arg Ala Leu Thr Phe Glu Leu Thr Leu Arg Tyr
385                 390                 395                 400

Pro Pro Glu Val Ser Val Ile Trp Thr Phe Ile Asn Gly Ser Gly Thr
                405                 410                 415
```

```
Leu Leu Cys Ala Ala Ser Gly Tyr Pro Gln Pro Asn Val Thr Trp Leu
            420                 425                 430
Gln Cys Ser Gly His Thr Asp Arg Cys Asp Glu Ala Gln Val Leu Gln
        435                 440                 445
Val Trp Asp Asp Pro Tyr Pro Glu Val Leu Ser Gln Glu Pro Phe His
    450                 455                 460
Lys Val Thr Val Gln Ser Leu Leu Thr Val Glu Thr Leu Glu His Asn
465                 470                 475                 480
Gln Thr Tyr Glu Cys Arg Ala His Asn Ser Val Gly Ser Gly Ser Trp
                485                 490                 495
Ala Phe Ile Pro Ile Ser Ala Gly Ala His Thr His Pro Pro Asp Glu
            500                 505                 510
Phe Leu Phe Thr Pro Val Val Ala Cys Met Ser Ile Met Ala Leu
        515                 520                 525
Leu Leu Leu Leu Leu Leu Leu Leu Tyr Lys Tyr Lys Gln Lys Pro
    530                 535                 540
Lys Tyr Gln Val Arg Trp Lys Ile Ile Glu Ser Tyr Glu Gly Asn Ser
545                 550                 555                 560
Tyr Thr Phe Ile Asp Pro Thr Gln Leu Pro Tyr Asn Glu Lys Trp Glu
                565                 570                 575
Phe Pro Arg Asn Asn Leu Gln Phe Gly Lys Thr Leu Gly Ala Gly Ala
            580                 585                 590
Phe Gly Lys Val Val Glu Ala Thr Ala Phe Gly Leu Gly Lys Glu Asp
        595                 600                 605
Ala Val Leu Lys Val Ala Val Lys Met Leu Lys Ser Thr Ala His Ala
    610                 615                 620
Asp Glu Lys Glu Ala Leu Met Ser Glu Leu Lys Ile Met Ser His Leu
625                 630                 635                 640
Gly Gln His Glu Asn Ile Val Asn Leu Leu Gly Ala Cys Thr His Gly
                645                 650                 655
Gly Pro Val Leu Val Ile Thr Glu Tyr Cys Cys Tyr Gly Asp Leu Leu
            660                 665                 670
Asn Phe Leu Arg Arg Lys Ala Glu Ala Met Leu Gly Pro Ser Leu Ser
        675                 680                 685
Pro Gly Gln Asp Pro Glu Gly Gly Val Asp Tyr Lys Asn Ile His Leu
    690                 695                 700
Glu Lys Lys Tyr Val Arg Arg Asp Ser Gly Phe Ser Ser Gln Gly Val
705                 710                 715                 720
Asp Thr Tyr Val Glu Met Arg Pro Val Ser Thr Ser Ser Asn Asp Ser
                725                 730                 735
Phe Ser Glu Gln Asp Leu Asp Lys Glu Asp Gly Arg Pro Leu Glu Leu
            740                 745                 750
Arg Asp Leu Leu His Phe Ser Ser Gln Val Ala Gln Gly Met Ala Phe
        755                 760                 765
Leu Ala Ser Lys Asn Cys Ile His Arg Asp Val Ala Ala Arg Asn Val
    770                 775                 780
Leu Leu Thr Asn Gly His Val Ala Lys Ile Gly Asp Phe Gly Leu Ala
785                 790                 795                 800
Arg Asp Ile Met Asn Asp Ser Asn Tyr Ile Val Lys Gly Asn Ala Arg
                805                 810                 815
Leu Pro Val Lys Trp Met Ala Pro Glu Ser Ile Phe Asp Cys Val Tyr
            820                 825                 830
Thr Val Gln Ser Asp Val Trp Ser Tyr Gly Ile Leu Leu Trp Glu Ile
```

```
                    835                 840                 845
Phe Ser Leu Gly Leu Asn Pro Tyr Pro Gly Ile Leu Val Asn Ser Lys
        850                 855                 860
Phe Tyr Lys Leu Val Lys Asp Gly Tyr Gln Met Ala Gln Pro Ala Phe
865                 870                 875                 880
Ala Pro Lys Asn Ile Tyr Ser Ile Met Gln Ala Cys Trp Ala Leu Glu
                885                 890                 895
Pro Thr His Arg Pro Thr Phe Gln Gln Ile Cys Ser Phe Leu Gln Glu
            900                 905                 910
Gln Ala Gln Glu Asp Arg Arg Glu Arg Asp Tyr Thr Asn Leu Pro Ser
        915                 920                 925
Ser Ser Arg Ser Gly Gly Ser Gly Ser Ser Ser Glu Leu Glu Glu
    930                 935                 940
Glu Ser Ser Ser Glu His Leu Thr Cys Cys Glu Gln Gly Asp Ile Ala
945                 950                 955                 960
Gln Pro Leu Leu Gln Pro Asn Asn Tyr Gln Phe Cys
                965                 970

<210> SEQ ID NO 3
<211> LENGTH: 20
<212> TYPE: PRT
<213> ORGANISM: Artificial sequence
<220> FEATURE:
<223> OTHER INFORMATION: Light chain leader sequence

<400> SEQUENCE: 3

Met Glu Thr Asp Thr Leu Leu Leu Trp Val Leu Leu Leu Trp Val Pro
1               5                   10                  15
Gly Ser Thr Gly
            20

<210> SEQ ID NO 4
<211> LENGTH: 19
<212> TYPE: PRT
<213> ORGANISM: Artificial sequence
<220> FEATURE:
<223> OTHER INFORMATION: Heavy chain leader sequence

<400> SEQUENCE: 4

Met Ala Val Leu Gly Leu Leu Leu Cys Leu Val Thr Phe Pro Ser Cys
1               5                   10                  15
Val Leu Ser

<210> SEQ ID NO 5
<211> LENGTH: 487
<212> TYPE: PRT
<213> ORGANISM: Artificial sequence
<220> FEATURE:
<223> OTHER INFORMATION: hCSF1R ECD.506

<400> SEQUENCE: 5

Ile Pro Val Ile Glu Pro Ser Val Pro Glu Leu Val Val Lys Pro Gly
1               5                   10                  15
Ala Thr Val Thr Leu Arg Cys Val Gly Asn Gly Ser Val Glu Trp Asp
            20                  25                  30
Gly Pro Pro Ser Pro His Trp Thr Leu Tyr Ser Asp Gly Ser Ser Ser
        35                  40                  45
Ile Leu Ser Thr Asn Asn Ala Thr Phe Gln Asn Thr Gly Thr Tyr Arg
    50                  55                  60
```

```
Cys Thr Glu Pro Gly Asp Pro Leu Gly Gly Ser Ala Ala Ile His Leu
 65                  70                  75                  80

Tyr Val Lys Asp Pro Ala Arg Pro Trp Asn Val Leu Ala Gln Glu Val
                 85                  90                  95

Val Val Phe Glu Asp Gln Asp Ala Leu Leu Pro Cys Leu Leu Thr Asp
            100                 105                 110

Pro Val Leu Glu Ala Gly Val Ser Leu Val Arg Val Arg Gly Arg Pro
            115                 120                 125

Leu Met Arg His Thr Asn Tyr Ser Phe Ser Pro Trp His Gly Phe Thr
        130                 135                 140

Ile His Arg Ala Lys Phe Ile Gln Ser Gln Asp Tyr Gln Cys Ser Ala
145                 150                 155                 160

Leu Met Gly Gly Arg Lys Val Met Ser Ile Ser Ile Arg Leu Lys Val
            165                 170                 175

Gln Lys Val Ile Pro Gly Pro Pro Ala Leu Thr Leu Val Pro Ala Glu
            180                 185                 190

Leu Val Arg Ile Arg Gly Glu Ala Ala Gln Ile Val Cys Ser Ala Ser
        195                 200                 205

Ser Val Asp Val Asn Phe Asp Val Phe Leu Gln His Asn Asn Thr Lys
    210                 215                 220

Leu Ala Ile Pro Gln Gln Ser Asp Phe His Asn Asn Arg Tyr Gln Lys
225                 230                 235                 240

Val Leu Thr Leu Asn Leu Asp Gln Val Asp Phe Gln His Ala Gly Asn
            245                 250                 255

Tyr Ser Cys Val Ala Ser Asn Val Gln Gly Lys His Ser Thr Ser Met
            260                 265                 270

Phe Phe Arg Val Val Glu Ser Ala Tyr Leu Asn Leu Ser Ser Glu Gln
        275                 280                 285

Asn Leu Ile Gln Glu Val Thr Val Gly Glu Gly Leu Asn Leu Lys Val
    290                 295                 300

Met Val Glu Ala Tyr Pro Gly Leu Gln Gly Phe Asn Trp Thr Tyr Leu
305                 310                 315                 320

Gly Pro Phe Ser Asp His Gln Pro Glu Pro Lys Leu Ala Asn Ala Thr
            325                 330                 335

Thr Lys Asp Thr Tyr Arg His Thr Phe Thr Leu Ser Leu Pro Arg Leu
            340                 345                 350

Lys Pro Ser Glu Ala Gly Arg Tyr Ser Phe Leu Ala Arg Asn Pro Gly
        355                 360                 365

Gly Trp Arg Ala Leu Thr Phe Glu Leu Thr Leu Arg Tyr Pro Pro Glu
    370                 375                 380

Val Ser Val Ile Trp Thr Phe Ile Asn Gly Ser Gly Thr Leu Leu Cys
385                 390                 395                 400

Ala Ala Ser Gly Tyr Pro Gln Pro Asn Val Thr Trp Leu Gln Cys Ser
            405                 410                 415

Gly His Thr Asp Arg Cys Asp Glu Ala Gln Val Leu Gln Val Trp Asp
            420                 425                 430

Asp Pro Tyr Pro Glu Val Leu Ser Gln Glu Pro Phe His Lys Val Thr
        435                 440                 445

Val Gln Ser Leu Leu Thr Val Glu Thr Leu Glu His Asn Gln Thr Tyr
    450                 455                 460

Glu Cys Arg Ala His Asn Ser Val Gly Ser Gly Ser Trp Ala Phe Ile
465                 470                 475                 480

Pro Ile Ser Ala Gly Ala His
```

-continued

485

<210> SEQ ID NO 6
<211> LENGTH: 719
<212> TYPE: PRT
<213> ORGANISM: Artificial sequence
<220> FEATURE:
<223> OTHER INFORMATION: hCSF1R ECD.506-Fc

<400> SEQUENCE: 6

```
Ile Pro Val Ile Glu Pro Ser Val Pro Glu Leu Val Val Lys Pro Gly
1               5                   10                  15

Ala Thr Val Thr Leu Arg Cys Val Gly Asn Gly Ser Val Glu Trp Asp
            20                  25                  30

Gly Pro Pro Ser Pro His Trp Thr Leu Tyr Ser Asp Gly Ser Ser Ser
        35                  40                  45

Ile Leu Ser Thr Asn Asn Ala Thr Phe Gln Asn Thr Gly Thr Tyr Arg
    50                  55                  60

Cys Thr Glu Pro Gly Asp Pro Leu Gly Gly Ser Ala Ala Ile His Leu
65                  70                  75                  80

Tyr Val Lys Asp Pro Ala Arg Pro Trp Asn Val Leu Ala Gln Glu Val
                85                  90                  95

Val Val Phe Glu Asp Gln Asp Ala Leu Leu Pro Cys Leu Leu Thr Asp
            100                 105                 110

Pro Val Leu Glu Ala Gly Val Ser Leu Val Arg Val Arg Gly Arg Pro
        115                 120                 125

Leu Met Arg His Thr Asn Tyr Ser Phe Ser Pro Trp His Gly Phe Thr
    130                 135                 140

Ile His Arg Ala Lys Phe Ile Gln Ser Gln Asp Tyr Gln Cys Ser Ala
145                 150                 155                 160

Leu Met Gly Gly Arg Lys Val Met Ser Ile Ser Ile Arg Leu Lys Val
                165                 170                 175

Gln Lys Val Ile Pro Gly Pro Pro Ala Leu Thr Leu Val Pro Ala Glu
            180                 185                 190

Leu Val Arg Ile Arg Gly Glu Ala Ala Gln Ile Val Cys Ser Ala Ser
        195                 200                 205

Ser Val Asp Val Asn Phe Asp Val Phe Leu Gln His Asn Asn Thr Lys
    210                 215                 220

Leu Ala Ile Pro Gln Gln Ser Asp Phe His Asn Asn Arg Tyr Gln Lys
225                 230                 235                 240

Val Leu Thr Leu Asn Leu Asp Gln Val Asp Phe Gln His Ala Gly Asn
                245                 250                 255

Tyr Ser Cys Val Ala Ser Asn Val Gln Gly Lys His Ser Thr Ser Met
            260                 265                 270

Phe Phe Arg Val Val Glu Ser Ala Tyr Leu Asn Leu Ser Ser Glu Gln
        275                 280                 285

Asn Leu Ile Gln Glu Val Thr Val Gly Glu Gly Leu Asn Leu Lys Val
    290                 295                 300

Met Val Glu Ala Tyr Pro Gly Leu Gln Gly Phe Asn Trp Thr Tyr Leu
305                 310                 315                 320

Gly Pro Phe Ser Asp His Gln Pro Glu Pro Lys Leu Ala Asn Ala Thr
                325                 330                 335

Thr Lys Asp Thr Tyr Arg His Thr Phe Thr Leu Ser Leu Pro Arg Leu
            340                 345                 350

Lys Pro Ser Glu Ala Gly Arg Tyr Ser Phe Leu Ala Arg Asn Pro Gly
```

```
                355                 360                 365
Gly Trp Arg Ala Leu Thr Phe Glu Leu Thr Leu Arg Tyr Pro Pro Glu
        370                 375                 380

Val Ser Val Ile Trp Thr Phe Ile Asn Gly Ser Gly Thr Leu Leu Cys
385                 390                 395                 400

Ala Ala Ser Gly Tyr Pro Gln Pro Asn Val Thr Trp Leu Gln Cys Ser
                405                 410                 415

Gly His Thr Asp Arg Cys Asp Glu Ala Gln Val Leu Gln Val Trp Asp
        420                 425                 430

Asp Pro Tyr Pro Glu Val Leu Ser Gln Glu Pro Phe His Lys Val Thr
                435                 440                 445

Val Gln Ser Leu Leu Thr Val Glu Thr Leu Glu His Asn Gln Thr Tyr
        450                 455                 460

Glu Cys Arg Ala His Asn Ser Val Gly Ser Gly Ser Trp Ala Phe Ile
465                 470                 475                 480

Pro Ile Ser Ala Gly Ala His Glu Pro Lys Ser Ser Asp Lys Thr His
                485                 490                 495

Thr Cys Pro Pro Cys Pro Ala Pro Glu Leu Leu Gly Gly Pro Ser Val
                500                 505                 510

Phe Leu Phe Pro Pro Lys Pro Lys Asp Thr Leu Met Ile Ser Arg Thr
        515                 520                 525

Pro Glu Val Thr Cys Val Val Val Asp Val Ser His Glu Asp Pro Glu
        530                 535                 540

Val Lys Phe Asn Trp Tyr Val Asp Gly Val Glu Val His Asn Ala Lys
545                 550                 555                 560

Thr Lys Pro Arg Glu Glu Gln Tyr Asn Ser Thr Tyr Arg Val Val Ser
                565                 570                 575

Val Leu Thr Val Leu His Gln Asp Trp Leu Asn Gly Lys Glu Tyr Lys
        580                 585                 590

Cys Lys Val Ser Asn Lys Ala Leu Pro Ala Pro Ile Glu Lys Thr Ile
        595                 600                 605

Ser Lys Ala Lys Gly Gln Pro Arg Glu Pro Gln Val Tyr Thr Leu Pro
610                 615                 620

Pro Ser Arg Asp Glu Leu Thr Lys Asn Gln Val Ser Leu Thr Cys Leu
625                 630                 635                 640

Val Lys Gly Phe Tyr Pro Ser Asp Ile Ala Val Glu Trp Glu Ser Asn
                645                 650                 655

Gly Gln Pro Glu Asn Asn Tyr Lys Thr Thr Pro Pro Val Leu Asp Ser
                660                 665                 670

Asp Gly Ser Phe Phe Leu Tyr Ser Lys Leu Thr Val Asp Lys Ser Arg
        675                 680                 685

Trp Gln Gln Gly Asn Val Phe Ser Cys Ser Val Met His Glu Ala Leu
        690                 695                 700

His Asn His Tyr Thr Gln Lys Ser Leu Ser Leu Ser Pro Gly Lys
705                 710                 715

<210> SEQ ID NO 7
<211> LENGTH: 506
<212> TYPE: PRT
<213> ORGANISM: Artificial sequence
<220> FEATURE:
<223> OTHER INFORMATION: cynoCSF1R ECD (with leader sequence)

<400> SEQUENCE: 7

Met Gly Pro Gly Val Leu Leu Leu Leu Leu Val Val Thr Ala Trp His
```

```
1               5                   10                  15
Gly Gln Gly Ile Pro Val Ile Glu Pro Ser Gly Pro Glu Leu Val Val
            20                  25                  30

Lys Pro Gly Glu Thr Val Thr Leu Arg Cys Val Gly Asn Gly Ser Val
            35                  40                  45

Glu Trp Asp Gly Pro Ile Ser Pro His Trp Thr Leu Tyr Ser Asp Gly
    50                  55                  60

Pro Ser Ser Val Leu Thr Thr Asn Ala Thr Phe Gln Asn Thr Arg
65                  70                  75                  80

Thr Tyr Arg Cys Thr Glu Pro Gly Asp Pro Leu Gly Gly Ser Ala Ala
                85                  90                  95

Ile His Leu Tyr Val Lys Asp Pro Ala Arg Pro Trp Asn Val Leu Ala
                100                 105                 110

Lys Glu Val Val Val Phe Glu Asp Gln Asp Ala Leu Leu Pro Cys Leu
                115                 120                 125

Leu Thr Asp Pro Val Leu Glu Ala Gly Val Ser Leu Val Arg Leu Arg
        130                 135                 140

Gly Arg Pro Leu Leu Arg His Thr Asn Tyr Ser Phe Ser Pro Trp His
145                 150                 155                 160

Gly Phe Thr Ile His Arg Ala Lys Phe Ile Gln Gly Gln Asp Tyr Gln
                165                 170                 175

Cys Ser Ala Leu Met Gly Ser Arg Lys Val Met Ser Ile Ser Ile Arg
                180                 185                 190

Leu Lys Val Gln Lys Val Ile Pro Gly Pro Pro Ala Leu Thr Leu Val
        195                 200                 205

Pro Ala Glu Leu Val Arg Ile Arg Gly Glu Ala Ala Gln Ile Val Cys
210                 215                 220

Ser Ala Ser Asn Ile Asp Val Asp Phe Asp Val Phe Leu Gln His Asn
225                 230                 235                 240

Thr Thr Lys Leu Ala Ile Pro Gln Arg Ser Asp Phe His Asp Asn Arg
                245                 250                 255

Tyr Gln Lys Val Leu Thr Leu Ser Leu Gly Gln Val Asp Phe Gln His
                260                 265                 270

Ala Gly Asn Tyr Ser Cys Val Ala Ser Asn Val Gln Gly Lys His Ser
                275                 280                 285

Thr Ser Met Phe Phe Arg Val Val Glu Ser Ala Tyr Leu Asp Leu Ser
        290                 295                 300

Ser Glu Gln Asn Leu Ile Gln Glu Val Thr Val Gly Glu Gly Leu Asn
305                 310                 315                 320

Leu Lys Val Met Val Glu Ala Tyr Pro Gly Leu Gln Gly Phe Asn Trp
                325                 330                 335

Thr Tyr Leu Gly Pro Phe Ser Asp His Gln Pro Glu Pro Lys Leu Ala
                340                 345                 350

Asn Ala Thr Thr Lys Asp Thr Tyr Arg His Thr Phe Thr Leu Ser Leu
            355                 360                 365

Pro Arg Leu Lys Pro Ser Glu Ala Gly Arg Tyr Ser Phe Leu Ala Arg
        370                 375                 380

Asn Pro Gly Gly Trp Arg Ala Leu Thr Phe Glu Leu Thr Leu Arg Tyr
385                 390                 395                 400

Pro Pro Glu Val Ser Val Ile Trp Thr Ser Ile Asn Gly Ser Gly Thr
                405                 410                 415

Leu Leu Cys Ala Ala Ser Gly Tyr Pro Gln Pro Asn Val Thr Trp Leu
                420                 425                 430
```

```
Gln Cys Ala Gly His Thr Asp Arg Cys Asp Glu Ala Gln Val Leu Gln
            435                 440                 445

Val Trp Val Asp Pro His Pro Glu Val Leu Ser Gln Glu Pro Phe Gln
    450                 455                 460

Lys Val Thr Val Gln Ser Leu Leu Thr Ala Glu Thr Leu Glu His Asn
465                 470                 475                 480

Gln Thr Tyr Glu Cys Arg Ala His Asn Ser Val Gly Ser Gly Ser Trp
                485                 490                 495

Ala Phe Ile Pro Ile Ser Ala Gly Ala Arg
            500                 505

<210> SEQ ID NO 8
<211> LENGTH: 740
<212> TYPE: PRT
<213> ORGANISM: Artificial sequence
<220> FEATURE:
<223> OTHER INFORMATION: cynoCSF1R ECD-Fc (with leader sequence)

<400> SEQUENCE: 8

Met Gly Pro Gly Val Leu Leu Leu Leu Val Val Thr Ala Trp His
1               5                   10                  15

Gly Gln Gly Ile Pro Val Ile Glu Pro Ser Gly Pro Glu Leu Val Val
                20                  25                  30

Lys Pro Gly Glu Thr Val Thr Leu Arg Cys Val Gly Asn Gly Ser Val
            35                  40                  45

Glu Trp Asp Gly Pro Ile Ser Pro His Trp Thr Leu Tyr Ser Asp Gly
    50                  55                  60

Pro Ser Ser Val Leu Thr Thr Thr Asn Ala Thr Phe Gln Asn Thr Arg
65                  70                  75                  80

Thr Tyr Arg Cys Thr Glu Pro Gly Asp Pro Leu Gly Gly Ser Ala Ala
                85                  90                  95

Ile His Leu Tyr Val Lys Asp Pro Ala Arg Pro Trp Asn Val Leu Ala
            100                 105                 110

Lys Glu Val Val Val Phe Glu Asp Gln Asp Ala Leu Leu Pro Cys Leu
        115                 120                 125

Leu Thr Asp Pro Val Leu Glu Ala Gly Val Ser Leu Val Arg Leu Arg
    130                 135                 140

Gly Arg Pro Leu Leu Arg His Thr Asn Tyr Ser Phe Ser Pro Trp His
145                 150                 155                 160

Gly Phe Thr Ile His Arg Ala Lys Phe Ile Gln Gly Gln Asp Tyr Gln
                165                 170                 175

Cys Ser Ala Leu Met Gly Ser Arg Lys Val Met Ser Ile Ser Ile Arg
            180                 185                 190

Leu Lys Val Gln Lys Val Ile Pro Gly Pro Pro Ala Leu Thr Leu Val
        195                 200                 205

Pro Ala Glu Leu Val Arg Ile Arg Gly Glu Ala Ala Gln Ile Val Cys
    210                 215                 220

Ser Ala Ser Asn Ile Asp Val Asp Phe Asp Val Phe Leu Gln His Asn
225                 230                 235                 240

Thr Thr Lys Leu Ala Ile Pro Gln Arg Ser Asp Phe His Asp Asn Arg
                245                 250                 255

Tyr Gln Lys Val Leu Thr Leu Ser Leu Gly Gln Val Asp Phe Gln His
            260                 265                 270

Ala Gly Asn Tyr Ser Cys Val Ala Ser Asn Val Gln Gly Lys His Ser
        275                 280                 285
```

```
Thr Ser Met Phe Phe Arg Val Glu Ser Ala Tyr Leu Asp Leu Ser
    290             295             300

Ser Glu Gln Asn Leu Ile Gln Glu Val Thr Val Gly Gly Leu Asn
305             310             315             320

Leu Lys Val Met Val Glu Ala Tyr Pro Gly Leu Gln Gly Phe Asn Trp
            325             330             335

Thr Tyr Leu Gly Pro Phe Ser Asp His Gln Pro Glu Pro Lys Leu Ala
            340             345             350

Asn Ala Thr Thr Lys Asp Thr Tyr Arg His Thr Phe Thr Leu Ser Leu
            355             360             365

Pro Arg Leu Lys Pro Ser Glu Ala Gly Arg Tyr Ser Phe Leu Ala Arg
    370             375             380

Asn Pro Gly Gly Trp Arg Ala Leu Thr Phe Glu Leu Thr Leu Arg Tyr
385             390             395             400

Pro Pro Glu Val Ser Val Ile Trp Thr Ser Ile Asn Gly Ser Gly Thr
            405             410             415

Leu Leu Cys Ala Ala Ser Gly Tyr Pro Gln Pro Asn Val Thr Trp Leu
            420             425             430

Gln Cys Ala Gly His Thr Asp Arg Cys Asp Glu Ala Gln Val Leu Gln
    435             440             445

Val Trp Val Asp Pro His Pro Glu Val Leu Ser Gln Glu Pro Phe Gln
    450             455             460

Lys Val Thr Val Gln Ser Leu Leu Thr Ala Glu Thr Leu Glu His Asn
465             470             475             480

Gln Thr Tyr Glu Cys Arg Ala His Asn Ser Val Gly Ser Gly Ser Trp
            485             490             495

Ala Phe Ile Pro Ile Ser Ala Gly Ala Arg Gly Ser Gly Pro Lys Ser
            500             505             510

Ser Asp Lys Thr His Thr Cys Pro Pro Cys Pro Ala Pro Glu Leu Leu
    515             520             525

Gly Gly Pro Ser Val Phe Leu Phe Pro Pro Lys Pro Lys Asp Thr Leu
    530             535             540

Met Ile Ser Arg Thr Pro Glu Val Thr Cys Val Val Val Asp Val Ser
545             550             555             560

His Glu Asp Pro Glu Val Lys Phe Asn Trp Tyr Val Asp Gly Val Glu
            565             570             575

Val His Asn Ala Lys Thr Lys Pro Arg Glu Glu Gln Tyr Asn Ser Thr
            580             585             590

Tyr Arg Val Val Ser Val Leu Thr Val Leu His Gln Asp Trp Leu Asn
    595             600             605

Gly Lys Glu Tyr Lys Cys Lys Val Ser Asn Lys Ala Leu Pro Ala Pro
    610             615             620

Ile Glu Lys Thr Ile Ser Lys Ala Lys Gly Gln Pro Arg Glu Pro Gln
625             630             635             640

Val Tyr Thr Leu Pro Pro Ser Arg Asp Glu Leu Thr Lys Asn Gln Val
            645             650             655

Ser Leu Thr Cys Leu Val Lys Gly Phe Tyr Pro Ser Asp Ile Ala Val
            660             665             670

Glu Trp Glu Ser Asn Gly Gln Pro Glu Asn Asn Tyr Lys Thr Thr Pro
    675             680             685

Pro Val Leu Asp Ser Asp Gly Ser Phe Phe Leu Tyr Ser Lys Leu Thr
    690             695             700
```

Val Asp Lys Ser Arg Trp Gln Gln Gly Asn Val Phe Ser Cys Ser Val
705                 710                 715                 720

Met His Glu Ala Leu His Asn His Tyr Thr Gln Lys Ser Leu Ser Leu
            725                 730                 735

Ser Pro Gly Lys
            740

<210> SEQ ID NO 9
<211> LENGTH: 122
<212> TYPE: PRT
<213> ORGANISM: Artificial sequence
<220> FEATURE:
<223> OTHER INFORMATION: Fab 0301 heavy chain variable region

<400> SEQUENCE: 9

Glu Val Gln Leu Gln Gln Ser Gly Pro Glu Leu Val Arg Pro Gly Ala
1               5                   10                  15

Ser Val Lys Met Ser Cys Lys Ala Ser Gly Tyr Thr Phe Thr Asp Asn
            20                  25                  30

Tyr Met Ile Trp Val Lys Gln Ser His Gly Lys Ser Leu Glu Trp Ile
        35                  40                  45

Gly Asp Ile Asn Pro Tyr Asn Gly Gly Thr Thr Phe Asn Gln Lys Phe
50                  55                  60

Lys Gly Lys Ala Thr Leu Thr Val Glu Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Glu Ser Pro Tyr Phe Ser Asn Leu Tyr Val Met Asp Tyr Trp
            100                 105                 110

Gly Gln Gly Thr Ser Val Thr Val Ser Ser
        115                 120

<210> SEQ ID NO 10
<211> LENGTH: 111
<212> TYPE: PRT
<213> ORGANISM: Artificial sequence
<220> FEATURE:
<223> OTHER INFORMATION: Fab 0301 light chain variable region

<400> SEQUENCE: 10

Asn Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Asn Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys His Leu Ser Asn
                85                  90                  95

Glu Asp Leu Ser Thr Phe Gly Gly Gly Thr Lys Leu Glu Ile Lys
            100                 105                 110

<210> SEQ ID NO 11
<211> LENGTH: 121
<212> TYPE: PRT
<213> ORGANISM: Artificial sequence

```
<220> FEATURE:
<223> OTHER INFORMATION: Fab 0302 heavy chain variable region

<400> SEQUENCE: 11

Glu Ile Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Ser Asp Phe
            20                  25                  30

Asn Ile His Trp Val Lys Gln Lys Pro Gly Gln Gly Leu Glu Trp Ile
        35                  40                  45

Gly Tyr Ile Asn Pro Tyr Thr Asp Val Thr Val Tyr Asn Glu Lys Phe
    50                  55                  60

Lys Gly Lys Ala Thr Leu Thr Ser Asp Arg Ser Ser Ser Thr Ala Tyr
65                  70                  75                  80

Met Asp Leu Ser Ser Leu Thr Ser Glu Asp Ser Ala Val Tyr Tyr Cys
                85                  90                  95

Ala Ser Tyr Phe Asp Gly Thr Phe Asp Tyr Ala Leu Asp Tyr Trp Gly
            100                 105                 110

Gln Gly Thr Ser Ile Thr Val Ser Ser
        115                 120

<210> SEQ ID NO 12
<211> LENGTH: 111
<212> TYPE: PRT
<213> ORGANISM: Artificial sequence
<220> FEATURE:
<223> OTHER INFORMATION: Fab 0302 light chain variable region

<400> SEQUENCE: 12

Asp Val Val Val Thr Gln Thr Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Leu Ser Phe Met Asn Trp Phe Gln Gln Lys Pro Gly Gln Pro Pro
        35                  40                  45

Lys Leu Leu Ile Tyr Thr Ala Ser Asn Leu Glu Ser Gly Ile Pro Ala
    50                  55                  60

Arg Phe Ser Gly Gly Gly Ser Arg Thr Asp Phe Thr Leu Thr Ile Asp
65                  70                  75                  80

Pro Val Glu Ala Asp Asp Ala Ala Thr Tyr Phe Cys Gln Gln Ser Lys
                85                  90                  95

Glu Leu Pro Trp Thr Phe Gly Gly Gly Thr Arg Leu Glu Ile Lys
            100                 105                 110

<210> SEQ ID NO 13
<211> LENGTH: 122
<212> TYPE: PRT
<213> ORGANISM: Artificial sequence
<220> FEATURE:
<223> OTHER INFORMATION: Fab 0311 heavy chain variable region

<400> SEQUENCE: 13

Glu Ile Gln Leu Gln Gln Ser Gly Pro Asp Leu Met Lys Pro Gly Ala
1               5                   10                  15

Ser Val Lys Met Ser Cys Lys Ala Ser Gly Tyr Ile Phe Thr Asp Tyr
            20                  25                  30

Asn Met His Trp Val Lys Gln Asn Gln Gly Lys Ser Leu Glu Trp Met
        35                  40                  45
```

Gly Glu Ile Asn Pro Asn Asn Gly Val Val Tyr Asn Gln Lys Phe
            50                  55                  60

Lys Gly Thr Thr Thr Leu Thr Val Asp Lys Ser Ser Thr Ala Tyr
 65                  70                  75                  80

Met Asp Leu His Ser Leu Thr Ser Glu Asp Ser Ala Val Tyr Tyr Cys
                 85                  90                  95

Thr Arg Ala Leu Tyr His Ser Asn Phe Gly Trp Tyr Phe Asp Ser Trp
                100                 105                 110

Gly Lys Gly Thr Thr Leu Thr Val Ser Ser
            115                 120

<210> SEQ ID NO 14
<211> LENGTH: 111
<212> TYPE: PRT
<213> ORGANISM: Artificial sequence
<220> FEATURE:
<223> OTHER INFORMATION: Fab 0311 light chain variable region

<400> SEQUENCE: 14

Asp Ile Val Leu Thr Gln Ser Pro Ala Ser Leu Ala Val Ser Leu Gly
 1               5                  10                  15

Gln Arg Ala Thr Ile Ser Cys Lys Ala Ser Gln Ser Val Asp Tyr Asp
             20                  25                  30

Gly Asp Ser His Met Asn Trp Tyr Gln Gln Lys Pro Gly Gln Pro Pro
         35                  40                  45

Lys Leu Leu Ile Tyr Thr Ala Ser Asn Leu Glu Ser Gly Ile Pro Ala
 50                  55                  60

Arg Phe Ser Gly Ser Gly Ser Gly Ala Asp Phe Thr Leu Thr Ile His
 65                  70                  75                  80

Pro Val Glu Glu Glu Asp Ala Ala Thr Tyr Tyr Cys Gln Gln Gly Asn
                 85                  90                  95

Glu Asp Pro Trp Thr Phe Gly Gly Gly Thr Arg Leu Glu Ile Lys
                100                 105                 110

<210> SEQ ID NO 15
<211> LENGTH: 10
<212> TYPE: PRT
<213> ORGANISM: Artificial sequence
<220> FEATURE:
<223> OTHER INFORMATION: 0301 heavy chain CDR1

<400> SEQUENCE: 15

Gly Tyr Thr Phe Thr Asp Asn Tyr Met Ile
 1               5                  10

<210> SEQ ID NO 16
<211> LENGTH: 17
<212> TYPE: PRT
<213> ORGANISM: Artificial sequence
<220> FEATURE:
<223> OTHER INFORMATION: 0301 heavy chain CDR

<400> SEQUENCE: 16

Asp Ile Asn Pro Tyr Asn Gly Gly Thr Thr Phe Asn Gln Lys Phe Lys
 1               5                  10                  15

Gly

<210> SEQ ID NO 17
<211> LENGTH: 13
<212> TYPE: PRT
<213> ORGANISM: Artificial sequence

```
<220> FEATURE:
<223> OTHER INFORMATION: 0301 heavy chain CDR3

<400> SEQUENCE: 17

Glu Ser Pro Tyr Phe Ser Asn Leu Tyr Val Met Asp Tyr
1               5                   10

<210> SEQ ID NO 18
<211> LENGTH: 15
<212> TYPE: PRT
<213> ORGANISM: Artificial sequence
<220> FEATURE:
<223> OTHER INFORMATION: 0301 light chain CDR1

<400> SEQUENCE: 18

Lys Ala Ser Gln Ser Val Asp Tyr Asp Gly Asp Asn Tyr Met Asn
1               5                   10                  15

<210> SEQ ID NO 19
<211> LENGTH: 7
<212> TYPE: PRT
<213> ORGANISM: Artificial sequence
<220> FEATURE:
<223> OTHER INFORMATION: 0301 light chain CDR2

<400> SEQUENCE: 19

Ala Ala Ser Asn Leu Glu Ser
1               5

<210> SEQ ID NO 20
<211> LENGTH: 9
<212> TYPE: PRT
<213> ORGANISM: Artificial sequence
<220> FEATURE:
<223> OTHER INFORMATION: 0301 light chain CDR3

<400> SEQUENCE: 20

His Leu Ser Asn Glu Asp Leu Ser Thr
1               5

<210> SEQ ID NO 21
<211> LENGTH: 10
<212> TYPE: PRT
<213> ORGANISM: Artificial sequence
<220> FEATURE:
<223> OTHER INFORMATION: 0302 heavy chain CDR1

<400> SEQUENCE: 21

Gly Tyr Thr Phe Ser Asp Phe Asn Ile His
1               5                   10

<210> SEQ ID NO 22
<211> LENGTH: 17
<212> TYPE: PRT
<213> ORGANISM: Artificial sequence
<220> FEATURE:
<223> OTHER INFORMATION: 0302 heavy chain CDR2

<400> SEQUENCE: 22

Tyr Ile Asn Pro Tyr Thr Asp Val Thr Val Tyr Asn Glu Lys Phe Lys
1               5                   10                  15

Gly

<210> SEQ ID NO 23
<211> LENGTH: 12
<212> TYPE: PRT
```

<213> ORGANISM: Artificial sequence
<220> FEATURE:
<223> OTHER INFORMATION: 0302 heavy chain CDR3

<400> SEQUENCE: 23

Tyr Phe Asp Gly Thr Phe Asp Tyr Ala Leu Asp Tyr
1               5                   10

<210> SEQ ID NO 24
<211> LENGTH: 15
<212> TYPE: PRT
<213> ORGANISM: Artificial sequence
<220> FEATURE:
<223> OTHER INFORMATION: 0302 light chain CDR1

<400> SEQUENCE: 24

Arg Ala Ser Glu Ser Val Asp Asn Tyr Gly Leu Ser Phe Met Asn
1               5                   10                  15

<210> SEQ ID NO 25
<211> LENGTH: 7
<212> TYPE: PRT
<213> ORGANISM: Artificial sequence
<220> FEATURE:
<223> OTHER INFORMATION: 0302 light chain CDR2

<400> SEQUENCE: 25

Thr Ala Ser Asn Leu Glu Ser
1               5

<210> SEQ ID NO 26
<211> LENGTH: 9
<212> TYPE: PRT
<213> ORGANISM: Artificial sequence
<220> FEATURE:
<223> OTHER INFORMATION: 0302 light chain CDR3

<400> SEQUENCE: 26

Gln Gln Ser Lys Glu Leu Pro Trp Thr
1               5

<210> SEQ ID NO 27
<211> LENGTH: 10
<212> TYPE: PRT
<213> ORGANISM: Artificial sequence
<220> FEATURE:
<223> OTHER INFORMATION: 0311 heavy chain CDR1

<400> SEQUENCE: 27

Gly Tyr Ile Phe Thr Asp Tyr Asn Met His
1               5                   10

<210> SEQ ID NO 28
<211> LENGTH: 17
<212> TYPE: PRT
<213> ORGANISM: Artificial sequence
<220> FEATURE:
<223> OTHER INFORMATION: 0311 heavy chain CDR2

<400> SEQUENCE: 28

Glu Ile Asn Pro Asn Asn Gly Val Val Val Tyr Asn Gln Lys Phe Lys
1               5                   10                  15

Gly

<210> SEQ ID NO 29
<211> LENGTH: 13

```
<212> TYPE: PRT
<213> ORGANISM: Artificial sequence
<220> FEATURE:
<223> OTHER INFORMATION: 0311 heavy chain CDR3

<400> SEQUENCE: 29

Ala Leu Tyr His Ser Asn Phe Gly Trp Tyr Phe Asp Ser
1               5                   10

<210> SEQ ID NO 30
<211> LENGTH: 15
<212> TYPE: PRT
<213> ORGANISM: Artificial sequence
<220> FEATURE:
<223> OTHER INFORMATION: 0311 light chain CDR1

<400> SEQUENCE: 30

Lys Ala Ser Gln Ser Val Asp Tyr Asp Gly Asp Ser His Met Asn
1               5                   10                  15

<210> SEQ ID NO 31
<211> LENGTH: 7
<212> TYPE: PRT
<213> ORGANISM: Artificial sequence
<220> FEATURE:
<223> OTHER INFORMATION: 0311 light chain CDR2

<400> SEQUENCE: 31

Thr Ala Ser Asn Leu Glu Ser
1               5

<210> SEQ ID NO 32
<211> LENGTH: 9
<212> TYPE: PRT
<213> ORGANISM: Artificial sequence
<220> FEATURE:
<223> OTHER INFORMATION: 0311 light chain CDR3

<400> SEQUENCE: 32

Gln Gln Gly Asn Glu Asp Pro Trp Thr
1               5

<210> SEQ ID NO 33
<211> LENGTH: 449
<212> TYPE: PRT
<213> ORGANISM: Artificial sequence
<220> FEATURE:
<223> OTHER INFORMATION: cAb 0301 heavy chain

<400> SEQUENCE: 33

Glu Val Gln Leu Gln Gln Ser Gly Pro Glu Leu Val Arg Pro Gly Ala
1               5                   10                  15

Ser Val Lys Met Ser Cys Lys Ala Ser Gly Tyr Thr Phe Thr Asp Asn
                20                  25                  30

Tyr Met Ile Trp Val Lys Gln Ser His Gly Lys Ser Leu Glu Trp Ile
            35                  40                  45

Gly Asp Ile Asn Pro Tyr Asn Gly Gly Thr Thr Phe Asn Gln Lys Phe
        50                  55                  60

Lys Gly Lys Ala Thr Leu Thr Val Glu Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Glu Ser Pro Tyr Phe Ser Asn Leu Tyr Val Met Asp Tyr Trp
                100                 105                 110
```

Gly Gln Gly Thr Ser Val Thr Val Ser Ser Ala Ser Thr Lys Gly Pro
            115                 120                 125

Ser Val Phe Pro Leu Ala Pro Cys Ser Arg Ser Thr Ser Glu Ser Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys

<210> SEQ ID NO 34
<211> LENGTH: 448
<212> TYPE: PRT
<213> ORGANISM: Artificial sequence
<220> FEATURE:
<223> OTHER INFORMATION: cAb 0301 light chain

<400> SEQUENCE: 34

Glu Ile Gln Leu Gln Gln Ser Gly Pro Glu Leu Val Lys Pro Gly Ala
1               5                   10                  15

-continued

```
Ser Val Lys Met Ser Cys Lys Ala Ser Gly Tyr Thr Phe Asp Phe
             20                  25                  30

Asn Ile His Trp Val Lys Gln Lys Pro Gly Gln Gly Leu Glu Trp Ile
         35                  40                  45

Gly Tyr Ile Asn Pro Tyr Thr Asp Val Thr Val Tyr Asn Glu Lys Phe
     50                  55                  60

Lys Gly Lys Ala Thr Leu Thr Ser Asp Arg Ser Ser Thr Ala Tyr
 65                  70                  75                  80

Met Asp Leu Ser Ser Leu Thr Ser Glu Asp Ser Ala Val Tyr Tyr Cys
                 85                  90                  95

Ala Ser Tyr Phe Asp Gly Thr Phe Asp Tyr Ala Leu Asp Tyr Trp Gly
             100                 105                 110

Gln Gly Thr Ser Ile Thr Val Ser Ser Ala Ser Thr Lys Gly Pro Ser
         115                 120                 125

Val Phe Pro Leu Ala Pro Cys Ser Arg Ser Thr Ser Glu Ser Thr Ala
     130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                 165                 170                 175

Val Leu Gln Ser Ser Gly Leu Tyr Ser Leu Ser Ser Val Val Thr Val
             180                 185                 190

Pro Ser Ser Ser Leu Gly Thr Lys Thr Tyr Thr Cys Asn Val Asp His
         195                 200                 205

Lys Pro Ser Asn Thr Lys Val Asp Lys Arg Val Glu Ser Lys Tyr Gly
 210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                 245                 250                 255

Thr Pro Glu Val Thr Cys Val Val Val Asp Val Ser Gln Glu Asp Pro
             260                 265                 270

Glu Val Gln Phe Asn Trp Tyr Val Asp Gly Val Glu Val His Asn Ala
         275                 280                 285

Lys Thr Lys Pro Arg Glu Glu Gln Phe Asn Ser Thr Tyr Arg Val Val
 290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                 325                 330                 335

Ile Ser Lys Ala Lys Gly Gln Pro Arg Glu Pro Gln Val Tyr Thr Leu
             340                 345                 350

Pro Pro Ser Gln Glu Glu Met Thr Lys Asn Gln Val Ser Leu Thr Cys
         355                 360                 365

Leu Val Lys Gly Phe Tyr Pro Ser Asp Ile Ala Val Glu Trp Glu Ser
 370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                 405                 410                 415

Arg Trp Gln Glu Gly Asn Val Phe Ser Cys Ser Val Met His Glu Ala
             420                 425                 430

Leu His Asn His Tyr Thr Gln Lys Ser Leu Ser Leu Ser Leu Gly Lys
```

-continued

```
            435                 440                 445
```

<210> SEQ ID NO 35
<211> LENGTH: 448
<212> TYPE: PRT
<213> ORGANISM: Artificial sequence
<220> FEATURE:
<223> OTHER INFORMATION: cAb 0302 heavy chain

<400> SEQUENCE: 35

```
Glu Ile Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Ser Asp Phe
            20                  25                  30

Asn Ile His Trp Val Lys Gln Lys Pro Gly Gln Gly Leu Glu Trp Ile
        35                  40                  45

Gly Tyr Ile Asn Pro Tyr Thr Asp Val Thr Val Tyr Asn Glu Lys Phe
    50                  55                  60

Lys Gly Lys Ala Thr Leu Thr Ser Asp Arg Ser Ser Thr Ala Tyr
65                  70                  75                  80

Met Asp Leu Ser Ser Leu Thr Ser Glu Asp Ser Ala Val Tyr Tyr Cys
                85                  90                  95

Ala Ser Tyr Phe Asp Gly Thr Phe Asp Tyr Ala Leu Asp Tyr Trp Gly
            100                 105                 110

Gln Gly Thr Ser Ile Thr Val Ser Ala Ser Thr Lys Gly Pro Ser
            115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
```

```
                        355                 360                 365
Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
                420                 425                 430

Leu His Asn His Tyr Thr Gln Lys Ser Leu Ser Leu Ser Leu Gly Lys
                435                 440                 445

<210> SEQ ID NO 36
<211> LENGTH: 218
<212> TYPE: PRT
<213> ORGANISM: Artificial sequence
<220> FEATURE:
<223> OTHER INFORMATION: cAb 0302 light chain

<400> SEQUENCE: 36

Asp Val Val Thr Gln Thr Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Leu Ser Phe Met Asn Trp Phe Gln Gln Lys Pro Gly Gln Pro Pro
        35                  40                  45

Lys Leu Leu Ile Tyr Thr Ala Ser Asn Leu Glu Ser Gly Ile Pro Ala
    50                  55                  60

Arg Phe Ser Gly Gly Gly Ser Arg Thr Asp Phe Thr Leu Thr Ile Asp
65                  70                  75                  80

Pro Val Glu Ala Asp Asp Ala Ala Thr Tyr Phe Cys Gln Gln Ser Lys
                85                  90                  95

Glu Leu Pro Trp Thr Phe Gly Gly Gly Thr Arg Leu Glu Ile Lys Arg
                100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
    210                 215

<210> SEQ ID NO 37
<211> LENGTH: 449
<212> TYPE: PRT
<213> ORGANISM: Artificial sequence
<220> FEATURE:
<223> OTHER INFORMATION: cAb 0311 heavy chain

<400> SEQUENCE: 37
```

Glu Ile Gln Leu Gln Gln Ser Gly Pro Asp Leu Met Lys Pro Gly Ala
1               5                   10                  15

Ser Val Lys Met Ser Cys Lys Ala Ser Gly Tyr Ile Phe Thr Asp Tyr
            20                  25                  30

Asn Met His Trp Val Lys Gln Asn Gln Gly Lys Ser Leu Glu Trp Met
        35                  40                  45

Gly Glu Ile Asn Pro Asn Asn Gly Val Val Tyr Asn Gln Lys Phe
    50                  55                  60

Lys Gly Thr Thr Thr Leu Thr Val Asp Lys Ser Ser Thr Ala Tyr
65                  70                  75                  80

Met Asp Leu His Ser Leu Thr Ser Glu Asp Ser Ala Val Tyr Tyr Cys
                85                  90                  95

Thr Arg Ala Leu Tyr His Ser Asn Phe Gly Trp Tyr Phe Asp Ser Trp
            100                 105                 110

Gly Lys Gly Thr Thr Leu Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
        180                 185                 190

Val Pro Ser Ser Ser Leu Gly Thr Lys Thr Tyr Thr Cys Asn Val Asp
    195                 200                 205

His Lys Pro Ser Asn Thr Lys Val Asp Lys Arg Val Glu Ser Lys Tyr
210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser Gln Glu Asp
        260                 265                 270

Pro Glu Val Gln Phe Asn Trp Tyr Val Asp Gly Val Glu Val His Asn
    275                 280                 285

Ala Lys Thr Lys Pro Arg Glu Glu Gln Phe Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
            325                 330                 335

Thr Ile Ser Lys Ala Lys Gly Gln Pro Arg Glu Pro Gln Val Tyr Thr
        340                 345                 350

Leu Pro Pro Ser Gln Glu Glu Met Thr Lys Asn Gln Val Ser Leu Thr
    355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
            405                 410                 415

Ser Arg Trp Gln Glu Gly Asn Val Phe Ser Cys Ser Val Met His Glu

```
                    420                 425                 430
Ala Leu His Asn His Tyr Thr Gln Lys Ser Leu Ser Leu Ser Leu Gly
            435                 440                 445
Lys

<210> SEQ ID NO 38
<211> LENGTH: 218
<212> TYPE: PRT
<213> ORGANISM: Artificial sequence
<220> FEATURE:
<223> OTHER INFORMATION: cAb 0311 light chain

<400> SEQUENCE: 38

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser His Met Asn Trp Tyr Gln Gln Lys Pro Gly Gln Pro Pro
        35                  40                  45

Lys Leu Leu Ile Tyr Thr Ala Ser Asn Leu Glu Ser Gly Ile Pro Ala
    50                  55                  60

Arg Phe Ser Gly Ser Gly Ser Gly Ala Asp Phe Thr Leu Thr Ile His
65                  70                  75                  80

Pro Val Glu Glu Glu Asp Ala Ala Thr Tyr Tyr Cys Gln Gln Gly Asn
                85                  90                  95

Glu Asp Pro Trp Thr Phe Gly Gly Thr Arg Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 39
<211> LENGTH: 122
<212> TYPE: PRT
<213> ORGANISM: Artificial sequence
<220> FEATURE:
<223> OTHER INFORMATION: h0301-H0 heavy chain variable region

<400> SEQUENCE: 39

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Asn
            20                  25                  30

Tyr Met Ile Trp Val Arg Gln Ala Pro Gly Gln Gly Leu Glu Trp Met
        35                  40                  45

Gly Asp Ile Asn Pro Tyr Asn Gly Gly Thr Thr Phe Asn Gln Lys Phe
```

```
                    50                  55                  60
Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Ser Pro Tyr Phe Ser Asn Leu Tyr Val Met Asp Tyr Trp
                100                 105                 110

Gly Gln Gly Thr Leu Val Thr Val Ser Ser
            115                 120

<210> SEQ ID NO 40
<211> LENGTH: 122
<212> TYPE: PRT
<213> ORGANISM: Artificial sequence
<220> FEATURE:
<223> OTHER INFORMATION: h0301-H1 heavy chain variable region

<400> SEQUENCE: 40

Gln Val Gln Leu Val Gln Ser Gly Ala Glu Val Lys Lys Pro Gly Ser
  1               5                  10                  15

Ser Val Lys Val Ser Cys Lys Ala Ser Gly Tyr Thr Phe Thr Asp Asn
                 20                  25                  30

Tyr Met Ile Trp Val Arg Gln Ala Pro Gly Gln Gly Leu Glu Trp Met
             35                  40                  45

Gly Asp Ile Asn Pro Tyr Asn Gly Gly Thr Thr Phe Asn Gln Lys Phe
     50                  55                  60

Lys Gly Arg Val Thr Ile Thr Val Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Ser Pro Tyr Phe Ser Asn Leu Tyr Val Met Asp Tyr Trp
                100                 105                 110

Gly Gln Gly Thr Leu Val Thr Val Ser Ser
            115                 120

<210> SEQ ID NO 41
<211> LENGTH: 122
<212> TYPE: PRT
<213> ORGANISM: Artificial sequence
<220> FEATURE:
<223> OTHER INFORMATION: h0301-H2 heavy chain variable region

<400> SEQUENCE: 41

Gln Val Gln Leu Val Gln Ser Gly Ala Glu Val Lys Lys Pro Gly Ser
  1               5                  10                  15

Ser Val Lys Val Ser Cys Lys Ala Ser Gly Tyr Thr Phe Thr Asp Asn
                 20                  25                  30

Tyr Met Ile Trp Val Arg Gln Ala Pro Gly Gln Gly Leu Glu Trp Ile
             35                  40                  45

Gly Asp Ile Asn Pro Tyr Asn Gly Gly Thr Thr Phe Asn Gln Lys Phe
     50                  55                  60

Lys Gly Arg Ala Thr Leu Thr Val Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Ser Pro Tyr Phe Ser Asn Leu Tyr Val Met Asp Tyr Trp
                100                 105                 110
```

Gly Gln Gly Thr Leu Val Thr Val Ser Ser
            115                 120

<210> SEQ ID NO 42
<211> LENGTH: 121
<212> TYPE: PRT
<213> ORGANISM: Artificial sequence
<220> FEATURE:
<223> OTHER INFORMATION: H0302-H1 heavy chain variable region

<400> SEQUENCE: 42

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asp Phe
            20                  25                  30

Asn Ile His Trp Val Arg Gln Ala Pro Gly Gln Gly Leu Glu Trp Met
        35                  40                  45

Gly Tyr Ile Asn Pro Tyr Thr Asp Val Thr Val Tyr Asn Glu Lys Phe
    50                  55                  60

Lys Gly Arg Val Thr Ile Thr Ser Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Tyr Phe Asp Gly Thr Phe Asp Tyr Ala Leu Asp Tyr Trp Gly
            100                 105                 110

Gln Gly Thr Leu Val Thr Val Ser Ser
            115                 120

<210> SEQ ID NO 43
<211> LENGTH: 121
<212> TYPE: PRT
<213> ORGANISM: Artificial sequence
<220> FEATURE:
<223> OTHER INFORMATION: H0302-H2 heavy chain variable region

<400> SEQUENCE: 43

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asp Phe
            20                  25                  30

Asn Ile His Trp Val Arg Gln Ala Pro Gly Gln Gly Leu Glu Trp Ile
        35                  40                  45

Gly Tyr Ile Asn Pro Tyr Thr Asp Val Thr Val Tyr Asn Glu Lys Phe
    50                  55                  60

Lys Gly Arg Ala Thr Leu Thr Ser Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Tyr Phe Asp Gly Thr Phe Asp Tyr Ala Leu Asp Tyr Trp Gly
            100                 105                 110

Gln Gly Thr Leu Val Thr Val Ser Ser
            115                 120

<210> SEQ ID NO 44
<211> LENGTH: 122
<212> TYPE: PRT
<213> ORGANISM: Artificial sequence
<220> FEATURE:
<223> OTHER INFORMATION: H0311-H1 heavy chain variable region

```
<400> SEQUENCE: 44

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ile Phe Thr Asp Tyr
            20                  25                  30

Asn Met His Trp Val Arg Gln Ala Pro Gly Gln Gly Leu Glu Trp Met
        35                  40                  45

Gly Glu Ile Asn Pro Asn Asn Gly Val Val Tyr Asn Gln Lys Phe
    50                  55                  60

Lys Gly Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ala Leu Tyr His Ser Asn Phe Gly Trp Tyr Phe Asp Ser Trp
            100                 105                 110

Gly Gln Gly Thr Leu Val Thr Val Ser Ser
        115                 120

<210> SEQ ID NO 45
<211> LENGTH: 122
<212> TYPE: PRT
<213> ORGANISM: Artificial sequence
<220> FEATURE:
<223> OTHER INFORMATION: H0311-H2 heavy chain variable region

<400> SEQUENCE: 45

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ile Phe Thr Asp Tyr
            20                  25                  30

Asn Met His Trp Val Arg Gln Ala Pro Gly Gln Gly Leu Glu Trp Met
        35                  40                  45

Gly Glu Ile Asn Pro Asn Asn Gly Val Val Val Tyr Asn Gln Lys Phe
    50                  55                  60

Lys Gly Thr Thr Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ala Leu Tyr His Ser Asn Phe Gly Trp Tyr Phe Asp Ser Trp
            100                 105                 110

Gly Gln Gly Thr Leu Val Thr Val Ser Ser
        115                 120

<210> SEQ ID NO 46
<211> LENGTH: 111
<212> TYPE: PRT
<213> ORGANISM: Artificial sequence
<220> FEATURE:
<223> OTHER INFORMATION: h0301-L0 light chain variable region

<400> SEQUENCE: 46

Glu Ile Val Leu Thr Gln Ser Pro Ala Thr Leu Ser Leu Ser Pro Gly
1               5                   10                  15

Glu Arg Ala Thr Leu Ser Cys Lys Ala Ser Gln Ser Val Asp Tyr Asp
            20                  25                  30

Gly Asp Asn Tyr Met Asn Trp Tyr Gln Gln Lys Pro Gly Gln Ala Pro
        35                  40                  45
```

Arg Leu Leu Ile Tyr Ala Ala Ser Asn Leu Glu Ser Gly Ile Pro Ala
        50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys His Leu Ser Asn
                85                  90                  95

Glu Asp Leu Ser Thr Phe Gly Gly Gly Thr Lys Val Glu Ile Lys
            100                 105                 110

<210> SEQ ID NO 47
<211> LENGTH: 111
<212> TYPE: PRT
<213> ORGANISM: Artificial sequence
<220> FEATURE:
<223> OTHER INFORMATION: h0301-L1 light chain variable region

<400> SEQUENCE: 47

Asn Ile Val Leu Thr Gln Ser Pro Ala Thr Leu Ser Leu Ser Pro Gly
1               5                   10                  15

Glu Arg Ala Thr Leu Ser Cys Lys Ala Ser Gln Ser Val Asp Tyr Asp
                20                  25                  30

Gly Asp Asn Tyr Met Asn Trp Tyr Gln Gln Lys Pro Gly Gln Ala Pro
            35                  40                  45

Arg Leu Leu Ile Tyr Ala Ala Ser Asn Leu Glu Ser Gly Ile Pro Ala
        50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys His Leu Ser Asn
                85                  90                  95

Glu Asp Leu Ser Thr Phe Gly Gly Gly Thr Lys Val Glu Ile Lys
            100                 105                 110

<210> SEQ ID NO 48
<211> LENGTH: 111
<212> TYPE: PRT
<213> ORGANISM: Artificial sequence
<220> FEATURE:
<223> OTHER INFORMATION: H0302-L0 light chain variable region

<400> SEQUENCE: 48

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
                20                  25                  30

Gly Leu Ser Phe Met Asn Trp Tyr Gln Gln Lys Pro Gly Gln Ala Pro
            35                  40                  45

Arg Leu Leu Ile Tyr Thr Ala Ser Asn Leu Glu Ser Gly Ile Pro Ala
        50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Ser Lys
                85                  90                  95

Glu Leu Pro Trp Thr Phe Gly Gln Gly Thr Lys Val Glu Ile Lys
            100                 105                 110

<210> SEQ ID NO 49
<211> LENGTH: 111
<212> TYPE: PRT
<213> ORGANISM: Artificial sequence

```
<220> FEATURE:
<223> OTHER INFORMATION: H0302-L1 light chain variable region

<400> SEQUENCE: 49

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
                20                  25                  30

Gly Leu Ser Phe Met Asn Trp Tyr Gln Gln Lys Pro Gly Gln Ala Pro
            35                  40                  45

Arg Leu Leu Ile Tyr Thr Ala Ser Asn Leu Glu Ser Gly Ile Pro Ala
        50                  55                  60

Arg Phe Ser Gly Ser Gly Ser Arg Thr Asp Phe Thr Leu Thr Ile Ser
65                  70                  75                  80

Ser Leu Glu Pro Glu Asp Phe Ala Val Tyr Tyr Cys Gln Gln Ser Lys
                85                  90                  95

Glu Leu Pro Trp Thr Phe Gly Gln Gly Thr Lys Val Glu Ile Lys
            100                 105                 110

<210> SEQ ID NO 50
<211> LENGTH: 111
<212> TYPE: PRT
<213> ORGANISM: Artificial sequence
<220> FEATURE:
<223> OTHER INFORMATION: H0302-L2 light chain variable region

<400> SEQUENCE: 50

Glu Ile Val Val Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
                20                  25                  30

Gly Leu Ser Phe Met Asn Trp Phe Gln Gln Lys Pro Gly Gln Ala Pro
            35                  40                  45

Arg Leu Leu Ile Tyr Thr Ala Ser Asn Leu Glu Ser Gly Ile Pro Ala
        50                  55                  60

Arg Phe Ser Gly Ser Gly Ser Arg Thr Asp Phe Thr Leu Thr Ile Ser
65                  70                  75                  80

Ser Leu Glu Pro Glu Asp Phe Ala Val Tyr Tyr Cys Gln Gln Ser Lys
                85                  90                  95

Glu Leu Pro Trp Thr Phe Gly Gln Gly Thr Lys Val Glu Ile Lys
            100                 105                 110

<210> SEQ ID NO 51
<211> LENGTH: 111
<212> TYPE: PRT
<213> ORGANISM: Artificial sequence
<220> FEATURE:
<223> OTHER INFORMATION: H0311-L0 light chain variable region

<400> SEQUENCE: 51

Glu Ile Val Leu Thr Gln Ser Pro Ala Thr Leu Ser Leu Ser Pro Gly
1               5                   10                  15

Glu Arg Ala Thr Leu Ser Cys Lys Ala Ser Gln Ser Val Asp Tyr Asp
                20                  25                  30

Gly Asp Ser His Met Asn Trp Tyr Gln Gln Lys Pro Gly Gln Ala Pro
            35                  40                  45

Arg Leu Leu Ile Tyr Thr Ala Ser Asn Leu Glu Ser Gly Ile Pro Ala
        50                  55                  60
```

```
Arg Phe Ser Gly Ser Gly Ser Gly Thr Asp Phe Thr Leu Thr Ile Ser
 65                  70                  75                  80

Ser Leu Glu Pro Glu Asp Phe Ala Val Tyr Tyr Cys Gln Gln Gly Asn
                 85                  90                  95

Glu Asp Pro Trp Thr Phe Gly Gln Gly Thr Lys Val Glu Ile Lys
            100                 105                 110
```

<210> SEQ ID NO 52
<211> LENGTH: 111
<212> TYPE: PRT
<213> ORGANISM: Artificial sequence
<220> FEATURE:
<223> OTHER INFORMATION: H0311-L1 light chain variable region

<400> SEQUENCE: 52

```
Asp Ile Val Leu Thr Gln Ser Pro Ala Thr Leu Ser Leu Ser Pro Gly
 1               5                  10                  15

Glu Arg Ala Thr Leu Ser Cys Lys Ala Ser Gln Ser Val Asp Tyr Asp
                20                  25                  30

Gly Asp Ser His Met Asn Trp Tyr Gln Gln Lys Pro Gly Gln Ala Pro
             35                  40                  45

Arg Leu Leu Ile Tyr Thr Ala Ser Asn Leu Glu Ser Gly Ile Pro Ala
 50                  55                  60

Arg Phe Ser Gly Ser Gly Ser Gly Ala Asp Phe Thr Leu Thr Ile Ser
 65                  70                  75                  80

Ser Leu Glu Pro Glu Asp Phe Ala Val Tyr Tyr Cys Gln Gln Gly Asn
                 85                  90                  95

Glu Asp Pro Trp Thr Phe Gly Gln Gly Thr Lys Val Glu Ile Lys
            100                 105                 110
```

<210> SEQ ID NO 53
<211> LENGTH: 449
<212> TYPE: PRT
<213> ORGANISM: Artificial sequence
<220> FEATURE:
<223> OTHER INFORMATION: h0301-H0 heavy chain

<400> SEQUENCE: 53

```
Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Thr Asp Asn
                20                  25                  30

Tyr Met Ile Trp Val Arg Gln Ala Pro Gly Gln Gly Leu Glu Trp Met
             35                  40                  45

Gly Asp Ile Asn Pro Tyr Asn Gly Gly Thr Thr Phe Asn Gln Lys Phe
 50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Ser Pro Tyr Phe Ser Asn Leu Tyr Val Met Asp Tyr Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Cys Ser Arg Ser Thr Ser Glu Ser Thr
            130                 135                 140

Ala Ala Leu Gly Cys Leu Val Lys Asp Tyr Phe Pro Glu Pro Val Thr
145                 150                 155                 160
```

-continued

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys

<210> SEQ ID NO 54
<211> LENGTH: 449
<212> TYPE: PRT
<213> ORGANISM: Artificial sequence
<220> FEATURE:
<223> OTHER INFORMATION: h0301-H1 heavy chain

<400> SEQUENCE: 54

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Asn
            20                  25                  30

Tyr Met Ile Trp Val Arg Gln Ala Pro Gly Gln Gly Leu Glu Trp Met
        35                  40                  45

Gly Asp Ile Asn Pro Tyr Asn Gly Gly Thr Thr Phe Asn Gln Lys Phe
    50                  55                  60

Lys Gly Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Glu Ser Pro Tyr Phe Ser Asn Leu Tyr Val Met Asp Tyr Trp
        100                 105                 110

Gly Gln Gly Thr Leu Val Thr Val Ser Ser Ala Ser Thr Lys Gly Pro
    115                 120                 125

Ser Val Phe Pro Leu Ala Pro Cys Ser Arg Ser Thr Ser Glu Ser Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys

<210> SEQ ID NO 55
<211> LENGTH: 449
<212> TYPE: PRT
<213> ORGANISM: Artificial sequence
<220> FEATURE:
<223> OTHER INFORMATION: h0301-H2 heavy chain

<400> SEQUENCE: 55

Gln Val Gln Leu Val Gln Ser Gly Ala Glu Val Lys Pro Gly Ser
1               5                   10                  15

Ser Val Lys Val Ser Cys Lys Ala Ser Gly Tyr Thr Phe Thr Asp Asn
            20                  25                  30

Tyr Met Ile Trp Val Arg Gln Ala Pro Gly Gln Gly Leu Glu Trp Ile
        35                  40                  45

Gly Asp Ile Asn Pro Tyr Asn Gly Gly Thr Thr Phe Asn Gln Lys Phe
50                  55                  60

Lys Gly Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Glu Ser Pro Tyr Phe Ser Asn Leu Tyr Val Met Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
        180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser Gln Glu Asp
        260                 265                 270

Pro Glu Val Gln Phe Asn Trp Tyr Val Asp Gly Val Glu Val His Asn
    275                 280                 285

Ala Lys Thr Lys Pro Arg Glu Glu Gln Phe Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
            325                 330                 335

Thr Ile Ser Lys Ala Lys Gly Gln Pro Arg Glu Pro Gln Val Tyr Thr
        340                 345                 350

Leu Pro Pro Ser Gln Glu Glu Met Thr Lys Asn Gln Val Ser Leu Thr
    355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

```
Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys

<210> SEQ ID NO 56
<211> LENGTH: 448
<212> TYPE: PRT
<213> ORGANISM: Artificial sequence
<220> FEATURE:
<223> OTHER INFORMATION: H0302-H1 heavy chain

<400> SEQUENCE: 56

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asp Phe
            20                  25                  30

Asn Ile His Trp Val Arg Gln Ala Pro Gly Gln Gly Leu Glu Trp Met
        35                  40                  45

Gly Tyr Ile Asn Pro Tyr Thr Asp Val Thr Val Tyr Asn Glu Lys Phe
    50                  55                  60

Lys Gly Arg Val Thr Ile Thr Ser Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Tyr Phe Asp Gly Thr Phe Asp Tyr Ala Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300
```

```
Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
                420                 425                 430

Leu His Asn His Tyr Thr Gln Lys Ser Leu Ser Leu Ser Leu Gly Lys
                435                 440                 445
```

<210> SEQ ID NO 57
<211> LENGTH: 448
<212> TYPE: PRT
<213> ORGANISM: Artificial sequence
<220> FEATURE:
<223> OTHER INFORMATION: H0302-H2 heavy chain

<400> SEQUENCE: 57

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asp Phe
            20                  25                  30

Asn Ile His Trp Val Arg Gln Ala Pro Gly Gln Gly Leu Glu Trp Ile
        35                  40                  45

Gly Tyr Ile Asn Pro Tyr Thr Asp Val Thr Val Tyr Asn Glu Lys Phe
    50                  55                  60

Lys Gly Arg Ala Thr Leu Thr Ser Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Tyr Phe Asp Gly Thr Phe Asp Tyr Ala Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220
```

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 58
<211> LENGTH: 449
<212> TYPE: PRT
<213> ORGANISM: Artificial sequence
<220> FEATURE:
<223> OTHER INFORMATION: H0311-H1 heavy chain

<400> SEQUENCE: 58

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ile Phe Thr Asp Tyr
            20                  25                  30

Asn Met His Trp Val Arg Gln Ala Pro Gly Gln Gly Leu Glu Trp Met
        35                  40                  45

Gly Glu Ile Asn Pro Asn Gly Val Val Tyr Asn Gln Lys Phe
50                  55                  60

Lys Gly Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ala Leu Tyr His Ser Asn Phe Gly Trp Tyr Phe Asp Ser Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

```
Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
                260                 265                 270

Pro Glu Val Gln Phe Asn Trp Tyr Val Asp Gly Val Glu Val His Asn
            275                 280                 285

Ala Lys Thr Lys Pro Arg Glu Glu Gln Phe Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Gln Glu Glu Met Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
                420                 425                 430

Ala Leu His Asn His Tyr Thr Gln Lys Ser Leu Ser Leu Ser Leu Gly
            435                 440                 445

Lys

<210> SEQ ID NO 59
<211> LENGTH: 449
<212> TYPE: PRT
<213> ORGANISM: Artificial sequence
<220> FEATURE:
<223> OTHER INFORMATION: H0311-H2 heavy chain

<400> SEQUENCE: 59

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ile Phe Thr Asp Tyr
                20                  25                  30

Asn Met His Trp Val Arg Gln Ala Pro Gly Gln Gly Leu Glu Trp Met
            35                  40                  45

Gly Glu Ile Asn Pro Asn Asn Gly Val Val Val Tyr Asn Gln Lys Phe
```

-continued

```
            50                  55                  60
Lys Gly Thr Thr Thr Leu Thr Val Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Thr Arg Ala Leu Tyr His Ser Asn Phe Gly Trp Tyr Phe Asp Ser Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Cys Ser Arg Ser Thr Ser Glu Ser Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
            195                 200                 205

His Lys Pro Ser Asn Thr Lys Val Asp Lys Arg Val Glu Ser Lys Tyr
210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
            275                 280                 285

Ala Lys Thr Lys Pro Arg Glu Glu Gln Phe Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
            435                 440                 445

Lys
```

<210> SEQ ID NO 60
<211> LENGTH: 218

<212> TYPE: PRT
<213> ORGANISM: Artificial sequence
<220> FEATURE:
<223> OTHER INFORMATION: h0301-L0 light chain

<400> SEQUENCE: 60

Glu Ile Val Leu Thr Gln Ser Pro Ala Thr Leu Ser Leu Ser Pro Gly
1               5                   10                  15

Glu Arg Ala Thr Leu Ser Cys Lys Ala Ser Gln Ser Val Asp Tyr Asp
            20                  25                  30

Gly Asp Asn Tyr Met Asn Trp Tyr Gln Gln Lys Pro Gly Gln Ala Pro
        35                  40                  45

Arg Leu Leu Ile Tyr Ala Ala Ser Asn Leu Glu Ser Gly Ile Pro Ala
50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys His Leu Ser Asn
                85                  90                  95

Glu Asp Leu Ser Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
        210                 215

<210> SEQ ID NO 61
<211> LENGTH: 218
<212> TYPE: PRT
<213> ORGANISM: Artificial sequence
<220> FEATURE:
<223> OTHER INFORMATION: h0301-L1 light chain

<400> SEQUENCE: 61

Asn Ile Val Leu Thr Gln Ser Pro Ala Thr Leu Ser Leu Ser Pro Gly
1               5                   10                  15

Glu Arg Ala Thr Leu Ser Cys Lys Ala Ser Gln Ser Val Asp Tyr Asp
            20                  25                  30

Gly Asp Asn Tyr Met Asn Trp Tyr Gln Gln Lys Pro Gly Gln Ala Pro
        35                  40                  45

Arg Leu Leu Ile Tyr Ala Ala Ser Asn Leu Glu Ser Gly Ile Pro Ala
50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys His Leu Ser Asn
                85                  90                  95

Glu Asp Leu Ser Thr Phe Gly Gly Gly Thr Lys Val Glu Ile Lys Arg
            100                 105                 110

Thr Val Ala Ala Pro Ser Val Phe Ile Phe Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
            165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
        210                 215

<210> SEQ ID NO 62
<211> LENGTH: 218
<212> TYPE: PRT
<213> ORGANISM: Artificial sequence
<220> FEATURE:
<223> OTHER INFORMATION: H0302-L0 light chain

<400> SEQUENCE: 62

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

Gly Leu Ser Phe Met Asn Trp Tyr Gln Gln Lys Pro Gly Gln Ala Pro
        35                  40                  45

Arg Leu Leu Ile Tyr Thr Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Ser Lys
                85                  90                  95

Glu Leu Pro Trp Thr Phe Gly Gln Gly Thr Lys Val Glu Ile Lys Arg
            100                 105                 110

Thr Val Ala Ala Pro Ser Val Phe Ile Phe Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
            165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
        210                 215

<210> SEQ ID NO 63
<211> LENGTH: 218
<212> TYPE: PRT
<213> ORGANISM: Artificial sequence
<220> FEATURE:
<223> OTHER INFORMATION: H0302-L1 light chain

<400> SEQUENCE: 63

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

Gly Leu Ser Phe Met Asn Trp Tyr Gln Gln Lys Pro Gly Gln Ala Pro
        35                  40                  45

Arg Leu Leu Ile Tyr Thr Ala Ser Asn Leu Glu Ser Gly Ile Pro Ala
    50                  55                  60

Arg Phe Ser Gly Ser Gly Ser Arg Thr Asp Phe Thr Leu Thr Ile Ser
65                  70                  75                  80

Ser Leu Glu Pro Glu Asp Phe Ala Val Tyr Tyr Cys Gln Gln Ser Lys
                85                  90                  95

Glu Leu Pro Trp Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 64
<211> LENGTH: 218
<212> TYPE: PRT
<213> ORGANISM: Artificial sequence
<220> FEATURE:
<223> OTHER INFORMATION: H0302-L2 light chain

<400> SEQUENCE: 64

Glu Ile Val Val Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

Gly Leu Ser Phe Met Asn Trp Phe Gln Gln Lys Pro Gly Gln Ala Pro
        35                  40                  45

Arg Leu Leu Ile Tyr Thr Ala Ser Asn Leu Glu Ser Gly Ile Pro Ala
    50                  55                  60

Arg Phe Ser Gly Ser Gly Ser Arg Thr Asp Phe Thr Leu Thr Ile Ser
65                  70                  75                  80

Ser Leu Glu Pro Glu Asp Phe Ala Val Tyr Tyr Cys Gln Gln Ser Lys
                85                  90                  95

Glu Leu Pro Trp Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln

```
            115                 120                 125
Leu Lys Ser Gly Thr Ala Ser Val Val Cys Leu Leu Asn Asn Phe Tyr
        130                 135                 140
Pro Arg Glu Ala Lys Val Gln Trp Lys Val Asp Asn Ala Leu Gln Ser
145                 150                 155                 160
Gly Asn Ser Gln Glu Ser Val Thr Glu Gln Asp Ser Lys Asp Ser Thr
                165                 170                 175
Tyr Ser Leu Ser Ser Thr Leu Thr Leu Ser Lys Ala Asp Tyr Glu Lys
            180                 185                 190
His Lys Val Tyr Ala Cys Glu Val Thr His Gln Gly Leu Ser Ser Pro
        195                 200                 205
Val Thr Lys Ser Phe Asn Arg Gly Glu Cys
    210                 215
```

<210> SEQ ID NO 65
<211> LENGTH: 218
<212> TYPE: PRT
<213> ORGANISM: Artificial sequence
<220> FEATURE:
<223> OTHER INFORMATION: H0311-L0 light chain

<400> SEQUENCE: 65

```
Glu Ile Val Leu Thr Gln Ser Pro Ala Thr Leu Ser Leu Ser Pro Gly
1               5                   10                  15
Glu Arg Ala Thr Leu Ser Cys Lys Ala Ser Gln Ser Val Asp Tyr Asp
            20                  25                  30
Gly Asp Ser His Met Asn Trp Tyr Gln Gln Lys Pro Gly Gln Ala Pro
        35                  40                  45
Arg Leu Leu Ile Tyr Thr Ala Ser Asn Leu Glu Ser Gly Ile Pro Ala
    50                  55                  60
Arg Phe Ser Gly Ser Gly Ser Gly Thr Asp Phe Thr Leu Thr Ile Ser
65                  70                  75                  80
Ser Leu Glu Pro Glu Asp Phe Ala Val Tyr Tyr Cys Gln Gln Gly Asn
                85                  90                  95
Glu Asp Pro Trp Thr Phe Gly Gln Gly Thr Lys Val Glu Ile Lys Arg
            100                 105                 110
Thr Val Ala Ala Pro Ser Val Phe Ile Phe Pro Pro Ser Asp Glu Gln
        115                 120                 125
Leu Lys Ser Gly Thr Ala Ser Val Val Cys Leu Leu Asn Asn Phe Tyr
    130                 135                 140
Pro Arg Glu Ala Lys Val Gln Trp Lys Val Asp Asn Ala Leu Gln Ser
145                 150                 155                 160
Gly Asn Ser Gln Glu Ser Val Thr Glu Gln Asp Ser Lys Asp Ser Thr
                165                 170                 175
Tyr Ser Leu Ser Ser Thr Leu Thr Leu Ser Lys Ala Asp Tyr Glu Lys
            180                 185                 190
His Lys Val Tyr Ala Cys Glu Val Thr His Gln Gly Leu Ser Ser Pro
        195                 200                 205
Val Thr Lys Ser Phe Asn Arg Gly Glu Cys
    210                 215
```

<210> SEQ ID NO 66
<211> LENGTH: 218
<212> TYPE: PRT
<213> ORGANISM: Artificial sequence
<220> FEATURE:
<223> OTHER INFORMATION: H0311-L1 light chain

<400> SEQUENCE: 66

Asp Ile Val Leu Thr Gln Ser Pro Ala Thr Leu Ser Leu Ser Pro Gly
1               5                   10                  15

Glu Arg Ala Thr Leu Ser Cys Lys Ala Ser Gln Ser Val Asp Tyr Asp
            20                  25                  30

Gly Asp Ser His Met Asn Trp Tyr Gln Gln Lys Pro Gly Gln Ala Pro
        35                  40                  45

Arg Leu Leu Ile Tyr Thr Ala Ser Asn Leu Glu Ser Gly Ile Pro Ala
    50                  55                  60

Arg Phe Ser Gly Ser Gly Ser Gly Ala Asp Phe Thr Leu Thr Ile Ser
65                  70                  75                  80

Ser Leu Glu Pro Glu Asp Phe Ala Val Tyr Tyr Cys Gln Gln Gly Asn
                85                  90                  95

Glu Asp Pro Trp Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 67
<211> LENGTH: 158
<212> TYPE: PRT
<213> ORGANISM: Homo sapiens
<220> FEATURE:
<221> NAME/KEY: MISC_FEATURE
<222> LOCATION: (1)..(158)
<223> OTHER INFORMATION: Human CSF1

<400> SEQUENCE: 67

Glu Glu Val Ser Glu Tyr Cys Ser His Met Ile Gly Ser Gly His Leu
1               5                   10                  15

Gln Ser Leu Gln Arg Leu Ile Asp Ser Gln Met Glu Thr Ser Cys Gln
            20                  25                  30

Ile Thr Phe Glu Phe Val Asp Gln Glu Gln Leu Lys Asp Pro Val Cys
        35                  40                  45

Tyr Leu Lys Lys Ala Phe Leu Leu Val Gln Asp Ile Met Glu Asp Thr
    50                  55                  60

Met Arg Phe Arg Asp Asn Thr Pro Asn Ala Ile Ala Ile Val Gln Leu
65                  70                  75                  80

Gln Glu Leu Ser Leu Arg Leu Lys Ser Cys Phe Thr Lys Asp Tyr Glu
                85                  90                  95

Glu His Asp Lys Ala Cys Val Arg Thr Phe Tyr Glu Thr Pro Leu Gln
            100                 105                 110

Leu Leu Glu Lys Val Lys Asn Val Phe Asn Glu Thr Lys Asn Leu Leu

```
            115                 120                 125
Asp Lys Asp Trp Asn Ile Phe Ser Lys Asn Cys Asn Asn Ser Phe Ala
    130                 135                 140

Glu Cys Ser Ser Gln Gly His Glu Arg Gln Ser Glu Gly Ser
145                 150                 155
```

<210> SEQ ID NO 68
<211> LENGTH: 222
<212> TYPE: PRT
<213> ORGANISM: Homo sapiens
<220> FEATURE:
<221> NAME/KEY: MISC_FEATURE
<222> LOCATION: (1)..(222)
<223> OTHER INFORMATION: Human IL-34

<400> SEQUENCE: 68

```
Asn Glu Pro Leu Glu Met Trp Pro Leu Thr Gln Asn Glu Glu Cys Thr
1               5                   10                  15

Val Thr Gly Phe Leu Arg Asp Lys Leu Gln Tyr Arg Ser Arg Leu Gln
            20                  25                  30

Tyr Met Lys His Tyr Phe Pro Ile Asn Tyr Lys Ile Ser Val Pro Tyr
        35                  40                  45

Glu Gly Val Phe Arg Ile Ala Asn Val Thr Arg Leu Gln Arg Ala Gln
    50                  55                  60

Val Ser Glu Arg Glu Leu Arg Tyr Leu Trp Val Leu Val Ser Leu Ser
65                  70                  75                  80

Ala Thr Glu Ser Val Gln Asp Val Leu Leu Glu Gly His Pro Ser Trp
                85                  90                  95

Lys Tyr Leu Gln Glu Val Gln Thr Leu Leu Leu Asn Val Gln Gln Gly
            100                 105                 110

Leu Thr Asp Val Glu Val Ser Pro Lys Val Glu Ser Val Leu Ser Leu
        115                 120                 125

Leu Asn Ala Pro Gly Pro Asn Leu Lys Leu Val Arg Pro Lys Ala Leu
    130                 135                 140

Leu Asp Asn Cys Phe Arg Val Met Glu Leu Leu Tyr Cys Ser Cys Cys
145                 150                 155                 160

Lys Gln Ser Ser Val Leu Asn Trp Gln Asp Cys Glu Val Pro Ser Pro
                165                 170                 175

Gln Ser Cys Ser Pro Glu Pro Ser Leu Gln Tyr Ala Ala Thr Gln Leu
            180                 185                 190

Tyr Pro Pro Pro Pro Trp Ser Pro Ser Ser Pro Pro His Ser Thr Gly
        195                 200                 205

Ser Val Arg Pro Val Arg Ala Gln Gly Glu Gly Leu Leu Pro
    210                 215                 220
```

<210> SEQ ID NO 69
<211> LENGTH: 25
<212> TYPE: PRT
<213> ORGANISM: Artificial sequence
<220> FEATURE:
<223> OTHER INFORMATION: Human acceptor A FR1

<400> SEQUENCE: 69

```
Gln Val Gln Leu Val Gln Ser Gly Ala Glu Val Lys Lys Pro Gly Ser
1               5                   10                  15

Ser Val Lys Val Ser Cys Lys Ala Ser
            20                  25
```

-continued

```
<210> SEQ ID NO 70
<211> LENGTH: 14
<212> TYPE: PRT
<213> ORGANISM: Artificial sequence
<220> FEATURE:
<223> OTHER INFORMATION: Human acceptor A FR2

<400> SEQUENCE: 70

Trp Val Arg Gln Ala Pro Gly Gln Gly Leu Glu Trp Met Gly
1               5                   10

<210> SEQ ID NO 71
<211> LENGTH: 32
<212> TYPE: PRT
<213> ORGANISM: Artificial sequence
<220> FEATURE:
<223> OTHER INFORMATION: Human acceptor A FR3

<400> SEQUENCE: 71

Arg Val Thr Ile Thr Ala Asp Lys Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 72
<211> LENGTH: 11
<212> TYPE: PRT
<213> ORGANISM: Artificial sequence
<220> FEATURE:
<223> OTHER INFORMATION: Human acceptor A FR4

<400> SEQUENCE: 72

Trp Gly Gln Gly Thr Leu Val Thr Val Ser Ser
1               5                   10

<210> SEQ ID NO 73
<211> LENGTH: 25
<212> TYPE: PRT
<213> ORGANISM: Artificial sequence
<220> FEATURE:
<223> OTHER INFORMATION: Human acceptor B FR1

<400> SEQUENCE: 73

Gln Val Gln Leu Val Gln Ser Gly Ala Glu Val Lys Lys Pro Gly Ser
1               5                   10                  15

Ser Val Lys Val Ser Cys Lys Ala Ser
            20                  25

<210> SEQ ID NO 74
<211> LENGTH: 14
<212> TYPE: PRT
<213> ORGANISM: Artificial sequence
<220> FEATURE:
<223> OTHER INFORMATION: Human acceptor B FR2

<400> SEQUENCE: 74

Trp Val Arg Gln Ala Pro Gly Gln Gly Leu Glu Trp Met Gly
1               5                   10

<210> SEQ ID NO 75
<211> LENGTH: 32
<212> TYPE: PRT
<213> ORGANISM: Artificial sequence
<220> FEATURE:
<223> OTHER INFORMATION: Human acceptor B FR3

<400> SEQUENCE: 75
```

Arg Val Thr Ile Thr Ala Asp Lys Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 76
<211> LENGTH: 11
<212> TYPE: PRT
<213> ORGANISM: Artificial sequence
<220> FEATURE:
<223> OTHER INFORMATION: Human acceptor B FR4

<400> SEQUENCE: 76

Trp Gly Gln Gly Thr Leu Val Thr Val Ser Ser
1               5                   10

<210> SEQ ID NO 77
<211> LENGTH: 25
<212> TYPE: PRT
<213> ORGANISM: Artificial sequence
<220> FEATURE:
<223> OTHER INFORMATION: Human acceptor C FR1

<400> SEQUENCE: 77

Gln Val Gln Leu Val Gln Ser Gly Ala Glu Val Lys Lys Pro Gly Ser
1               5                   10                  15

Ser Val Lys Val Ser Cys Lys Ala Ser
            20                  25

<210> SEQ ID NO 78
<211> LENGTH: 14
<212> TYPE: PRT
<213> ORGANISM: Artificial sequence
<220> FEATURE:
<223> OTHER INFORMATION: Human acceptor C FR2

<400> SEQUENCE: 78

Trp Val Arg Gln Ala Pro Gly Gln Gly Leu Glu Trp Met Gly
1               5                   10

<210> SEQ ID NO 79
<211> LENGTH: 32
<212> TYPE: PRT
<213> ORGANISM: Artificial sequence
<220> FEATURE:
<223> OTHER INFORMATION: Human acceptor C FR3

<400> SEQUENCE: 79

Arg Val Thr Ile Thr Ala Asp Lys Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 80
<211> LENGTH: 11
<212> TYPE: PRT
<213> ORGANISM: Artificial sequence
<220> FEATURE:
<223> OTHER INFORMATION: Human acceptor C FR4

<400> SEQUENCE: 80

Trp Gly Gln Gly Thr Leu Val Thr Val Ser Ser
1               5                   10

```
<210> SEQ ID NO 81
<211> LENGTH: 23
<212> TYPE: PRT
<213> ORGANISM: Artificial sequence
<220> FEATURE:
<223> OTHER INFORMATION: Human acceptor D FR1

<400> SEQUENCE: 81

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 82
<211> LENGTH: 15
<212> TYPE: PRT
<213> ORGANISM: Artificial sequence
<220> FEATURE:
<223> OTHER INFORMATION: Human acceptor D FR2

<400> SEQUENCE: 82

Trp Tyr Gln Gln Lys Pro Gly Gln Ala Pro Arg Leu Leu Ile Tyr
1               5                   10                  15

<210> SEQ ID NO 83
<211> LENGTH: 32
<212> TYPE: PRT
<213> ORGANISM: Artificial sequence
<220> FEATURE:
<223> OTHER INFORMATION: Human acceptor D FR3

<400> SEQUENCE: 83

Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
            20                  25                  30

<210> SEQ ID NO 84
<211> LENGTH: 10
<212> TYPE: PRT
<213> ORGANISM: Artificial sequence
<220> FEATURE:
<223> OTHER INFORMATION: Human acceptor D FR4

<400> SEQUENCE: 84

Phe Gly Gly Gly Thr Lys Val Glu Ile Lys
1               5                   10

<210> SEQ ID NO 85
<211> LENGTH: 23
<212> TYPE: PRT
<213> ORGANISM: Artificial sequence
<220> FEATURE:
<223> OTHER INFORMATION: Human acceptor E FR1

<400> SEQUENCE: 85

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 86
<211> LENGTH: 15
<212> TYPE: PRT
<213> ORGANISM: Artificial sequence
<220> FEATURE:
```

<223> OTHER INFORMATION: Human acceptor E FR2

<400> SEQUENCE: 86

Trp Tyr Gln Gln Lys Pro Gly Gln Ala Pro Arg Leu Leu Ile Tyr
1               5                   10                  15

<210> SEQ ID NO 87
<211> LENGTH: 32
<212> TYPE: PRT
<213> ORGANISM: Artificial sequence
<220> FEATURE:
<223> OTHER INFORMATION: Human acceptor E FR3

<400> SEQUENCE: 87

Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
            20                  25                  30

<210> SEQ ID NO 88
<211> LENGTH: 10
<212> TYPE: PRT
<213> ORGANISM: Artificial sequence
<220> FEATURE:
<223> OTHER INFORMATION: Human acceptor E FR4

<400> SEQUENCE: 88

Phe Gly Gln Gly Thr Lys Val Glu Ile Lys
1               5                   10

<210> SEQ ID NO 89
<211> LENGTH: 23
<212> TYPE: PRT
<213> ORGANISM: Artificial sequence
<220> FEATURE:
<223> OTHER INFORMATION: Human acceptor F FR1

<400> SEQUENCE: 89

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 90
<211> LENGTH: 15
<212> TYPE: PRT
<213> ORGANISM: Artificial sequence
<220> FEATURE:
<223> OTHER INFORMATION: Human acceptor F FR2

<400> SEQUENCE: 90

Trp Tyr Gln Gln Lys Pro Gly Gln Ala Pro Arg Leu Leu Ile Tyr
1               5                   10                  15

<210> SEQ ID NO 91
<211> LENGTH: 32
<212> TYPE: PRT
<213> ORGANISM: Artificial sequence
<220> FEATURE:
<223> OTHER INFORMATION: Human acceptor F FR3

<400> SEQUENCE: 91

Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys

<210> SEQ ID NO 92
<211> LENGTH: 10
<212> TYPE: PRT
<213> ORGANISM: Artificial sequence
<220> FEATURE:
<223> OTHER INFORMATION: Human acceptor F FR4

<400> SEQUENCE: 92

Phe Gly Gln Gly Thr Lys Val Glu Ile Lys
1               5                   10

<210> SEQ ID NO 93
<211> LENGTH: 719
<212> TYPE: PRT
<213> ORGANISM: Artificial sequence
<220> FEATURE:
<223> OTHER INFORMATION: mCSF1R ECD-Fc

<400> SEQUENCE: 93

Ala Pro Val Ile Glu Pro Ser Gly Pro Glu Leu Val Val Glu Pro Gly
1               5                   10                  15

Glu Thr Val Thr Leu Arg Cys Val Ser Asn Gly Ser Val Glu Trp Asp
                20                  25                  30

Gly Pro Ile Ser Pro Tyr Trp Thr Leu Asp Pro Glu Ser Pro Gly Ser
            35                  40                  45

Thr Leu Thr Thr Arg Asn Ala Thr Phe Lys Asn Thr Gly Thr Tyr Arg
        50                  55                  60

Cys Thr Glu Leu Glu Asp Pro Met Ala Gly Ser Thr Thr Ile His Leu
65                  70                  75                  80

Tyr Val Lys Asp Pro Ala His Ser Trp Asn Leu Leu Ala Gln Glu Val
                85                  90                  95

Thr Val Val Glu Gly Gln Glu Ala Val Leu Pro Cys Leu Ile Thr Asp
                100                 105                 110

Pro Ala Leu Lys Asp Ser Val Ser Leu Met Arg Glu Gly Gly Arg Gln
            115                 120                 125

Val Leu Arg Lys Thr Val Tyr Phe Phe Ser Pro Trp Arg Gly Phe Ile
        130                 135                 140

Ile Arg Lys Ala Lys Val Leu Asp Ser Asn Thr Tyr Val Cys Lys Thr
145                 150                 155                 160

Met Val Asn Gly Arg Glu Ser Thr Ser Thr Gly Ile Trp Leu Lys Val
                165                 170                 175

Asn Arg Val His Pro Glu Pro Pro Gln Ile Lys Leu Glu Pro Ser Lys
            180                 185                 190

Leu Val Arg Ile Arg Gly Glu Ala Ala Gln Ile Val Cys Ser Ala Thr
        195                 200                 205

Asn Ala Glu Val Gly Phe Asn Val Ile Leu Lys Arg Gly Asp Thr Lys
    210                 215                 220

Leu Glu Ile Pro Leu Asn Ser Asp Phe Gln Asp Asn Tyr Tyr Lys Lys
225                 230                 235                 240

Val Arg Ala Leu Ser Leu Asn Ala Val Asp Phe Gln Asp Ala Gly Ile
                245                 250                 255

Tyr Ser Cys Val Ala Ser Asn Asp Val Gly Thr Arg Thr Ala Thr Met
            260                 265                 270

Asn Phe Gln Val Val Glu Ser Ala Tyr Leu Asn Leu Thr Ser Glu Gln
        275                 280                 285

-continued

```
Ser Leu Leu Gln Glu Val Ser Val Gly Asp Ser Leu Ile Leu Thr Val
    290                 295                 300
His Ala Asp Ala Tyr Pro Ser Ile Gln His Tyr Asn Trp Thr Tyr Leu
305                 310                 315                 320
Gly Pro Phe Phe Glu Asp Gln Arg Lys Leu Glu Phe Ile Thr Gln Arg
                325                 330                 335
Ala Ile Tyr Arg Tyr Thr Phe Lys Leu Phe Leu Asn Arg Val Lys Ala
            340                 345                 350
Ser Glu Ala Gly Gln Tyr Phe Leu Met Ala Gln Asn Lys Ala Gly Trp
        355                 360                 365
Asn Asn Leu Thr Phe Glu Leu Thr Leu Arg Tyr Pro Pro Glu Val Ser
    370                 375                 380
Val Thr Trp Met Pro Val Asn Gly Ser Asp Val Leu Phe Cys Asp Val
385                 390                 395                 400
Ser Gly Tyr Pro Gln Pro Ser Val Thr Trp Met Glu Cys Arg Gly His
                405                 410                 415
Thr Asp Arg Cys Asp Glu Ala Gln Ala Leu Gln Val Trp Asn Asp Thr
            420                 425                 430
His Pro Glu Val Leu Ser Gln Lys Pro Phe Asp Lys Val Ile Ile Gln
        435                 440                 445
Ser Gln Leu Pro Ile Gly Thr Leu Lys His Asn Met Thr Tyr Phe Cys
    450                 455                 460
Lys Thr His Asn Ser Val Gly Asn Ser Ser Gln Tyr Phe Arg Ala Val
465                 470                 475                 480
Ser Leu Gly Gln Ser Lys Gln Glu Pro Lys Ser Ser Asp Lys Thr His
                485                 490                 495
Thr Cys Pro Pro Cys Pro Ala Pro Glu Leu Leu Gly Gly Pro Ser Val
            500                 505                 510
Phe Leu Phe Pro Pro Lys Pro Lys Asp Thr Leu Met Ile Ser Arg Thr
        515                 520                 525
Pro Glu Val Thr Cys Val Val Val Asp Val Ser His Glu Asp Pro Glu
    530                 535                 540
Val Lys Phe Asn Trp Tyr Val Asp Gly Val Glu Val His Asn Ala Lys
545                 550                 555                 560
Thr Lys Pro Arg Glu Glu Gln Tyr Asn Ser Thr Tyr Arg Val Val Ser
                565                 570                 575
Val Leu Thr Val Leu His Gln Asp Trp Leu Asn Gly Lys Glu Tyr Lys
            580                 585                 590
Cys Lys Val Ser Asn Lys Ala Leu Pro Ala Pro Ile Glu Lys Thr Ile
        595                 600                 605
Ser Lys Ala Lys Gly Gln Pro Arg Glu Pro Gln Val Tyr Thr Leu Pro
    610                 615                 620
Pro Ser Arg Asp Glu Leu Thr Lys Asn Gln Val Ser Leu Thr Cys Leu
625                 630                 635                 640
Val Lys Gly Phe Tyr Pro Ser Asp Ile Ala Val Glu Trp Glu Ser Asn
                645                 650                 655
Gly Gln Pro Glu Asn Asn Tyr Lys Thr Thr Pro Pro Val Leu Asp Ser
            660                 665                 670
Asp Gly Ser Phe Phe Leu Tyr Ser Lys Leu Thr Val Asp Lys Ser Arg
        675                 680                 685
Trp Gln Gln Gly Asn Val Phe Ser Cys Ser Val Met His Glu Ala Leu
    690                 695                 700
His Asn His Tyr Thr Gln Lys Ser Leu Ser Leu Ser Pro Gly Lys
```

<210> SEQ ID NO 94
<211> LENGTH: 327
<212> TYPE: PRT
<213> ORGANISM: Artificial sequence
<220> FEATURE:
<223> OTHER INFORMATION: Human IgG4 S241P

<400> SEQUENCE: 94

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 95
<211> LENGTH: 107
<212> TYPE: PRT

-continued

```
<213> ORGANISM: Homo sapiens
<220> FEATURE:
<221> NAME/KEY: MISC_FEATURE
<222> LOCATION: (1)..(107)
<223> OTHER INFORMATION: Human Ig-kappa

<400> SEQUENCE: 95

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

ANTI-CSF1R ANTIBODIES FOR TREATING PVNS

CROSS-REFERENCE TO RELATED APPLICATIONS

The present application claims the benefit of priority of US Provisional Application Nos. 62/095,297, filed Dec. 22, 2014, and 62/163,251, filed May 18, 2015, both of which are incorporated by reference herein in their entirety for any purpose.

SEQUENCE LISTING

The present application is filed with a Sequence Listing in electronic format. The Sequence Listing is provided as a file entitled "2015-12-08_01134-0037 00PCT_SeqList_ST25.txt" created on Dec. 8, 2015, which is 146,937 bytes in size. The information in the electronic format of the sequence listing is incorporated herein by reference in its entirety.

TECHNICAL FIELD

Methods of treating pigmented villonodular synovitis (PVNS) with antibodies that bind colony stimulating factor 1 receptor (CSF1R) are provided.

BACKGROUND

Colony stimulating factor 1 receptor (referred to herein as CSF1R; also referred to in the art as FMS, FIM2, C-FMS, M-CSF receptor, and CD115) is a single-pass transmembrane receptor with an N-terminal extracellular domain (ECD) and a C-terminal intracellular domain with tyrosine kinase activity. Ligand binding of CSF1 or the interleukin 34 ligand (referred to herein as IL-34; Lin et al., Science 320: 807-11 (2008)) to CSF1R leads to receptor dimerization, upregulation of CSF1R protein tyrosine kinase activity, phosphorylation of CSF1R tyrosine residues, and downstream signaling events. CSF1R activation by CSF1 or IL-34 leads to the trafficking, survival, proliferation, and differentiation of monocytes and macrophages, as well as other monocytic cell lineages such as osteoclasts, dendritic cells, and microglia.

Pigmented villonodular synovitis (PVNS) is a solid tumor of the synovium with features of both reactive inflammation and clonal neoplastic proliferation in which colony stimulating factor-1 (CSF1) is over expressed. A common translocation of the CSF1 gene (1p13) to the COL6A3 promoter (2q35) is present in approximately 60% of PVNS patients. The translocation is accompanied by CSF1 overexpression in the synovium. In addition, approximately 40% of PVNS patients have CSF1 overexpression in the absence of an identified CSF1 translocation. The consistent presence of CSF1 overexpression in all cases of PVNS and reactive synovitis suggests both an important role for CSF1 in the spectrum of synovial pathologies and the utility of targeting the CSF1/CSF1R interaction therapeutically. See West et al., 2006, Proc. Natl. Acad. Sci USA, 103: 690-695.

In PVNS, CSF1 overexpression is present in a minority of synovial cells, whereas the majority of the cellular infiltrate expresses CSF1R but not CSF1. This has been characterized as a tumor-landscaping effect with aberrant CSF1 expression in the tumor cells, leading to the abnormal accumulation of non-neoplastic cells that form a mass.

Surgery is the treatment of choice for patients with localized PVNS. Recurrences occur in 8-20% of patients and are often managed by re-excision. Diffuse tenosynovial giant cell tumor (TGCT/PVNS or PVNS/dtTGCT) tends to recur more often (33-50%) and has a much more aggressive clinical course. Patients are often symptomatic and require multiple surgical procedures during their lifetime. For patients with unresectable disease or multiple recurrences, systemic therapy using CSF1R inhibitors may help delay or avoid surgical procedures and improve functional outcomes. See Ravi et al., 2011, Am. J. Pathol., 179: 240-247.

Imatinib, a non-specific inhibitor of CSF1R, has undergone evaluation in PVNS patients. Twenty-nine patients from 12 institutions in Europe, Australia, and the United States were included. The median age was 41 years and the most common site of disease was the knee (n=17; 59%). Two patients had metastatic disease to the lung and/or bone. Five of 27 evaluable patients had complete (n=1) or partial (n=4) responses per RECIST for an overall response rate of 19%. Twenty of 27 patients (74%) had stable disease. Symptomatic improvement was noted in 16 of 22 patients (73%) who were assessable for symptoms. Despite a high rate of symptomatic improvement and an overall favorable safety profile, 10 patients discontinued treatment for toxicity or other reasons.

Alternative, less toxic treatments for PVNS are needed.

SUMMARY

In some embodiments, methods of treating a proliferative disorder involving a synovial joint and/or tendon sheath in a subject are provided, comprising administering to the subject an effective amount of an antibody that binds CSF1R. In some embodiments, the proliferative disorder is selected from pigmented villonodular synovitis (PVNS), giant cell tumor of the tendon sheath (GCTTS), and tenosynovial giant cell tumor (TGCT) such as diffuse type tenosynovial gian cell tumor (dtTGCT). In some embodiments, the disorder is pigmented villonodular synovitis/ diffuse type tenosynovial gian cell tumor (PVNS/dtTGCT). In some embodiments, methods of treating pigmented villonodular synovitis (PVNS) in a subject are provided, comprising administering to the subject an effective amount of an antibody that binds CSF1R.

In some embodiments, the antibody is administered once per week, once per two weeks, once per three weeks, or once per month. In some embodiments, the antibody is administered at a dose of at least 1, at least 2, at least 3, at least 4, at least 5, at least 6, at least 7, at least 8, at least 10, at least 12, at least 15, at least 16, at least 20, at least 30, at least 40, at least 50, or at least 100 mg/kg. In some embodiments, the antibody is administered at a dose of 1, 2, 3, or 4 mg/kg.

In some embodiments, the PVNS tumor volume is reduced by at least 30% or at least 40% or at least 50% or at least 60% or at least 70% after administration of at least two, at least three, at least four, at least five, at least six, at least seven, at least eight, at least nine, or at least ten doses of the antibody that binds CSF1R. In some embodiments, the tumor volume is tumor volume in a single joint. In some embodiments, the single join is selected from a hip joint and a knee joint. In some embodiments, the tumor volume is total tumor volume in all joints affected by PVNS. In some embodiments, the subject experiences one or more than one of the following improvements in symptoms: (a) a reduction in joint pain, (b) an increase range of motion in a joint, and (c) an increase in functional capacity of a joint, following at least one dose of the antibody.

In some embodiments, prior to administering the first dose of the antibody, the subject received a first therapy selected from surgical synovectomy, radiation beam therapy, radio isotope synovectomy, and joint replacement. In some embodiments, the PVNS recurred or progressed after the first therapy. In some embodiments, the antibody is administered prior to a therapy selected from surgical synovectomy, radiation beam therapy, radio isotope synovectomy, and joint replacement. In some embodiments, the tumor is unresectable. In some embodiments, the subject has not received prior therapy with imatinib or nilotinib, while in other embodiments the subject has received prior treatment with imatinib or nilotinib. In some embodiments, the subject has not received prior treatment with a CSF1R inhibitor, while in other embodiments the subject has received prior treatment with a CSF1R inhibitor.

In any of the compositions or methods described herein, the antibody heavy chain and/or the antibody light chain of the anti-CSF1R antibody may have the structure described below.

In any of the compositions or methods described herein, the anti-CSF1R antibody heavy chain may comprise a sequence that is at least 90%, at least 95%, at least 97%, at least 99%, or 100% identical to a sequence selected from SEQ ID NOs: 9, 11, 13, and 39 to 45. In any of the methods described herein, the anti-CSF1R antibody light chain may comprise a sequence that is at least 90%, at least 95%, at least 97%, at least 99%, or 100% identical to a sequence selected from SEQ ID NOs: 10, 12, 14, and 46 to 52. In any of the compositions or methods described herein, the anti-CSF1R antibody heavy chain may comprise a sequence that is at least 90%, at least 95%, at least 97%, at least 99%, or 100% identical to a sequence selected from SEQ ID NOs: 9, 11, 13, and 39 to 45, and the anti-CSF1R antibody light chain may comprise a sequence that is at least 90%, at least 95%, at least 97%, at least 99%, or 100% identical to a sequence selected from SEQ ID NOs: 10, 12, 14, and 46 to 52.

In any of the compositions or methods described herein, the anti-CSF1R antibody HC CDR1, HC CDR2, and HC CDR3 may comprise a set of sequences selected from: (a) SEQ ID NOs: 15, 16, and 17; (b) SEQ ID NOs: 21, 22, and 23; and (c) SEQ ID NOs: 27, 28, and 29. In any of the compositions or methods described herein, the anti-CSF1R antibody LC CDR1, LC CDR2, and LC CDR3 may comprise a set of sequences selected from: (a) SEQ ID NOs: 18, 19, and 20; (b) SEQ ID NOs: 24, 25, and 26; and (c) SEQ ID NOs: 30, 31, and 32.

In any of the compositions or methods described herein, the anti-CSF1R antibody heavy chain may comprise an HC CDR1, HC CDR2, and HC CDR3, wherein the HC CDR1, HC CDR2, and HC CDR3 comprise a set of sequences selected from: (a) SEQ ID NOs: 15, 16, and 17; (b) SEQ ID NOs: 21, 22, and 23; and (c) SEQ ID NOs: 27, 28, and 29; and the light chain may comprise an LC CDR1, LC CDR2, and LC CDR3, wherein the LC CDR1, LC CDR2, and LC CDR3 comprise a set of sequences selected from: (a) SEQ ID NOs: 18, 19, and 20; (b) SEQ ID NOs: 24, 25, and 26; and (c) SEQ ID NOs: 30, 31, and 32.

In any of the compositions or methods described herein, the anti-CSF1R antibody may comprise: (a) a heavy chain comprising a sequence that is at least 95%, at least 97%, at least 99%, or 100% identical to SEQ ID NO: 9 and a light chain comprising a sequence that is at least 95%, at least 97%, at least 99%, or 100% identical to SEQ ID NO: 10; (b) a heavy chain comprising a sequence that is at least 95%, at least 97%, at least 99%, or 100% identical to SEQ ID NO: 11 and a light chain comprising a sequence that is at least 95%, at least 97%, at least 99%, or 100% identical to SEQ ID NO: 12; (c) a heavy chain comprising a sequence that is at least 95%, at least 97%, at least 99%, or 100% identical to SEQ ID NO: 13 and a light chain comprising a sequence that is at least 95%, at least 97%, at least 99%, or 100% identical to SEQ ID NO: 14; (d) a heavy chain comprising a sequence that is at least 95%, at least 97%, at least 99%, or 100% identical to SEQ ID NO: 39 and a light chain comprising a sequence that is at least 95%, at least 97%, at least 99%, or 100% identical to SEQ ID NO: 46; (e) a heavy chain comprising a sequence that is at least 95%, at least 97%, at least 99%, or 100% identical to SEQ ID NO: 40 and a light chain comprising a sequence that is at least 95%, at least 97%, at least 99%, or 100% identical to SEQ ID NO: 46; (f) a heavy chain comprising a sequence that is at least 95%, at least 97%, at least 99%, or 100% identical to SEQ ID NO: 41 and a light chain comprising a sequence that is at least 95%, at least 97%, at least 99%, or 100% identical to SEQ ID NO: 46; (g) a heavy chain comprising a sequence that is at least 95%, at least 97%, at least 99%, or 100% identical to SEQ ID NO: 39 and a light chain comprising a sequence that is at least 95%, at least 97%, at least 99%, or 100% identical to SEQ ID NO: 47; (h) a heavy chain comprising a sequence that is at least 95%, at least 97%, at least 99%, or 100% identical to SEQ ID NO: 40 and a light chain comprising a sequence that is at least 95%, at least 97%, at least 99%, or 100% identical to SEQ ID NO: 47; (i) a heavy chain comprising a sequence that is at least 95%, at least 97%, at least 99%, or 100% identical to SEQ ID NO: 41 and a light chain comprising a sequence that is at least 95%, at least 97%, at least 99%, or 100% identical to SEQ ID NO: 47; and (j) a heavy chain comprising a sequence that is at least 95%, at least 97%, at least 99%, or 100% identical to SEQ ID NO: 42 and a light chain comprising a sequence that is at least 95%, at least 97%, at least 99%, or 100% identical to SEQ ID NO: 48; (k) a heavy chain comprising a sequence that is at least 95%, at least 97%, at least 99%, or 100% identical to SEQ ID NO: 42 and a light chain comprising a sequence that is at least 95%, at least 97%, at least 99%, or 100% identical to SEQ ID NO: 49; (l) a heavy chain comprising a sequence that is at least 95%, at least 97%, at least 99%, or 100% identical to SEQ ID NO: 42 and a light chain comprising a sequence that is at least 95%, at least 97%, at least 99%, or 100% identical to SEQ ID NO: 50; (m) a heavy chain comprising a sequence that is at least 95%, at least 97%, at least 99%, or 100% identical to SEQ ID NO: 43 and a light chain comprising a sequence that is at least 95%, at least 97%, at least 99%, or 100% identical to SEQ ID NO: 48; (n) a heavy chain comprising a sequence that is at least 95%, at least 97%, at least 99%, or 100% identical to SEQ ID NO: 43 and a light chain comprising a sequence that is at least 95%, at least 97%, at least 99%, or 100% identical to SEQ ID NO: 49; (o) a heavy chain comprising a sequence that is at least 95%, at least 97%, at least 99%, or 100% identical to SEQ ID NO: 43 and a light chain comprising a sequence that is at least 95%, at least 97%, at least 99%, or 100% identical to SEQ ID NO: 50; (p) a heavy chain comprising a sequence that is at least 95%, at least 97%, at least 99%, or 100% identical to SEQ ID NO: 44 and a light chain comprising a sequence that is at least 95%, at least 97%, at least 99%, or 100% identical to SEQ ID NO: 51; (q) a heavy chain comprising a sequence that is at least 95%, at least 97%, at least 99%, or 100% identical to SEQ ID NO: 44 and a light chain comprising a sequence that is at least 95%, at least 97%, at least 99%, or 100% identical to SEQ ID NO: 52; (r) a heavy chain comprising a sequence that is at least 95%, at least 97%, at least 99%, or 100% identical to SEQ ID NO: 45 and a light chain comprising a sequence that is at least 95%, at least 97%, at least 99%, or 100% identical to SEQ ID NO: 51; or (s) a heavy chain comprising a sequence that is at least 95%, at least 97%, at least 99%, or 100% identical to SEQ ID NO: 45 and a light chain comprising a sequence that is at least 95%, at least 97%, at least 99%, or 100% identical to SEQ ID NO: 52.

In any of the compositions or methods described herein, the anti-CSF1R antibody may comprise: (a) a heavy chain comprising a heavy chain (HC) CDR1 having the sequence of SEQ ID NO: 15, an HC CDR2 having the sequence of SEQ ID NO: 16, and an HC CDR3 having the sequence of SEQ ID NO: 17, and a light chain comprising a light chain (LC) CDR1 having the sequence of SEQ ID NO: 18, a LC CDR2 having the sequence of SEQ ID NO: 19, and a LC CDR3 having the sequence of SEQ ID NO: 20; (b) a heavy chain comprising a heavy chain (HC) CDR1 having the sequence of SEQ ID NO: 21, an HC CDR2 having the sequence of SEQ ID NO: 22, and an HC CDR3 having the sequence of SEQ ID NO: 23, and a light chain comprising a light chain (LC) CDR1 having the sequence of SEQ ID NO: 24, a LC CDR2 having the sequence of SEQ ID NO: 25, and a LC CDR3 having the sequence of SEQ ID NO: 26; or (c) a heavy chain comprising a heavy chain (HC) CDR1 having the sequence of SEQ ID NO: 27, an HC CDR2 having the sequence of SEQ ID NO: 28, and an HC CDR3 having the sequence of SEQ ID NO: 29, and a light chain comprising a light chain (LC) CDR1 having the sequence of SEQ ID NO: 30, a LC CDR2 having the sequence of SEQ ID NO: 31, and a LC CDR3 having the sequence of SEQ ID NO: 32.

In any of the compositions or methods described herein, the anti-CSF1R antibody may comprise: (a) a heavy chain comprising a sequence of SEQ ID NO: 53 and a light chain comprising a sequence of SEQ ID NO: 60; (b) a heavy chain comprising a sequence of SEQ ID NO: 53 and a light chain comprising a sequence of SEQ ID NO: 61; or (c) a heavy chain comprising a sequence of SEQ ID NO: 58 and a light chain comprising a sequence of SEQ ID NO: 65. In some embodiments, an antibody comprises a heavy chain and a light chain, wherein the antibody comprises: (a) a heavy chain consisting of the sequence of SEQ ID NO: 53 and a light chain consisting of the sequence of SEQ ID NO: 60; (b) a heavy chain consisting of the sequence of SEQ ID NO: 53 and a light chain consisting of the sequence of SEQ ID NO: 61; or (c) a heavy chain consisting of the sequence of SEQ ID NO: 58 and a light chain consisting of the sequence of SEQ ID NO: 65.

In any of the compositions or methods described herein, the anti-CSF1R antibody may be a humanized antibody. In any of the compositions or methods described herein, the anti-CSF1R antibody may be any of huAb1, huAb2, huAb3, huAb4, huAb5 huAb6, huAb7, huAb8, huAb9, huAb10, huAb11, huAb12, huAb13, huAb14 huAb15, or huAb16. (See FIGS. 1-2.) In any of the compositions or methods described herein, the anti-CSF1R antibody may be selected from a Fab, an Fv, an scFv, a Fab', and a (Fab')$_2$. In any of the compositions or methods described herein, the anti-CSF1R antibody may be a chimeric antibody. In any of the compositions or methods described herein, the anti-CSF1R antibody may be selected from an IgA, an IgG, and an IgD. In any of the compositions or methods described herein, the anti-CSF1R antibody may be an IgG. In any of the methods described herein, the antibody may be an IgG1 or IgG2.

In any of the compositions or methods described herein, the anti-CSF1R antibody may bind to human CSF1R and/or binds to cynomolgus CSF1R. In any of the compositions or methods described herein, the anti-CSF1R antibody may block ligand binding to CSF1R. In any of the compositions or methods described herein, the anti-CSF1R antibody may block binding of CSF1 and/or IL-34 to CSF1R. In any of the compositions or methods described herein, the anti-CSF1R antibody may block binding of both CSF1 and IL-34 to CSF1R. In any of the compositions or methods described herein, the anti-CSF1R antibody may inhibit ligand-induced CSF1R phosphorylation. In any of the compositions or methods described herein, the anti-CSF1R antibody may inhibit CSF1- and/or IL-34-induced CSF1R phosphorylation. In any of the compositions or methods described herein, the anti-CSF1R antibody may bind to human CSF1R with an affinity ($K_D$) of less than 1 nM. In any of the compositions or methods described herein, the anti-CSF1R antibody may inhibit monocyte proliferation and/or survival responses in the presence of CSF1 or IL-34.

BRIEF DESCRIPTION OF THE FIGURES

FIG. 1A-C show an alignment of the humanized heavy chain variable regions for each of humanized antibodies huAb1 to huAb16, as discussed in Example 1. Boxed residues are amino acids in the human acceptor sequence that were changed back to the corresponding mouse residue.

Figure 2A:
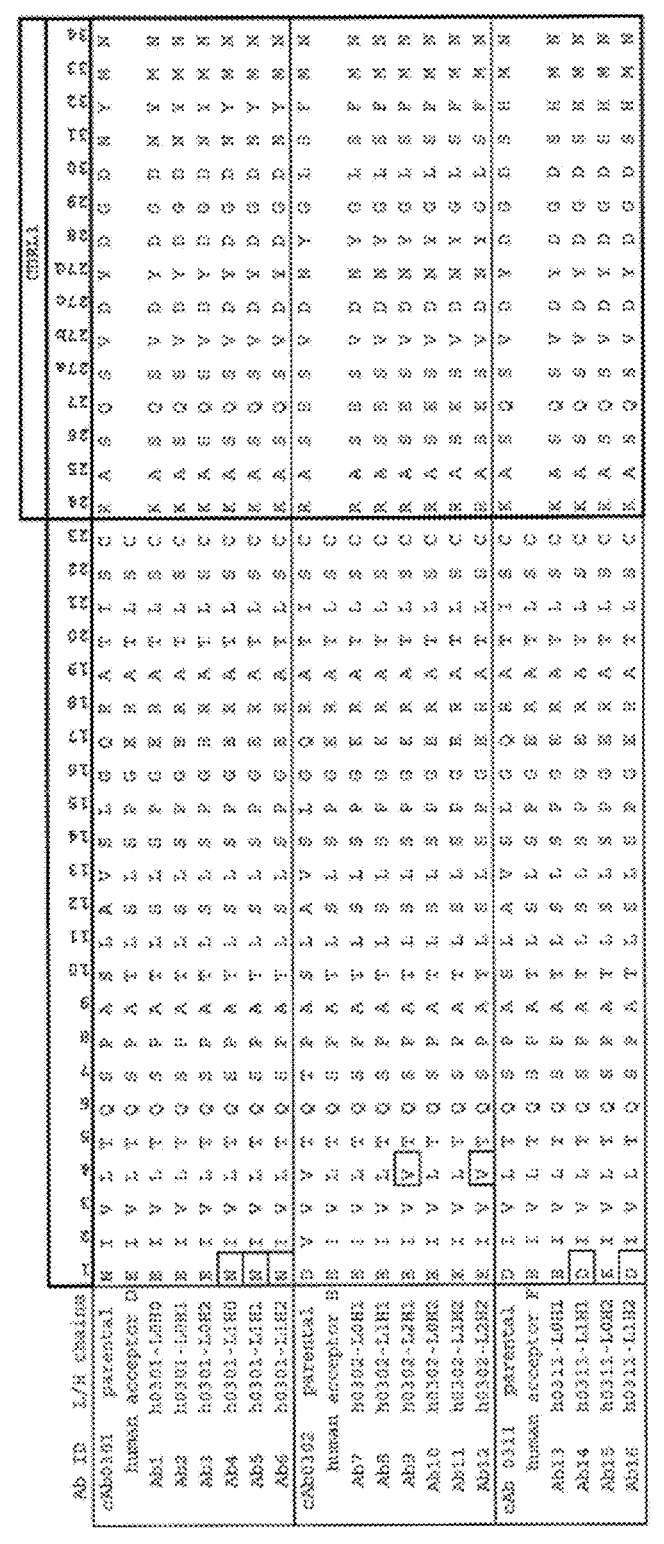
Figure 2B:
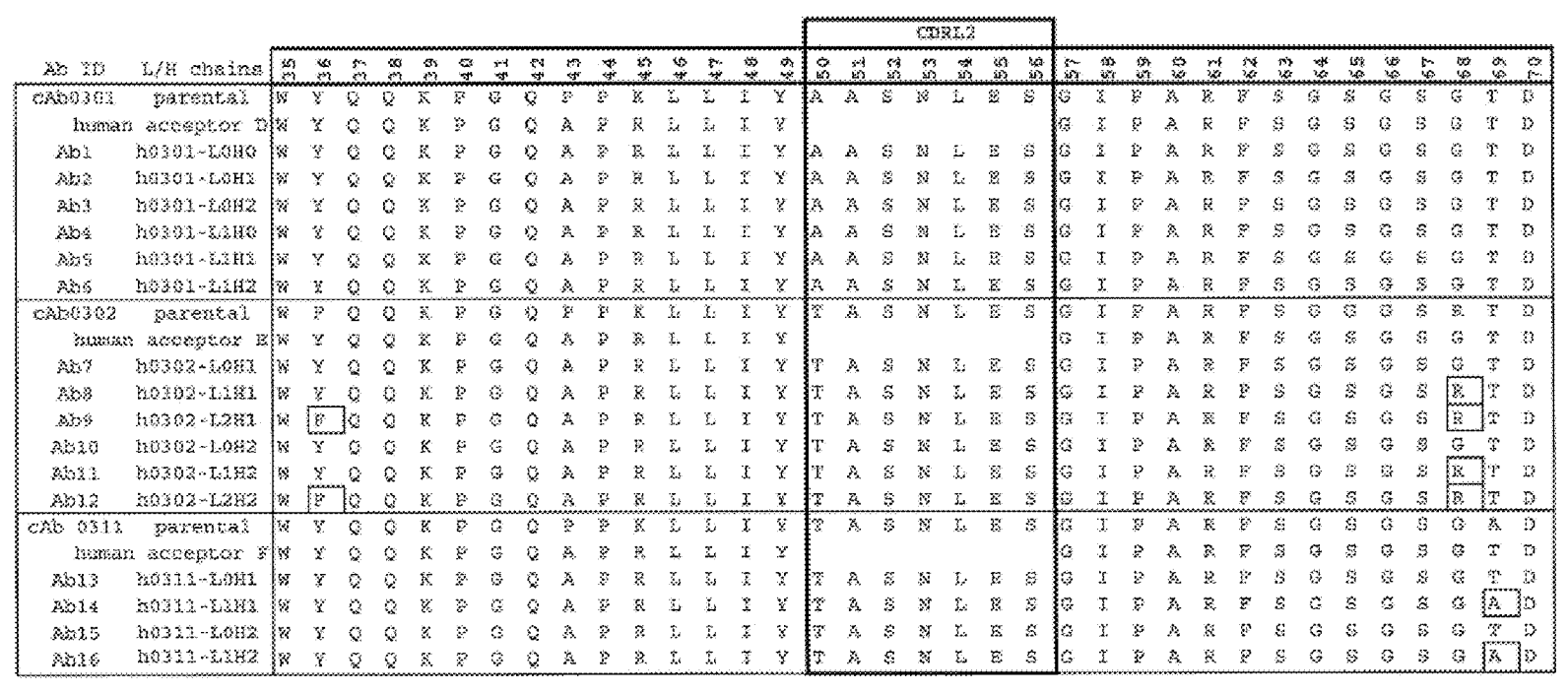
Figure 2C:
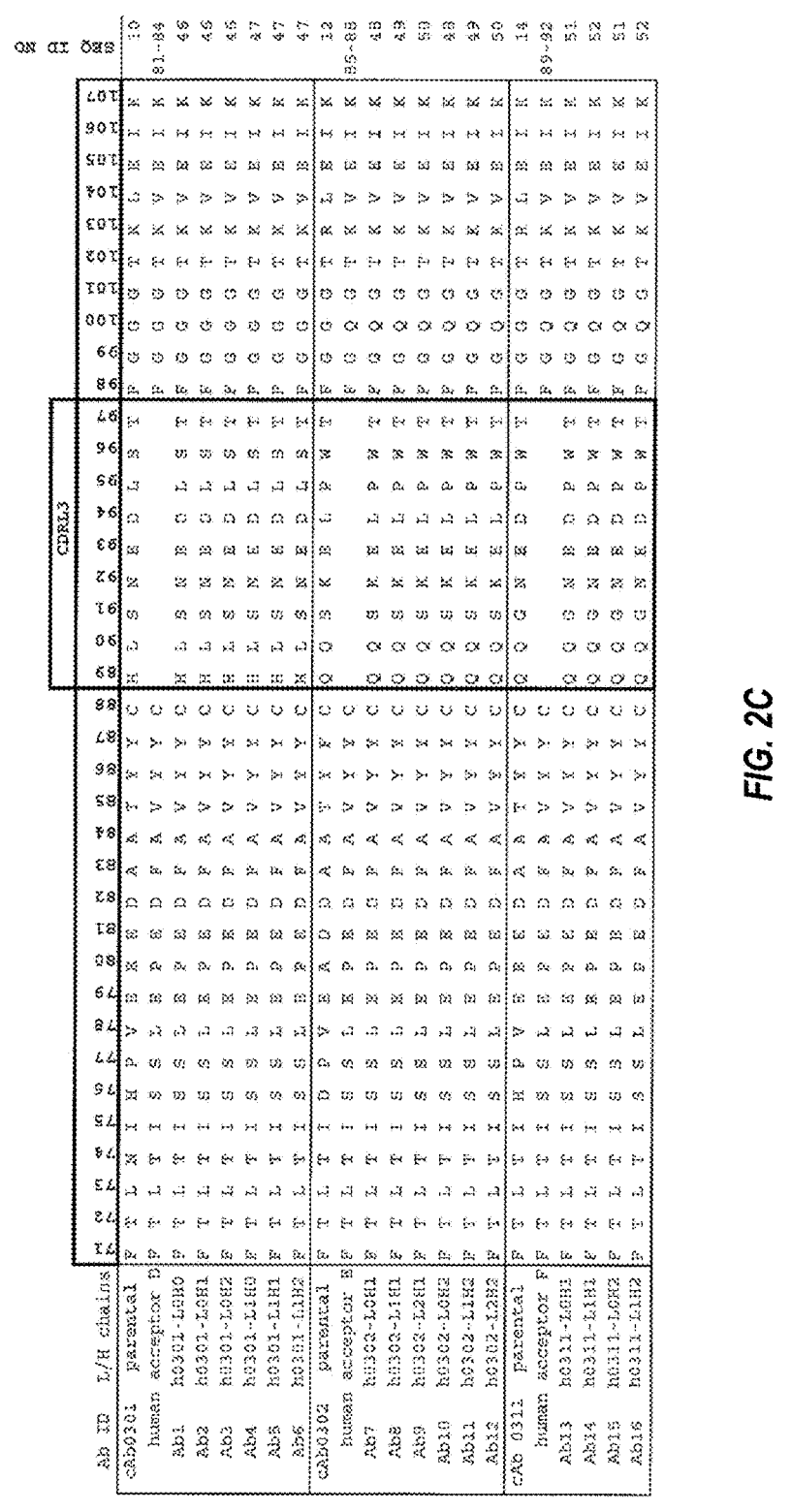

FIG. 2A-C show an alignment of the humanized light chain variable regions for each of humanized antibodies huAb1 to huAb16, as discussed in Example 1. Boxed amino acids are residues in the human acceptor sequence that were changed back to the corresponding mouse residue.

DETAILED DESCRIPTION

Figure 3:
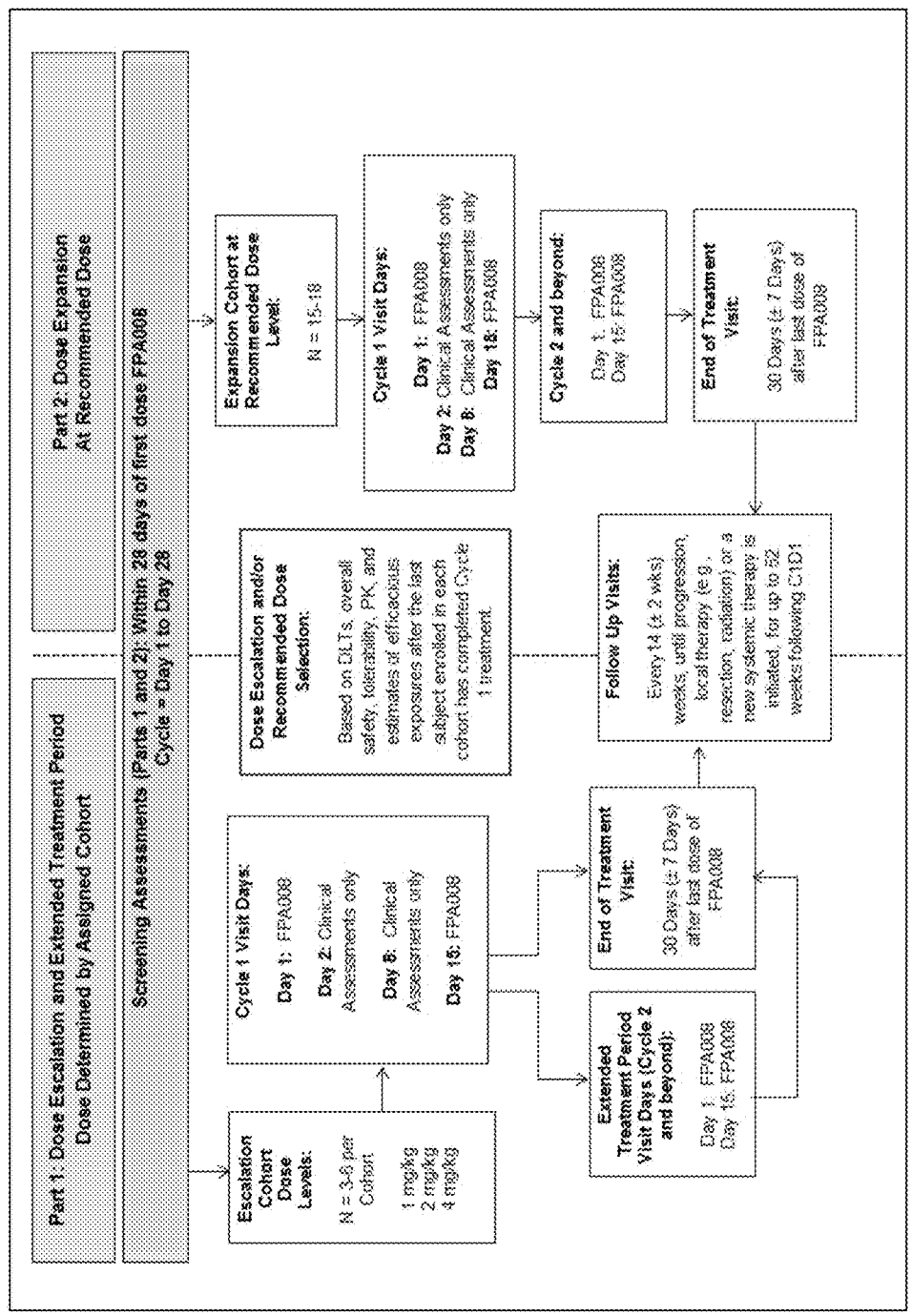
FIG. 3 shows a schematic diagram of the clinical trial summarized in Examples 4 and 5 using antibody huAb1, also known as FPA008.

The present invention provides methods of treating PVNS in a subject comprising administering an anti-CSF1R antibody to the subject.

The section headings used herein are for organizational purposes only and are not to be construed as limiting the subject matter described. All references cited herein, including patent applications and publications, are incorporated herein by reference in their entireties for any purpose.

Definitions

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular.

Exemplary techniques used in connection with recombinant DNA, oligonucleotide synthesis, tissue culture and transformation (e.g., electroporation, lipofection), enzymatic reactions, and purification techniques are known in the art. Many such techniques and procedures are described, e.g., in Sambrook et al. *Molecular Cloning: A Laboratory Manual* (2nd ed., Cold Spring Harbor Laboratory Press, Cold Spring Harbor, N.Y. (1989)), among other places. In addition, exemplary techniques for chemical syntheses, chemical analyses, pharmaceutical preparation, formulation, and delivery, and treatment of patients are also known in the art.

In this application, the use of "or" means "and/or" unless stated otherwise. In the context of a multiple dependent claim, the use of "or" refers back to more than one preceding independent or dependent claim in the alternative only. Also, terms such as "element" or "component" encompass both elements and components comprising one unit and elements and components that comprise more than one subunit unless specifically stated otherwise.

As utilized in accordance with the present disclosure, the following terms, unless otherwise indicated, shall be understood to have the following meanings:

The terms "nucleic acid molecule" and "polynucleotide" may be used interchangeably, and refer to a polymer of nucleotides. Such polymers of nucleotides may contain natural and/or non-natural nucleotides, and include, but are not limited to, DNA, RNA, and PNA. "Nucleic acid sequence" refers to the linear sequence of nucleotides that comprise the nucleic acid molecule or polynucleotide.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present invention, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

The term "CSF1R" refers herein to the full-length CSF1R, which includes the N-terminal ECD, the transmembrane domain, and the intracellular tyrosine kinase domain, with or without an N-terminal leader sequence. In some embodiments, the CSF1R is a human CSF1R having the amino acid sequence of SEQ ID NO: 1 or SEQ ID NO: 2.

With reference to anti-CSF1R antibodies the term "blocks binding of" a ligand, such as CSF1 and/or IL-34, and grammatical variants thereof, are used to refer to the ability to inhibit the interaction between CSF1R and a CSF1R ligand, such as CSF1 and/or IL-34. Such inhibition may occur through any mechanism, including direct interference with ligand binding, e.g., because of overlapping binding sites on CSF1R, and/or conformational changes in CSF1R induced by the antibody that alter ligand affinity, etc. Antibodies and antibody fragments referred to as "functional" are characterized by having such properties.

The term "antibody" as used herein refers to a molecule comprising at least complementarity-determining region (CDR) 1, CDR2, and CDR3 of a heavy chain and at least CDR1, CDR2, and CDR3 of a light chain, wherein the molecule is capable of binding to antigen. The term antibody includes, but is not limited to, fragments that are capable of binding antigen, such as Fv, single-chain Fv (scFv), Fab, Fab', and (Fab')$_2$. The term antibody also includes, but is not limited to, chimeric antibodies, humanized antibodies, and antibodies of various species such as mouse, human, cynomolgus monkey, etc.

In some embodiments, an antibody comprises a heavy chain variable region and a light chain variable region. In some embodiments, an antibody comprises at least one heavy chain comprising a heavy chain variable region and at least a portion of a heavy chain constant region, and at least one light chain comprising a light chain variable region and at least a portion of a light chain constant region. In some embodiments, an antibody comprises two heavy chains, wherein each heavy chain comprises a heavy chain variable region and at least a portion of a heavy chain constant region, and two light chains, wherein each light chain comprises a light chain variable region and at least a portion of a light chain constant region. As used herein, a single-chain Fv (scFv), or any other antibody that comprises, for example, a single polypeptide chain comprising all six CDRs (three heavy chain CDRs and three light chain CDRs) is considered to have a heavy chain and a light chain. In some such embodiments, the heavy chain is the region of the antibody that comprises the three heavy chain CDRs and the light chain in the region of the antibody that comprises the three light chain CDRs.

Figure 1A:
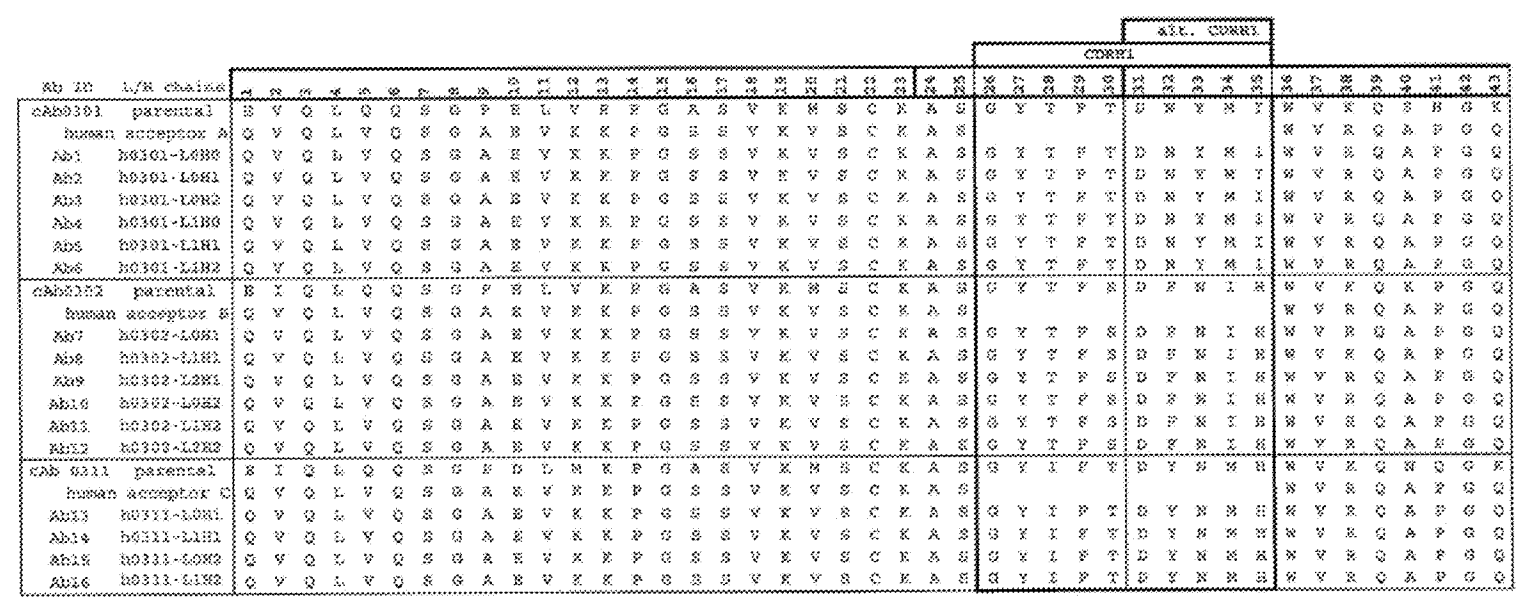

The term "heavy chain variable region" as used herein refers to a region comprising heavy chain CDR1, framework (FR) 2, CDR2, FR3, and CDR3. In some embodiments, a heavy chain variable region also comprises at least a portion of an FR1 and/or at least a portion of an FR4. In some embodiments, a heavy chain CDR1 corresponds to Kabat residues 26 to 35; a heavy chain CDR2 corresponds to Kabat residues 50 to 65; and a heavy chain CDR3 corresponds to Kabat residues 95 to 102. See, e.g., Kabat Sequences of Proteins of Immunological Interest (1987 and 1991, NIH, Bethesda, Md.); and FIG. 1. In some embodiments, a heavy chain CDR1 corresponds to Kabat residues 31 to 35; a heavy chain CDR2 corresponds to Kabat residues 50 to 65; and a heavy chain CDR3 corresponds to Kabat residues 95 to 102. See id.

The term "heavy chain constant region" as used herein refers to a region comprising at least three heavy chain constant domains, $C_H1$, $C_H2$, and $C_H3$. Nonlimiting exemplary heavy chain constant regions include γ, δ, and α. Nonlimiting exemplary heavy chain constant regions also include ε and μ. Each heavy constant region corresponds to an antibody isotype. For example, an antibody comprising a γ constant region is an IgG antibody, an antibody comprising a δ constant region is an IgD antibody, and an antibody comprising an α constant region is an IgA antibody. Further, an antibody comprising μ constant region is an IgM antibody, and an antibody comprising an ε constant region is an IgE antibody. Certain isotypes can be further subdivided into subclasses. For example, IgG antibodies include, but are not limited to, IgG1 (comprising a $γ_1$ constant region), IgG2 (comprising a $γ_2$ constant region), IgG3 (comprising a $γ_3$ constant region), and IgG4 (comprising a $γ_4$ constant region) antibodies; IgA antibodies include, but are not limited to, IgA1 (comprising an $α_1$ constant region) and IgA2 (comprising an $α_2$ constant region) antibodies; and IgM antibodies include, but are not limited to, IgM1 and IgM2.

In some embodiments, a heavy chain constant region comprises one or more mutations (or substitutions), additions, or deletions that confer a desired characteristic on the antibody. A nonlimiting exemplary mutation is the S241P mutation in the IgG4 hinge region (between constant domains $C_H1$ and $C_H2$), which alters the IgG4 motif CPSCP to CPPCP, which is similar to the corresponding motif in IgG1. That mutation, in some embodiments, results in a more stable IgG4 antibody. See, e.g., Angal et al., *Mol. Immunol.* 30: 105-108 (1993); Bloom et al., *Prot. Sci.* 6: 407-415 (1997); Schuurman et al., *Mol. Immunol.* 38: 1-8 (2001).

The term "heavy chain" as used herein refers to a polypeptide comprising at least a heavy chain variable region, with or without a leader sequence. In some embodiments, a heavy chain comprises at least a portion of a heavy chain constant region. The term "full-length heavy chain" as used herein refers to a polypeptide comprising a heavy chain variable region and a heavy chain constant region, with or without a leader sequence.

The term "light chain variable region" as used herein refers to a region comprising light chain CDR1, framework (FR) 2, CDR2, FR3, and CDR3. In some embodiments, a light chain variable region also comprises an FR1 and/or an FR4. In some embodiments, a light chain CDR1 corresponds to Kabat residues 24 to 34; a light chain CDR2 corresponds to Kabat residues 50 to 56; and a light chain CDR3 corresponds to Kabat residues 89 to 97. See, e.g., Kabat Sequences of Proteins of Immunological Interest (1987 and 1991, NIH, Bethesda, Md.); and FIG. 1.

The term "light chain constant region" as used herein refers to a region comprising a light chain constant domain, $C_L$. Nonlimiting exemplary light chain constant regions include λ and κ.

The term "light chain" as used herein refers to a polypeptide comprising at least a light chain variable region, with or without a leader sequence. In some embodiments, a light chain comprises at least a portion of a light chain constant region. The term "full-length light chain" as used herein refers to a polypeptide comprising a light chain variable region and a light chain constant region, with or without a leader sequence.

A "chimeric antibody" as used herein refers to an antibody comprising at least one variable region from a first species (such as mouse, rat, cynomolgus monkey, etc.) and at least one constant region from a second species (such as human, cynomolgus monkey, etc.). In some embodiments, a chimeric antibody comprises at least one mouse variable region and at least one human constant region. In some embodiments, a chimeric antibody comprises at least one cynomolgus variable region and at least one human constant region. In some embodiments, a chimeric antibody comprises at least one rat variable region and at least one mouse constant region. In some embodiments, all of the variable regions of a chimeric antibody are from a first species and all of the constant regions of the chimeric antibody are from a second species.

A "humanized antibody" as used herein refers to an antibody in which at least one amino acid in a framework region of a non-human variable region has been replaced with the corresponding amino acid from a human variable region. In some embodiments, a humanized antibody comprises at least one human constant region or fragment thereof. In some embodiments, a humanized antibody is a Fab, an scFv, a (Fab')$_2$, etc.

A "CDR-grafted antibody" as used herein refers to a humanized antibody in which the complementarity determining regions (CDRs) of a first (non-human) species have been grafted onto the framework regions (FRs) of a second (human) species.

A "human antibody" as used herein refers to antibodies produced in humans, antibodies produced in non-human animals that comprise human immunoglobulin genes, such as XenoMouse®, and antibodies selected using in vitro methods, such as phage display, wherein the antibody repertoire is based on a human immunoglobulin sequences.

The term "leader sequence" refers to a sequence of amino acid residues located at the N terminus of a polypeptide that facilitates secretion of a polypeptide from a mammalian cell. A leader sequence may be cleaved upon export of the polypeptide from the mammalian cell, forming a mature protein. Leader sequences may be natural or synthetic, and they may be heterologous or homologous to the protein to which they are attached. Exemplary leader sequences include, but are not limited to, antibody leader sequences, such as, for example, the amino acid sequences of SEQ ID NOs: 3 and 4, which correspond to human light and heavy chain leader sequences, respectively. Nonlimiting exemplary leader sequences also include leader sequences from heterologous proteins. In some embodiments, an antibody lacks a leader sequence. In some embodiments, an antibody comprises at least one leader sequence, which may be selected from native antibody leader sequences and heterologous leader sequences.

The term "vector" is used to describe a polynucleotide that may be engineered to contain a cloned polynucleotide or polynucleotides that may be propagated in a host cell. A vector may include one or more of the following elements: an origin of replication, one or more regulatory sequences (such as, for example, promoters and/or enhancers) that regulate the expression of the polypeptide of interest, and/or one or more selectable marker genes (such as, for example, antibiotic resistance genes and genes that may be used in colorimetric assays, e.g., β-galactosidase). The term "expression vector" refers to a vector that is used to express a polypeptide of interest in a host cell.

A "host cell" refers to a cell that may be or has been a recipient of a vector or isolated polynucleotide. Host cells may be prokaryotic cells or eukaryotic cells. Exemplary eukaryotic cells include mammalian cells, such as primate or non-primate animal cells; fungal cells, such as yeast; plant cells; and insect cells. Nonlimiting exemplary mammalian cells include, but are not limited to, NSO cells, PER.C6® cells (Crucell), and 293 and CHO cells, and their derivatives, such as 293-6E and DG44 cells, respectively.

The term "isolated" as used herein refers to a molecule that has been separated from at least some of the components with which it is typically found in nature. For example, a polypeptide is referred to as "isolated" when it is separated from at least some of the components of the cell in which it was produced. Where a polypeptide is secreted by a cell after expression, physically separating the supernatant containing the polypeptide from the cell that produced it is considered to be "isolating" the polypeptide. Similarly, a polynucleotide is referred to as "isolated" when it is not part of the larger polynucleotide (such as, for example, genomic DNA or mitochondrial DNA, in the case of a DNA polynucleotide) in which it is typically found in nature, or is separated from at least some of the components of the cell in which it was produced, e.g., in the case of an RNA polynucleotide. Thus, a DNA polynucleotide that is contained in a vector inside a host cell may be referred to as "isolated" so long as that polynucleotide is not found in that vector in nature.

The term "elevated level" means a higher level of a protein in a particular tissue of a subject relative to the same tissue in a control, such as an individual or individuals who are not suffering from PVNS or other condition described herein. The elevated level may be the result of any mechanism, such as increased expression, increased stability, decreased degradation, increased secretion, decreased clearance, etc., of the protein.

The term "reduce" or "reduces" means to lower the level of a protein in a particular tissue of a subject by at least 10%. In some embodiments, an agent, such as an antibody that binds CSF1R, reduces the level of a protein in a particular tissue of a subject by at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, or at least 90%. In some embodiments, the level of a protein is reduced relative to the level of the protein prior to contacting with an agent, such as an antibody that binds CSF1R.

The term "resistant," when used in the context of resistance to a therapeutic agent, means a decreased response or lack of response to a standard dose of the therapeutic agent, relative to the subject's response to the standard dose of the therapeutic agent in the past, or relative to the expected response of a similar subject with a similar disorder to the standard dose of the therapeutic agent. Thus, in some embodiments, a subject may be resistant to therapeutic agent although the subject has not previously been given the therapeutic agent, or the subject may develop resistance to the therapeutic agent after having responded to the agent on one or more previous occasions.

The terms "subject" and "patient" are used interchangeably herein to refer to a human. In some embodiments, methods of treating other mammals, including, but not limited to, rodents, simians, felines, canines, equines, bovines, porcines, ovines, caprines, mammalian laboratory animals, mammalian farm animals, mammalian sport animals, and mammalian pets, are also provided.

The term "sample," as used herein, refers to a composition that is obtained or derived from a subject that contains a cellular and/or other molecular entity that is to be characterized, quantitated, and/or identified, for example based on physical, biochemical, chemical and/or physiological characteristics. An exemplary sample is a tissue sample.

The term "tissue sample" refers to a collection of similar cells obtained from a tissue of a subject. The source of the tissue sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, synovial fluid, or interstitial fluid; cells from any time in gestation or development of the subject. In some embodiments, a tissue sample is a synovial biopsy tissue sample and/or a synovial fluid sample. In some embodiments, a tissue sample is a synovial fluid sample. The tissue sample may also be primary or cultured cells or cell lines. Optionally, the tissue sample is obtained from a disease tissue/organ. The tissue sample may contain compounds that are not naturally intermixed with the tissue in nature such as preservatives, anticoagulants, buffers, fixatives, nutrients, antibiotics, or the like. A "control sample" or "control tissue", as used herein, refers to a sample, cell, or tissue obtained from a source known, or believed, not to be afflicted with the disease for which the subject is being treated.

For the purposes herein a "section" of a tissue sample means a part or piece of a tissue sample, such as a thin slice of tissue or cells cut from a solid tissue sample.

The term "pigmented villonodular synovitis" or "PVNS" as used herein refers to a condition in which the synovium thickens and overgrows in one or more joints. Localized PVNS typically involves the tendons that support the joint and/or occurs in one area of the joint, while diffuse PVNS is more widespread and may involve the entire joint. Diffuse PVNS typically affects large joints, such as the hip and/or knee joints, while localized (or nodular) PVNS typically occurs in smaller joints such as the hands and feet. The benign growth (sometimes referred to as a benign tumor) may progress, leading to damage to adjacent bone and/or arthritis. The methods of treating PVNS disclosed in the present application can also be used in treating other proliferative disorders that involve synovial joints and tendon sheaths, such as giant cell tumor of the tendon sheath (GCTTS) and tenosynovial giant cell tumor (TGCT) such as diffuse type tenosynovial giant cell tumor (dtTGCT).

An agent "antagonizes" factor activity when the agent neutralizes, blocks, inhibits, abrogates, reduces, and/or interferes with the activity of the factor, including its binding to one or more receptors when the factor is a ligand.

"Treatment," as used herein, refers to both therapeutic treatment and prophylactic or preventative measures, wherein the object is to prevent or slow down (lessen) the targeted pathologic condition or disorder. In certain embodiments, the term "treatment" covers any administration or application of a therapeutic for disease in a mammal, including a human, and includes inhibiting or slowing the disease or progression of the disease; partially or fully relieving the disease, for example, by causing regression, or restoring or repairing a lost, missing, or defective function; stimulating an inefficient process; or causing the disease plateau to have reduced severity. The term "treatment" also includes reducing the severity of any phenotypic characteristic and/or reducing the incidence, degree, or likelihood of that characteristic. Those in need of treatment include those already with the disorder as well as those prone to have the disorder or those in whom the disorder is to be prevented.

The term "effective amount" or "therapeutically effective amount" refers to an amount of a drug effective to treat a disease or disorder in a subject. In certain embodiments, an effective amount refers to an amount effective, at dosages and for periods of time necessary, to achieve the desired therapeutic or prophylactic result. A therapeutically effective amount of an anti-CSF1R antibody of the invention may vary according to factors such as the disease state, age, sex, and weight of the individual, and the ability of the antibody or antibodies to elicit a desired response in the individual. A therapeutically effective amount encompasses an amount in which any toxic or detrimental effects of the antibody or antibodies are outweighed by the therapeutically beneficial effects. In some embodiments, the expression "effective amount" refers to an amount of the antibody that is effective for treating PVNS.

A "prophylactically effective amount" refers to an amount effective, at dosages and for periods of time necessary, to achieve the desired prophylactic result. Typically, but not necessarily, since a prophylactic dose is used in subjects prior to or at an earlier stage of disease, the prophylactically effective amount would be less than the therapeutically effective amount.

Administration "in combination with" one or more further therapeutic agents includes simultaneous (concurrent) and consecutive (sequential) administration in any order.

A "pharmaceutically acceptable carrier" refers to a non-toxic solid, semisolid, or liquid filler, diluent, encapsulating material, formulation auxiliary, or carrier conventional in the art for use with a therapeutic agent that together comprise a "pharmaceutical composition" for administration to a subject. A pharmaceutically acceptable carrier is non-toxic to recipients at the dosages and concentrations employed and is compatible with other ingredients of the formulation. The pharmaceutically acceptable carrier is appropriate for the formulation employed. For example, if the therapeutic agent is to be administered orally, the carrier may be a gel capsule. If the therapeutic agent is to be administered subcutaneously, the carrier ideally is not irritable to the skin and does not cause injection site reaction.

Anti-CSF1R Antibodies

Anti-CSF1R antibodies include, but are not limited to, humanized antibodies, chimeric antibodies, mouse antibodies, human antibodies, and antibodies comprising the heavy chain and/or light chain CDRs discussed herein.

Exemplary Humanized Antibodies

In some embodiments, humanized antibodies that bind CSF1R are provided. Humanized antibodies are useful as therapeutic molecules because humanized antibodies reduce or eliminate the human immune response to non-human antibodies (such as the human anti-mouse antibody (HAMA) response), which can result in an immune response to an antibody therapeutic, and decreased effectiveness of the therapeutic.

Nonlimiting exemplary humanized antibodies include huAb1 through huAb16, described herein. Nonlimiting exemplary humanized antibodies also include antibodies comprising a heavy chain variable region of an antibody selected from huAb1 to huAb16 and/or a light chain variable region of an antibody selected from huAb1 to huAb16. Nonlimiting exemplary humanized antibodies include antibodies comprising a heavy chain variable region selected from SEQ ID NOs: 39 to 45 and/or a light chain variable region selected from SEQ ID NOs: 46 to 52. Exemplary humanized antibodies also include, but are not limited to, humanized antibodies comprising heavy chain CDR1, CDR2, and CDR3, and/or light chain CDR1, CDR2, and CDR3 of an antibody selected from 0301, 0302, and 0311.

In some embodiments, a humanized anti-CSF1R antibody comprises heavy chain CDR1, CDR2, and CDR3 and/or a light chain CDR1, CDR2, and CDR3 of an antibody selected from 0301, 0302, and 0311. Nonlimiting exemplary humanized anti-CSF1R antibodies include antibodies comprising sets of heavy chain CDR1, CDR2, and CDR3 selected from: SEQ ID NOs: 15, 16, and 17; SEQ ID NOs: 21, 22, and 23; and SEQ ID NOs: 27, 28, and 29. Nonlimiting exemplary humanized anti-CSF1R antibodies also include antibodies comprising sets of light chain CDR1, CDR2, and CDR3 selected from: SEQ ID NOs: 18, 19, and 20; SEQ ID NOs: 24, 25, and 26; and SEQ ID NOs: 30, 31, and 32.

Nonlimiting exemplary humanized anti-CSF1R antibodies include antibodies comprising the sets of heavy chain CDR1, CDR2, and CDR3, and light chain CDR1, CDR2, and CDR3 in Table 1 (SEQ ID NOs shown; see Table 8 for sequences). Each row of Table 1 shows the heavy chain CDR1, CDR2, and CDR3, and light chain CDR1, CDR2, and CDR3 of an exemplary antibody.

TABLE 1

Heavy chain and light chain CDRs

| Ab | Heavy chain | | | Light chain | | |
|---|---|---|---|---|---|---|
|  | CDR1 SEQ ID | CDR2 SEQ ID | CDR3 SEQ ID | CDR1 SEQ ID | CDR2 SEQ ID | CDR3 SEQ ID |
| 0301 | 15 | 16 | 17 | 18 | 19 | 20 |
| 0302 | 21 | 22 | 23 | 24 | 25 | 26 |
| 0311 | 27 | 28 | 29 | 30 | 31 | 32 |

Further Exemplary Humanized Antibodies

In some embodiments, a humanized anti-CSF1R antibody comprises a heavy chain comprising a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 9, 11, 13, and 39 to 45, and wherein the antibody binds CSF1R. In some embodiments, a humanized anti-CSF1R antibody comprises a light chain comprising a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 10, 12, 14, and 46 to 52, wherein the antibody binds CSF1R. In some embodiments, a humanized anti-CSF1R antibody comprises a heavy chain comprising a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 9, 11, 13, and 39 to 45; and a light chain comprising a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 10, 12, 14, and 46 to 52; wherein the antibody binds CSF1R.

As used herein, whether a particular polypeptide is, for example, at least 95% identical to an amino acid sequence can be determined using, e.g., a computer program. When determining whether a particular sequence is, for example, 95% identical to a reference sequence, the percentage of identity is calculated over the full length of the reference amino acid sequence.

In some embodiments, a humanized anti-CSF1R antibody comprises at least one of the CDRs discussed herein. That is, in some embodiments, a humanized anti-CSF1R antibody comprises at least one CDR selected from a heavy chain CDR1 discussed herein, a heavy chain CDR2 discussed herein, a heavy chain CDR3 discussed herein, a light chain CDR1 discussed herein, a light chain CDR2 discussed herein, and a light chain CDR3 discussed herein. Further, in some embodiments, a humanized anti-CSF1R antibody comprises at least one mutated CDR based on a CDR discussed herein, wherein the mutated CDR comprises 1, 2, 3, or 4 amino acid substitutions relative to the CDR discussed herein. In some embodiments, one or more of the amino acid substitutions are conservative amino acid substitutions. One skilled in the art can select one or more suitable conservative amino acid substitutions for a particular CDR sequence, wherein the suitable conservative amino acid substitutions are not predicted to significantly alter the binding properties of the antibody comprising the mutated CDR.

Exemplary humanized anti-CSF1R antibodies also include antibodies that compete for binding to CSF1R with an antibody described herein. Thus, in some embodiments, a humanized anti-CSF1R antibody is provided that competes for binding to CSF1R with an antibody selected from Fabs 0301, 0302, and 0311; and bivalent (i.e., having two heavy chains and two light chains) antibody versions of those Fabs.

Exemplary Humanized Antibody Constant Regions

In some embodiments, a humanized antibody described herein comprises one or more human constant regions. In some embodiments, the human heavy chain constant region is of an isotype selected from IgA, IgG, and IgD. In some embodiments, the human light chain constant region is of an isotype selected from κ and λ. In some embodiments, a humanized antibody described herein comprises a human IgG constant region. In some embodiments, a humanized antibody described herein comprises a human IgG4 heavy chain constant region. In some such embodiments, a humanized antibody described herein comprises an S241P mutation in the human IgG4 constant region. In some embodiments, a humanized antibody described herein comprises a human IgG4 constant region and a human κ light chain.

The choice of heavy chain constant region can determine whether or not an antibody will have effector function in vivo. Such effector function, in some embodiments, includes antibody-dependent cell-mediated cytotoxicity (ADCC) and/or complement-dependent cytotoxicity (CDC), and can result in killing of the cell to which the antibody is bound. In some methods of treatment, including methods of treating some tumors, cell killing may be desirable, for example, when the antibody binds to a cell that supports the maintenance or growth of the tumor. Exemplary cells that may support the maintenance or growth of a tumor include, but are not limited to, tumor cells themselves, cells that aid in the recruitment of vasculature to the tumor, and cells that provide ligands, growth factors, or counter-receptors that support or promote tumor growth or tumor survival. In some embodiments, when effector function is desirable, an anti-CSF1R antibody comprising a human IgG1 heavy chain or a human IgG3 heavy chain is selected.

In some methods of treatment, effector function may not be desirable. For example, in some embodiments, it may be desirable that antibodies used in the treatment of PVNS do not have effector function. Accordingly, in some embodiments, an anti-CSF1R antibody that lacks significant effector function is used in treatment of PVNS. In some embodiments, an anti-CSF1R antibody for treatment of PVNS comprises a human IgG4 or IgG2 heavy chain constant region. In some embodiments, an IgG4 constant region comprises an S241P mutation.

An antibody may be humanized by any method. Nonlimiting exemplary methods of humanization include methods described, e.g., in U.S. Pat. Nos. 5,530,101; 5,585,089; 5,693,761; 5,693,762; 6,180,370; Jones et al., Nature 321: 522-525 (1986); Riechmann et al., Nature 332: 323-27 (1988); Verhoeyen et al., Science 239: 1534-36 (1988); and U.S. Publication No. US 2009/0136500.

As noted above, a humanized antibody is an antibody in which at least one amino acid in a framework region of a non-human variable region has been replaced with the amino acid from the corresponding location in a human framework region. In some embodiments, at least two, at least three, at least four, at least five, at least six, at least seven, at least eight, at least nine, at least 10, at least 11, at least 12, at least 15, or at least 20 amino acids in the framework regions of a non-human variable region are replaced with an amino acid from one or more corresponding locations in one or more human framework regions.

In some embodiments, some of the corresponding human amino acids used for substitution are from the framework regions of different human immunoglobulin genes. That is, in some such embodiments, one or more of the non-human amino acids may be replaced with corresponding amino acids from a human framework region of a first human antibody or encoded by a first human immunoglobulin gene, one or more of the non-human amino acids may be replaced with corresponding amino acids from a human framework region of a second human antibody or encoded by a second human immunoglobulin gene, one or more of the non-human amino acids may be replaced with corresponding amino acids from a human framework region of a third human antibody or encoded by a third human immunoglobulin gene, etc. Further, in some embodiments, all of the corresponding human amino acids being used for substitution in a single framework region, for example, FR2, need not be from the same human framework. In some embodiments, however, all of the corresponding human amino acids being used for substitution are from the same human antibody or encoded by the same human immunoglobulin gene.

In some embodiments, an antibody is humanized by replacing one or more entire framework regions with corresponding human framework regions. In some embodiments, a human framework region is selected that has the highest level of homology to the non-human framework region being replaced. In some embodiments, such a humanized antibody is a CDR-grafted antibody.

In some embodiments, following CDR-grafting, one or more framework amino acids are changed back to the corresponding amino acid in a mouse framework region. Such "back mutations" are made, in some embodiments, to retain one or more mouse framework amino acids that appear to contribute to the structure of one or more of the CDRs and/or that may be involved in antigen contacts and/or appear to be involved in the overall structural integrity of the antibody. In some embodiments, ten or fewer, nine or fewer, eight or fewer, seven or fewer, six or fewer, five or fewer, four or fewer, three or fewer, two or fewer, one, or zero back mutations are made to the framework regions of an antibody following CDR grafting.

In some embodiments, a humanized antibody also comprises a human heavy chain constant region and/or a human light chain constant region.

Exemplary Chimeric Antibodies

In some embodiments, an anti-CSF1R antibody is a chimeric antibody. In some embodiments, an anti-CSF1R antibody comprises at least one non-human variable region and at least one human constant region. In some such embodiments, all of the variable regions of an anti-CSF1R antibody are non-human variable regions, and all of the constant regions of an anti-CSF1R antibody are human constant regions. In some embodiments, one or more variable regions of a chimeric antibody are mouse variable regions. The human constant region of a chimeric antibody need not be of the same isotype as the non-human constant region, if any, it replaces. Chimeric antibodies are discussed, e.g., in U.S. Pat. No. 4,816,567; and Morrison et al. Proc. Natl. Acad. Sci. USA 81: 6851-55 (1984).

Nonlimiting exemplary chimeric antibodies include chimeric antibodies comprising the heavy and/or light chain variable regions of an antibody selected from 0301, 0302, and 0311. Additional nonlimiting exemplary chimeric antibodies include chimeric antibodies comprising heavy chain CDR1, CDR2, and CDR3, and/or light chain CDR1, CDR2, and CDR3 of an antibody selected from 0301, 0302, and 0311.

Nonlimiting exemplary chimeric anti-CSF1R antibodies include antibodies comprising the following pairs of heavy and light chain variable regions: SEQ ID NOs: 9 and 10; SEQ ID NOs: 11 and 12; and SEQ ID NOs: 13 and 14.

Nonlimiting exemplary anti-CSF1R antibodies include antibodies comprising a set of heavy chain CDR1, CDR2, and CDR3, and light chain CDR1, CDR2, and CDR3 shown above in Table 1.

Further Exemplary Chimeric Antibodies

In some embodiments, a chimeric anti-CSF1R antibody comprises a heavy chain comprising a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 9, 11, 13, and 39 to 45, wherein the antibody binds CSF1R. In some embodiments, a chimeric anti-CSF1R antibody comprises a light chain comprising a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 10, 12, 14, and 46 to 52, wherein the antibody binds CSF1R. In some embodiments, a chimeric anti-CSF1R antibody comprises a heavy chain comprising a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 9, 11, 13, and 39 to 45; and a light chain comprising a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 10, 12, 14, and 46 to 52; wherein the antibody binds CSF1R.

In some embodiments, a chimeric anti-CSF1R antibody comprises at least one of the CDRs discussed herein. That is, in some embodiments, a chimeric anti-CSF1R antibody comprises at least one CDR selected from a heavy chain CDR1 discussed herein, a heavy chain CDR2 discussed herein, a heavy chain CDR3 discussed herein, a light chain CDR1 discussed herein, a light chain CDR2 discussed herein, and a light chain CDR3 discussed herein. Further, in some embodiments, a chimeric anti-CSF1R antibody comprises at least one mutated CDR based on a CDR discussed herein, wherein the mutated CDR comprises 1, 2, 3, or 4 amino acid substitutions relative to the CDR discussed herein. In some embodiments, one or more of the amino acid substitutions are conservative amino acid substitutions. One skilled in the art can select one or more suitable conservative amino acid substitutions for a particular CDR sequence, wherein the suitable conservative amino acid substitutions are not predicted to significantly alter the binding properties of the antibody comprising the mutated CDR.

Exemplary chimeric anti-CSF1R antibodies also include chimeric antibodies that compete for binding to CSF1R with an antibody described herein. Thus, in some embodiments, a chimeric anti-CSF1R antibody is provided that competes for binding to CSF1R with an antibody selected from Fabs 0301, 0302, and 0311; and bivalent (i.e., having two heavy chains and two light chains) antibody versions of those Fabs.

Exemplary Chimeric Antibody Constant Regions

In some embodiments, a chimeric antibody described herein comprises one or more human constant regions. In some embodiments, the human heavy chain constant region is of an isotype selected from IgA, IgG, and IgD. In some embodiments, the human light chain constant region is of an isotype selected from κ and λ. In some embodiments, a chimeric antibody described herein comprises a human IgG constant region. In some embodiments, a chimeric antibody described herein comprises a human IgG4 heavy chain constant region. In some such embodiments, a chimeric antibody described herein comprises an S241P mutation in the human IgG4 constant region. In some embodiments, a chimeric antibody described herein comprises a human IgG4 constant region and a human κ light chain.

As noted above, whether or not effector function is desirable may depend on the particular method of treatment intended for an antibody. Thus, in some embodiments, when effector function is desirable, a chimeric anti-CSF1R antibody comprising a human IgG1 heavy chain constant region or a human IgG3 heavy chain constant region is selected. In some embodiments, when effector function is not desirable, a chimeric anti-CSF1R antibody comprising a human IgG4 or IgG2 heavy chain constant region is selected.

Exemplary Human Antibodies

Human antibodies can be made by any suitable method. Nonlimiting exemplary methods include making human antibodies in transgenic mice that comprise human immunoglobulin loci. See, e.g., Jakobovits et al., *Proc. Natl. Acad. Sci. USA* 90: 2551-55 (1993); Jakobovits et al., *Nature* 362: 255-8 (1993); Lonberg et al., *Nature* 368: 856-9 (1994); and U.S. Pat. Nos. 5,545,807; 6,713,610; 6,673,986; 6,162,963; 5,545,807; 6,300,129; 6,255,458; 5,877,397; 5,874,299; and 5,545,806.

Nonlimiting exemplary methods also include making human antibodies using phage display libraries. See, e.g., Hoogenboom et al., *J. Mol. Biol.* 227: 381-8 (1992); Marks et al., *J. Mol. Biol.* 222: 581-97 (1991); and PCT Publication No. WO 99/10494.

In some embodiments, a human anti-CSF1R antibody binds to a polypeptide having the sequence of SEQ ID NO: 1. Exemplary human anti-CSF1R antibodies also include antibodies that compete for binding to CSF1R with an antibody described herein. Thus, in some embodiments, a human anti-CSF1R antibody is provided that competes for binding to CSF1R with an antibody selected from Fabs 0301, 0302, and 0311, and bivalent (i.e., having two heavy chains and two light chains) antibody versions of those Fabs.

In some embodiments, a human anti-CSF1R antibody comprises one or more human constant regions. In some embodiments, the human heavy chain constant region is of an isotype selected from IgA, IgG, and IgD. In some embodiments, the human light chain constant region is of an isotype selected from κ and λ. In some embodiments, a human antibody described herein comprises a human IgG constant region. In some embodiments, a human antibody described herein comprises a human IgG4 heavy chain constant region. In some such embodiments, a human antibody described herein comprises an S241P mutation in the human IgG4 constant region. In some embodiments, a human antibody described herein comprises a human IgG4 constant region and a human κ light chain.

In some embodiments, when effector function is desirable, a human anti-CSF1R antibody comprising a human IgG1 heavy chain constant region or a human IgG3 heavy chain constant region is selected. In some embodiments, when effector function is not desirable, a human anti-CSF1R antibody comprising a human IgG4 or IgG2 heavy chain constant region is selected.

Additional Exemplary Anti-CSF1R Antibodies

Exemplary anti-CSF1R antibodies also include, but are not limited to, mouse, humanized, human, chimeric, and engineered antibodies that comprise, for example, one or more of the CDR sequences described herein. In some embodiments, an anti-CSF1R antibody comprises a heavy chain variable region described herein. In some embodiments, an anti-CSF1R antibody comprises a light chain variable region described herein. In some embodiments, an anti-CSF1R antibody comprises a heavy chain variable region described herein and a light chain variable region described herein. In some embodiments, an anti-CSF1R antibody comprises heavy chain CDR1, CDR2, and CDR3 described herein. In some embodiments, an anti-CSF1R antibody comprises light chain CDR1, CDR2, and CDR3 described herein. In some embodiments, an anti-CSF1R antibody comprises heavy chain CDR1, CDR2, and CDR3 described herein and light chain CDR1, CDR2, and CDR3 described herein.

In some embodiments, an anti-CSF1R antibody comprises a heavy chain variable region of an antibody selected from Fabs 0301, 0302, and 0311. Nonlimiting exemplary anti-CSF1R antibodies also include antibodies comprising a heavy chain variable region of an antibody selected from humanized antibodies huAb1 to huAb16. Nonlimiting exemplary anti-CSF1R antibodies include antibodies comprising a heavy chain variable region comprising a sequence selected from SEQ ID NOs: 9, 11, 13, and 39 to 45.

In some embodiments, an anti-CSF1R antibody comprises a light chain variable region of an antibody selected from Fabs 0301, 0302, and 0311. Nonlimiting exemplary anti-CSF1R antibodies also include antibodies comprising a light chain variable region of an antibody selected from humanized antibodies huAb1 to huAb16. Nonlimiting exemplary anti-CSF1R antibodies include antibodies comprising a light chain variable region comprising a sequence selected from SEQ ID NOs: 10, 12, 14, and 46 to 52.

In some embodiments, an anti-CSF1R antibody comprises a heavy chain variable region and a light chain variable region of an antibody selected from Fabs 0301, 0302, and 0311. Nonlimiting exemplary anti-CSF1R antibodies also include antibodies comprising a heavy chain variable region and a light chain variable region of an antibody selected from humanized antibodies huAb1 to huAb16. Nonlimiting exemplary anti-CSF1R antibodies include antibodies comprising the following pairs of heavy and light chain variable regions: SEQ ID NOs: 9 and 10; SEQ ID NOs: 11 and 12; and SEQ ID NOs: 13 and 14; SEQ ID NOs: 39 and 40; SEQ ID NOs: 41 and 42; SEQ ID NOs: 43 and 44; SEQ ID NOs: 45 and 46; SEQ ID NOs: 47 and 48; SEQ ID NOs: 49 and 50; and SEQ ID NOs: 51 and 52. Nonlimiting exemplary anti-CSF1R antibodies also include antibodies comprising the following pairs of heavy and light chains: SEQ ID NOs: 33 and 34; SEQ ID NOs: 35 and 36; and SEQ ID NOs: 37 and 38.

In some embodiments, an anti-CSF1R antibody comprises heavy chain CDR1, CDR2, and CDR3 of an antibody selected from Fabs 0301, 0302, and 0311. Nonlimiting exemplary anti-CSF1R antibodies include antibodies comprising sets of heavy chain CDR1, CDR2, and CDR3 selected from: SEQ ID NOs: 15, 16, and 17; SEQ ID NOs: 21, 22, and 23; and SEQ ID NOs: 27, 28, and 29.

In some embodiments, an anti-CSF1R antibody comprises light chain CDR1, CDR2, and CDR3 of an antibody selected from Fabs 0301, 0302, and 0311. Nonlimiting exemplary anti-CSF1R antibodies include antibodies comprising sets of light chain CDR1, CDR2, and CDR3 selected from: SEQ ID NOs: 18, 19, and 20; SEQ ID NOs: 24, 25, and 26; and SEQ ID NOs: 30, 31, and 32.

In some embodiments, an anti-CSF1R antibody comprises heavy chain CDR1, CDR2, and CDR3, and light chain CDR1, CDR2, and CDR3 of an antibody selected from Fabs 0301, 0302, and 0311.

Nonlimiting exemplary anti-CSF1R antibodies include antibodies comprising the sets of heavy chain CDR1, CDR2, and CDR3, and light chain CDR1, CDR2, and CDR3 shown above in Table 1.

Further Exemplary Antibodies

In some embodiments, an anti-CSF1R antibody comprises a heavy chain comprising a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 9, 11, 13, and 39 to 45, wherein the antibody binds CSF1R. In some embodiments, an anti-CSF1R antibody comprises a light chain comprising a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 10, 12, 14, and 46 to 52, wherein the antibody binds CSF1R. In some embodiments, an anti-CSF1R antibody comprises a heavy chain comprising a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 9, 11, 13, and 39 to 45; and a light chain comprising a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 10, 12, 14, and 46 to 52; wherein the antibody binds CSF1R.

In some embodiments, an anti-CSF1R antibody comprises at least one of the CDRs discussed herein. That is, in some embodiments, an anti-CSF1R antibody comprises at least one CDR selected from a heavy chain CDR1 discussed herein, a heavy chain CDR2 discussed herein, a heavy chain CDR3 discussed herein, a light chain CDR1 discussed herein, a light chain CDR2 discussed herein, and a light chain CDR3 discussed herein. Further, in some embodiments, an anti-CSF1R antibody comprises at least one mutated CDR based on a CDR discussed herein, wherein the mutated CDR comprises 1, 2, 3, or 4 amino acid substitutions relative to the CDR discussed herein. In some embodiments, one or more of the amino acid substitutions are conservative amino acid substitutions. One skilled in the art can select one or more suitable conservative amino acid substitutions for a particular CDR sequence, wherein the suitable conservative amino acid substitutions are not predicted to significantly alter the binding properties of the antibody comprising the mutated CDR.

Exemplary anti-CSF1R antibodies also include antibodies that compete for binding to CSF1R with an antibody described herein. Thus, in some embodiments, an anti-CSF1R antibody is provided that competes for binding to CSF1R with an antibody selected from Fabs 0301, 0302, and 0311, and bivalent (i.e., having two heavy chains and two light chains) antibody versions of those Fabs.

Exemplary Antibody Constant Regions

In some embodiments, an antibody described herein comprises one or more human constant regions. In some embodiments, the human heavy chain constant region is of an isotype selected from IgA, IgG, and IgD. In some embodiments, the human light chain constant region is of an isotype selected from κ and λ. In some embodiments, an antibody described herein comprises a human IgG constant region. In some embodiments, an antibody described herein comprises a human IgG4 heavy chain constant region. In some such embodiments, an antibody described herein comprises an S241P mutation in the human IgG4 constant region. In some embodiments, an antibody described herein comprises a human IgG4 constant region and a human κ light chain.

As noted above, whether or not effector function is desirable may depend on the particular method of treatment intended for an antibody. Thus, in some embodiments, when effector function is desirable, an anti-CSF1R antibody comprising a human IgG1 heavy chain constant region or a human IgG3 heavy chain constant region is selected. In some embodiments, when effector function is not desirable, an anti-CSF1R antibody comprising a human IgG4 or IgG2 heavy chain constant region is selected.

Exemplary Anti-CSF1R Heavy Chain Variable Regions

In some embodiments, anti-CSF1R antibody heavy chain variable regions are provided. In some embodiments, an anti-CSF1R antibody heavy chain variable region is a mouse variable region, a human variable region, or a humanized variable region.

An anti-CSF1R antibody heavy chain variable region comprises a heavy chain CDR1, FR2, CDR2, FR3, and CDR3. In some embodiments, an anti-CSF1R antibody heavy chain variable region further comprises a heavy chain FR1 and/or FR4. Nonlimiting exemplary heavy chain variable regions include, but are not limited to, heavy chain variable regions having an amino acid sequence selected from SEQ ID NOs: 9, 11, 13, and 39 to 45.

In some embodiments, an anti-CSF1R antibody heavy chain variable region comprises a CDR1 comprising a sequence selected from SEQ ID NOs: 15, 21, and 27.

In some embodiments, an anti-CSF1R antibody heavy chain variable region comprises a CDR2 comprising a sequence selected from SEQ ID NOs: 16, 22, and 28.

In some embodiments, an anti-CSF1R antibody heavy chain variable region comprises a CDR3 comprising a sequence selected from SEQ ID NOs: 17, 23, and 29.

Nonlimiting exemplary heavy chain variable regions include, but are not limited to, heavy chain variable regions comprising sets of CDR1, CDR2, and CDR3 selected from: SEQ ID NOs: 15, 16, and 17; SEQ ID NOs: 21, 22, and 23; and SEQ ID NOs: 27, 28, and 29.

In some embodiments, an anti-CSF1R antibody heavy chain comprises a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 9, 11, 13, and 39 to 45, wherein the heavy chain, together with a light chain, is capable of forming an antibody that binds CSF1R.

In some embodiments, an anti-CSF1R antibody heavy chain comprises at least one of the CDRs discussed herein. That is, in some embodiments, an anti-CSF1R antibody heavy chain comprises at least one CDR selected from a heavy chain CDR1 discussed herein, a heavy chain CDR2 discussed herein, and a heavy chain CDR3 discussed herein. Further, in some embodiments, an anti-CSF1R antibody heavy chain comprises at least one mutated CDR based on a CDR discussed herein, wherein the mutated CDR comprises 1, 2, 3, or 4 amino acid substitutions relative to the CDR discussed herein. In some embodiments, one or more of the amino acid substitutions are conservative amino acid substitutions. One skilled in the art can select one or more suitable conservative amino acid substitutions for a particular CDR sequence, wherein the suitable conservative amino acid substitutions are not predicted to significantly alter the binding properties of the heavy chain comprising the mutated CDR.

In some embodiments, a heavy chain comprises a heavy chain constant region. In some embodiments, a heavy chain comprises a human heavy chain constant region. In some embodiments, the human heavy chain constant region is of an isotype selected from IgA, IgG, and IgD. In some embodiments, the human heavy chain constant region is an IgG constant region. In some embodiments, a heavy chain comprises a human igG4 heavy chain constant region. In some such embodiments, the human IgG4 heavy chain constant region comprises an S241P mutation.

In some embodiments, when effector function is desirable, a heavy chain comprises a human IgG1 or IgG3 heavy chain constant region. In some embodiments, when effector function is less desirable, a heavy chain comprises a human IgG4 or IgG2 heavy chain constant region.

Exemplary Anti-CSF1R Light Chain Variable Regions

In some embodiments, anti-CSF1R antibody light chain variable regions are provided. In some embodiments, an anti-CSF1R antibody light chain variable region is a mouse variable region, a human variable region, or a humanized variable region.

An anti-CSF1R antibody light chain variable region comprises a light chain CDR1, FR2, CDR2, FR3, and CDR3. In some embodiments, an anti-CSF1R antibody light chain variable region further comprises a light chain FR1 and/or FR4. Nonlimiting exemplary light chain variable regions include light chain variable regions having an amino acid sequence selected from SEQ ID NOs: 10, 12, 14, and 46 to 52.

In some embodiments, an anti-CSF1R antibody light chain variable region comprises a CDR1 comprising a sequence selected from SEQ ID NOs: 18, 24 and 30.

In some embodiments, an anti-CSF1R antibody light chain variable region comprises a CDR2 comprising a sequence selected from SEQ ID NOs: 19, 25, and 31.

In some embodiments, an anti-CSF1R antibody light chain variable region comprises a CDR3 comprising a sequence selected from SEQ ID NOs: 20, 26, and 32.

Nonlimiting exemplary light chain variable regions include, but are not limited to, light chain variable regions comprising sets of CDR1, CDR2, and CDR3 selected from: SEQ ID NOs: 18, 19, and 20; SEQ ID NOs: 24, 25, and 26; and SEQ ID NOs: 30, 31, and 32.

In some embodiments, an anti-CSF1R antibody light chain comprises a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 10, 12, 14, and 46 to 52, wherein the light chain, together with a heavy chain, is capable of forming an antibody that binds CSF1R.

In some embodiments, an anti-CSF1R antibody light chain comprises at least one of the CDRs discussed herein. That is, in some embodiments, an anti-CSF1R antibody light chain comprises at least one CDR selected from a light chain CDR1 discussed herein, a light chain CDR2 discussed herein, and a light chain CDR3 discussed herein. Further, in some embodiments, an anti-CSF1R antibody light chain comprises at least one mutated CDR based on a CDR discussed herein, wherein the mutated CDR comprises 1, 2, 3, or 4 amino acid substitutions relative to the CDR discussed herein. In some embodiments, one or more of the amino acid substitutions are conservative amino acid substitutions. One skilled in the art can select one or more suitable conservative amino acid substitutions for a particular CDR sequence, wherein the suitable conservative amino acid substitutions are not predicted to significantly alter the binding properties of the light chain comprising the mutated CDR.

In some embodiments, a light chain comprises a human light chain constant region. In some embodiments, a human light chain constant region is selected from a human κ and a human λ light chain constant region.

Exemplary Additional CSF1R Binding Molecules

In some embodiments, additional molecules that bind CSF1R are provided. Such molecules include, but are not limited to, non-canonical scaffolds, such as anti-calins, adnectins, ankyrin repeats, etc. See, e.g., Hosse et al., *Prot. Sci.* 15:14 (2006); Fiedler, M. and Skerra, A., "Non-Antibody Scaffolds," pp. 467-499 in Handbook of Therapeutic Antibodies, Dubel, S., ed., Wiley-VCH, Weinheim, Germany, 2007.

Exemplary Properties of Anti-CSF1R Antibodies

In some embodiments, an antibody having a structure described above binds to the CSF1R with a binding affinity ($K_D$) of less than 1 nM, blocks binding of CSF1 and/or IL-34 to CSF1R, and inhibits CSF1R phosphorylation induced by CSF1 and/or IL-34.

In some embodiments, an anti-CSF1R antibody binds to the extracellular domain of CSF1R (CSF1R-ECD). In some embodiments, an anti-CSF1R antibody has a binding affinity ($K_D$) for CSF1R of less than 1 nM, less than 0.5 nM, less than 0.1 nM, or less than 0.05 nM. In some embodiments, an anti-CSF1R antibody has a $K_D$ of between 0.01 and 1 nM, between 0.01 and 0.5 nM, between 0.01 and 0.1 nM, between 0.01 and 0.05 nM, or between 0.02 and 0.05 nM.

In some embodiments, an anti-CSF1R antibody blocks ligand binding to CSF1R. In some embodiments, an anti-CSF1R antibody blocks binding of CSF1 to CSF1R. In some embodiments, an anti-CSF1R antibody blocks binding of IL-34 to CSF1R. In some embodiments, an anti-CSF1R antibody blocks binding of both CSF1 and IL-34 to CSF1R. In some embodiments, an antibody that blocks ligand binding binds to the extracellular domain of CSF1R. In some embodiments, an antibody blocks ligand binding to CSF1R when it reduces the amount of detectable binding of a ligand to CSF1R by at least 50%, using the assay described, e.g., U.S. Pat. No. 8,206,715 B2, Example 7, which is incorporated herein by reference for any purpose. In some embodiments, an antibody reduces the amount of detectable binding of a ligand to CSF1R by at least 60%, at least 70%, at least 80%, or at least 90%. In some such embodiments, the antibody is said to block ligand binding by at least 50%, at least 60%, at least 70%, etc.

In some embodiments, an anti-CSF1R antibody inhibits ligand-induced CSF1R phosphorylation. In some embodiments, an anti-CSF1R antibody inhibits CSF1-induced CSF1R phosphorylation. In some embodiments, an anti-CSF1R antibody inhibits IL-34-induced CSF1R phosphorylation. In some embodiments, an anti-CSF1R antibody inhibits both CSF1-induced and IL-34-induced CSF1R phosphorylation. In some embodiments, an antibody is considered to "inhibit ligand-induced CSF1R phosphorylation" when it reduces the amount of detectable ligand-induced CSF1R phosphorylation by at least 50%, using the assay described, e.g., U.S. Pat. No. 8,206,715 B2, Example 6, which is incorporated herein by reference for any purpose. In some embodiments, an antibody reduces the amount of detectable ligand-induced CSF1R phosphorylation by at least 60%, at least 70%, at least 80%, or at least 90%. In some such embodiments, the antibody is said to inhibit ligand-induced CSF1R phosphorylation by at least at least 50%, at least 60%, at least 70%, etc.

In some embodiments, an antibody inhibits monocyte proliferation and/or survival responses in the presence of CSF1 and/or IL-34. In some embodiments, an antibody is considered to "inhibit monocyte proliferation and/or survival responses" when it reduces the amount of monocyte proliferation and/or survival responses in the presence of CSF1 and/or IL-34 by at least 50%, using the assay described, e.g., U.S. Pat. No. 8,206,715 B2, Example 10, which is incorporated herein by reference for any purpose. In some embodiments, an antibody reduces the amount of monocyte proliferation and/or survival responses in the presence of CSF1 and/or IL-34 by at least 60%, at least 70%, at least 80%, or at least 90%. In some such embodiments, the antibody is said to inhibit monocyte proliferation and/or survival responses by at least at least 50%, at least 60%, at least 70%, etc.

Exemplary Antibody Conjugates

In some embodiments, an antibody is conjugated to a label and/or a cytotoxic agent. As used herein, a label is a moiety that facilitates detection of the antibody and/or facilitates detection of a molecule to which the antibody binds. Nonlimiting exemplary labels include, but are not limited to, radioisotopes, fluorescent groups, enzymatic groups, chemiluminescent groups, biotin, epitope tags, metal-binding tags, etc. One skilled in the art can select a suitable label according to the intended application.

As used herein, a cytotoxic agent is a moiety that reduces the proliferative capacity of one or more cells. A cell has reduced proliferative capacity when the cell becomes less able to proliferate, for example, because the cell undergoes apoptosis or otherwise dies, the cell fails to proceed through the cell cycle and/or fails to divide, the cell differentiates, etc. Nonlimiting exemplary cytotoxic agents include, but are not limited to, radioisotopes, toxins, and chemotherapeutic agents. One skilled in the art can select a suitable cytotoxic according to the intended application.

In some embodiments, a label and/or a cytotoxic agent is conjugated to an antibody using chemical methods in vitro. Nonlimiting exemplary chemical methods of conjugation are known in the art, and include services, methods and/or reagents commercially available from, e.g., Thermo Scientific Life Science Research Produces (formerly Pierce; Rockford, Ill.), Prozyme (Hayward, Calif.), SACRI Antibody Services (Calgary, Canada), AbD Serotec (Raleigh, N.C.), etc. In some embodiments, when a label and/or cytotoxic agent is a polypeptide, the label and/or cytotoxic agent can be expressed from the same expression vector with at least one antibody chain to produce a polypeptide comprising the label and/or cytotoxic agent fused to an antibody chain. One skilled in the art can select a suitable method for conjugating a label and/or cytotoxic agent to an antibody according to the intended application.

Exemplary Leader Sequences

In order for some secreted proteins to express and secrete in large quantities, a leader sequence from a heterologous protein may be desirable. In some embodiments, a leader sequence is selected from SEQ ID NOs: 3 and 4, which are light chain and heavy chain leader sequences, respectively. In some embodiments, employing heterologous leader sequences may be advantageous in that a resulting mature polypeptide may remain unaltered as the leader sequence is removed in the ER during the secretion process. The addition of a heterologous leader sequence may be required to express and secrete some proteins.

Certain exemplary leader sequence sequences are described, e.g., in the online Leader sequence Database maintained by the Department of Biochemistry, National University of Singapore. See Choo et al., *BMC Bioinformatics*, 6: 249 (2005); and PCT Publication No. WO 2006/081430.

Nucleic Acid Molecules Encoding Antibodies

Nucleic acid molecules comprising polynucleotides that encode one or more chains of an antibody are provided. In some embodiments, a nucleic acid molecule comprises a polynucleotide that encodes a heavy chain or a light chain of an antibody. In some embodiments, a nucleic acid molecule comprises both a polynucleotide that encodes a heavy chain and a polynucleotide that encodes a light chain, of an antibody. In some embodiments, a first nucleic acid molecule comprises a first polynucleotide that encodes a heavy chain and a second nucleic acid molecule comprises a second polynucleotide that encodes a light chain.

In some such embodiments, the heavy chain and the light chain are expressed from one nucleic acid molecule, or from two separate nucleic acid molecules, as two separate polypeptides. In some embodiments, such as when an antibody is an scFv, a single polynucleotide encodes a single polypeptide comprising both a heavy chain and a light chain linked together.

In some embodiments, a polynucleotide encoding a heavy chain or light chain of an antibody comprises a nucleotide sequence that encodes a leader sequence, which, when translated, is located at the N terminus of the heavy chain or light chain. As discussed above, the leader sequence may be the native heavy or light chain leader sequence, or may be another heterologous leader sequence.

Nucleic acid molecules may be constructed using recombinant DNA techniques conventional in the art. In some embodiments, a nucleic acid molecule is an expression vector that is suitable for expression in a selected host cell.

Antibody Expression and Production

Vectors

Vectors comprising polynucleotides that encode antibody heavy chains and/or light chains are provided. Vectors comprising polynucleotides that encode antibody heavy chains and/or light chains are also provided. Such vectors include, but are not limited to, DNA vectors, phage vectors, viral vectors, retroviral vectors, etc. In some embodiments, a vector comprises a first polynucleotide sequence encoding a heavy chain and a second polynucleotide sequence encoding a light chain. In some embodiments, the heavy chain and light chain are expressed from the vector as two separate polypeptides. In some embodiments, the heavy chain and light chain are expressed as part of a single polypeptide, such as, for example, when the antibody is an scFv.

In some embodiments, a first vector comprises a polynucleotide that encodes a heavy chain and a second vector comprises a polynucleotide that encodes a light chain. In some embodiments, the first vector and second vector are transfected into host cells in similar amounts (such as similar molar amounts or similar mass amounts). In some embodiments, a mole- or mass-ratio of between 5:1 and 1:5 of the first vector and the second vector is transfected into host cells. In some embodiments, a mass ratio of between 1:1 and 1:5 for the vector encoding the heavy chain and the vector encoding the light chain is used. In some embodiments, a mass ratio of 1:2 for the vector encoding the heavy chain and the vector encoding the light chain is used.

In some embodiments, a vector is selected that is optimized for expression of polypeptides in CHO or CHO-derived cells, or in NSO cells. Exemplary such vectors are described, e.g., in Running Deer et al., *Biotechnol. Prog.* 20:880-889 (2004).

In some embodiments, a vector is chosen for in vivo expression of antibody heavy chains and/or antibody light chains in animals, including humans. In some such embodiments, expression of the polypeptide is under the control of a promoter that functions in a tissue-specific manner. For example, liver-specific promoters are described, e.g., in PCT Publication No. WO 2006/076288.

Host Cells

In various embodiments, antibody heavy chains and/or light chains may be expressed in prokaryotic cells, such as bacterial cells; or in eukaryotic cells, such as fungal cells (such as yeast), plant cells, insect cells, and mammalian cells. Such expression may be carried out, for example, according to procedures known in the art. Exemplary eukaryotic cells that may be used to express polypeptides include, but are not limited to, COS cells, including COS 7 cells; 293 cells, including 293-6E cells; CHO cells, including CHO—S and DG44 cells; PER.C6® cells (Crucell); and NSO cells. In some embodiments, antibody heavy chains and/or light chains may be expressed in yeast. See, e.g., U.S. Publication No. US 2006/0270045 A1. In some embodiments, a particular eukaryotic host cell is selected based on its ability to make desired post-translational modifications to the antibody heavy chains and/or light chains. For example, in some embodiments, CHO cells produce polypeptides that have a higher level of sialylation than the same polypeptide produced in 293 cells.

Introduction of one or more nucleic acids into a desired host cell may be accomplished by any method, including but not limited to, calcium phosphate transfection, DEAE-dextran mediated transfection, cationic lipid-mediated transfection, electroporation, transduction, infection, etc. Nonlimiting exemplary methods are described, e.g., in Sambrook et al., *Molecular Cloning, A Laboratory Manual*, $3^{rd}$ ed. Cold Spring Harbor Laboratory Press (2001). Nucleic acids may be transiently or stably transfected in the desired host cells, according to any suitable method.

In some embodiments, one or more polypeptides may be produced in vivo in an animal that has been engineered or transfected with one or more nucleic acid molecules encoding the polypeptides, according to any suitable method.

Purification of Antibodies

Antibodies may be purified by any suitable method. Such methods include, but are not limited to, the use of affinity matrices or hydrophobic interaction chromatography. Suitable affinity ligands include the antigen and ligands that bind antibody constant regions. For example, a Protein A, Protein G, Protein A/G, or an antibody affinity column may be used to bind the constant region and to purify an antibody. Hydrophobic interactive chromatography, for example, a butyl or phenyl column, may also suitable for purifying some polypeptides. Many methods of purifying polypeptides are known in the art.

Cell-Free Production of Antibodies

In some embodiments, an antibody is produced in a cell-free system. Nonlimiting exemplary cell-free systems are described, e.g., in Sitaraman et al., *Methods Mol. Biol.* 498: 229-44 (2009); Spirin, *Trends Biotechnol.* 22: 538-45 (2004); Endo et al., *Biotechnol. Adv.* 21: 695-713 (2003).

Therapeutic Compositions and Methods

Methods of Treating Pigmented Villonodular Synovitis (PVNS) and Other Conditions In some embodiments, methods for treating PVNS are provided, comprising administering an effective amount of an anti-CSF1R antibody. In some embodiments, the PVNS is diffuse PVNS. In some such embodiments, the PVNS is in a hip and/or knee joint. In some such embodiments, the PVNS is in a hand or foot joint. In some embodiments, methods of treating other proliferative disorders that involve synovial joints and tendon sheaths, such as giant cell tumor of the tendon sheath (GCTTS) and, tenosynovial giant cell tumor (TGCT) are provided, comprising administering an effective amount of an anti-CSF1R antibody. In some embodiments, the antibody is administered at a dose described herein, and for example, at a dose of at least 1, at least 2, at least 4, at least 8, at least 10, at least 12, at least 16, at least 20, at least 30, at least 40, at least 50, or at least 100 mg/kg. In some embodiments, the antibody is administered at a dose described herein, and for example, at a dose of 1 mg/kg, 2 mg/kg, or 4 mg/kg. In some embodiments, the antibody is administered with a frequency described herein, and for example, once every two weeks, once every three weeks, once every four weeks, once every five weeks, once every six weeks, once every eight weeks, or once every ten weeks. In some embodiments, at least two, at least three, at least four, at least five, at least six, at least seven, at least eight, at least nine, at least ten, at least 11, or at least 12 doses may be administered during a course of antibody treatment.

In some embodiments, treatment of PVNS with an antibody that binds CSF1R results in a reduction of tumor volume score of at least 30% or at least 40% or at least 50% or at least 60% or at least 70% after at least two or at least three or at least four doses of the antibody. Tumor volume score may be measured, for example, using MRI to assess the tumor volume in an affected joint. In some embodiments, the tumor volume score is measured in one affected joint. In some embodiments, the tumor volume score is measured as the total tumor volume in one or more affected joints.

The anti-CSF1R antibodies may be administered prior to, concurrently with, and/or following at least one additional therapy. Nonlimiting exemplary additional therapies include surgical synovectomy, radiation beam therapy, radio isotope synovectomy, and joint replacement.

In some embodiments, the anti-CSF1R antibody blocks binding of CSF1 and/or IL-34 to CSF1R and/or inhibits CSF1R phosphorylation induced by CSF1 and/or IL-34. In some embodiments, the anti-CSF1R antibody blocks binding of CSF1 and IL-34 to CSF1R and/or inhibits CSF1R phosphorylation induced by CSF1 and/or IL-34. In some embodiments, the anti-CSF1R antibody comprises the CDRs of, or the variable regions of, an antibody selected from huAb1 to huAb16, described herein. In some embodiments, the anti-CSF1R antibody comprises the CDRs of, or the variable regions of, huAb1.

Routes of Administration and Carriers

In various embodiments, antibodies may be administered in vivo by various routes, including, but not limited to, oral, intra-arterial, parenteral, intranasal, intramuscular, intracardiac, intraventricular, intratracheal, buccal, rectal, intraperitoneal, intradermal, topical, transdermal, and intrathecal, or otherwise by implantation or inhalation. The subject compositions may be formulated into preparations in solid, semi-solid, liquid, or gaseous forms; including, but not limited to, tablets, capsules, powders, granules, ointments, solutions, suppositories, enemas, injections, inhalants, and aerosols. A nucleic acid molecule encoding an antibody may be coated onto gold microparticles and delivered intradermally by a particle bombardment device, or "gene gun," as described in the literature (see, e.g., Tang et al., *Nature* 356:152-154 (1992)). The appropriate formulation and route of administration may be selected according to the intended application.

In various embodiments, compositions comprising antibodies are provided in formulations with a wide variety of pharmaceutically acceptable carriers (see, e.g., Gennaro, *Remington: The Science and Practice of Pharmacy with Facts and Comparisons: Drugfacts Plus,* 20$^{th}$ ed. (2003); Ansel et al., Pharmaceutical Dosage Forms and Drug Delivery Systems, 7$^{th}$ ed., Lippencott Williams and Wilkins (2004); Kibbe et al., *Handbook of Pharmaceutical Excipients,* 3$^{rd}$ ed., Pharmaceutical Press (2000)). Various pharmaceutically acceptable carriers, which include vehicles, adjuvants, and diluents, are available. Moreover, various pharmaceutically acceptable auxiliary substances, such as Ph adjusting and buffering agents, tonicity adjusting agents, stabilizers, wetting agents and the like, are also available. Non-limiting exemplary carriers include saline, buffered saline, dextrose, water, glycerol, ethanol, and combinations thereof.

In various embodiments, compositions comprising antibodies may be formulated for injection, including subcutaneous administration, by dissolving, suspending, or emulsifying them in an aqueous or nonaqueous solvent, such as vegetable or other oils, synthetic aliphatic acid glycerides, esters of higher aliphatic acids, or propylene glycol; and if desired, with conventional additives such as solubilizers, isotonic agents, suspending agents, emulsifying agents, stabilizers and preservatives. In various embodiments, the compositions may be formulated for inhalation, for example, using pressurized acceptable propellants such as dichlorodifluoromethane, propane, nitrogen, and the like. The compositions may also be formulated, in various embodiments, into sustained release microcapsules, such as with biodegradable or non-biodegradable polymers. A non-limiting exemplary biodegradable formulation includes poly lactic acid-glycolic acid polymer. A non-limiting exemplary non-biodegradable formulation includes a polyglycerin fatty acid ester. Certain methods of making such formulations are described, for example, in EP 1 125 584 A1.

Pharmaceutical packs and kits comprising one or more containers, each containing one or more doses of an antibody or combination of antibodies are also provided. In some embodiments, a unit dosage is provided wherein the unit dosage contains a predetermined amount of a composition comprising an antibody or combination of antibodies, with or without one or more additional agents. In some embodiments, such a unit dosage is supplied in single-use prefilled syringe for injection. In various embodiments, the composition contained in the unit dosage may comprise saline, sucrose, or the like; a buffer, such as phosphate, or the like; and/or be formulated within a stable and effective Ph range. Alternatively, in some embodiments, the composition may be provided as a lyophilized powder that may be reconstituted upon addition of an appropriate liquid, for example, sterile water. In some embodiments, the composition comprises one or more substances that inhibit protein aggregation, including, but not limited to, sucrose and arginine. In some embodiments, a composition of the invention comprises heparin and/or a proteoglycan.

Pharmaceutical compositions are administered in an amount effective for treatment or prophylaxis of the specific indication. The therapeutically effective amount is typically dependent on the weight of the subject being treated, his or her physical or health condition, the extensiveness of the condition to be treated, or the age of the subject being treated. In general, antibodies may be administered in an amount in the range of about 10 µg/kg body weight to about 100 mg/kg body weight per dose. In some embodiments, antibodies may be administered in an amount in the range of about 50 µg/kg body weight to about 5 mg/kg body weight per dose. In some embodiments, antibodies may be administered in an amount in the range of about 100 µg/kg body weight to about 10 mg/kg body weight per dose. In some embodiments, antibodies may be administered in an amount in the range of about 100 µg/kg body weight to about 20 mg/kg body weight per dose. In some embodiments, antibodies may be administered in an amount in the range of about 0.5 mg/kg body weight to about 20 mg/kg body weight per dose. In some embodiments, antibodies may be administered at a dose of at least 1, at least 2, at least 4, at least 8, at least 10, at least 12, at least 16, at least 20, at least 30, at least 40, at least 50, or at least 100 mg/kg. In some embodiments, antibodies may be administered at a dose of 1 mg/kg, 2 mg/kg, or 4 mg/kg.

The antibody compositions may be administered as needed to subjects. Determination of the frequency of administration may be made by persons skilled in the art, such as an attending physician based on considerations of the condition being treated, age of the subject being treated, severity of the condition being treated, general state of health of the subject being treated and the like. In some embodiments, an effective dose of an antibody is administered to a subject one or more times. In various embodiments, an effective dose of an antibody is administered to the subject once a month, less than once a month, such as, for example, every two months or every three months. In other embodiments, an effective dose of an antibody is administered more than once a month, such as, for example, every three weeks, every two weeks or every week. In some embodiments, an effective dose of an antibody is administered once per 1, 2, 3, 4, or 5 weeks. In some embodiments, an effective dose of an antibody is administered twice or three times per week. An effective dose of an antibody is administered to the subject at least once. In some embodiments, the effective dose of an antibody may be administered multiple times, including for periods of at least a month, at least six months, or at least a year.

Combination Therapy

Antibodies may be administered alone or with other modes of treatment. They may be provided before, substantially contemporaneous with, or after other modes of treatment, for example, surgery, radiation therapy, joint replacement, and/or another therapeutic agent. In some embodiments, the PVNS has recurred or progressed following a therapy selected from surgery, radiation therapy, joint replacement, administration of another therapeutic agent, or a combination thereof.

In some embodiments, the anti-CSF1R antibody is administered before, concurrently, or after at least one treatment selected from surgical synovectomy, radiation beam therapy, radio isotope synovectomy, and joint replacement.

EXAMPLES

The examples discussed below are intended to be purely exemplary of the invention and should not be considered to limit the invention in any way. The examples are not intended to represent that the experiments below are all or the only experiments performed. Efforts have been made to ensure accuracy with respect to numbers used (for example, amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1: Humanized Anti-CSF1R Antibodies

Various humanized anti-CSF1R antibodies were developed previously. See, e.g., PCT Publication No. WO 2011/140249.

Figure 1B:
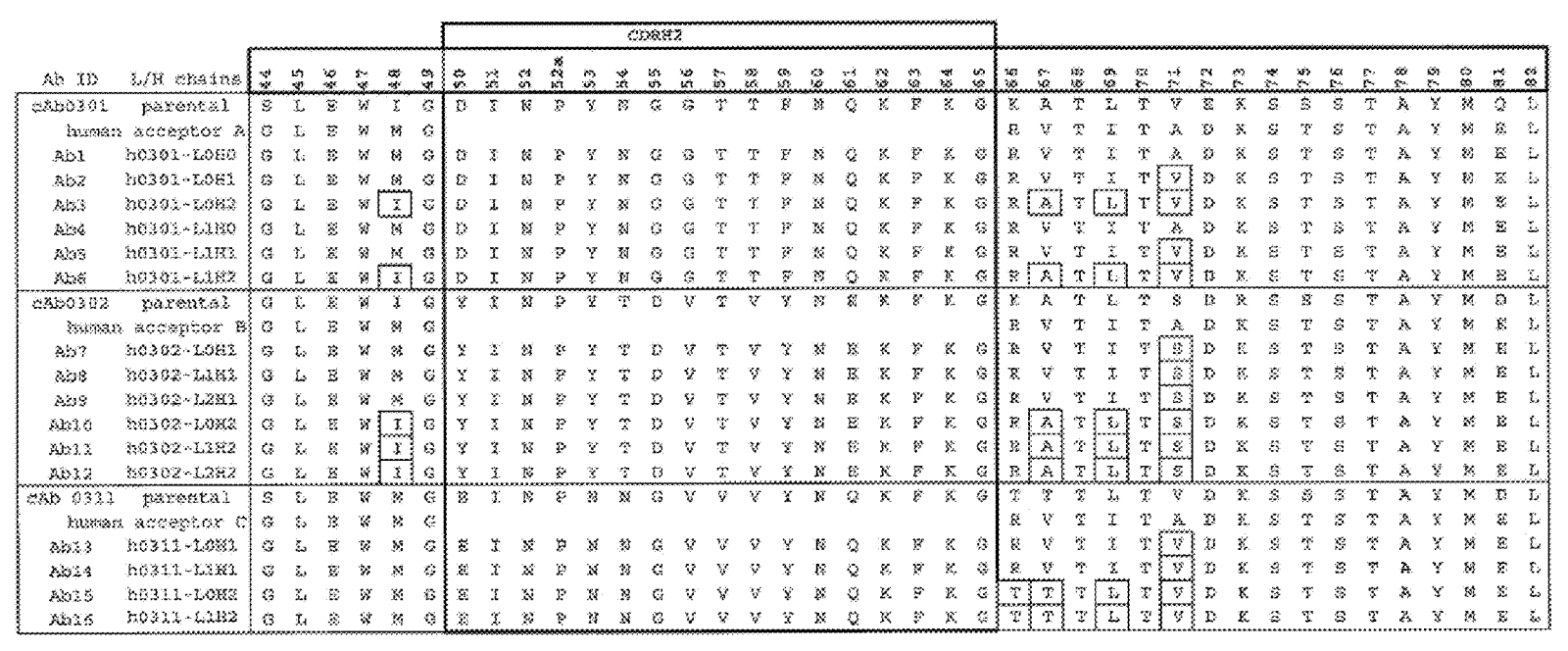
Figure 1C:
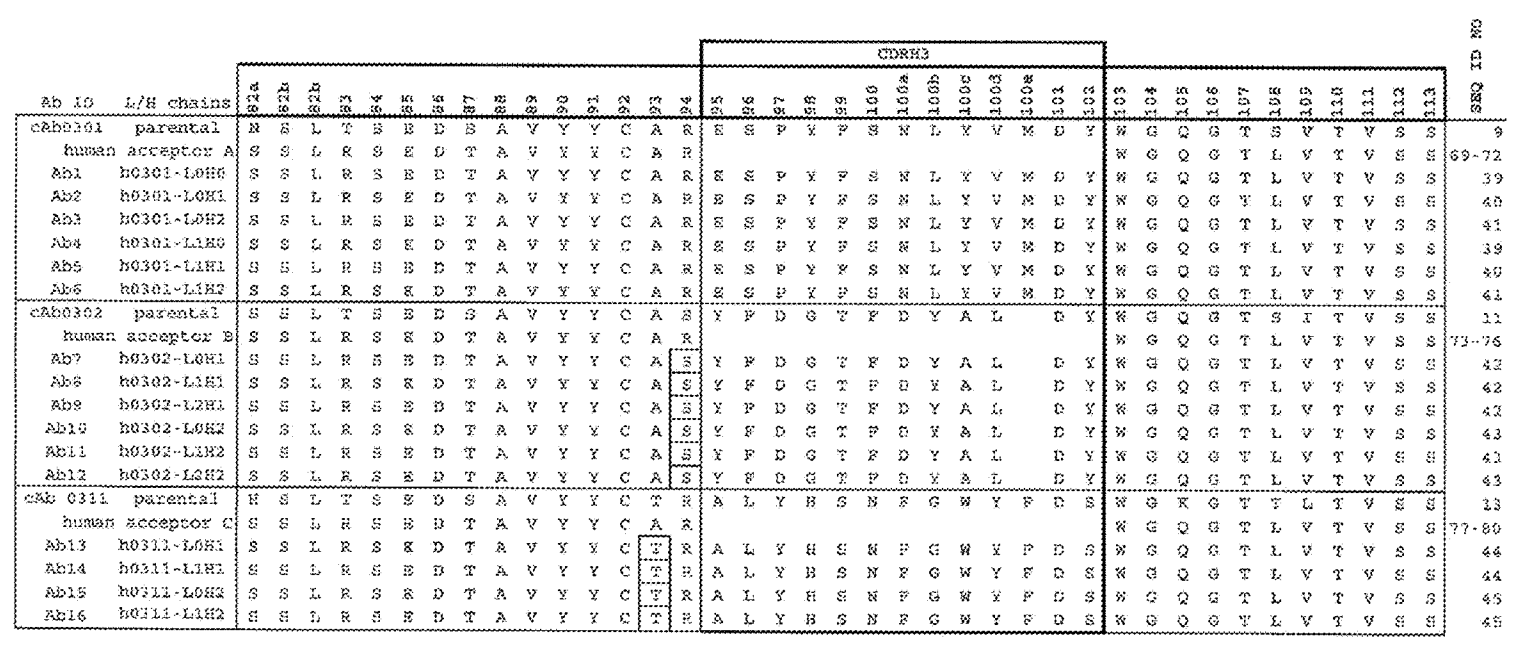

The sequences for each of the humanized heavy chain variable regions and humanized light chain variable regions, aligned with the sequences of the parental chimeric antibody variable regions and the sequences of the human acceptor variable framework regions are shown in FIGS. 1 (heavy chains) and 2 (light chains). The changes in humanized variable region sequences relative to the human acceptor variable framework region sequences are boxed. Each of the CDRs for each of the variable regions is shown in a boxed region, and labeled as "CDR" above the boxed sequences.

Table 8, below, shows the full sequences for the humanized heavy chains and humanized light chains of antibodies huAb1 to huAb16. The name and SEQ ID Nos of the humanized heavy chain and humanized light chain of each of those antibodies is shown in Table

TABLE 3

Humanized heavy chains and light chains of huAb1 to huAb16

| Humanized antibody | Humanized HC | SEQ ID NO | Humanized LC | SEQ ID NO |
|---|---|---|---|---|
| huAb1 | h0301-H0 | 53 | h0301-L0 | 60 |
| huAb2 | h0301-H1 | 54 | h0301-L0 | 60 |
| huAb3 | h0301-H2 | 55 | h0301-L0 | 60 |
| huAb4 | h0301-H0 | 53 | h0301-L1 | 61 |
| huAb5 | h0301-H1 | 54 | h0301-L1 | 61 |
| huAb6 | h0301-H2 | 55 | h0301-L1 | 61 |
| huAb7 | h0302-H1 | 56 | h0302-L0 | 62 |
| huAb8 | h0302-H1 | 56 | h0302-L1 | 63 |
| huAb9 | h0302-H1 | 56 | h0302-L2 | 64 |
| huAb10 | h0302-H2 | 57 | h0302-L0 | 62 |
| huAb11 | h0302-H2 | 57 | h0302-L1 | 63 |
| huAb12 | h0302-H2 | 57 | h0302-L2 | 64 |
| huAb13 | h0311-H1 | 58 | h0311-L0 | 65 |
| huAb14 | h0311-H1 | 58 | h0311-L1 | 66 |
| huAb15 | h0311-H2 | 59 | h0311-L0 | 65 |
| huAb16 | h0311-H2 | 59 | h0311-L1 | 66 |

The 16 humanized antibodies were tested for binding to human, cynomolgus monkey, and mouse CSF1R ECD, as described previously. See, e.g., PCT Publication No. WO 2011/140249. The antibodies were found to bind to both human and cynomolgus monkey CSF1R ECD, but not to mouse CSF1R ECD. The humanized antibodies were also found to block binding of CSF1 and IL-34 to both human and cynomolgus CSF1R and to inhibit CSF1-induced and IL-34-induced phosphorylation of human CSF1R expressed in CHO cells. See, e.g., PCT Publication No. WO 2011/140249.

The $k_a$, $k_d$, and $K_D$ for binding to human CSF1R ECD were previously determined and are shown in Table 4. See, e.g., PCT Publication No. WO 2011/140249.

TABLE 4

Humanized antibody binding affinity for human CSF1R

| huAb | $k_a$ ($M^{-1} s^{-1}$) | $K_d$ ($s^{-1}$) | $K_D$ (Nm) |
|---|---|---|---|
| huAb 0301-L0H0 | $3.22 \times 10^6$ | $1.11 \times 10^{-03}$ | 0.35 |
| huAb 0301-L0H1 | $3.56 \times 10^6$ | $1.22 \times 10^{-03}$ | 0.34 |
| huAb 0301-L0H2 | $2.32 \times 10^6$ | $6.60 \times 10^{-04}$ | 0.28 |
| huAb 0301-L1H0 | $3.29 \times 10^6$ | $1.15 \times 10^{-03}$ | 0.35 |
| huAb 0301-L1H1 | $2.87 \times 10^6$ | $9.21 \times 10^{-04}$ | 0.32 |
| huAb 0301-L1H2 | $2.95 \times 10^6$ | $7.42 \times 10^{-04}$ | 0.25 |
| huAb 0302-L0H1 | $3.54 \times 10^6$ | $3.69 \times 10^{-03}$ | 1.04 |
| huAb 0302-L1H1 | $3.47 \times 10^6$ | $4.04 \times 10^{-03}$ | 1.17 |
| huAb 0302-L2H1 | $1.60 \times 10^6$ | $9.14 \times 10^{-04}$ | 0.57 |
| huAb 0302-L0H2 | $3.40 \times 10^6$ | $1.79 \times 10^{-03}$ | 0.53 |
| huAb 0302-L1H2 | $2.71 \times 10^6$ | $1.53 \times 10^{-03}$ | 0.56 |
| huAb 0302-L2H2 | $1.84 \times 10^6$ | $8.40 \times 10^{-04}$ | 0.46 |
| huAb 0311-L0H1 | $1.22 \times 10^6$ | $5.40 \times 10^{-04}$ | 0.44 |
| huAb 0311-L1H1 | $1.32 \times 10^6$ | $6.64 \times 10^{-04}$ | 0.50 |
| huAb 0311-L0H2 | $1.34 \times 10^6$ | $4.73 \times 10^{-04}$ | 0.35 |
| huAb 0311-L1H2 | $1.51 \times 10^6$ | $6.09 \times 10^{-04}$ | 0.40 |

Example 2: Pharmacokinetics and Pharmacodynamics of Anti-CSF1R Antibody

The pharmacokinetics (PK) and toxicokinetics (TK) of huAb1 have been investigated in 3 intravenous (IV) studies in cynomolgus monkeys. The dose range studied was 3-150 mg/kg after a single dose and 3-150 mg/kg after repeat doses. The duration of infusion was 30 minutes. The dosing interval in the repeat-dose studies was once a week with each animal receiving a total of 4 doses.

The single and repeat-dose PK of a chimeric surrogate antibody was studied in SCID mice to help elucidate the mechanism of huAb1 clearance and better understand the mechanism of the prolonged exposure observed in the monkeys in the recovery group of the GLP toxicology study relative to the monkeys in the single-dose PK study.

The PK profile following a single 30-minute IV infusion of huAb1 in cynomolgus monkeys was characterized by a rapid distribution, followed by a slower terminal phase that ended with an accelerated depletion of huAb1 from the plasma, consistent with target-mediated clearance.

The rapid decrease may be due in part to huAb1 antibodies in addition to target-mediated clearance. However, a single dose administration of a chimeric surrogate antibody in SCID mice, which lack the ability to mount an ADA response, showed a similar profile and supported the contribution of target-mediated clearance to total clearance of huAb1, especially at low doses.

The observed maximum plasma concentration (Cmax) increased proportionally to dose at all dose levels tested, while area under plasma concentratin-time curve from time zero extrapolated to infinity (AUC∞) increases were greater than dose proportional from 3 mg/kg to 10 mg/kg and were dose proportional from 10 mg/kg to 150 mg/kg. The half-life (t½) prior to the accelerated terminal decline ranged from 1-12 days and the total clearance ranged from 0.14-1.25 mL/h/kg. In summary, huAb1 has saturable nonlinear clearance in cynomolgus monkeys.

The effects of huAb1 on various pharmacodynamics (PD) markers known to be modulated in vivo by CSF1R inhibition were examined in 3 cynomolgus monkey studies. These markers include CSF1, CD16$^+$ monocytes, and bone resorption markers.

CSF1 levels: Plasma or serum levels of CSF1 are a measure of huAb1 target engagement. CSF1 is cleared from circulation under normal physiological conditions by macrophages (primarily splenic macrophages and liver Kupffer cells) via CSF1R-mediated endocytosis and intracellular degradation. Steady state levels of CSF1 in normal individuals are <huAb1 binds to and prevents CSF1 being cleared by s CSF1R, resulting in a large, rapid increase in circulating CSF1 concentration, after which CSF1 levels reach a new steady state of approximately 10 µg/ml. In the pilot toxicology study, plasma CSF1 and plasma huAb1 samples were obtained at trough (7 days post-dose) following once-a-week dosing for 4 weeks in cynomolgus monkeys. The data show that a minimum biological effect occurred at 5 µg/mL huAb1, and a half-maximal response ($EC_{50}$) was 8 µg/mL huAb1.

CD16$^+$ monocytes: In the GLP toxicology study, CD16$^+$ monocytes were reduced in monkeys receiving 4 weekly IV infusions of 50 mg/kg or 150 mg/kg huAb1, consistent with CSF1R pathways supporting the growth and maintenance of this monocyte subpopulation in vivo. CD16$^+$ monocyte reduction occurred within 1 week of dosing and was sustained throughout the dosing and exposure periods. The CD16$^+$ monocytes were restored to normal baseline levels after huAb1 cleared. The CD16$^-$ monocyte subpopulation remained unaffected by administration of huAb1.

Bone resorption markers: Plasma and urine markers of bone resorption were evaluated in monkeys following repeat dosing with huAb1. Urine NTx, plasma CTx, and TRAP5b were all decreased. The effects were reversible upon clearance of huAb1.

Example 3: Treatment of PVNS with an Anti-CSF1R Antibody huAb1 antibody (an antibody comprising heavy chain and light chain variable regions of SEQ ID NOs: 53 and 60, respectively) is administered to patients with PVNS at increasing dosages ranging from 1 mg/kg to 4 mg/kg. huAb1 is administered every 2 weeks. Patients are treated in 28-day cycles, with each cycle consisting of 2 doses on day 1 and day 15. After completing a cycle a patient may be administered an increased dose in the next cycle.

Patients are monitored for symptomatic improvement and tumor volume score (TVS). Baseline and post-treatment tumor tissue resections and synovial fluid may be obtained from patients before and after beginning huAb1 treatment. Patients are additionally monitored for overall response, immune-related response, and overall survival.

MRI tumor assessments are performed within 28 days prior to first dose of huAb1, and then at certain time intervals following the first dose (e.g., 4, 8, 16, and 24 weeks, and every 12-16 thereafter). Clinical assessment of health outcomes (e.g., function and symptoms) are also done every 4 weeks after the first dose. Response to huAb1 is evaluated using RECIST for measurable disease.

Patients may be classified according to their best overall tumor response (complete response [CR], partial response [PR], stable disease [SD], or progressive disease [PD]). Frequencies, proportions, and exact 95% CI of patients, when appropriate, stratified by their best overall tumor response are calculated. Patients with a best overall tumor response of CR or PR with duration of at least 4 weeks (28 days) are further classified as having an objective tumor response.

Patients will be classified for response by RECIST and the Tumor Volume Score. The Tumor Volume Score classifies response according to the following definitions: Complete Response [(CR) lesion completely gone after treatment cycle], Partial Response [(PR)≥50% decrease in volume score relative to Baseline], Progressive Disease [(PD)≥30% increase in volume relative to lowest score during the treatment whether at baseline or some other visit] or Stable Disease [(SD) does not meet any of the prior criteria based on score].

Duration of response is calculated as the number of days from the first documentation of overall response (CR or PR) to the first documentation of disease progression.

Example 4: Summary of a Phase I/II Clinical Trial in Patients with Pigmented Villonodular Synovitis (PVNS)/Diffuse Type Tensosynovial Giant Cell Tumor (dt-TGCT)

A phase I/II clinical trial is conducted in patients with one or both of pigmented villonodular synovitis (PVNS) and diffuse type tensynovial giant cell tumor (dt-TGCT) using huAb1 (also known as FPA008). The objective of phase I will be to determine a recommended dose of huAb1 in the patients, while phase II will be conducted to estimate the objective response rate (ORR) of huAb1 in the patients. ORR=complete response (CR)+partial response (PR). The study will also characterize the safety and tolerability of huAb1 in the patients as well as determine the duration of response in responding patients and assess the pharmacokinetics of huAb1 in the patients. In addition, the study will assess the pharmacodynamics of huAb1 as measured by changes in serum levels of CSF1, IL34, TRAP5b, CTx, and whole blood CD14+/CD16+ monocyte subsets; evaluate synovial biopsies by immunohistochemistry (IHC) for CSF1, CSF1R and CD68; evaluate synovial fluid for huAb1 concentration and changes in cellularity; and assess functional outcomes as measured by the Ogilvie-Harris score developed specifically for PVNS (Ogilvie-Harris, 1992; Rhee, 2010) and by the EQ-5D-5L score (Rabin, 2001; Herdmann, 2011).

The phase I/II study is open label and patients will be enrolled into either phase but not both. Patients are treated with huAb1 every 2 weeks in 28 day cycles. Treatments may be continued after one 28-day cycle. For example, the first dose cycle may be used for a safety and pharmacokinetic assessment, but patients may participate in an extended treatment period of, for example, 1, 2, or 3, additional 28-day cycles or until disease progression (if before 24 weeks), unacceptable toxicity, patient or physician decision to discontinue, or termination of the study.

In phase I, 3 patients are enrolled in each of 3 cohorts, the cohorts administered 1 mg/Kg huAb1, 2 mg/Kg huAb1, or 4 mg/Kg huAb1, respectively. Additional cohorts may be added and an intermediate 3 mg/Kg huAb1 cohort may be added. If dose escalation continues higher than 4 mg/kg, the recommended dose (RD) for phase II may or may not be a maximum tolerated dose (MTD), assuming that an MTD is identified in phase I, but would not be higher than the MTD. The phase II study is based on the dose selected from the phase I results, or a dose anticipated to be less than or equal to 4 mg/Kg. The phase II dose will be identified based on overall safety, tolerability, objective response, PK, PD and estimates of efficacious exposures extrapolated from non-clinical data.

The phase II study duration is 24 weeks and involves 30 patients.

Treated patients are 18 or more years of age and have a histologically confirmed diagnosis of inoperable PVNS/dt-TGCT or potentially resectable tumor that would result in unacceptable functional loss or morbidity as determined by a qualified surgeon or multi-disciplinary tumor board. Patients may have measurable PVNS/dt-TGCT by RECIST 1.1 on MRI.

Treated patients have not received prior therapy with an anti-CSF1R antibody or with PLX3397 unless discontinued for intolerance. Patients may have received prior therapy with imatinib or nilotinib, however. Patients have not had any surgical procedure of the involved joint within 12 weeks prior to first study dose administration.

Pharmacokinetic parameters will be assessed in the patients. The following PK parameters will be derived from concentration-time data for FPA008, when appropriate and applicable (other parameters, such as accumulation ratio and half-life, may also be calculated): Area under serum concentration-time curve (AUC); Maximum serum concentration ($C_{max}$); Minimum serum concentration ($C_{min}$); Clearance (CL); Volume of distribution at steady state ($V_{ss}$).

Pharmacodynamic (PD) parameters are also assessed: Serum—CSF1 and IL34 ligand concentration, CTx, and TRAP5b bone resorption marker concentrations; Whole blood—$CD14^+/CD16^+$ monocyte subsets; Synovium (optional)—evaluate synovial biopsy for CSF1 gene translocation (if not previously done), baseline and on treatment synovial biopsy, IHC for: CSF1 and CSF1R and/or for CD68; Synovial fluid (optional)—huAb1 concentration; cellular component for above markers by IHC.

Immunogenicity is assessed, for example, by collecting blood samples and assaying samples for anti-drug antibodies to huAb1.

Responsiveness is assessed, for example, by the following: MRI of affected joints will be performed at Screening, 4, 8, and 16 weeks (or until treatment discontinuation) following the start of treatment. Response per MRI will be assessed using RECIST 1.1 and TVS based on independent central radiology review. In addition, if there is a good tumor response rate, changes in surrounding bone and other joint tissues may be evaluated based on the whole organ MRI score (WORMS) and rheumatoid arthritis MRI score (RAMRIS). Clinical assessment of health outcomes (function, symptoms) will be done at Screening, C1D15 (pre-dose), C2D1 (pre-dose), and then on Day 1 (pre-dose) for all subsequent cycles through 24 weeks or until treatment is discontinued. Patients who have not progressed at Treatment Completion/Early Termination and agree to continue participation in the study are to be followed (MRI and assessment of health outcomes) every 14 (±2) weeks until progression, the patient undergoes local therapy (e.g., resection, radiation) or a new systemic therapy is initiated, for up to 52 weeks following C1D1.

Safety is assessed by monitoring adverse events and changes in physical examinations, vital signs, 12-lead ECGs, and clinical laboratory measurements.

All analyses will be descriptive and will be presented by dose group and overall as appropriate. Patient data from the Phase 2 will be summarized as a separate group. All patients dosed at the RD will also be summarized. Because of the low number of patients that may be enrolled at lower dose levels, some dose levels may be combined for summarization. Missing values in the efficacy data will be treated as missing; no efficacy data will be imputed.

Data collected in this study will be presented using summary tables and patient data listings. Continuous variables will be summarized using descriptive statistics, specifically the mean, median, standard deviation (SD), minimum, and maximum. Categorical variables will be summarized by frequencies and percentages. 95% confidence intervals will be presented where appropriate. Response rates and the corresponding confidence interval (CI) will be used to access efficacy. It is anticipated that there will a total of approximately 33 to 36 patients treated at the RD overall. Table 6 displays the corresponding 95% confidence interval and the precision for various sample sizes and observed response rates. PK parameters will be calculated using non-compartmental analysis methods, though compartmental analysis methods may be employed if appropriate.

Example 5: Phase I/II Clinical Trial in Patients with Pigmented Villonodular Synovitis (PVNS)/Diffuse Type Tensosynovial Giant Cell Tumor (dt-TGCT)

1. Introduction
1.1. PVNS Background

Pigmented villonodular synovitis (PVNS) is a benign neoplasm of the synovium with features of both reactive inflammation and clonal neoplastic proliferation in which colony stimulating factor-1 (CSF1) is over expressed. A common translocation of the CSF1 gene (1p13) to the COL6A3 promoter (2q35) is present in approximately 60% of PVNS patients. The translocation is accompanied by CSF1 overexpression in the synovium. In addition, approximately 40% of PVNS patients have CSF1 overexpression in the absence of an identified CSF1 translocation. The consistent presence of CSF1 overexpression in all cases of PVNS and reactive synovitis suggests both an important role for CSF1 in the spectrum of synovial pathologies and the utility of targeting the CSF1/CSF1R interaction therapeutically (West, 2006).

In PVNS, CSF1 overexpression is present in a minority of synovial cells, whereas the majority of the cellular infiltrate expresses CSF1R but not CSF1. This has been characterized as a tumor-landscaping effect with aberrant CSF1 expression in the neoplastic cells, leading to the abnormal accumulation of non-neoplastic cells that form a mass.

Surgery is the treatment of choice for patients with localized PVNS. Recurrences occur in 8-20% of patients and are easily managed by re-excision. PVNS/dt-TGCT tends to recur more often (33-50%) and has a much more aggressive clinical course. Patients are often symptomatic and require multiple surgical procedures during their lifetime. For patients with unresectable disease or multiple recurrences, systemic therapy using CSF1R inhibitors may help delay or avoid surgical procedures and improve functional outcomes (Ravi, 2011).

Imatinib, a non-specific inhibitor of CSF1R, has undergone evaluation in 29 PVNS patients. The median age was 41 years and the most common site of disease was the knee (n=17; 59%). Five of 27 evaluable patients had complete (n=1) or partial (n=4) responses per RECIST for an overall response rate of 19%. Twenty of 27 patients (74%) had stable disease. Symptomatic improvement was noted in 16 of 22 patients (73%) who were assessable for symptoms. Despite a high rate of symptomatic improvement and an overall favorable safety profile, 10 patients discontinued treatment for either toxicity or other reasons (Cassier, 2012).

Recently two studies of potent inhibitors of CSF1 signaling have shown preliminary but compelling clinical activity in patients with PVNS. PLX3397, a CSF1R kinase inhibitor, and RG7155, a monoclonal antibody targeting CSF1R have been evaluated in patients with PVNS (Cassier, 2014; Tap, 2014). In both studies, a majority of patients with PVNS responded to treatment based on RECIST, FDG-PET, and/or total volume score, which is a measure of disease volume by MRI.

In PVNS, overexpression of CSF1 by a minority of cells leads to recruitment of CSF1R-expressing cells that make up the bulk of the tumor mass. FPA008 antagonizes CSF1R activation and should result in the reduction of CSF1R-expressing cells in the tumor thereby providing clinical benefit.

1.2. FPA008: Description of the Molecule

HuAB1, also called FPA008, is a humanized IgG4 monoclonal antibody with a single amino acid substitution in the hinge region to prevent hemi-dimer exchange. FPA008 has high affinity binding to human colony stimulating factor 1 receptor (CSF1R), a receptor tyrosine kinase.

1.2.1. Nonclinical Studies with FPA008
1.2.1.1. FPA008 Inhibition of CSF1R Signaling FPA008 inhibited both CSF1 and IL34-induced CSF1R phosphorylation in a cell line engineered to overexpress CSF1R (CHO-CSF1R), demonstrating FPA008 blocks the activation of ligand-induced CSF1R signaling pathways. FPA008 also inhibits CSF1 and IL34-induced proliferation/survival of peripheral blood monocytes in vitro, demonstrating FPA008 inhibits not only the initiation of CSF1 and IL34 signaling pathways, but also the subsequent physiologic responses of primary human monocytes to these ligands (for further details, see the FPA008 Investigator's Brochure [IB]).

1.2.2. Nonclinical Pharmacokinetics and Pharmacodynamics
1.2.2.1. Pharmacokinetics The pharmacokinetics (PK) and toxicokinetics (TK) of FPA008 have been investigated in 4 intravenous (IV) studies in cynomolgus monkeys. The dose range studied was 3-150 mg/kg after a single intravenous bolus dose and 3-150 mg/kg after repeat intravenous infusion doses. The duration of infusion was 30 minutes. The dosing interval in the repeat-dose studies was once a week with each animal receiving a total of 4 doses in two studies and 13 doses in one study.

The PK profile following a single IV bolus administration of FPA008 in cynomolgus monkeys was characterized by a rapid distribution, followed by a slower terminal phase that ended with an accelerated depletion of FPA008 from the plasma, consistent with target-mediated clearance.

The rapid decrease may be due in part to anti-FPA008 antibodies in addition to target-mediated clearance. However, a single dose administration of cmFPA008 in SCID mice, which lack the ability to mount an ADA response, showed a similar profile and supported the contribution of target-mediated clearance to total clearance of FPA008, especially at low doses.

The observed maximum plasma concentration ($C_{max}$) increased proportionally to dose at all dose levels tested, while area under plasma concentration-time curve from time zero extrapolated to infinity ($AUC_\infty$) increases were greater than dose proportional from 3 mg/kg to 10 mg/kg and were dose proportional from 10 mg/kg to 150 mg/kg. The half-life ($t_{1/2}$) prior to the accelerated terminal decline ranged from 1-12 days and the total clearance ranged from 0.14-1.25 mL/h/kg. In summary, FPA008 has saturable target-mediated clearance in cynomolgus monkeys.

1.2.2.2. Pharmacodynamics

The effects of FPA008 on various pharmacodynamics (PD) markers known to be modulated in vivo by CSF1R inhibition were examined in 3 cynomolgus monkey studies (details are provided in Section 5.1.1.7 of the IB). These markers include CSF1, $CD16^+$ monocytes, and bone resorption markers. IL34 was not measured in monkeys due to lack of an appropriate assay.

CSF1 Levels:

Plasma or serum levels of CSF1 are a measure of FPA008 target engagement. CSF1 is cleared from circulation under normal physiological conditions by macrophages (primarily splenic macrophages and liver Kupffer cells) via CSF1R-mediated endocytosis and intracellular degradation (Bartocci, 1987). Steady state levels of CSF1 in normal individuals are <1 ng/ml. FPA008 binds to and prevents CSF1 being cleared by CSF1R, resulting in a large, rapid increase in circulating CSF1 concentration, after which CSF1 levels reach a new steady state of approximately 10 µg/ml. In the pilot toxicology study, plasma CSF1 and plasma FPA008 samples were obtained at trough (7 days post-dose) following once-a-week dosing for 4 weeks in cynomolgus monkeys. The data show that a minimum biological effect occurred at 5 µg/mL FPA008, and a half-maximal response ($EC_{50}$) was 8 µg/mL FPA008. While FPA008 elevates CSF1, FivePrime believes that these elevations will have no consequence because:

CSF1R is the only identified receptor through which CSF1 signals and this is antagonized by FPA008.

The levels of CSF1 fall concomitantly with the clearance of FPA008.

In the presence of FPA008, when CSF1 is elevated, the potential for extremely high concentrations of CSF1 to displace FPA008 from the CSF1R receptor was evaluated in the FPA008 cell potency assay. The data showed that concentrations as high as 10 µg/mL CSF1 had no impact on FPA008 potency or maximal inhibition of CSF1R signaling.

No rebound increase in CD16$^+$ monocytes was observed once FPA008 is cleared in preclinical in vivo studies.

CD16$^+$ Monocytes:

In the GLP toxicology study, CD16$^+$ monocytes were reduced in monkeys receiving 4 weekly IV infusions of 50 mg/kg or 150 mg/kg FPA008, consistent with CSF1R pathways being necessary to support the growth and maintenance of this monocyte subpopulation in vivo. CD16$^+$ monocyte reduction occurred within 1 week of dosing and was sustained throughout the dosing and exposure periods. The CD16$^+$ monocytes were restored to normal baseline levels after FPA008 cleared. The CD16$^-$ monocyte subpopulation remained unaffected by administration of FPA008.

Bone Resorption Markers:

Plasma and urine markers of bone resorption were evaluated in monkeys following repeat dosing with FPA008. Urine NTX, plasma CTx, and TRAP5b were all decreased. The effects were reversible upon clearance of FPA008.

1.2.3. Nonclinical Toxicology Studies and Findings

Full details of the nonclinical toxicology studies are provided in Section 5.3 of the IB. All toxicity studies were performed in cynomolgus monkey since FPA008 is not cross-reactive to rodents but shows similar in vitro binding affinity to cynomolgus monkey and human CSF1R and similar tissue binding profile in a tissue cross reactivity study comparing a panel of human and cynomolgus monkey tissues. Four nonclinical in vivo toxicology studies were performed using FPA008: A single-dose pharmacokinetic (PK)/tolerability study with doses of 3, 10, 30, and 150 mg/kg, a dose range finding repeat-dose toxicity study with 4 weekly IV doses of 3, 10, and 150 mg/kg, a repeat-dose GLP toxicity study with 4 weekly IV doses of 50 mg/kg and 150 mg/kg and a 30 week recovery phase, and a subchronic repeat-dose GLP toxicity study with 13 weekly IV doses of 20, 50, and 100 mg/kg and a 29-week recovery phase.

In the in vivo toxicology studies in cynomolgus monkeys, FPA008 was generally well tolerated. Test article-related findings included clinical observations, hematology and clinical chemistry changes, and histologic changes. The majority of these observations were considered non-adverse.

1.2.3.1. Periorbital Edema

The most prominent physical finding was reversible periorbital edema, seen after prolonged exposure to FPA008. The onset of the edema did not show a clear relationship to exposure levels, however edema resolved after systemic clearance of the drug. Periorbital edema is a known side effect with drugs affecting the CSF1 pathway (Ries, 2014).

1.2.3.2. Monocyte Depletion

The main hematologic change was a decrease in circulating CD16$^+$ monocytes, which was considered a pharmacodynamic (PD) effect. The decreased cell numbers normalized with clearance of FPA008 from circulation.

1.2.3.3. Enzyme Elevations

FPA008-related clinical chemistry effects included reversible increased alanine transaminase (ALT), aspartate transaminase (AST), and creatine kinase (CK) serum levels. These laboratory abnormalities were not associated with any histopathological evidence of liver, cardiac, or muscle tissue injury at terminal or recovery necropsy. Cardiac troponin, skeletal troponin, myoglobin, and aldolase were also measured during the in-life portion of the study, and no changes were detected in any of these parameters further confirming the lack of any liver or muscle injury. The increased serum levels are attributed to diminished clearance of the ALT, AST, and CK molecules from serum due to a reduced number of liver Kupffer cells (Radi, 2011). Accordingly, the ALT, AST, and CK elevations are considered non-toxic and an indirect PD effect of FPA008 exposure.

1.2.3.4. Accumulation of Extracellular Matrix

The most noteworthy histopathological finding in both pivotal studies at terminal necropsy was the observation of reversible expansion of the submucosal collagen fibers by clear space and varying amounts of a blue, granular extracellular matrix (ECM). This finding was present in a large variety of tissues and was generally minimal to mild in severity. It was most prominently seen in the esophagus. This change was not associated with inflammatory cells or with any sign of degeneration or other alteration of the collagen fibers, fibroblasts, or the smooth muscle cells within the area of expansion. A similar observation was also noted in op/op mice that lack functional CSF1 (Radi, 2009). In this publication, the authors postulated that the reduction of tissue macrophages likely causes the observed accumulation of ECM due to a decreased clearance of glycosaminoglycans by macrophages. Glycosaminoglycans, especially hyaluronic acid, are prominent in connective tissue and are normally catabolized by macrophages (Radi, 2009). This change is considered to be an indirect PD effect of FPA008. There was no evidence that the accumulation of the blue granular ECM was adverse; there were no associated clinical observations or organ weight changes that correlated to the histopathologic observations. In addition, these changes in the ECM were reversible during a drug-free recovery period, and therefore, were considered non-adverse.

1.2.3.5. Other Findings

Unique to the 4-week GLP study was a finding in a single female dosed with 150 mg/kg. At terminal sacrifice microscopic evidence of mild inflammation of the epicardium and vacuolation of cardiac myocytes was seen. The significance of this finding is unknown, but association with FPA008 cannot be excluded. Chronic, mild epicardial inflammation can be a background lesion in nonhuman primates. However, vacuolation of a cell can be an early sign of a non-specific, cellular response to injurious stimuli. Vacuolation of myocytes was not found in any of the other dosed animals. It is important to note that this vacuolation did not lead to degeneration or necrosis, and did not cause changes in recorded ECGs. No cardiac changes were detected in any animals at recovery or in the 13-week toxicity study. This event was considered an adverse finding in the 4-week toxicity study.

Also unique to the 4-week study was increased spleen organ weights with corresponding histopathological findings of minimal to mild follicular hyperplasia in female animals. The finding was considered of low toxicological significance and non-adverse, and no spleen hyperplasia was seen in the 13-week toxicity study.

As macrophages engulf pathogens to destroy them (Dale, 2008), treatment with FPA008 may be associated with an increased risk of susceptibility to intracellular pathogens such as *Mycobacterium tuberculosis, Listeria monocytogenes, Leishmania*, and others. While no spontaneous infections have been noted in FPA008 animal studies to date, clinical study protocols will contain exclusion criteria for those patients at greatest risk. Patients will be monitored regularly for adverse events and infections while on study.

1.2.3.6. Summary

The no-observable-adverse-effect level (NOAEL) for FPA008 was determined to be 100 mg/kg when administered for 13 weekly doses to cynomolgus monkeys.

1.3. Clinical Experience with FPA008

FPA008 is currently being evaluated in a double-blind, randomized, placebo-controlled first-in-human trial designed in 3 parts to study safety, pharmacokinetics (PK), and PD biomarkers. In Part 1, 8 healthy volunteers were randomized (3:1) to receive a single intravenous infusion of FPA008 or placebo, per dose cohort of 0.2, 1, 3, or 10 mg/kg. In Part 2, 8 healthy volunteers were randomized (3:1) to receive 2 doses of FPA008 or placebo administered 14 days apart, at 1 mg/kg or 3 mg/kg. Dose escalation decisions were based on the incidence of dose limiting toxicities (DLTs) plus attributed adverse events beyond the DLT period. Part 3 consists of an open-label evaluation of 3 dose levels in RA patients whose disease is not responding to disease modifying anti-rheumatic drugs (DMARDs) and on a stable dose of methotrexate. Three subjects per dose level will receive 2 doses of FPA008 administered intravenously 14 days apart in the open-label part. Thereafter, 30 new subjects will be randomized (2:2:1) to one of two dose levels of FPA008 or placebo, respectively, and receive 3 doses administered intravenously every 14 days. No clinical safety data are yet available for Part 3 patients.

Forty-eight healthy volunteers completed Parts 1 and 2 of the study; 36 of these subjects received FPA008 and 12 received placebo. FPA008 was well tolerated in healthy volunteers up to 3 mg/kg dual doses. The most common FPA008 treatment-related toxicities were pruritus, eyelid edema along with facial swelling, fatigue, and headache. The events were Grade 1 or 2, and self-limited. At 10 mg/kg, all 6 active subjects experienced moderate (Grade 2) eyelid edema or facial swelling, some accompanied with swelling in hands and feet, blurry vision, and weight gain. The events lasted up to 3 months and coincided with prolonged PK exposure at this dose level. No adverse events met protocol definitions for dose-limiting toxicities.

Dose-dependent elevations of CK up to 6.8 times the upper limit of normal and lactate dehydrogenase (LDH) up to 2.2 times the upper limit of normal were noted at 1 mg/kg and above; AST elevation up to 2.1 times the upper limit of normal occurred at 3 mg/kg and above and occurred in a greater percentage of volunteers with increasing dose; and mild ALT elevation up to 1.2 times the upper limit of normal occurred at 10 mg/kg in 1 subject. Peak values occurred 2-8 weeks following drug administration, typically with normalization by 12 weeks. These elevations were not associated with clinical signs/symptoms or abnormalities in total bilirubin, CK isoenzymes, or troponin. They were reversible and were expected due to FPA008-mediated inhibition of Kupffer cells responsible for their clearance (Radi, 2011) and are considered to be a pharmacologic effect of inhibiting CSF1R rather than representing tissue injury.

The adverse event profile observed in this study is relatively similar to what has been reported in other compounds targeting the CSF1R pathway (Cassier, 2014; Tap, 2014).

FPA008 exhibited saturable target-mediated clearance in the dose range tested. The PK characteristics observed in healthy volunteers support dosing of FPA008 once every 2 weeks or less frequently to maintain desired drug exposure. Reduction of CD16$^+$ monocytes, decreased bone turnover biomarkers (CTx, TRAP5b), and dose-dependent increase in serum CSF1 and IL34 concentrations were observed.

1.4. Risk-Benefit Assessment

The safety, PK, and PD of FPA008 in healthy volunteers were generally predicted based on the nonclinical toxicology studies of FPA008. More details on the toxicology studies are provided in the IB.

In the nonclinical toxicology studies, FPA008 was well tolerated in animals at high doses up to 100 mg/kg for up to 13 weekly doses. PD effects (CSF1 and CD16$^+$ monocytes) occurred at drug exposure levels well below those associated with adverse events or abnormal laboratory findings.

Evidence from mouse models to evaluate potential risk of pharmacologically mediated toxicity associated with interruption of CSF1 and IL34 signaling has shown that the deletion of CSF1, IL34, or CSF1R is non-lethal. Mice deficient in CSF1 show a loss of bone osteoclasts and display deficiency in some myeloid cells at birth (Yoshida, 1990); mice deficient in IL34 lack Langerhans cells in the epidermis and microglia in some areas of the brain (Wang, 2012; Greter, 2012); and mice deficient in CSF1R display both osteoporosis and deficiency of Langerhans cells and microglia (Hamilton, 2013).

Binding of FPA008 to CSF1R does not produce an agonist effect as demonstrated by experiments conducted at FivePrime (details provided in the IB). Additionally, FPA008 is an IgG4 antibody, and in vitro testing has confirmed that it has no specific antibody-dependent cell-mediated cytotoxicity (ADCC) or complement-dependent cytotoxicity (CDC) activity.

Although PVNS is managed by local intervention in most patients, some patients present with or have chronic or recurrent disease that is not well managed by surgery or other available therapies. Imatinib is effective in a minority of patients but has some on-target and off-target toxicities that limit its usefulness. Preliminary reports of specific CSF1R inhibitors suggest that FPA008 may be a beneficial treatment for non-surgical PVNS, which can be a debilitating disease.

2. Study Objectives and Endpoints

2.1. Primary Objective

Phase 1: To determine the recommended dose (RD) of FPA008 in patients with PVNS/dt-TGCT Phase 2: To estimate the objective response rate (ORR=CR+PR) of FPA008 in patients with PVNS/dt-TGCT

2.2. Secondary Objectives

To characterize the safety and tolerability of FPA008 in patients with PVNS/dt-TGCT To determine the duration of response in responding patients To assess the pharmacokinetics of FPA008 in patients with PVNS/dt-TGCT

2.3. Exploratory Objective

To assess the pharmacodynamics of FPA008 as measured by changes in serum levels of CSF1, IL34, TRAP5b, CTx, and whole blood CD14$^+$/CD16$^+$ monocyte subsets To evaluate synovial biopsies by immunohistochemistry (IHC) for CSF1, CSF1R and CD68 markers in selected patients To evaluate synovial fluid for FPA008 concentration and changes in cellularity in selected patients To assess functional outcomes as measured by the Ogilvie-Harris score developed specifically for PVNS and by the EQ-5D-5L score

2.4. Primary Study Endpoints

Phase 1: The incidence of Grade 3 and Grade 4 adverse events (AEs) and clinical laboratory abnormalities defined as dose-limiting toxicities (DLTs)

Phase 2: The incidence of confirmed objective responses per RECIST 1.1

2.5. Secondary Endpoints

PK parameters

The incidence of AEs, clinical laboratory abnormalities, and ECG abnormalities

Duration of response per RECIST 1.1

2.6. Exploratory Endpoints

PD parameters

Symptom and Functional Outcomes as measured by the Ogilvie-Harris score developed specifically for PVNS and by the EQ-5D-5L score 3. Overall Design and Plan of the Study 3.1. Overview This is a Phase 1/2 study. Phase 1 is a dose escalation, open-label, safety, tolerability, PK, and PD study of FPA008. Patients will be enrolled into either Phase 1 or Phase 2 of the study, but not both.

Enrolled patients will be treated in 28-day cycles. Each cycle will consist of 2 doses: on Day 1 and Day 15.

3.1.1. Screening Period

All Screening evaluations must be completed and reviewed by the Investigator and Medical Monitor to confirm that patients meet all eligibility criteria before the first infusion of FPA008 (Appendix 1). Written informed consent for participation in the study must be obtained before performing any study specific Screening tests or procedures. Screening assessments will be performed within 28 days prior to the first dose of FPA008 unless otherwise specified.

Study-procedure-related AEs that occur after signing of the informed consent form and before administration of the first FPA008 dose will be collected during this period.

3.1.2. Phase 1 (Dose Escalation)

Dose escalation will continue until either the MTD or maximum feasible dose is reached, with a minimum of 3 patients enrolled in each cohort. The anticipated dose levels and schedules are: Dose level 1: 1 mg/kg q2w; Dose level 2: 2 mg/kg q2w; Dose level 3: 4 mg/kg q2w.

All dose escalation decisions will be based on assessment of DLTs, overall safety, and tolerability and will be made after the last patient enrolled in each cohort has completed the first treatment cycle. Dose escalation decisions will be agreed upon between the Investigators and the Sponsor. Prior to initiating each new dose level or expanding an existing dose level, a safety teleconference will be held wherein Investigators and the Sponsor review patient data, including, but not limited to, demographics, FPA008 dosing, concomitant medications, hematology and serum chemistry, and AEs; and confer and document agreement that dose escalation or expanding an existing dose level is considered appropriate. If the Sponsor and Investigators collectively agree that following review of safety and pharmacokinetic data, that a different dose escalation scheme should be used than the one outlined, this will be permitted. Review of safety, PK and PD parameters may inform decisions to add cohorts with alternative dose levels or dose regimens (e.g., less frequent dosing or with a loading dose) in order to reach an optimal target exposure.

The following algorithm will be used for dose escalation decisions:

TABLE 1

Dose-Escalation Considerations

| Number of Patients with DLT at a Given Dose Level | Dose Escalation Decision Rule |
| --- | --- |
| 0/3 | Escalation will occur to the next higher dose cohort |
| 1/3 | Enroll three more patients in same cohort |
| ≥2/3 | Stop enrollment. Enter three more patients at dose level below, if only three were previously entered |
| 1/6 | Open next cohort |
| ≥2/6 | Stop enrollment. Enter 3 more patients at a dose level below or at an intermediate dose level if the current dose level is ≥50% higher than the previous dose level in the same manner as described above. |

The MTD is defined as the highest dose associated with DLTs in less than 33% of patients receiving FPA008 administered on Days 1 and 15 of a 28-day cycle. This will normally be the dose recommended for further study (RD); however, based on review of safety and PK data, the RD could be lower than the MTD. If the MTD is not reached, and the highest evaluated FPA008 dose is well tolerated, the data will be reviewed to assess whether further dose escalations are warranted. The protocol may be amended if additional dose escalation is considered appropriate.

If the MTD is not reached during Phase 1, or subsequent cycles of treatment in Phase 1 provide additional insight on the safety profile, an RD may be selected based on overall tolerability, safety, and PK.

If a patient does not receive 2 doses and does not complete the safety and PK assessment in Cycle 1 for reasons other than toxicity (e.g., disease progression or withdrawal of consent), then an additional patient will be enrolled into the cohort so that the cohort has at least three patients evaluable for tolerability through Cycle 1. All such discussions and decisions will be documented as part of the dose escalation decision-making process.

Intra-patient dose escalation above the starting dose for each patient is not permitted.

If a patient's dose is decreased for an adverse event, dose escalation to the originally assigned dose may occur after resolution of the AE and after discussion with and approval by the Sponsor. Recurrence of the AE to greater than Grade 2 will result in permanent dose reduction without the opportunity for re-escalation.

On completion of Cycle 1 (Safety and PK Assessment Period), Phase 1 patients may participate in an Extended Treatment Period, which begins on Day 1 of Cycle 2. FPA008 will be administered every 2 weeks in 4-week cycles for up to 24 weeks or until disease progression (if before 24 weeks), unacceptable toxicity, patient or physician decision to discontinue, death, or Sponsor termination of the study, assuming no limitations with availability of drug supply, or other issues that may preclude the Sponsor from providing FPA008.

3.1.3. Phase 2

Enrollment in Phase 2 will begin when the RD has been identified by the CRC, based on overall safety, tolerability, objective response, PK, PD and estimates of efficacious exposures extrapolated from nonclinical data. The RD is anticipated to be ≤4 mg/kg. However, it is possible that PVNS/dt-TGCT patients may have different drug exposure relative to healthy volunteers. If dose escalation continues higher than 4 mg/kg, the RD may or may not be an MTD, if an MTD is identified in Phase 1. For example, if an MTD is not reached, or if exposure at the MTD is much higher than the level believed to be required for efficacy, or if subsequent cycles of treatment provide additional insight on the safety profile, then the RD may be a different, though not higher, dose than the MTD.

Treatment is planned to continue every 2 weeks for up to 24 weeks (no more than 12 doses) or until disease progression.

If a patient appears to have stable or improving symptoms with stable measurable disease or better by MRI, but is having intolerable or Grade 3 or greater adverse events, dose reduction by 25-50% may be allowed with Sponsor agreement.

3.2. Procedures

Patients will undergo safety evaluations (DLTs and other AEs, vital signs, ECGs, clinical laboratory tests), determination of ECOG performance status (PS), and physical examinations (Appendix 1). Additionally, blood samples will be collected for PK and PD analyses for all patients (Appendix 2).

MRI of affected joints will be performed at Screening, 4, 8, and 16 weeks following the start of treatment. An MRI should also be performed at the 30 days (±7 days) and 90 days (±7 days) End of Treatment Follow-up Visits unless already performed within the previous 6 weeks or if tumor progression was previously determined. Patients who have not progressed and enter Long-Term Follow-up should have MRI every 14 (±2) weeks until progression, the patient undergoes local therapy (e.g., resection, radiation) or a new systemic therapy is initiated, for up to 52 weeks following C1D1. Response per MRI will be assessed using RECIST 1.1 and TVS based on independent central radiology review.

Clinical assessment of health outcomes (function, symptoms) will be done every 4 weeks after the first administration of study drug.

Safety will be assessed by monitoring AEs and changes in physical examinations, weight, vital signs, 12-lead ECGs, and laboratory measurements. Assessment of AEs will follow the guidelines provided in the National Cancer Institute (NCI)—Common Terminology Criteria for Adverse Events (CTCAE), version 4.03. Blood samples will also be drawn at scheduled time points (Appendix 2) during the study for determination of drug serum concentration, and anti-drug antibodies (ADAs) (i.e., antibody response to FPA008).

In patients who have archival tumor tissue available and who have signed the Optional Research Sample Informed Consent Form, the tissue will be evaluated for CSF1 gene translocation if not previously done (Appendix 1). In addition, CSF1 and CSF1R and CD68 markers and will be determined.

For patients who sign the applicable Optional Research Sample Informed Consent Form, baseline tumor tissue resections (≥0.5 cm to ≤2 cm) and synovial fluid (if applicable) will be obtained from patients prior to starting FPA008 treatment and after eligibility criteria have been fulfilled. The baseline tissue sample will be reviewed by a pathologist to determine whether the tissue is evaluable. If the Screening tissue sample is evaluable, a subsequent biopsy will be performed before the Cycle 2, Day 1 administration of FPA008 (Appendix 1).

Patients enrolled in Phase 1 or Phase 2 of the study may continue treatment with FPA008 in 28-day cycles for up to 24 weeks or until disease progression, intolerable toxicity, patient or physician decision to discontinue, or Sponsor termination of the study. Responding patients who discontinue treatment while still in response (CR, PR or SD) should get follow-up scans at 14 (±2)-week intervals during the Long-Term Follow-up Period to determine the duration of response, unless other therapy is started for the treatment of PVNS/dt-TGCT or consent is withdrawn.

All patients should return to the clinic for three End of Treatment Follow-Up visits irrespective of whether a patient is withdrawn or withdraws at a planned visit or mid-cycle.

AEs will be assessed from the time the first dose of FPA008 is administered through 90 days (±7 days) after the last dose of FPA008 (see Section 6.2.1.1). All serious adverse events (SAEs) will be collected after signing of the informed consent form through 90 days (±7 days) after the last dose (see Section 6.2.1.1).

3.3. Rationale for the Study Design

The Phase 1 component of this study is a dose escalation, open-label study to assess the safety, PK, PD, and preliminary efficacy of FPA008 in patients with PVNS/dt-TGCT. The 3+3 dose escalation design is standard for early stage trials of novel anticancer treatments.

The Phase 2 component is a single-stage trial designed to estimate the objective response rate with a precision of approximately 20%, assuming the response rate is similar to that reported for PLX3397 and RG.7155, other potent inhibitors of the CSF1R signaling pathway. The Phase 2 component will also allow a more thorough investigation of the safety, PK, and biological effects of FPA008 in the target population for future trials.

4. Study Eligibility and Withdrawal Criteria 4.1. Planned Number of Patients and Study Centers Phase 1: Approximately 12-15 patients with PVNS/dt-TGCT will be enrolled. Enrollment in Phase 1 will continue until the MTD has been reached or until the RD for Phase 2 has been defined.

Phase 2: Approximately 30 patients with PVNS/dt-TGCT will be enrolled. The study will be conducted at approximately 12 investigational centers in North America, Europe, and Asia.

4.2. Inclusion Criteria for Study Participation

Patients enrolling into Phase 1 or 2 must meet all of the following inclusion criteria:

1. Understand and sign an Institutional Review Board/Independent Ethics Committee-approved informed consent form prior to any study-specific evaluation
2. Age≥18 years
3. Histologically confirmed diagnosis of inoperable PVNS/dt-TGCT or potentially resectable tumor that would result in unacceptable functional loss or morbidity as determined by a qualified surgeon or multi-disciplinary tumor board (must be documented in the CRF during screening)
4. Measurable PVNS/dt-TGCT by RECIST 1.1 on MRI
5. ECOG performance status≤1
6. Willing and able to comply with all study procedures
7. In sexually-active patients (i.e., females of childbearing potential, who have not undergone menopause as defined by 12 consecutive months of amenorrhea or had a permanent sterilization procedure and males, who have not had a permanent sterilization procedure), willingness to use 2 effective methods of contraception, of which one must be a physical barrier method (condom, diaphragm, or cervical/vault cap) until 6 months after the last dose of FPA008. Other effective forms of contraception are permanent sterilization (hysterectomy and/or bilateral oophorectomy, or bilateral tubal ligation with surgery, or vasectomy) at least 6 months prior to Screening. Females<55 years of age should have FSH>40. Female patients of childbearing potential must be on stable oral contraceptive therapy or intrauterine or implant device for at least 90 days prior to the study, or abstain from sexual intercourse as a way of living.

No waivers of these inclusion criteria will be permitted.

4.3. Exclusion Criteria for Study Participation

Patients enrolling into Phase 1 or 2 will be excluded if any of the following criteria apply:
1. Prior therapy with an anti-CSF1R antibody
2. Prior therapy with PLX3397 unless discontinued for intolerance (i.e., non-progression on prior kinase inhibitor); prior therapy with imatinib or nilotinib is allowed
3. CK and liver function tests (including ALT, AST, and total bilirubin), outside of the range of local laboratory normal at Screening
4. Inadequate organ or bone marrow function defined as: hemoglobin<10 g/dL, absolute neutrophil count<$1.5 \times 10^9$/L, platelet count<$100 \times 10^9$/L, serum creatinine>1.5×ULN or calculated creatinine clearance<30 mL/min
5. Any surgical procedure of the involved joint within 12 weeks prior to first study dose administration (except baseline synovium biopsy, if performed)
6. Current or history of clinically significant muscle disorders (e.g., myositis), recent unresolved muscle injury, or any condition known to elevate serum CK levels
7. History of congestive heart failure or myocardial infarction<1 year prior to first study dose administration
8. Decreased cardiac function with NYHA>Class 2
9. Uncontrolled or significant heart disorder such as unstable angina
10. Significant abnormalities on ECG at Screening. QTcF>450 msec for males or >470 msec for females at Screening
11. Contraindications to MRI and use of intravenous gadolinium-based contrast agents
12. History of severe allergic, anaphylactic, or other infusion related reaction to a previous biologic agent
13. Treatment with any anticancer therapy or participation in another therapeutic clinical study with investigational drugs≤28 days prior to first dose of FPA008
14. Known history of ADAs to previous biologic agents
15. Known history of sensitivity to Tween 20 (polysorbate 20)
16. Consumption of non-pasteurized milk on a regular basis, or known significant risk of exposure to opportunistic intracellular infections such as *listeria*, or other such pathogens.
17. Receipt of any vaccine within 28 days prior to first day of treatment. The effect of FPA008 on mounting an immunologic vaccine response is not known. Flu or other vaccinations may be administered while on study but the impact of FPA008 on the safety and efficacy of the vaccination is unknown.
18. Current unresolved infection or history of chronic active clinically significant infection (viral [e.g., HBV, HCV], bacterial, fungal, or other), which in the opinion of the Investigator would place the patient at risk from exposure to a CSF1R inhibitor
19. Known positive test for human immunodeficiency virus (HIV)
20. Active TB
21. Positive test for latent TB at Screening (Quantiferon test)
22. History of prior malignancy, except:
    Curatively treated non-melanoma skin malignancy
    Cervical cancer in situ
    Solid tumor treated curatively more than 2 years previously without evidence of recurrence
23. Lack of peripheral venous access or any condition that would interfere with drug administration or collection of study samples
24. Any uncontrolled medical condition or psychiatric disorder which in the opinion of the Investigator would pose a risk to patient safety or interfere with study participation or interpretation of individual patient results
25. Inability to perform and/or comply with study and follow-up procedures.

No waivers of these exclusion criteria will be permitted.

4.4. Patient Withdrawal and Replacement

The patient has the right to stop treatment or to withdraw from the study at any time. Patients may continue to repeat cycles (up to 6 cycles) of FPA008 treatment until at least one of the following criteria applies:

Consent withdrawal at the patient's request or at the request of their legally authorized representative Progression of patient's underlying disease Any event that would pose an unacceptable safety risk to the patient An intercurrent illness that would affect assessments of the clinical status to a significant degree and require discontinuation of therapy A positive pregnancy test at any time during the study At the specific request of the Sponsor or its authorized representative (for example, if the study is terminated for reasons of patient safety).

The date and reason for cessation of FPA008 will be documented, and the Investigator must make every effort to perform the End of Treatment Follow-Up visits. Patients will be followed for 90 days (±7 days) after the last dose of FPA008 for safety; those with ongoing SAEs will be followed until either resolution or stabilization.

Data from patients who discontinue prematurely will remain part of the study database.

4.5. Patient Identification and Enrollment

Patients must be able to provide written informed consent and meet all inclusion criteria and none of the exclusion criteria. No waivers of inclusion or exclusion criteria will be granted by the Investigator and Sponsor or its designee for any patient enrolled in the study. Before enrolling a patient, all eligibility criteria must be satisfied. Patients who qualify for Phase 1 of the study will be enrolled into the first available cohort. In Phase 2, a cohort of approximately 30 patients will be enrolled. A total of approximately 42-45 patients will be enrolled in the study.

The Investigator may repeat qualifying lab tests and vitals/ECGs prior to enrollment if a non-qualifying finding is considered an error or an acute finding is likely to meet eligibility criteria on repeat testing.

5. Study Drug 5.1. FPA008 Drug Product

The investigational drug product in this study is FPA008. The investigational supply of FPA008 will be provided to the study centers by the Sponsor (or designee) and will be administered to patients in the clinical study by a trained healthcare professional.

A brief description of the FPA008 drug product is provided below:

Formulation: FPA008 drug substance is comprised of 20 mg/mL FPA008 in a pH 6.3 buffer containing 20 mM L-histidine, 142 mM L-arginine, and 0.01% polysorbate 20.

How Supplied: FPA008 drug product is supplied for IV administration as a sterile, aqueous, colorless, pyrogen-free solution in 5 mL ISO6R Type 1 glass vials fitted with butyl rubber stoppers and flip-up aluminum seals.

Each vial contains a minimum of 5 mL of a 20 mg/mL solution of FPA008 (approximately 100 mg per vial).

Storage Conditions: 2-8° C. (36-46° F.).

FPA008 vials and cartons will be labeled according to local regulations.

5.2. Administration

The dose of FPA008 will be administered based on weight to patients in this study.

A research pharmacist (or other responsible personnel) will prepare the solution for administration. After calculating the number of vials, based on the patient's weight, the study drug product will be diluted in approximately 100 mL of 0.9% sodium chloride solution. Prepared FPA008 should be administered≤6 hours after preparation (ambient temperature). The IV administration set for FPA008 infusion must contain a 0.22 µm in-line filter or a 0.22 µm syringe filter. FPA008 will be administered under medical supervision over approximately 30-minute IV infusion via a peripheral vein or central venous catheter.

If a patient experiences an infusion reaction prior to completion of the infusion, the infusion must be stopped, and the patient should be promptly managed according to signs and symptoms, and local clinical protocol. The infusion may be restarted at a slower rate if all signs and symptoms have resolved. If the signs and symptoms do not resolve, the infusion should not be restarted. Patient should be kept under close observation for at least 1 hour after the end of study drug infusion.

All vials are for single use only. Instructions on study drug preparation and administration will be provided in a Pharmacy Manual.

5.3. Starting Dose and Dose Modifications

The starting dose level of FPA008 and subsequent dose escalations between cohorts in Phase 1 are described in Section 3.1.2. The dose of FPA008 in Phase 2 will be determined by evaluation of the data from Phase 1 of the study.

5.3.1. Dose Escalation of FPA008 Between Cohorts

Dose escalation to the next cohort will only start after the preceding dose cohort has completed the DLT period. Twenty-eight days (DLT period) of safety data must be available for at least 3 safety-evaluable patients prior to a potential dose-escalation decision by the CRC per the CRC Charter. In the event that a patient in a cohort is lacking adequate safety data (e.g., due to early withdrawal from study or poor compliance with the protocol), an additional patient will be enrolled to the cohort.

Dose escalation in each successive dose cohort will proceed in a stepwise fashion. All relevant safety information for the first cohort or the preceding dose cohort will be reviewed by the CRC.

Dose escalation is planned to continue until dose-limiting toxicities occur in 2 or more patients in a cohort. The decision to discontinue dose escalation will be made jointly by the Sponsor and Investigator(s) based on reaching the MTD or a dose level that shows an adequate pharmacodynamic effect.

In Cohort 1, 3 patients will be enrolled initially at a starting dose of 1 mg/kg FPA008, given by infusion. The occurrence of DLTs (Section 5.3.3) will determine whether the dose will be escalated in subsequent cohorts.

The dose escalation decision rules are summarized in Table 2.

TABLE 2

Decision Criteria for Escalation

| Number of Patients with DLTs | Action |
|---|---|
| 0/3 | Open next cohort |
| 1/3 | Enroll 3 more in same cohort |
| ≥2/3 | Stop enrollment. Enter 3 more patients at dose level below, if only 3 were previously entered |
| 1/6 | Open next cohort |
| ≥2/6 | Stop enrollment. Enter 3 more patients at a dose level below or at an intermediate dose level if the current dose level is ≥50% higher than the previous dose level. |

5.3.1.1. Maximum Tolerated Dose

The selection of the RD will be based on clinical response data as well as PK and PD profiles. The Sponsor and Investigators may decide to discontinue dose escalation before reaching the highest planned dose of 4 mg/kg or, potentially, evaluate a higher (>4 mg/kg) or intermediate (3 mg/kg) dose if the safety, PK, and PD data support evaluation of different dose levels.

Escalation to an MTD is not intended, however, may occur. If so, the MTD is defined as the highest dose associated with DLTs in Cycle 1 in less than 33% of patients receiving FPA008 administered on Day 1 and Day 15 of a planned 28-day cycle.

If the MTD is not reached during Phase 1 or subsequent cycles of treatment in Phase 1 provide additional insight regarding the safety profile, the RD may be selected depending on overall tolerability, PK, and estimates of efficacious exposures extrapolated from ongoing clinical evaluations.

5.3.1.2. Toxicity at Lowest Dose Level

If the first dose level of 1 mg/kg is, unexpectedly, found to exceed an MTD, then decisions on how to proceed will be based on safety, tolerability, and PK data; and will be agreed on between the Investigators and the Sponsor.

A lower dose level may be chosen as the next cohort.

5.3.2. Dose Escalation within a Cohort

Intra-patient dose escalation above the starting dose is not permitted. If a patient's dose is decreased for an AE, dose escalation to the originally assigned dose may occur after resolution of the AE and after discussion with and approval by the Sponsor. Recurrence of the AE to greater than Grade 2 will result in permanent dose reduction without re-escalation.

5.3.3. Dose-Limiting Toxicity

DLTs are defined as any of the following events that occur during Cycle 1 of treatment and are assessed by the Investigator with concurrence by the CRC as related to FPA008. As applicable, events will be classified according to the NCI CTCAE (Version 4.03).

Any Grade≥3 related event except the following:
  For elevations in ALT, AST, or CK without associated clinical or laboratory abnormality, the following DLT definitions apply:
    CK associated DLT: CK>10× the upper limit of normal (ULN)
    ALT or AST associated DLT:
      ALT or AST>8×ULN
      ALT or AST>3×ULN and associated total bilirubin>2×ULN Phase 1 patients who experience a DLT during the DLT assessment period (Cycle 1) will be removed from study treatment. Patients experiencing toxicity in cycles after Cycle 1 that would be considered dose limiting during the DLT assessment period are not required to discontinue study participation in the study.

5.3.4. Dose Modification Criteria

Dose reductions may be permitted for patients on prolonged treatment beyond the DLT period in Phase 1 or any patient in Phase 2 per the following guidelines. If dose reductions or interruptions that do not fall within these guidelines are being considered by the Investigator, these will require discussion with and approval by the Sponsor.

Patients may miss up to 2 consecutive doses (up to 6 weeks between doses) for adverse or other events and may resume the study drug if the event returns to baseline or ≤Grade 1 within 6 weeks of treatment interruption. Omission of additional dosing longer than 6 weeks for adverse events will necessitate the patient's discontinuation from the study unless allowed by the Sponsor. Patients may miss doses in the course of participation in the study, including missed doses for scheduled vacations or other personal reasons as needed, but not more than 2 doses sequentially.

The Cycle 2, Day 1 infusion of FPA008 can only be administered after completion of the 28-day DLT window. All subsequent infusions can be administered with a ±3 day window. Patients should not have 2 doses of FPA008 within 7 days. The first dose of each cycle is considered Day 1 of each cycle, cycles will repeat every 28 days unless there is a treatment delay. Patients can have treatment delay of Day 1 of the subsequent cycle as long as the Day 1 treatment is within 6 weeks of the last treatment.

If a patient has an elevation of CK>5×ULN but<10×ULN, the next scheduled study treatment may be delayed up to a maximum of 28 days from the last administered treatment dose, based on Investigator assessment of accompanying signs, symptoms, and additional laboratory findings (Table 3).

In the event of ALT or AST elevations:
At any time, if the elevation in ALT or AST is >3×ULN and accompanied by an elevation in total bilirubin of >2×ULN, FPA008 should be held, and the patient should be withdrawn into safety follow-up.
If ALT or AST is elevated>3×ULN but<5×ULN without bilirubin>2×ULN, the test should be repeated at the next scheduled visit and if ALT or AST are persistently high but still<5×ULN, the dose can be delayed up to a maximum of 28 days. The minimum interval between 2 consecutive doses cannot be less than 7 days.
If a patient has an elevation of ALT or AST>5×ULN but<8×ULN, the next scheduled study treatment may be delayed up to a maximum of 28 days from the last administered treatment dose, based on Investigator assessment of accompanying signs, symptoms, and additional laboratory findings.
If a patient experiences a Grade 3 or higher ALT or AST adverse event attributed to study treatment, or ALT or AST elevation>8×ULN regardless of attribution, the study drug should be discontinued and the patient should be withdrawn from study treatment. Withdrawal from treatment should also occur for patients with ALT or AST elevations>3×ULN accompanied by an elevation in total bilirubin of >2×ULN.

In the event of CK elevations:
Treatment should be discontinued for a CK elevation>10× ULN

TABLE 3

Dose Delay and Modification Guidelines for Study Drug-Related Events other than ALT, AST and CK

| Toxicity Grade | FPA008 Dose | Dose Schedule |
|---|---|---|
| 1 | Continue 100% of dose | No delay or missed dose required |
| 2 | Continue 100% of dose | No delay or missed dose required |
| 3 | Phase 1: May continue at next lower dose level evaluated (e.g., if a Grade 3 AE occurs at 2 mg/kg, patient may continue at 1 mg/kg) following recovery to baseline or Grade 1; If at lowest dose level evaluated (i.e., 1 mg/kg), use Phase 2 dose modification guideline Phase 2: Continue 75% of starting dose following recovery to baseline or Grade 1 | Up to 2 missed doses allowed without Sponsor approval to continue |
| 4 | Phase 1: May continue at next lower dose level evaluated (e.g., if a Grade 3 AE occurs at 2 mg/kg, patient may continue at 1 mg/kg) following recovery to baseline or Grade 1; If at lowest dose level evaluated use Phase 2 Phase 2: Continue 50-75% of starting dose following recovery to baseline or Grade 1 | Up to 2 missed doses allowed without Sponsor approval to continue |

Note:
Table 3 applies to adverse events other than the ALT, AST, and CK rules above.

If a patient's dose is decreased for an adverse event, dose escalation to the originally assigned dose may occur after resolution of the AE and after discussion with and approval by the Sponsor. Recurrence of the AE to greater than Grade 2 will result in permanent dose reduction without re-escalation.

5.3.5. Dose Interruptions During Study Drug Infusion

Infusion of FPA008 must be stopped if any AE≥Grade 3 occurs during the infusion. If bronchospasm or dyspnea occurs in a patient during infusion, the infusion should be stopped.

In addition, at the Investigator's discretion, the infusion rate may be reduced or stopped if a less severe AE (Grade 1 or 2) occurs during the infusion. If a Grade 3 or less severe AE resolves within 6 hours, the infusion may be restarted at half the previous rate. If the same AE appears again with the same severity at any time during the restarted infusion, the infusion should be discontinued, and no further dosing of study drug will occur without consultation with the Sponsor (or designee).

If a patient experiences an infusion reaction, the patient's vital signs (temperature, blood pressure, pulse, and respiration rate) should be monitored during the infusion, as well as every 30 minutes after the infusion for a minimum of 1 hour and until resolution of the infusion reaction.

Systemic hypersensitivity reactions should be managed under the direct supervision of a physician and according to treatment protocols in effect at the investigational site. However, in the absence of such a protocol, the standardized treatment protocol provided in Appendix 6 should be used.

5.4. Blinding and Breaking the Blind

Blinding and breaking the blind are not applicable as this is an open-label study.

5.5. Drug Accountability

The Investigator or appropriately qualified staff is responsible for maintaining accurate study drug accountability records throughout the study.

The Investigator is responsible for returning all unused study drug to the Sponsor (or designee), and must verify that no remaining supplies are in the Investigator's possession. The study site is permitted to destroy used or partially used study drug vials according to the site policy once Sponsor (or designee) approval of its documented destruction procedure has been obtained. Accurate records of all study drug received at, dispensed from, returned to, and disposed of by the study site should be reconciled and recorded by using a drug inventory log during and on completion of the study.

5.6. Investigational Product Compliance

Only qualified trained site personnel may administer FPA008. Pharmacy personnel trained in the study requirements will monitor compliance with the treatment assignments. FPA008 will be infused over approximately 30 minutes via a peripheral vein or central venous catheter by a trained healthcare professional. Records of study medication administered (date, start and stop time, and dose administered relative to time of preparation) will be recorded on the patient's electronic case report form (eCRF).

5.7. Concomitant Medication and Treatment

All concomitant medications including herbal and other non-traditional remedies are to be captured on the eCRF. The following parameters will be collected: generic name, route of administration, start date, stop date, dosage, frequency, and indication. Any changes in the dosage or regimen of a concomitant medication also must be recorded on the eCRF.

At Screening, patients will be asked what medications they have taken during the previous 28 days. At each subsequent study visit, patients will be asked about any changes in concomitant medications since the previous visit.

Throughout the study, Investigators may prescribe any concomitant medications or treatments deemed necessary to provide adequate supportive care except for the following:

- Other experimental drugs or devices
- Other systemic medication for treatment of PVNS such as imatinib or nilotinib
- Chronic daily corticosteroids≥10 mg/kg prednisone (or equivalent)

If a patient uses a prohibited medication or undergoes tumor resection, the Sponsor should be consulted for a decision on whether the patient should be withdrawn from the study.

Patients may initiate or continue pain medications as dictated by standard clinical practice. Transfusions are permitted as needed.

No routine premedication will be administered for the initial FPA008 dose. If a patient develops nausea, vomiting, or other infusion-related AEs, the patient may be premedicated with antiemetics, steroids, or antihistamines prior to subsequent infusions of FPA008 at the discretion of the Investigator. The treatment will be administered according to the institution's standard practice, and should be captured on the patient's eCRF.

6. Parameters and Methods of Assessment

Safety of FPA008 will be assessed by monitoring AEs and changes in physical examinations (including weight), vital signs, 12-lead ECGs, disease related signs and symptoms, and clinical laboratory measurements. Blood samples will be evaluated for immunogenicity.

6.1. Tumor Response Parameters

MRI will be performed at Screening (within 28 days prior to first dose), 4, 8, and 16 weeks following the start of treatment (Appendix 1). MRIs should be completed within 1 week of dose administration when re-imaging is scheduled. All patients should have tumor response parameters assessed at the 30 days (±7 days) and 90 days (±7 days) End of Treatment Follow-up Visits, unless a tumor assessment has been performed within the previous 6 weeks or if tumor progression was previously determined.

Clinical assessment of health outcomes (function, symptoms) will be done at Screening, C1D15 (pre-dose), C2D1 (pre-dose), and then on Day 1 (pre-dose) for all subsequent cycles through 24 weeks or until treatment is discontinued.

Patients who have not progressed after the End of Treatment Follow-up Period are to be followed every 14 weeks (±2 weeks) (see section 7.2.10) until progression, the patient undergoes local therapy (e.g., resection, radiation) or a new systemic therapy is initiated, for up to 52 weeks following C1D1.

Response will be evaluated using RECIST 1.1 (Eisenhauer, 2009) and the Total Volume Score (Tap, 2014) for radiologically measurable disease. MRI will be used for radiologic measurement of tumor.

Linear measurements of diffuse PVNS are complicated by a number of factors. Since the tumors are characteristically amorphous and can fluctuate in shape, correlation of serial linear measurements with changes in tumor volume depends on where the measurements are made. However, poor contrast between the tumor and adjacent tissue in certain locations limits where these measurements can be made accurately. Additionally, linear measurements are highly vulnerable to variations in the plane of section on serially acquired images. Nevertheless, given the longstanding tradition of RECIST in oncology clinical trials, linear measurements of up to two measurable tumor locations per joint or tendon sheath, as per RECIST 1.1 guidelines, will be used in this study as a reference.

Radiologic response will also be assessed by the TVS. The TVS has been used in a recent study of PVNS that showed a treatment effect of a CSF1R tyrosine kinase inhibitor.

The clinical impact of PVNS is believed to stem primarily from the mass effect and local structural damage caused by tumor growth within limited articular and peri-articular spaces. Tumor growth interferes with joint flexion and can also destroy the structural and functional integrity of joints as tumor invades local bones and soft tissues. The goals of imaging in clinical trials of PVNS are thus to monitor changes in the volume of the tumor and to monitor any associated damage to local tissues.

Volumetric quantification of diffuse PVNS is complicated by irregular shape of the tumor, heterogeneous contrast between the tumor and its surrounding structures, and variable enhancement by intravenous gadolinium-based contrast agents. Tumor margins are thus difficult to delineate in certain locations, making automated segmentation unreliable and manual segmentation subjective. Hemosiderin deposition usually does not improve contrast substantially, as the distribution of hemosiderin is variable, heterogeneous, and not always confined to the tumor. Additionally, discriminating viable tumor from inactive scar tissue or intra- and peri-lesional fluid collections can be difficult. Under such circumstances, visual scoring using semi-quantitative ordinal scales is usually more reliable than volumetric quantification, as has been the experience with synovial thickening assessments in clinical trials of arthritis. Trials employing MRI for evaluation of anti-inflammatory therapy for arthritis have been based on semi-quantitative scoring.

The TVS scale is based on 10% increments of the estimated volume of the maximally distended synovial cavity, which varies from joint to joint, or of the maximally distended tendon sheath (assumed to be three times the diameter of the involved tendon). Thus, a tumor that is equal to the volume of a maximally distended synovial cavity or tendon sheath would be scored 10, whereas a tumor that was 70% of that volume would be scored 7, and a tumor twice that volume would be scored 20.

Individual patient outcomes by TVS are classified according to the following criteria:
Complete Response (CR): lesion completely gone
Partial Response (PR): ≥50% decrease in volume score relative to baseline
Progressive Disease (PD): ≥30% increase in volume relative to lowest score during the study whether at baseline or some other visit
Stable Disease (SD): does not meet any of the prior criteria based on score during study.
Note: Tumor assessments performed as part of the patient's standard of care within 28 days (4 weeks) of the first dose of FPA008 do not need to be repeated during Screening.

6.2. Safety Parameters 6.2.1. Laboratory Parameters

Laboratory assessments will be performed locally at each study site's laboratory by means of their established methods. Before starting the study, the Investigator will provide the Sponsor (and/or designee) with a list of the normal ranges and units of measurement.

Blood samples should be taken using standard venipuncture techniques. The following laboratory parameters (Table 5) will be determined in accordance with the Schedule of Assessments (Appendix 1):

TABLE 5

| Laboratory Assessments | |
|---|---|
| Hematology: Complete blood cell (CBC) with differential: | |
| white blood cells (WBC) | platelets |
| ANC | hemoglobin |
| neutrophils (%) | hematocrit |
| eosinophils (%) | red blood cells (RBC) |
| basophils (%) | RBC indices: |
| lymphocytes (%) | mean corpuscular volume (MCV) |
| monocytes (%) | mean corpuscular hemoglobin (MCH) |
| | mean corpuscular hemoglobin concentration (MCHC) |
| Urinalysis: | |
| Dipstick (appearance, color, pH, specific gravity, ketones, protein, glucose, bilirubin, nitrite, urobilinogen, and occult blood) | |
| If dipstick is positive (2+ or greater) for blood or protein, perform a microscopic examination. | |
| Clinical chemistry: | |
| albumin | alkaline phosphatase |
| glucose | ALT (SGPT) |
| lactate dehydrogenase (LDH) | AST (SGOT) |
| Troponins (cardiac and skeletal) | CK isoenzymes (if CK abnormal) |
| blood urea nitrogen (BUN) | potassium |
| calcium | sodium |
| chloride | total bilirubin |
| carbon dioxide ($CO_2$) | total cholesterol |
| creatinine | total protein |
| direct bilirubin | uric acid |
| phosphate | CK (creatinine kinase) |

TABLE 5-continued

| Laboratory Assessments | |
|---|---|
| Other chemistry tests: | |
| Magnesium | |
| Coagulation: | |
| INR | APTT |
| PT | |
| Serum pregnancy test: | |
| For females of childbearing potential only. | |
| Other test: | |
| Antinuclear antibodies (ANA) | |

Abnormal laboratory results that lead to a change in patient treatment management (e.g., dose delay, requirement for additional medication or monitoring) are considered clinically significant for the purposes of this study and will be recorded on the AE page of the eCRF. Values meeting SAE criteria must be reported as SAEs.

The Investigator's determination of relationship of the AE to drug therapy and counter measures undertaken will be documented and noted on the eCRF.

6.2.2. Vital Signs

Vital signs will include sitting blood pressure, pulse, respiration rate, and temperature. All vital signs will be obtained after the patient has been resting for at least 5 minutes. Vital signs will be performed in accordance with the Schedule of Assessments (Appendix 1).

6.2.3. Electrocardiograms

Twelve-lead ECGs will be performed in accordance with the Schedule of Assessments (Appendix 1). The Investigator must review the ECG, document this review in the source documents, and record any clinically significant changes that occur during the study as an AE in the eCRF.

6.2.4. Pregnancy

Pregnancy is an exclusion criterion and women of childbearing potential must not be considering getting pregnant during the study. A negative serum pregnancy test fewer than 5 days prior to first dosing with FPA008 treatment is mandatory. Patients of reproductive potential (males and females) must practice 2 effective contraception methods (Section 4.2). during the study and for 6 months after last treatment.

6.2.5. Physical Examinations

Physical examinations will be performed in accordance with the Schedule of Assessments (Appendix 1).

A complete physical examination including height and weight will be performed at Screening. Complete physical examinations should be conducted per the Schedule of Events (Appendix 1).

6.2.6. Immunogenicity

Immunogenicity, defined as an immune response to FPA008, will be assessed by measurement of total anti-FPA008 antibodies from all patients. Immunogenicity testing will consist of screening, confirmation, and titration.

Samples for immunogenicity assessment will be drawn from each patient at the time points designated in Appendix 2. Samples for immunogenicity testing will be collected and processed according to the instruction provided in the Laboratory Manual.

6.2.7. ECOG Performance Status

ECOG performance status will be assessed at Screening, within 72 hours prior to dosing, and through the End of Treatment Follow-up Period (Appendix 1).

6.3. Pharmacokinetic Parameters

In this study, samples for the determination of serum FPA008 will be collected as outlined in Appendix 2. The sampling will allow determination of the exposure (AUC), $C_{max}$, $C_{min}$ (trough concentration), CL, and $V_{ss}$. Other PK parameters, such as accumulation ratio and half-life, may also be calculated as data allow.

These samples will be collected and processed according to the instructions provided in a separate Laboratory Manual.

6.4. Pharmacodynamic Parameters

The following exploratory endpoints will be assessed (Appendix 2):
- Serum: CSF1 and IL34 ligand concentration, CTx, and TRAP5b bone resorption marker concentrations
- Whole blood—$CD14^+/CD16^+$ monocyte subsets levels The following procedures (see Appendix 1) only apply to patients who sign the applicable Optional Research Informed Consent Form; the purpose of these procedures is to understand the impact of FPA008 on changes in local biomarkers of inflammation (synovium and synovial fluid) and distribution of FPA008 to the involved joint (synovial fluid):
- Synovium (optional)
- Evaluate synovial biopsy for CSF1 gene translocation (if not previously done) at pretreatment
- Baseline and on treatment synovial biopsy, IHC for:
- CSF1 and CSF1R
- CD68
- Synovial fluid (optional)
- FPA008 concentration; cellular component for above markers by IHC.

6.5. Patient and Clinician Reported Outcome Measures

Clinical assessment of health outcomes (function, symptoms) will be done at Screening, C1D15 (pre-dose), C2D1 (pre-dose), and then on Day 1 (pre-dose) for all subsequent cycles through 24 weeks or until treatment is discontinued, and through the End of Treatment Follow-up Period. Patients who have not progressed and enter Long-Term Follow-up are to be followed every 14 weeks (±2 weeks) until progression, the patient undergoes local therapy (e.g., resection, radiation) or a new systemic therapy is initiated, for up to 52 weeks following C1D1. The following tools will be used to collect exploratory endpoint data on symptom and functional outcomes:

- Ogilvie-Harris (OH) Scale (Appendix 4): This tool was developed specifically for patients with PVNS (Ogilvie-Harris, 1992) and has been used in other PVNS publications (De Ponti, 2003; Rhee, 2010). Characteristics of this tool include the following:
- It is a clinician reported outcome (CRO) measure
- It is based on a 0-3 interval scale for each of the 4 domains:
- Pain
- Synovitis/effusion
- Range of motion
- Functional capacity
- It uses lower end of the scale (score min=0) indicating severe disability, pain and functional loss and the higher values (score max=12) indicating no disability. Scores can be summed and classified as follows:
- Poor condition (0-3 points)
- Fair condition (4-6 points)
- Good condition (7-9 points)
- Excellent condition (10-12 points)

Is selected for this study relative to other location-specific outcome measures (such as the WOMAC, KOOS, etc.) because:
- It can be used in any joint affected by PVNS
- It is specific to the disease of PVNS by addressing the symptomology of PVNS (pain and synovitis/effusion)
- It has a low respondent burden—4 "questions"
- Has, however, only been published in patients with PVNS of the knee and has not been validated against a gold-standard outcomes measure such as the SF-36 or EQ-5D-5L scales. Thus the EQ-5D-5L scale (a patient-reported outcome) will also be used in this study.
- EQ-5D-5L (Appendix 5): This is a well-known generic measure of health status originally published in 2001 (Rabin) which includes the following characteristics:
- Has been used in numerous diseases and chronic conditions in multiple countries
- Is a patient reported outcome (PRO) measure
- Is used as a functional assessment in an active PVNS clinical trial (MCS110, Novartis)
- Is based on a 0-5 interval scale for each of the 5 domains with the lower end of the scale (score min=0) anchored at death (or worse than death) health state and the higher values (score max=100) anchored at perfect health state:
  (1) Mobility
  (2) Self-care
  (3) Usual activities
  (4) Pain/discomfort
  (5) Anxiety/depression
- It also uses a VAS to measure the responders current health on a 20-cm vertical line with 0="worst imaginable health" and 100="best imaginable health"
- It has been validated in multiple countries and is available in 119 languages. It has a low respondent burden with only 6 questions and is available in several media (paper, web, and tablet).

7. Study Conduct

7.1. Overview of Patient Assessments

After an initial Screening period of up to 28 days (4 weeks), patients will be treated with FPA008 every 2 weeks (±3 days) in 28-day cycles, and FPA008 will be administered over approximately 30 minutes. All time points of assessments should be completed in the timeframe stated. Assessments performed prior to the patient signing the informed consent are acceptable only if confirmed to have been standard of care.

The schedule of detailed patient assessments is shown in Appendix 1 and Appendix 2. Instructions for the sampling and processing of PK, PD, and immunogenicity data are described in a separate, protocol-specific laboratory manual.

7.2. Study Assessments and Procedures by Visit

7.2.1. Screening Period (Day −28 to Day 0)

Patients who have fully consented to participation in the study will undergo Screening assessments within 28 days (4 weeks) prior to administration of the first infusion of FPA008 (unless otherwise stated). To determine if the patient meets all the inclusion criteria and does not violate the exclusion criteria, the following procedures will be performed (Appendix 1):
- Written, signed informed consent must be collected prior to any study-specific procedures
- Complete medical and disease history
- Demographic and baseline characteristics
- Vital signs (sitting blood pressure, pulse, respiration rate, and temperature [° C.] after 5 minutes rest)

Complete physical examination, including height and weight

ECOG performance status evaluation 12-lead ECG (required at Screening, and if clinically indicated during the study)

AE reporting, if applicable

Document prior and concurrent medications

Quantiferon test (for latent TB)

Clinical safety labs as outlined in Table 5 (including ANA)

Ogilvie-Harris and EQ-5D-5L assessments

Optional archival tissue

Optional synovial biopsy

Optional synovial fluid aspirate

Serum pregnancy test (beta-human chorionic gonadotropin [β-HCG]), ≤5 days prior to Cycle 1, Day 1, for women of childbearing potential Radiological imaging: MRI of the involved joint(s) is to be performed within 28 days prior to the first infusion of FPA008. If the MRI is performed as part of the patient's standard of care within 28 days of the first study infusion it does not need to be repeated if the documentation of results is provided and is adequate for an assessment.

Note: A protocol-specific patient registration form must be submitted to the Sponsor (or designee) to confirm patient eligibility prior to initiation of study treatment.

7.2.2. Treatment Allocation (Dosing Assignment)

This is an open-label study. Enrollment numbers will be faxed or emailed to the Investigator (or designee). The Sponsor (or designee) will maintain records of the number of patients treated within a specific cohort and will determine to which treatment cohort newly enrolled patients will be assigned.

7.2.3. Phases 1 and 2: Cycle 1, Day 1

The following procedures will be performed:

Prior to FPA008 infusion (within 72 hours unless otherwise stated):

Verification of eligibility

Update medical and disease history to capture any changes from Screening

AE reporting, if applicable

Review of concomitant medications

Record weight

Vital signs (sitting blood pressure, pulse, respiration rate, and temperature [° C.] after 5 minutes rest)

ECOG performance status evaluation

Clinical safety labs with the exception of urinalysis and ANA as outlined in Table 5

Serum β-hCG (evaluated by local laboratories) will be performed 5 days prior to the first dose of FPA008 only on women of childbearing potential PK, ADA, serum biomarkers and CD14$^+$/CD16$^+$ monocytes sample collections (within 4 hours) as outlined in Appendix 2.

Study drug administration: Administer FPA008, by IV infusion over approximately 30 minutes Post FPA008 administration:

PK, serum biomarkers and CD14$^+$/CD16$^+$ monocytes sample collections (±5 min) as outlined in Appendix 2.

Post-dose Vital signs (sitting heart rate, blood pressure, respiration rate, and temperature [° C.] after 5 minutes rest) at the following time points after completion of the IV infusion:

5 minutes, 15 minutes, 30 minutes, and 1 hour

AE reporting, if applicable

Review of concomitant medications

7.2.4. Phases 1 and 2: Cycle 1, Day 2

PK, serum biomarkers, and CD14$^+$/CD16$^+$ monocytes sample collections as outlined in Appendix 2.

AE reporting, if applicable

Review of concomitant medications

7.2.5. Phases 1 and 2: Cycle 1, Day 8

Study patients will return to the study center on Day 8 (±2 days). No treatment will be administered.

The following assessments will be completed:

Vital signs (sitting blood pressure, pulse, respiration rate, and temperature [° C.] after 5 minutes rest)

Clinical safety labs with the exception of ANA, as outlined in Table 5

PK, serum biomarkers, CD14$^+$/CD16$^+$ monocytes sample collections as outlined in Appendix 2.

AE reporting, if applicable

Review of concomitant medications

7.2.6. Phases 1 and 2: Cycle 1, Day 15

Study patients will return to the study center on Day 15, and the following assessments will be completed.

Prior to FPA008 infusion (within 72 hours unless otherwise stated):

Record weight

Vital signs (sitting blood pressure, heart rate, respiration rate, and temperature [° C.] after 5 minutes rest)

Clinical safety labs with exception of urinalysis and ANA as outlined in Table 5

Ogilvie-Harris and EQ-5D-5L assessments

PK, ADA, serum biomarkers and CD14$^+$/CD16$^+$ monocytes sample collections (within 4 hours) as outlined in Appendix 2

Update medical and disease history

AE reporting, if applicable

Review of concomitant medications

Study drug administration: Administer FPA008, by IV infusion over 30 minutes

Post FPA008 administration:

PK sample collection 15 minutes (±5 min) after end of infusion (as outlined in Appendix 2)

Post-dose Vital signs (sitting heart rate, blood pressure, respiration rate, and temperature [° C.] after 5 minutes rest) at the following time points after completion of the IV infusion:

5 minutes, 15 minutes, 30 minutes, and 1 hour 12-lead ECG (within approximately 30 minutes post-dose after PK/PD sample collection)

AE reporting, if applicable

Review of concomitant medications

7.2.7. Phase 1: End of Cycle 1

For Phase 1 patients, if at the end of Cycle 1 the Investigator determines that the patient may benefit from continued dosing with FPA008, entry into the Extended Treatment Period may be offered.

If the patient is continuing onto the Extended Treatment Period (Cycle 2 and beyond), proceed to procedures outlined in Section 7.2.8.

If the patient does not qualify to receive further doses of FPA008, the patient will return to the clinic for the End of Treatment Follow-up Visits.

7.2.8. Phase 1 Extended Treatment/Phase 2 Cycle 2 and Subsequent Cycles

Phase 1 Extended treatment may begin on Cycle 2, Day 1. Dosing will be discontinued if the patient experiences either disease progression or unacceptable toxicity.

At each infusion visit, patients are to remain at the study site after each administration of FPA008 until completion of all post-dose assessments for safety monitoring. The following assessments will be performed at each visit unless otherwise noted ((Appendix 1):

7.2.8.1. Phases 1 and 2: Cycle 2 and Subsequent Cycles, Day 1

Prior to each infusion of study drug (within hours unless otherwise stated):
- Vital signs (sitting heart rate, blood pressure, respiration rate, and temperature [° C.] after 5 minutes rest)
- Complete physical examination including weight at Cycle 2, 4, and 6
- ECOG performance status evaluation
- Ogilvie-Harris and EQ-5D-5L assessments
- Clinical safety labs with the exception of urinalysis and ANA as outlined in Table 5
- PK, ADA, serum biomarkers and $CD14^+/CD16^+$ monocytes sample collections (within ≤4 hours) on Day 1 of Cycles 2, 3, and 5, as outlined in Appendix 2
- MRI of the involved joint(s) using the same physical or radiologic parameter(s) used to evaluate baseline tumor measurements are to be done within 1 week of C2D1, C3D1, and C5D1
- Optional synovial biopsy up to −2 days prior to dose administration (Cycle 2 only) as outlined in Appendix 1
- Optional synovial fluid aspirate up to −2 days prior to dose administration (Cycle 2 only) as outlined in Appendix 1
- AE reporting, if applicable
- Review of concomitant medications Study drug administration: Administer FPA008, by IV infusion over approximately 30 minutes Post study drug administration:
- Post-dose Vital signs (sitting heart rate, blood pressure, respiration rate, and temperature [° C.] after 5 minutes rest) at the following time points after completion of the IV infusion:
  5 minutes, 15 minutes, 30 minutes, and 1 hour
- PK sample collection 15 minutes (±5 min) after end of infusion on Day 1 of Cycles 3, and 5 (Appendix 1).
- AE reporting, if applicable
- Review of concomitant medication

7.2.8.2. Phases 1 and 2: Cycle 2 and Subsequent Cycles, Day 15

Prior to each infusion of study drug (within hours unless otherwise stated):
- Vital signs (sitting heart rate, blood pressure, respiration rate, and temperature [° C.] after 5 minutes rest)
- Clinical safety labs with the exception of urinalysis and ANA as outlined in Table 5
- AE reporting, if applicable
- Review of concomitant medications Study drug administration:
- Administer FPA008, by IV infusion over approximately 30 minutes Post study drug administration:
- Post-dose Vital signs (sitting heart rate, blood pressure, respiration rate, and temperature [° C.] after 5 minutes rest) at the following time points after completion of the IV infusion:
  5 minutes, 15 minutes, 30 minutes, and 1 hour
- 12-lead ECG (within approximately 30 minutes post-dose after PK/PD sample collection)
- AE reporting, if applicable
- Review of concomitant medication

7.2.9. End of Treatment Follow-Up Period

Patients will return to the study center three times, approximately 30 days (±7 days), 60 days (±7 days), and 90 days (±7 days) after their last infusion of FPA008, to complete the End of Treatment Follow-up Period.

The following assessments will be performed:
- Vital signs (sitting pulse, blood pressure, respiration rate, and temperature [° C.] after 5 minutes rest)
- 12-lead ECG at the 30 days (±7 days) End of Treatment Follow-up Visit only
- Complete physical examination at the 30 days (±7 days) End of Treatment Follow-up Visit only. Weight is to be recorded at all visits
- ECOG performance status evaluation
- Clinical safety labs as outlined in Table 5 (including ANA at the 30 days (±7 days) End of Treatment Follow-up Visit only)
- PK, ADA, serum biomarkers and $CD14^+/CD16^+$ monocytes sample collections as outlined in Appendix 2
- Serum β-hCG (evaluated by local laboratories) in women of child-bearing potential
- MRI of the involved joint(s), Ogilvie-Harris, and EQ-5D-5L assessments at the 30 days (±7 days) and 90 days (±7 days) End of Treatment Follow-up Visits. These can be omitted if performed within 6 weeks prior or if tumor progression was previously determined.) Patients who have not progressed at treatment discontinuation and agree to continue participation in the study are to be followed every 14 (±2) weeks until progression, the patient undergoes local therapy (e.g., resection, radiation) or a new systemic therapy is initiated, for up to 52 weeks following C1D1.
- AE reporting, if applicable
- Review of concomitant medications

7.2.10. Long-Term Follow Up Period

Patients who have not progressed should continue onto Long-Term Follow-up after completing the End-of-Treatment Follow-up Period. Patients will be followed every 14 weeks (±2 weeks) until progression, the patient undergoes local therapy (e.g., resection, radiation) or a new systemic therapy is initiated, for up to 52 weeks following C1D1.

The following assessments will be performed:
- Clinical safety labs with the exception of urinalysis and ANA
- PK, ADA, serum biomarkers and $CD14^+/CD16^+$ monocytes sample collections as outlined in Appendix 2
- MRI of the involved joint(s), Ogilvie-Harris, and EQ-5D-5L assessments
- AE reporting for ongoing adverse events thought to be related to study treatment, if applicable
- Reporting of concomitant medications (local therapy (e.g., resection, radiation) or a new systemic therapy only)

8. Statistical Methods

Before database lock, a separate statistical analysis plan (SAP) will be finalized, providing detailed methods for the analyses outlined below.

Any deviations from the planned analyses will be described and justified in the final integrated study report.

8.1. Study Patients

8.1.1. Disposition of Patients

The number and percentage of patients evaluable for DLT, safety, efficacy, PK and PD will be presented. Reasons for withdrawal will also be summarized.

8.1.2. Protocol Deviations

A summary of the number and percentage of patients with protocol deviations by type of deviation will be provided. Deviations will be defined in the SAP prior to database lock.

8.1.3. Analysis Populations

The following analysis populations are defined for the study:

Safety Population—all patients who have received any portion of at least one dose of FPA008.

DLT-Evaluable Population—all patients enrolled into Phase 1 of the study who received at least 2 doses of FPA008 and completed Cycle 1 of treatment, or who experienced a DLT in Cycle 1.

PK-Evaluable Population—all patients who have received at least one dose of FPA008 and have had adequate PK assessments drawn for determination of the PK profile.

Efficacy-Evaluable Population—all patients who met eligibility criteria, received at least 1 dose of FPA008, have measurable tumor lesions at baseline, and have at least 1 post-baseline disease assessment.

Intent-to-Treat Population (ITT)—all enrolled patients. Patient without post-baseline disease assessment will be considered as non-responder.

8.2. General Considerations

All analyses will be descriptive and will be presented by dose group and overall as appropriate. Patient data from Phase 2 will be summarized as a separate group. All patients dosed at the RD will also be summarized. Data collected in this study will be presented using summary tables and patient data listings. Continuous variables will be summarized using descriptive statistics, specifically the number of valid cases, arithmetic mean, median, standard deviation (SD), minimum, and maximum. Categorical variables will be summarized by frequencies and percentages.

A change to the data analysis methods described in the protocol will require a protocol amendment only if it alters a principal feature of the protocol. The SAP will be finalized prior to database lock. Any changes to the methods described in the final SAP will be described and justified in the clinical study report.

8.3. Demographics, Baseline Characteristics, and Concomitant Medications

Demographic data, medical history, other baseline characteristics, concomitant disease, and concomitant medication will be summarized by cohort and overall. To determine whether the criteria for study conduct are met, corresponding tables and listings will be provided. These will include an assessment of protocol deviations, study drug accountability, and other data that may impact the general conduct of the study.

8.4. Treatment Compliance

Treatment administration will be summarized by cohort including dose administration, dose modifications or delays, cumulative dose, average dose, number of infusions, and the duration of therapy.

8.5. Analyses of Tumor Response

Patients will be classified according to their best overall tumor response (complete response [CR], partial response [PR], stable disease [SD], or progressive disease [PD]). Frequencies, proportions, and exact 95% CI of patients, when appropriate, stratified by their best overall tumor response will be calculated. Patients with a best overall tumor response of CR or PR with duration of at least 4 weeks (28 days) will be further classified as having an objective tumor response. Listing of patients with an objective tumor response will be presented.

Patients will be classified for response by RECIST 1.1 and the Total Volume Score. The Tumor Volume Score classifies response according to the following definitions: Complete Response [(CR) lesion completely gone by the end of the study], Partial Response [(PR)≥50% decrease in volume score relative to baseline], Progressive Disease [(PD)≥30% increase in volume relative to lowest score during the study whether at baseline or some other visit] or Stable Disease [(SD) does not meet any of the prior criteria based on score during study].

In addition to local review, all MRI scans will be centrally reviewed, and concordance between the local and central assessments of tumor response will be determined.

Duration of response will be calculated as the number of days from the first documentation of overall response (CR or PR) to the first documentation of disease progression or death, whichever comes first. Patients who are alive and progression-free at the time of data analysis will be censored at the time of their last assessment for tumor response.

In patients who respond adequately such that a decision is made to resect residual disease, the duration of response will be censored at the time of the surgical procedure.

8.6. Safety Analyses

Safety analyses will be performed separately within both phases of the study and for all patients combined. Data from all patients that receive any portion of at least 1 dose of FPA008 will be included in the safety analyses. AEs, clinical laboratory information, vital signs, ECOG performance status, weight, ECGs, and concomitant medications/procedures will be tabulated and summarized.

AEs will be summarized overall and with separate summaries for serious AEs, AEs leading to discontinuation, AEs leading to death, and NCI CTCAE Version 4.03 Grade 3 or higher AEs.

Weight and vital signs will be summarized descriptively (N, mean, standard deviation, median, minimum, and maximum). ECOG performance status will be summarized categorically and descriptively.

Shift tables displaying patient counts and percentages classified by baseline grade and maximum grade on treatment will be provided for laboratory data by cohort and overall. A marked laboratory change is defined as a shift from a baseline Grade 0 to Grade 3 (non-hematologic) or Grade 4 (hematologic) on treatment, or a shift from a baseline Grade 1 to Grade 4 on treatment. The number and percentage of patients with marked laboratory changes will be tabulated by cohort and overall.

8.7. Efficacy Analysis

Efficacy analyses will be descriptive. The overall response rate will be summarized with frequencies and percentages. The duration of response for CR and PR patients will be summarized with descriptive statistics (N, arithmetic mean, standard deviation, median, minimum, and maximum) as well as categorically. Response and duration of response will be determined using RECIST 1.1. Kaplan-Meier methodology will be used to summarize duration of response and PFS.

8.8. Pharmacokinetic Analyses

Individual and mean (±SD) serum FPA008 concentration-time data will be tabulated and plotted by dose level. FPA008 PK parameters will be calculated from the serum drug concentration-time data using a non-compartmental analysis (NCA) method with intravenous infusion input in Phoenix WinNonLin (Certara L P, St. Louis, Mo.). Alternative methods may be considered. Estimated individual and mean (±SD) PK parameters will be tabulated and summarized by dose level. Other descriptive statistics might be reported for serum FPA008 concentration-time data and estimated PK parameters. Dose proportionality, drug accumulation, and attainment of steady state will be evaluated whenever it is possible.

The impact of immunogenicity on FPA008 exposure will be assessed.

8.9. Interim Analyses

No formal interim analysis is planned.

Safety data will be reviewed on a routine basis by the Sponsor and CRO. In Phase 1, the Sponsor (and/or designee) and Investigator(s) will review safety data from each dose cohort prior to dose escalation or de-escalation. Adverse event data from the extended treatment period will be presented to the medical monitors when available.

8.10. Determination of Sample Size

Three patients per dose group, with a sample size increase to 6 in the case of DLT, is generally accepted as adequate to determine the safety of escalating doses of novel oncologic drugs. If a DLT is observed in 1 of 3 patients, then 3 additional patients will be enrolled at that same dose level. Dose escalation will continue until 2 of 3-6 patients treated at a dose level experience a DLT. The MTD is defined as the maximum dose at which<33% of patients experience a DLT during Cycle 1. After the MTD is determined, additional patients may be recruited at that dose level to further characterize the safety, PK, PD, and preliminary efficacy of FPA008. It is anticipated that 12-15 patients may be enrolled in Phase 1.

For the objective of estimating the ORR of FPA008 in patients with PVNS/dt-TGCT, it is estimated that approximately 30 patients will be enrolled in Phase 2. In addition, a total of approximately 33 to 36 patients will be enrolled at the RD overall. The following Table 6 displays the corresponding 95% CI and the precision for various sample sizes and observed response rates (Agresti, 1998).

TABLE 6

Probability of Responders

| Sample Size | Observed Response Rate | 95% CI | Precision (longest one-sided CI length) |
|---|---|---|---|
| 30 | 15/30 (50%) | 33.2% to 66.9% | ~17% |
|  | 16/30 (53%) | 36.1% to 69.8% | ~17% |
|  | 17/30 (57%) | 39.2% to 72.6% | ~18% |
|  | 18/30 (60%) | 42.3% to 75.4% | ~18% |
|  | 19/30 (63%) | 45.5% to 78.2% | ~17% |
|  | 20/30 (67%) | 48.7% to 80.9% | ~18% |
|  | 21/30 (70%) | 52.0% to 83.5% | ~18% |
|  | 22/30 (73%) | 55.4% to 86.0% | ~18% |
|  | 23/30 (77%) | 58.8% to 88.5% | ~18% |
|  | 24/30 (80%) | 62.3% to 90.9% | ~18% |
| 35 | 17/35 (49%) | 33.0% to 64.4% | ~16% |
|  | 18/35 (51%) | 35.6% to 67.0% | ~16% |
|  | 19/35 (54%) | 38.2% to 69.5% | ~16% |
|  | 20/35 (57%) | 40.8% to 72.0% | ~16% |
|  | 21/35 (60%) | 43.5% to 74.5% | ~16% |
|  | 22/35 (63%) | 46.3% to 76.9% | ~17% |
|  | 23/35 (66%) | 49.1% to 79.2% | ~17% |
|  | 24/35 (69%) | 51.9% to 81.6% | ~17% |
|  | 25/35 (71%) | 54.8% to 83.8% | ~16% |
|  | 26/35 (74%) | 57.8% to 86.0% | ~16% |
|  | 27/35 (77%) | 60.7% to 88.2% | ~16% |
|  | 28/35 (80%) | 63.8% to 90.3% | ~16% |
| 40 | 20/40 (50%) | 35.2% to 64.8% | ~15% |
|  | 21/40 (53%) | 37.5% to 67.1% | ~15% |
|  | 22/40 (55%) | 39.8% to 69.3% | ~15% |
|  | 23/40 (58%) | 42.2% to 71.5% | ~16% |
|  | 24/40 (60%) | 44.6% to 73.7% | ~15% |
|  | 25/40 (63%) | 47.0% to 75.8% | ~16% |
|  | 26/40 (65%) | 49.5% to 77.9% | ~16% |
|  | 27/40 (68%) | 51.9% to 80.0% | ~16% |
|  | 28/40 (70%) | 54.5% to 82.0% | ~16% |
|  | 29/40 (73%) | 57.0% to 84.0% | ~16% |
|  | 30/40 (75%) | 59.6% to 86.0% | ~16% |
|  | 31/40 (78%) | 62.3% to 87.9% | ~16% |
|  | 32/40 (80%) | 65.0% to 89.8% | ~15% |

REFERENCES

Agresti A, Coull B. Approximate is better than "exact" for interval estimation of binomial proportions. J Am Stat Assoc, 1998; 52:119-26.

Bartocci A, Mastrogiannis D, Migliorati G, Stockert R, Wolkoff A, Stanley E. Macrophages specifically regulate the concentration of their own growth factor in the circulation. Proc Natl Acad Sci, 1987; 84:6179-6183.

Cassier P, Gelderblom H, Stacchiotti S, Thomas D, Maki R, Kroep J, et al. Efficacy of imatinib mesylate for the treatment of locally advanced and/or metastatic tenosynovial giant cell tumor/pigmented villonodular synovitis. Cancer, 2012; 118; 1649-55.

Cassier P, Gomez-Roca C, Italiano A, Cannarile M, Ries C, Brillouet A, et al. Phase 1 study of RG7155, a novel anti-CSF1R antibody, in patients with locally advanced pigmented villonodular synovitis (PVNS). J Clin Oncol suppl, 2014; 32:5 abstract 10504.

Dale D, Boxer L, Liles W. The phagocytes: neutrophils and monocytes. Blood, 2008; 112(4):935-45.

De Ponti A, Sansone V, Malcherè M. Result of arthroscopic treatment of pigmented villonodular synovitis of the knee. Arthroscopy, 2003; 6:602-7.

Eisenhauer E, Therasse P, Bogaerts J, Schwartz L, Sargent D, Ford R, et al. New response evaluation criteria in solid tumours: revised RECIST guideline (version 1.1). Eur J Cancer, 2009; 45:228-247.

Greter M, Lelios I, Pelczar P, Hoeffel G, Price J, Leboeuf M, et al. Stroma-derived Interleukin-34 controls the development and maintenance of Langerhans cells and the maintenance of microglia. Immunity, 2012; 37:1050-1060.

Hamilton J, Achuthan A. Colony stimulating factors and myeloid cell biology in health and disease. Trends in Immunology, 2013; 34:81-89.

Herdman M, Gudex C, Lloyd A, Janssen M, Kind P, Parkin D, et al. Development and preliminary testing of the new five-level version of EQ-5D (EQ-5D-5L). Qual Life Res, 2011; 20:1727-36.

Ogilvie-Harris D, McLean J, Zarnett M. Pigmented villonodular synovitis of the knee. The results of total arthroscopic synovectomy, partial arthroscopic synovectomy, and arthroscopic local excision. J Bone Joint Surg Am, 1992; 74:119-123.

Rabin R, de Charro F. EQ-5D: A measure of health status of the EuroQoL Group. Ann Med, 2001; 33:337-343.

Radi Z, Guzman R, Bell R. Increased connective tissue extracellular matrix in the op/op model of osteopetrosis. Pathobiology, 2009; 76:199-203

Radi Z, Koza-Taylor P, Bell R, Obert L, Runnels H, Beebe J, et al. Increased serum enzyme levels associated with Kupffer cell reduction with no signs of hepatic or skeletal muscle injury. Am J Pathol, 2011; 179: 240-47.

Ravi V, Wang W-L, Lewis, V. Treatment of tenosynovial giant cell tumor and pigmented villonodular synovitis. Curr Opin Oncol, 2011; 23:361-6.

Rhee P C, Sassoon A A, Sayeed S A, Stuart M S, Dahm D L. Arthroscopic treatment of localized pigmented villonodular synovitis: long-term functional results. Am J Orthop 2010 September; 39(9):E90-4.

Ries C, Cannarile M, Hoves S, Benz J, Wartha K, Runza V, et al. Targeting tumor-associated macrophages with anti-CSF-1R antibody reveals a strategy for cancer therapy. Cancer Cell, 2014; 25:846-59.

Tap W D, Anthony S P, Chmielowski B et al. A pilot study of PLX3397, a selective colony-stimulating factor 1 receptor (CSF1R) kinase inhibitor, in pigmented villonodular synovitis (PVNS). J Clin Oncol 2014; 32:5s (suppl; abstr 10503).

Wang Y, Szretter K, Vermi W, Gilfillan S, Rossini C, Cella M, et al. IL-34 is a tissue-restricted ligand of CSF1R required for the development of Langerhans cells and microglia. Nat Immunol, 2012; 13:753-762.

West R, Rubin B, Miller M, Subramanian S, Kaygusuz G, Montgomery K, et al. A landscape effect in tenosynovial giant-cell tumor from activation of CSF1 expression by a translocation in a minority of tumor cells. Proc Natl Acad Sci USA, 2006; 103:690-5.

Yoshida H, Hayashi S, Kunisada T, Ogawa M, Nishikawa S, Okamura H, et al. The murine mutation osteopetrosis is in the coding region of the macrophage colony stimulating factor gene. Nature, 1990; 345:442-444.

LIST OF ABBREVIATIONS AND DEFINITIONS

ADA Anti-drug antibody
ADCC Antibody-dependent cell-mediated cytotoxicity
AE Adverse event
ALT Alanine transaminase
ANC Absolute neutrophil count
ANOVA Analysis of variance
AST Aspartate transaminase
AUC Area under serum concentration-time curve
β-HCG Beta-human chorionic gonadotropin
BUN Blood urea nitrogen
CBC Complete blood count
CK Creatinine kinase
$C_{max}$ Maximum serum concentration
$C_{min}$ Minimum serum concentration
CL Clearance
$CO_2$ Carbon dioxide (bicarbonate)
CR Complete response
CRC Cohort Review Committee
CRO Clinician reported outcome
CRO Contract research organization
CSF1 Colony stimulating factor-1
CT Computed tomography
CTx Collagen-type I C-terminal telopeptide
CTCAE Common Terminology Criteria for Adverse Events
DLT Dose-limiting toxicity
dt-TGCT Diffuse type tenosynovial giant cell tumor
eCRF Electronic case report form
ECG Electrocardiogram
ECOG Eastern Cooperative Oncology Group
FDA Food and Drug Administration
FNA Fine needle aspiration
GCP Good Clinical Practice
GLP Good Laboratory Practice
HIV Human immunodeficiency virus
IB Investigator's Brochure
ICF Informed consent form
ICH International Conference on Harmonization
IEC Independent Ethics Committee
IHC Immunohistochemistry
IND Investigational New Drug (application)
INR International normalized ratio
IRB Institutional Review Board
IV Intravenous
LDH Lactate dehydrogenase
LVEF Left ventricular ejection fraction
MCH Mean corpuscular haemoglobin
MCHC Mean corpuscular hemoglobin concentration
MCV Mean corpuscular volume
MRI Magnetic resonance imaging
MTD Maximum tolerated dose
NCI National Cancer Institute
NOAEL No observed adverse effect level
NTX N-terminal telopeptide
NYHA New York Heart Association
ORR Objective response rate
PD Progressive disease
PD Pharmacodynamic
PET Positron emission tomography
PFS Progression free survival
PK Pharmacokinetic
PR Partial response
PRO Patient reported outcome
PS Performance status
PT Prothrombin time
PTT Partial thromboplastin time
PVNS Pigmented villonodular synovitis
QTc Corrected QT interval
RBC Red blood cell
RD Recommended dose
RECIST Response Evaluation Criteria in Solid Tumors
SAE Serious adverse event
SAP Statistical analysis plan
SD Stable disease
$t_{1/2}$ Half-life
TB Tuberculosis
TRAP5b Tartrate resistant acid phosphatase 5b
TVS Tumor volume score
ULN Upper limit of normal
$V_{ss}$ Volume of distribution at steady state
WBC White blood cell

APPENDIX 1

Schedule of Assessments

| Procedure[a,b] | Screening Day −28 to Day 0 Week 0 | Phases 1 and 2: Cycle 1 | | | | Phase 1 Extended Treatment Period/Phase 2 Cycle 2 and Subsequent Cycles | | End of Treatment Follow-up Period[s] | Long-Term Follow Up Period[t] |
|---|---|---|---|---|---|---|---|---|---|
| | | Day 1 Week 1 | Day 2 | Day 8 Week 2 | Day 15 Week 3 | Day 1 ≥Week 4 | Day 15 | | |
| Informed Consent | x | | | | | | | | |
| Review/Confirm Eligibility Criteria | x | x | | | | | | | |
| Medical History/Demographics | x | x | | | | | | | |
| Physical Examination[c] | x | | | | | x | | x | |
| Height and Weight[d] | x | x | | | x | x | | x | |
| Vital Signs[e] | x | x | | x | x | x | x | x | |
| ECOG Performance Status | x | x | | | | x | | x | |
| Screening Labs[f] | x | | | | | | | | |

APPENDIX 1-continued

Schedule of Assessments

| Procedure[a,b] | Screening Day −28 to Day 0 Week 0 | Phases 1 and 2: Cycle 1 | | | | Phase 1 Extended Treatment Period/Phase 2 Cycle 2 and Subsequent Cycles | | End of Treatment Follow-up Period[s] | Long-Term Follow Up Period[t] |
|---|---|---|---|---|---|---|---|---|---|
| | | Day 1 Week 1 | Day 2 | Day 8 Week 2 | Day 15 Week 3 | Day 1 ≥Week 4 | Day 15 | | |
| Clinical Safety Labs[g] | x | x | | x | x | x | x | x | x |
| 12-Lead ECG[h] | x | | | | x | | x | x | |
| MRI of Involved Joint(s)[i] | x | | | | | x | | x | x |
| Serum Pregnancy Test[j] | x | x | | | | | | x | |
| Ogilvie-Harris/EQ-5D-5L Assessments[k] | x | | | | x | x | | x | x |
| Optional Archival Tumor Tissue[l] | x | | | | | | | | |
| Optional Synovial Biopsy[m] | x | | | | | x | | | |
| Optional Synovial Fluid Sampling[n] | x | | | | | x | | | |
| ADA Sampling[o] | | x | | | x | x | | x | x |
| PK and Serum Biomarkers Sampling[o] | | x | x | x | x | x | | x | x |
| CD14+/16+ Monocyte Sampling[p] | | x | x | x | x | x | | x | x |
| Antinuclear Antibody (ANA)[q] | x | | | | | | | x | |
| FPA008 Study Drug Administration[r] | | x | | | x | x | x | | |
| Adverse events | x------------------------------------------------------------------------x | | | | | | | x | x[t] |
| Prior/Concomitant Medications | x------------------------------------------------------------------------x | | | | | | | x | x[u] |

Notes for Schedule of Assessments

[a]Unless specified, procedure is to be completed within ±72 hours of scheduled time point and to be synchronized with administration day of FPA008 infusion.

[b]Any clinical assessment, laboratory study, or additional non-specified tests may be obtained at any time, if clinically indicated.

[c]Complete physical examination will be performed at Screening, Day 1 of Cycle 2, 4, 6, at the 30 days (±7 days) End of Treatment Follow-up Visit, and as determined by the Investigator, particularly to follow physical findings to resolution. Targeted physical exams should be conducted at any time to follow up on AE reports.

[d]Height is only required to be recorded at Screening. Weight is to be recorded Cycle 1, Days 1 and 15, and on Day 1 of subsequent cycles and at the End of Treatment Follow-up Visits.

[e]Vital signs include pulse, blood pressure, respiration rate, and temperature in the sitting position. Measure prior to dose and after completion of the IV infusion at the following time points: 5 minutes, 15 minutes, 30 minutes, and 1 h post-dose.

[f]Screening labs to include the Quantiferon test (for latent TB), and all women of childbearing potential (including those who have had a tubal ligation <6 months of first dose of FPA008) will have a serum pregnancy test.

[g]Clinical Safety Labs (Table 5):
Hematology including CBC with differential, platelets, hemoglobin, hematocrit, RBC, and RBC indices.
Chemistry including CK (creatine kinase), AST (aspartate transaminase), ALT (alanine transaminase), troponins (cardiac and skeletal), CK isoenzymes, carbon dioxide, bilirubin (direct and total), BUN (blood urea nitrogen), calcium, chloride, creatinine, glucose, LDH (lactate dehydrogenase), phosphate, potassium, sodium, magnesium, and, if applicable, serum pregnancy. Additional tests may be obtained at any time, if clinically indicated.
Urinalysis will only be done at Screening and at the End of Treatment Follow-up Visits, and may be repeated at any time if clinically indicated.
Coagulation including INR, PTT and APTT.

[h]Obtain ECG records at Screening, approximately 30 minutes post-dose on Day 15 for all cycles, and at the 30 days (±7 days) End of Treatment Follow-up Visit. Additional ECGs should be obtained at any time, and/or if serum CK or cardiac troponin is elevated; if abnormal (excluding sinus tachycardia), ECGs should be obtained (if clinically indicated), until the abnormality is resolved or clinically stable. ECGs for each patient should be obtained from the same machine whenever possible. To minimize variability, it is important that patients be in a resting position for approximately ≥5 minutes prior to each ECG evaluation. Body position should be consistently maintained for each ECG evaluation to prevent changes in heart rate. Environmental distractions (e.g., television, radio, conversation) should be avoided during the pre-ECG resting period and during ECG recording.

[i]MRI of the affected joint(s) will be performed during Screening and within 7 days of the following: 4 (C2D1), 8 (C3D1), and 16 (C5D1) weeks. Patients should have an MRI done at the 30 days (±7 days) and 90 days (±7 days) End of Treatment Follow-up Visits, unless it was already performed within the previous 6 weeks or if tumor progression was previously determined. Patients who have not progressed and enter Long-Term Follow-up should have MRI performed every 14 weeks (±2 weeks) for duration of response until progression, the patient undergoes local therapy (e.g., resection, radiation) or a new systemic therapy is initiated, for up to 52 weeks following C1D1. Response per MRI will be assessed using RECIST 1.1 and TVS based on independent central radiology review.

[j]All women of childbearing potential (including those who have had a tubal ligation <6 months of first dose of FPA008) will have a serum pregnancy test at Screening and at End of Treatment Follow-up Visits.

[k]The Ogilvie-Harris and EQ-5D-5L assessments will be performed at Screening, C1D15 (pre-dose), C2D1 (pre-dose), and then on Day 1 (pre-dose) for all subsequent cycles through 24 weeks, or until treatment is discontinued. These can be omitted if performed within 6 weeks prior to the End of Treatment Follow-up Visits. Patients who have not progressed and enter Long-Term Follow-up are to be followed every 14 weeks (±2 weeks) until progression, the patient undergoes local therapy (e.g., resection, radiation) or a new systemic therapy is initiated, for up to 52 weeks following C1D1.

[l]Optional archival tumor tissue will be collected at Screening, if available.

[m]Optional synovial biopsies will be collected at Screening and up to −2 days prior to the C2D1 dose administration.

[n]Optional synovial fluid aspirate will be extracted at Screening and up to −2 days prior to the C2D1 dose administration.

[o]Blood samples will be collected for PK, ADA, and PD. Refer to Appendix 2 for collection times.

[p]Whole blood will be collected and shipped overnight to the testing facility for analysis of CD14+/16+ monocytes. Refer to Appendix 2 for collection times.

[q] ANA testing will be performed at Screening and at the 30 days (±7 days) End of Treatment Follow-up Visit.

[r]FPA008 study drug will be administered every 2 weeks (±3 days) in 28-day cycles for 24 weeks. The Cycle 2, Day 1 infusion of FPA008 can only be administered after completion of the 28-day DLT window. All subsequent infusions can be administered with a ±3 day window. Patients should not have 2 doses of FPA008 within 7 days. The first dose of each cycle is considered Day 1 of each cycle, cycles will repeat every 28 days unless there is a treatment delay. Patients can have treatment delay of Day 1 of the subsequent cycle as long as the Day 1 treatment is within 6 weeks of the last treatment. FPA008 will be administered over approximately 30 minutes.

[s]Performed at 30 days (±7 days), 60 days (±7 days) and 90 days (±7 days) after the last dose of study treatment for all patients who complete the treatment period or who terminate early. All adverse events (including serious adverse events), regardless of attribution, will be recorded until 90 days after the last dose of study treatment. Ongoing adverse events will be followed until the event has resolved to baseline grade, the event is assessed by the Investigator as stable, there is a satisfactory explanation for the changes observed, the patient is lost to follow-up, or the patient withdraws consent.

[t]Patients who have not progressed should continue onto Long-Term Follow-up after completing the End-of-Treatment Follow-up Period. Patients are to be followed every 14 weeks (±2 weeks) until progression, the patient undergoes local therapy (e.g., resection, radiation) or a new systemic therapy is initiated, for up to 52 weeks following C1D1.

[u]Only ongoing adverse events thought to be related to study treatment should be followed during the Long-Term Follow-up Period.

v. Only local therapy (e.g., resection, radiation) or a new systemic therapy will be recorded during the Long-Term Follow-up Period.

APPENDIX 2

Study Flowchart for Pharmacokinetic, Immunogenicity, and Pharmacodynamic Blood Sample Collections

| Study Cycle | Study Day | Time Point | Type of Sample |
|---|---|---|---|
| Cycle 1 | Day 1 (First Dose) | ≤4 hours Prior to infusion | FPA008 PK (serum) ADA (serum) |

APPENDIX 2-continued

Study Flowchart for Pharmacokinetic, Immunogenicity, and Pharmacodynamic Blood Sample Collections

| Study Cycle | Study Day | Time Point | Type of Sample |
|---|---|---|---|
| | | | Serum Biomarkers (serum) |
| | | | $CD14^+/CD16^+$ (whole blood) |
| | | 15 minutes after end of infusion (±5 minutes) | FPA008 PK (serum) |
| | | 4 hours after end of infusion (±5 minutes) | Serum Biomarkers (serum) |
| | | | FPA008 PK (serum) |
| | | | Serum Biomarkers (serum) |
| | | | $CD14^+/CD16^+$ (whole blood) |
| | Day 2 | 24 hours after infusion (±2 hours) | FPA008 PK (serum) |
| | | | Serum Biomarkers (serum) |
| | | | $CD14^+/CD16^+$ (whole blood) |
| | Day 8 | 168 hours after infusion (±24 hours) | FPA008 PK (serum) |
| | | | Serum Biomarkers (serum) |
| | | | $CD14^+/CD16^+$ (whole blood) |
| | Day 15 (Second Dose) | ≤4 hours Prior to infusion | FPA008 PK (serum) |
| | | | ADA (serum) |
| | | | Serum Biomarkers (serum) |
| | | | $CD14^+/CD16^+$ (whole blood) |
| | | 15 minutes after end of infusion (±5 minutes) | FPA008 PK (serum) |
| Cycle 2 | Day 1 (First Dose) | ≤4 hours Prior to infusion | FPA008 PK (serum) |
| | | | ADA (serum) |
| | | | Serum Biomarkers (serum) |
| | | | $CD14^+/CD16^+$ (whole blood) |
| Cycle 3, and 5* | Day 1 (First Dose) | ≤4 hours Prior to infusion | FPA008 PK (serum) |
| | | | ADA (serum) |
| | | | Serum Biomarkers (serum) |
| | | | $CD14^+/CD16^+$ (whole blood) |
| | | 15 minutes after end of infusion (±5 minutes) | FPA008 PK (serum) |
| End of Treatment Follow-up and Long-Term Follow Up | Not applicable | Not applicable | FPA008 PK (serum) |
| | | | ADA (serum) |
| | | | Serum Biomarkers (serum) |
| | | | $CD14^+/CD16^+$ (whole blood) |

*The 15-minute post infusion PK blood draw is not required if FPA008 is not administered.

APPENDIX 3

ECOG Performance Status

| Grade | Performance Status Criteria |
|---|---|
| 0 | Fully active, able to carry on all pre-disease activities without restriction. |
| 1 | Restricted in physically strenuous activity but ambulatory and able to carry out work of a light sedentary nature (light housework, office work). |
| 2 | Ambulatory and capable of all self-care but unable to carry out any work activities. Up and about more than 50% of waking hours. |
| 3 | Capable of only limited self-care, confined to bed or chair more than 50% of waking hours. |
| 4 | Completely disabled. Cannot carry on any self-care. Totally confined to bed or chair. |

Appendix 4: Ogilvie-Harris Score for PVNS
  Pain
    Severe (0 point)
    Moderate (1 point)
    Slight (2 points)
    None (3 points)
  Synovitis/effusion
    Severe (0 point)
    Moderate (1 point)
    Slight (2 points)
    None (3 points)
  Range of Motion (*Normal=150°)
    >20% loss (0 point)
    10%-20% loss (1 point)
    0%-10% loss (2 points)
    No Loss (3 points)
      *Example: loss of 15° flexion or extension=loss of 10% (150−(150−15)/150)=10%
  Functional capacity
    Minimal activity (0 point)
    Some activity (1 point)
    Most activities (2 points)
    All activities (3 points)

Appendix 5: EQ-5D-5L
Under each heading, please tick the ONE box that best describes your health TODAY
  Mobility
    I have no problems in walking about
    I have slight problems in walking about
    I have moderate problems in walking about
    I have severe problems in walking about
    I am unable to walk about
  Self-Care
    I have no problems washing or dressing myself
    I have slight problems washing or dressing myself
    I have moderate problems washing or dressing myself
    I have severe problems washing or dressing myself
    I am unable to wash or dress myself
  Usual Activities (e.g. work, study, housework, family or leisure activities)
    I have no problems doing my usual activities
    I have slight problems doing my usual activities
    I have moderate problems doing my usual activities
    I have severe problems doing my usual activities
    I am unable to do my usual activities Pain/Discomfort
I have no pain or discomfort
I have slight pain or discomfort
I have moderate pain or discomfort
I have severe pain or discomfort
I have extreme pain or discomfort
Anxiety/Depression
I am not anxious or depressed
I am slightly anxious or depressed
I am moderately anxious or depressed
I am severely anxious or depressed
I am extremely anxious or depressed
We would like to know how good or bad your health is TODAY.
This scale is numbered from 0 to 100.
100 means the best health you can imagine.
0 means the worst health you can imagine.
Mark an X on the scale to indicate how your health is TODAY.
Now, please write the number you marked on the scale in the box below.

Appendix 6: Management of Systemic Hypersensitivity Reactions

Staff administering study drug are required to closely monitor all patients for possible systemic hypersensitivity reactions (e.g., generalized exanthema, urticaria, paraesthesia, bronchoconstriction, palpitations) over the first 180 minutes after infusion, paying particular attention to those patients with a history of asthma or systemic reactions to allergenic injections.

All systemic hypersensitivity manifestations will be captured on the appropriate eCRF page(s) and identified as being due to a hypersensitivity reaction.

Systemic hypersensitivity reactions will be managed according to treatment protocols in effect at the investigational site. In the absence of such a protocol, the following standardized treatment protocol will be used:

Clinically mild reactions (e.g., generalized rash or itching, hives) are treated as soon as possible with Benadryl® (diphenhydramine hydrochloride) 25 to 50 mg, orally or IV at the Investigator's discretion. The period of observation is extended beyond 3 hours, as necessary, until symptoms and signs have resolved or stabilized. Patients who have experienced a clinically mild reaction may continue to have study drug administered.

Clinically moderate reactions (e.g., hypotension, shortness of breath, facial edema) are treated immediately and supportive care measures instituted as medically indicated (e.g., IV fluids, corticosteroids, vasopressors, oxygen, bronchodilators, diphenhydramine, and acetaminophen). Vital signs are monitored at 10-minute intervals until they have normalized. The period of observation is extended beyond 3 hours, if necessary, until symptoms and signs have resolved. In the event of a clinically moderate reaction, the patient should receive no further treatment with study drug.

Clinically severe reactions (e.g., marked hypotension, syncope, severe bronchoconstriction, tongue or throat swelling, significant angioedema) are treated immediately, under the direct supervision of the investigator, and supportive care measures instituted as medically indicated (e.g., IV fluids, corticosteroids, vasopressors, oxygen, bronchodilators, diphenhydramine, and acetaminophen). Vital signs and systems are monitored at a minimum of 10-minute intervals for as long as the investigator considers it necessary to ensure patient safety. In the event of a clinically severe reaction, the patient should receive no further treatment with study drug.

These clinical classifications are for the purpose of recommending treatment for patients who experience systemic hypersensitivity reactions. These classifications will not be used to grade the severity of the systemic hypersensitivity event within the eCRF. The severity of these events will be documented per the grading system presented in NCI CTCAE v4.03.

Preliminary data from this trial shows that pateints under treatment with a dose as low as 1 mg/kg demonstrated clinical improvement in some parameters according to the Ogilive-Harris Score for PVNS, including:
1) reducing pain, for example, from severe (0 points) to none (3 points),
2) enhancing range of motion, for example, from loss more than 20% to no loss, and
3) increasing functional capacity, for example, from capable of having some activity to capable of have all activity.

An improving effect of the treatment was also seen with EQ-5D-5L Eveluation as least some of the petiants receiving the treatment had improved ability in washing and dressing and other self-care activity.

Table of Sequences

Table 5 provides certain sequences discussed herein. All polypeptide and antibody sequences are shown without leader sequences, unless otherwise indicated.

TABLE 5

Sequences and Descriptions

| SEQ ID NO | Description | Sequence |
|---|---|---|
| 1 | hCSF1R (full-length, no leader sequence) | IPVIEPSVPE LVVKPGATVT LRCVGNGSVE WDGPPSPHWT LYSDGSSSIL STNNATFQNT GTYRCTEPGD PLGGSAAIHL YVKDPARPWN VLAQEVVVFE DQDALLPCLL TDPVLEAGVS LVRVRGRPLM RHTNYSFSPW HGFTIHRAKF IQSQDYQCSA LMGGRKVMSI SIRLKVQKVI PGPPALTLVP AELVRIRGEA AQIVCSASSV DVNFDVFLQH NNTKLAIPQQ SDFHNNRYQK VLTLNLDQVD FQHAGNYSCV ASNVQGKHST SMFFRVVESA YLNLSSEQNL IQEVTVGEGL NLKVMVEAYP GLQGFNWTYL GPFSDHQPEP KLANATTKDT YRHTFTLSLP RLKPSEAGRY SFLARNPGGW RALTFELTLR YPPEVSVIWT FINGSGTLLC AASGYPQPNV TWLQCSGHTD RCDEAQVLQV WDDPYPEVLS QEPPHKVTVQ SLLTVETLEH NQTYECRAHN SVGSGSWAFI PISAGAHTHP PDEFLFTPVV VACMSIMALL LLLLLLLLYK YKQKPKYQVR WKIIESYEGN SYTFIDPTQL PYNEKWEFPR NNLQFGKTLG AGAFGKVVEA TAFGLGKEDA VLKVAVKMLK STAHADEKEA LMSELKIMSH LGQHENIVNL LGACTHGGPV LVITEYCCYG DLLNFLRRKA EAMLGPSLSP GQDPEGGVDY KNIHLEKKYV RRDSGFSSQG |

TABLE 5-continued

Sequences and Descriptions

| SEQ ID NO | Description | Sequence |
|---|---|---|
| | | VDTYVEMRPV STSSNDSFSE QDLDKEDGRP LELRDLLHFS SQVAQGMAFL ASKNCIHRDV AARNVLLTNG HVAKIGDFGL ARDIMNDSNY IVKGNARLPV KWMAPESIFD CVYTVQSDVW SYGILLWEIF SLGLNPYPGI LVNSKFYKLV KDGYQMAQPA FAPKNIYSIM QACWALEPTH RPTFQQICSF LQEQAQEDRR ERDYTNLPSS SRSGGSGSSS SELEEESSSE HLTCCEQGDI AQPLLQPNNY QFC |
| 2 | hCSF1R (full-length, + leader sequence) | MGPGVLLLLL VATAWHGQGI PVIEPSVPEL VVKPGATVTL RCVGNGSVEW DGPPSPHWTL YSDGSSSILS TNNATFQNTG TYRCTEPGDP LGGSAAIHLY VKDPARPWNV LAQEVVVFED QDALLPCLLT DPVLEAGVSL VRVRGRPLMR HTNYSFSPWH GFTIHRAKFI QSQDYQCSAL MGGRKVMSIS IRLKVQKVIP GPPALTLVPA ELVRIRGEAA QIVCSASSVD VNFDVFLQHN NTKLAIPQQS DFHNNRYQKV LTLNLDQVDF QHAGNYSCVA SNVQGKHSTS MFFRVVESAY LNLSSEQNLI QEVTVGEGLN LKVMVEAYPG LQGFNWTYLG PFSDHQPEPK LANATTKDTY RHTFTLSLPR LKPSEAGRYS FLARNPGGWR ALTFELTLRY PPEVSVIWTF INGSGTLLCA ASGYPQPNVT WLQCSGHTDR CDEAQVLQVW DDPYPEVLSQ EPFHKVTVQS LLTVETLEHN QTYECRAHNS VGSGSWAFIP ISAGAHTHPP DEFLFTPVVV ACMSIMALLL LLLLLLLYKY KQKPKYQVRW KIIESYEGNS YTFIDPTQLP YNEKWEFPRN NLQFGKTLGA GAFGKVVEAT AFGLGKEDAV LKVAVKMLKS TAHADEKEAL MSELKIMSHL GQHENIVNLL GACTHGGPVL VITEYCCYGD LLNFLRRKAE AMLGPSLSPG QDPEGGVDYK NIHLEKKYVR RDSGFSSQGV DTYVEMRPVS TSSNDSFSEQ DLDKEDGRPL ELRDLLHFSS QVAQGMAFLA SKNCIHRDVA ARNVLLTNGH VAKIGDFGLA RDIMNDSNYI VKGNARLPVK WMAPESIFDC VYTVQSDVWS YGILLWEIFS LGLNPYPGIL VNSKFYKLVK DGYQMAQPAF APKNIYSIMQ ACWALEPTHR PTFQQICSFL QEQAQEDRRE RDYTNLPSSS RSGGSGSSSS ELEEESSSEH LTCCEQGDIA QPLLQPNNYQ FC |
| 5 | hCSF1R ECD.506 | IPVIEPSVPE LVVKPGATVT LRCVGNGSVE WDGPPSPHWT LYSDGSSSIL STNNATFQNT GTYRCTEPGD PLGGSAAIHL YVKDPARPWN VLAQEVVVFE DQDALLPCLL TDPVLEAGVS LVRVRGRPLM RHTNYSFSPW HGFTIHRAKF IQSQDYQCSA LMGGRKVMSI SIRLKVQKVI PGPPALTLVP AELVRIRGEA AQIVCSASSV DVNFDVFLQH NNTKLAIPQQ SDFHNNRYQK VLTLNLDQVD FQHAGNYSCV ASNVQGKHST SMFFRVVESA YLNLSSEQNL IQEVTVGEGL NLKVMVEAYP GLQGFNWTYL GPFSDHQPEP KLANATTKDT YRHTFTLSLP RLKPSEAGRY SFLARNPGGW RALTFELTLR YPPEVSVIWT FINGSGTLLC AASGYPQPNV TWLQCSGHTD RCDEAQVLQV WDDPYPEVLS QEPFHKVTVQ SLLTVETLEH NQTYECRAHN SVGSGSWAFI PISAGAH |
| 6 | hCSF1R ECD.506-Fc | IPVIEPSVPE LVVKPGATVT LRCVGNGSVE WDGPPSPHWT LYSDGSSSIL STNNATFQNT GTYRCTEPGD PLGGSAAIHL YVKDPARPWN VLAQEVVVFE DQDALLPCLL TDPVLEAGVS LVRVRGRPLM RHTNYSFSPW HGFTIHRAKF IQSQDYQCSA LMGGRKVMSI SIRLKVQKVI PGPPALTLVP AELVRIRGEA AQIVCSASSV DVNFDVFLQH NNTKLAIPQQ SDFHNNRYQK VLTLNLDQVD FQHAGNYSCV ASNVQGKHST SMFFRVVESA YLNLSSEQNL IQEVTVGEGL NLKVMVEAYP GLQGFNWTYL GPFSDHQPEP KLANATTKDT YRHTFTLSLP RLKPSEAGRY SFLARNPGGW RALTFELTLR YPPEVSVIWT FINGSGTLLC AASGYPQPNV TWLQCSGHTD RCDEAQVLQV WDDPYPEVLS QEPFHKVTVQ SLLTVETLEH NQTYECRAHN SVGSGSWAFI PISAGAHEPK SSDKTHTCPP CPAPELLGGP SVFLFPPKPK DTLMISRTPE VTCVVVDVSH EDPEVKFNWY VDGVEVHNAK TKPREEQYNS TYRVVSVLTV LHQDWLNGKE YKCKVSNKAL PAPIEKTISK AKGQPREPQV YTLPPSRDEL TKNQVSLTCL VKGFYPSDIA VEWESNGQPE NNYKTTPPVL DSDGSFFLYS KLTVDKSRWQ QGNVFSCSVM HEALHNHYTQ KSLSLSPGK |
| 7 | CynoCSF1R ECD (with leader sequence) | MGPGVLLLLL VVTAWHGQGI PVIEPSGPEL VVKPGETVTL RCVGNGSVEW DGPISPHWTL YSDGPSSVLT TTNATFQNTR TYRCTEPGDP LGGSAAIHLY VKDPARPWNV LAKEVVVFED QDALLPCLLT DPVLEAGVSL VRLRGRPLLR HTNYSFSPWH GFTIHRAKFI QGQDYQCSAL MGSRKVMSIS IRLKVQKVIP GPPALTLVPA ELVRIRGEAA QIVCSASNID VDFDVFLQHN TTKLAIPQRS DFHDNRYQKV LTLSLGQVDF QHAGNYSCVA SNVQGKHSTS MFFRVVESAY LDLSSEQNLI QEVTVGEGLN LKVMVEAYPG LQGFNWTYLG PFSDHQPEPK LANATTKDTY RHTFTLSLPR LKPSEAGRYS FLARNPGGWR ALTFELTLRY PPEVSVIWTS INGSGTLLCA ASGYPQPNVT WLQCAGHTDR CDEAQVLQVW VDPHPEVLSQ EPFQKVTVQS LLTAETLEHN QTYECRAHNS VGSGSWAFIP ISAGAR |
| 8 | CynoCSF1R ECD-Fc (with leader sequence) | MGPGVLLLLL VVTAWHGQGI PVIEPSGPEL VVKPGETVTL RCVGNGSVEW DGPISPHWTL YSDGPSSVLT TTNATFQNTR TYRCTEPGDP LGGSAAIHLY VKDPARPWNV LAKEVVVFED QDALLPCLLT DPVLEAGVSL VRLRGRPLLR HTNYSFSPWH GFTIHRAKFI QGQDYQCSAL MGSRKVMSIS IRLKVQKVIP GPPALTLVPA ELVRIRGEAA QIVCSASNID VDFDVFLQHN TTKLAIPQRS DFHDNRYQKV LTLSLGQVDF QHAGNYSCVA SNVQGKHSTS MFFRVVESAY |

TABLE 5-continued

Sequences and Descriptions

| SEQ ID NO | Description | Sequence |
|---|---|---|
|  |  | LDLSSEQNLI QEVTVGEGLN LKVMVEAYPG LQGFNWTYLG PFSDHQPEPK LANATTKDTY RHTFTLSLPR LKPSEAGRYS FLARNPGGWR ALTFELTLRY PPEVSVIWTS INGSGTLLCA ASGYPQPNVT WLQCAGHTDR CDEAQVLQVW VDPHPEVLSQ EPFQKVTVQS LLTAETLEHN QTYECRAHNS VGSGSWAFIP ISAGARGSEP KSSDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSRDE LTKNQVSLTC LVKGFYPSDI AVEWESNGQP ENNYKTTPPV LDSDGSFFLY SKLTVDKSRW QQGNVFSCSV MHEALHNHYT QKSLSLSPGK |
| 3 | Light chain leader sequence | METDTLLLWV LLLWVPGSTG |
| 4 | Heavy chain leader sequence | MAVLGLLLCL VTFPSCVLS |
| 9 | Fab 0301 heavy chain variable region | EVQLQQSGPE LVRPGASVKM SCKASGYTFT DNYMIWVKQS HGKSLEWIGD INPYNGGTTF NQKFKGKATL TVEKSSSTAY MQLNSLTSED SAVYYCARES PYFSNLYVMD YWGQGTSVTV SS |
| 10 | Fab 0301 light chain variable region | NIVLTQSPAS LAVSLGQRAT ISCKASQSVD YDGDNYMNWY QQKPGQPPKL LIYAASNLES GIPARFSGSG SGTDFTLNIH PVEEEDAATY YCHLSNEDLS TFGGGTKLEI K |
| 11 | Fab 0302 heavy chain variable region | EIQLQQSGPE LVKPGASVKM SCKASGYTFS DFNIHWVKQK PGQGLEWIGY INPYTDVTVY NEKFKGKATL TSDRSSSTAY MDLSSLTSED SAVYYCASYF DGTFDYALDY WGQGTSITVS S |
| 12 | Fab 0302 light chain variable region | DVVVTQTPAS LAVSLGQRAT ISCRASESVD NYGLSFMNWF QQKPGQPPKL LIYTASNLES GIPARFSGGG SRTDFTLTID PVEADDAATY FCQQSKELPW TFGGGTRLEI K |
| 13 | Fab 0311 heavy chain variable region | EIQLQQSGPD LMKPGASVKM SCKASGYIFT DYNMHWVKQN QGKSLEWMGE INPNNGVVVY NQKFKGTTTL TVDKSSSTAY MDLHSLTSED SAVYYCTRAL YHSNFGWYFD SWGKGTTLTV SS |
| 14 | Fab 0311 light chain variable region | DIVLTQSPAS LAVSLGQRAT ISCKASQSVD YDGDSHMNWY QQKPGQPPKL LIYTASNLES GIPARFSGSG SGADFTLTIH PVEEEDAATY YCQQGNEDPW TFGGGTRLEI K |
| 15 | 0301 heavy chain CDR1 | GYTFTDNYMI |
| 16 | 0301 heavy chain CDR2 | DINPYNGGTT FNQKFKG |
| 17 | 0301 heavy chain CDR3 | ESPYFSNLYV MDY |
| 18 | 0301 light chain CDR1 | KASQSVDYDG DNYMN |
| 19 | 0301 light chain CDR2 | AASNLES |
| 20 | 0301 light chain CDR3 | HLSNEDLST |
| 21 | 0302 heavy chain CDR1 | GYTFSDFNIH |
| 22 | 0302 heavy chain CDR2 | YINPYTDVTV YNEKFKG |
| 23 | 0302 heavy chain CDR3 | YFDGTFDYAL DY |

TABLE 5-continued

Sequences and Descriptions

| SEQ ID NO | Description | Sequence |
|---|---|---|
| 24 | 0302 light chain CDR1 | RASESVDNYG LSFMN |
| 25 | 0302 light chain CDR2 | TASNLES |
| 26 | 0302 light chain CDR3 | QQSKELPWT |
| 27 | 0311 heavy chain CDR1 | GYIFTDYNMH |
| 28 | 0311 heavy chain CDR2 | EINPNNGVW YNQKFKG |
| 29 | 0311 heavy chain CDR3 | ALYHSNFGWY FDS |
| 30 | 0311 light chain CD R1 | KASQSVDYDG DSHMN |
| 31 | 0311 light chain CDR2 | TASNLES |
| 32 | 0311 light chain CDR3 | QQGNEDPWT |
| 33 | cAb 0301 heavy chain | EVQLQQSGPE LVRPGASVKM SCKASGYTFT DNYMIWVKQS HGKSLEWIGD INPYNGGTTF NQKFKGKATL TVEKSSSTAY MQLNSLTSED SAVYYCARES PYFSNLYVMD YWGQGTSVTV SSASTKGPSV FPLAPCSRST SESTAALGCL VKDYFPEPVT VSWNSGALTS GVHTFPAVLQ SSGLYSLSSV VTVPSSSLGT KTYTCNVDHK PSNTKVDKRV ESKYGPPCPP CPAPEFLGGP SVFLFPPKPK DTLMISRTPE VTCVVVDVSQ EDPEVQFNWY VDGVEVHNAK TKPREEQFNS TYRVVSVLTV LHQDWLNGKE YKCKVSNKGL PSSIEKTISK AKGQPREPQV YTLPPSQEEM TKNQVSLTCL VKGFYPSDIA VEWESNGQPE NNYKTTPPVL DSDGSFFLYS RLTVDKSRWQ EGNVFSCSVM HEALHNHYTQ KSLSLSLGK |
| 34 | cAb 0301 light chain | NIVLTQSPAS LAVSLGQRAT ISCKASQSVD YDGDNYMNWY QQKPGQPPKL LIYAASNLES GIPARFSGSG SGTDFTLNIH PVEEEDAATY YCHLSNEDLS TFGGGTKLEI KRTVAAPSVF IFPPSDEQLK SGTASVVCLL NNFYPREAKV QWKVDNALQS GNSQESVTEQ DSKDSTYSLS STLTLSKADY EKHKVYACEV THQGLSSPVT KSFNRGEC |
| 35 | cAb 0302 heavy chain | EIQLQQSGPE LVKPGASVKM SCKASGYTFS DFNIHWVKQK PGQGLEWIGY INPYTDVTVY NEKFKGKATL TSDRSSSTAY MDLSSLTSED SAVYYCASYF DGTFDYALDY WGQGTSITVS SASTKGPSVF PLAPCSRSTS ESTAALGCLV KDYFPEPVTV SWNSGALTSG VHTFPAVLQS SGLYSLSSVV TVPSSSLGTK TYTCNVDHKP SNTKVDKRVE SKYGPPCPPC PAPEFLGGPS VFLFPPKPKD TLMISRTPEV TCVVVDVSQE DPEVQFNWYV DGVEVHNAKT KPREEQFNST YRVVSVLTVL HQDWLNGKEY KCKVSNKGLP SSIEKTISKA KGQPREPQVY TLPPSQEEMT KNQVSLTCLV KGFYPSDIAV EWESNGQPEN NYKTTPPVLD SDGSFFLYSR LTVDKSRWQE GNVFSCSVMH EALHNHYTQK SLSLSLGK |
| 36 | cAb 0302 light chain | DVVVTQTPAS LAVSLGQRAT ISCRASESVD NYGLSFMNVV QQKPGQPPKL LIYTASNLES GIPARFSGGG SRTDFTLTID PVEADDAATY FCQQSKELPW TFGGGTRLEI KRTVAAPSVF IFPPSDEQLK SGTASVVCLL NNFYPREAKV QWKVDNALQS GNSQESVTEQ DSKDSTYSLS STLTLSKADY EKHKVYACEV THQGLSSPVT KSFNRGEC |
| 37 | cAb 0311 heavy chain | EIQLQQSGPD LMKPGASVKM SCKASGYIFT DYNMHWVKQN QGKSLEWMGE INPNNGVVVY NQKFKGTTTL TVDKSSSTAY MDLHSLTSED SAVYYCTRAL YHSNFGWYFD SWGKGTTLTV SSASTKGPSV FPLAPCSRST SESTAALGCL VKDYFPEPVT VSWNSGALTS GVHTFPAVLQ SSGLYSLSSV VTVPSSSLGT KTYTCNVDHK PSNTKVDKRV ESKYGPPCPP CPAPEFLGGP SVFLFPPKPK DTLMISRTPE VTCVVVDVSQ EDPEVQFNWY VDGVEVHNAK TKPREEQFNS TYRVVSVLTV LHQDWLNGKE YKCKVSNKGL PSSIEKTISK AKGQPREPQV YTLPPSQEEM TKNQVSLTCL VKGFYPSDIA VEWESNGQPE NNYKTTPPVL DSDGSFFLYS RLTVDKSRWQ EGNVFSCSVM HEALHNHYTQ KSLSLSLGK |
| 38 | cAb 0311 light chain | DIVLTQSPAS LAVSLGQRAT ISCKASQSVD YDGDSHMNWY QQKPGQPPKL LIYTASNLES GIPARFSGSG SGADPTLTIH PVEEEDAATY YCQQGNEDPW TFGGGTRLEI KRTVAAPSVF IFPPSDEQLK SGTASVVCLL NNFYPREAKV QWKVDNALQS GNSQESVTEQ DSKDSTYSLS STLTLSKADY EKHKVYACEV THQGLSSPVT KSFNRGEC |

TABLE 5-continued

Sequences and Descriptions

| SEQ ID NO | Description | Sequence |
|---|---|---|
| 39 | h0301-H0 heavy chain variable region | QVQLVQSGAE VKKPGSSVKV SCKASGYTFT DNYMIWVRQA PGQGLEWMGD INPYNGGTTF NQKFKGRVTI TADKSTSTAY MELSSLRSED TAVYYCARES PYFSNLYVMD YWGQGTLVTV SS |
| 40 | h0301-H1 heavy chain variable region | QVQLVQSGAE VKKPGSSVKV SCKASGYTFT DNYMIWVRQA PGQGLEWMGD INPYNGGTTF NQKFKGRVTI TVDKSTSTAY MELSSLRSED TAVYYCARES PYFSNLYVMD YWGQGTLVTV SS |
| 41 | h0301-H2 heavy chain variable region | QVQLVQSGAE VKKPGSSVKV SCKASGYTFT DNYMIWVRQA PGQGLEWIGD INPYNGGTTF NQKFKGRATL TVDKSTSTAY MELSSLRSED TAVYYCARES PYFSNLYVMD YWGQGTLVTV SS |
| 42 | H0302-H1 heavy chain variable region | QVQLVQSGAE VKKPGSSVKV SCKASGYTFS DFNIHWVRQA PGQGLEWMGY INPYTDVTVY NEKFKGRVTI TSDKSTSTAY MELSSLRSED TAVYYCASYF DGTFDYALDY WGQGTLVTVS S |
| 43 | H0302-H2 heavy chain variable region | QVQLVQSGAE VKKPGSSVKV SCKASGYTFS DFNIHWVRQA PGQGLEWIGY INPYTDVTVY NEKFKGRATL TSDKSTSTAY MELSSLRSED TAVYYCASYF DGTFDYALDY WGQGTLVTVS S |
| 44 | H0311-H1 heavy chain variable region | QVQLVQSGAE VKKPGSSVKV SCKASGYIFT DYNMHWVRQA PGQGLEWMGE INPNNGVVVY NQKFKGRVTI TVDKSTSTAY MELSSLRSED TAVYYCTRAL YHSNFGWYFD SWGQGTLVTV SS |
| 45 | H0311-H2 heavy chain variable region | QVQLVQSGAE VKKPGSSVKV SCKASGYIFT DYNMHWVRQA PGQGLEWMGE INPNNGVVVY NQKFKGTTTL TVDKSTSTAY MELSSLRSED TAVYYCTRAL YHSNFGWYFD SWGQGTLVTV SS |
| 46 | h0301-L0 light chain variable region | EIVLTQSPAT LSLSPGERAT LSCKASQSVD YDGDNYMNWY QQKPGQAPRL LIYAASNLES GIPARFSGSG SGTDFTLTIS SLEPEDFAVY YCHLSNEDLS TFGGGTKVEI K |
| 47 | h0301-L1 light chain variable region | NIVLTQSPAT LSLSPGERAT LSCKASQSVD YDGDNYMNWY QQKPGQAPRL LIYAASNLES GIPARFSGSG SGTDFTLTIS SLEPEDFAVY YCHLSNEDLS TFGGGTKVEI K |
| 48 | H0302-L0 light chain variable region | EIVLTQSPAT LSLSPGERAT LSCRASESVD NYGLSFMNWY QQKPGQAPRL LIYTASNLES GIPARFSGSG SGTDFTLTIS SLEPEDFAVY YCQQSKELPW TFGQGTKVEI K |
| 49 | H0302-L1 light chain variable region | EIVLTQSPAT LSLSPGERAT LSCRASESVD NYGLSFMNWY QQKPGQAPRL LIYTASNLES GIPARFSGSG SRTDFTLTIS SLEPEDFAVY YCQQSKELPW TFGQGTKVEI K |
| 50 | H0302-L2 light chain variable region | EIVLTQSPAT LSLSPGERAT LSCRASESVD NYGLSFMNWF QQKPGQAPRL LIYTASNLES GIPARFSGSG SRTDFTLTIS SLEPEDFAVY YCQQSKELPW TFGQGTKVEI K |
| 51 | H0311-L0 light chain variable region | EIVLTQSPAT LSLSPGERAT LSCKASQSVD YDGDSHMNWY QQKPGQAPRL LIYTASNLES GIPARFSGSG SGTDFTLTIS SLEPEDFAVY YCQQGNEDPW TFGQGTKVEI K |
| 52 | H0311-L1 light chain variable region | DIVLTQSPAT LSLSPGERAT LSCKASQSVD YDGDSHMNWY QQKPGQAPRL LIYTASNLES GIPARFSGSG SGADFTLTIS SLEPEDFAVY YCQQGNEDPW TFGQGTKVEI K |
| 53 | h0301-H0 heavy chain | QVQLVQSGAE VKKPGSSVKV SCKASGYTFT DNYMIWVRQA PGQGLEWMGD INPYNGGTTF NQKFKGRVTI TADKSTSTAY MELSSLRSED TAVYYCARES PYFSNLYVMD YWGQGTLVTV SSASTKGPSV FPLAPCSRST SESTAALGCL VKDYFPEPVT VSWNSGALTS GVHTFPAVLQ SSGLYSLSSV VTVPSSSLGT |

TABLE 5-continued

Sequences and Descriptions

| SEQ ID NO | Description | Sequence |
|---|---|---|
| | | KTYTCNVDHK PSNTKVDKRV ESKYGPPCPP CPAPEFLGGP SVFLFPPKPK DTLMISRTPE VTCVVVDVSQ EDPEVQFNWY VDGVEVHNAK TKPREEQFNS TYRVVSVLTV LHQDWLNGKE YKCKVSNKGL PSSIEKTISK AKGQPREPQV YTLPPSQEEM TKNQVSLTCL VKGFYPSDIA VEWESNGQPE NNYKTTPPVL DSDGSFFLYS RLTVDKSRWQ EGNVFSCSVM HEALHNHYTQ KSLSLSLGK |
| 54 | h0301-H1 heavy chain | QVQLVQSGAE VKKPGSSVKV SCKASGYTFT DNYMIWVRQA PGQGLEWMGD INPYNGGTTF NQKFKGRVTI TVDKSTSTAY MELSSLRSED TAVYYCARES PYFSNLYVMD YWGQGTLVTV SSASTKGPSV FPLAPCSRST SESTAALGCL VKDYFPEPVT VSWNSGALTS GVHTFPAVLQ SSGLYSLSSV VTVPSSSLGT KTYTCNVDHK PSNTKVDKRV ESKYGPPCPP CPAPEFLGGP SVFLFPPKPK DTLMISRTPE VTCVVVDVSQ EDPEVQFNWY VDGVEVHNAK TKPREEQFNS TYRVVSVLTV LHQDWLNGKE YKCKVSNKGL PSSIEKTISK AKGQPREPQV YTLPPSQEEM TKNQVSLTCL VKGFYPSDIA VEWESNGQPE NNYKTTPPVL DSDGSFFLYS RLTVDKSRWQ EGNVFSCSVM HEALHNHYTQ KSLSLSLGK |
| 55 | h0301-H2 heavy chain | QVQLVQSGAE VKKPGSSVKV SCKASGYTFT DNYMIWVRQA PGQGLEWIGD INPYNGGTTF NQKFKGRATL TVDKSTSTAY MELSSLRSED TAVYYCARES PYFSNLYVMD YWGQGTLVTV SSASTKGPSV FPLAPCSRST SESTAALGCL VKDYFPEPVT VSWNSGALTS GVHTFPAVLQ SSGLYSLSSV VTVPSSSLGT KTYTCNVDHK PSNTKVDKRV ESKYGPPCPP CPAPEFLGGP SVFLFPPKPK DTLMISRTPE VTCVVVDVSQ EDPEVQFNWY VDGVEVHNAK TKPREEQFNS TYRVVSVLTV LHQDWLNGKE YKCKVSNKGL PSSIEKTISK AKGQPREPQV YTLPPSQEEM TKNQVSLTCL VKGFYPSDIA VEWESNGQPE NNYKTTPPVL DSDGSFFLYS RLTVDKSRWQ EGNVFSCSVM HEALHNHYTQ KSLSLSLGK |
| 56 | H0302-H1 heavy chain | QVQLVQSGAE VKKPGSSVKV SCKASGYTFS DFNIHWVRQA PGQGLEWMGY INPYTDVTVY NEKFKGRVTI TSDKSTSTAY MELSSLRSED TAVYYCASYF DGTFDYALDY WGQGTLVTVS SASTKGPSVF PLAPCSRSTS ESTAALGCLV KDYFPEPVTV SWNSGALTSG VHTFPAVLQS SGLYSLSSVV TVPSSSLGTK TYTCNVDHKP SNTKVDKRVE SKYGPPCPPC PAPEFLGGPS VFLFPPKPKD TLMISRTPEV TCVVVDVSQE DPEVQFNWYV DGVEVHNAKT KPREEQFNST YRVVSVLTVL HQDWLNGKEY KCKVSNKGLP SSIEKTISKA KGQPREPQVY TLPPSQEEMT KNQVSLTCLV KGFYPSDIAV EWESNGQPEN NYKTTPPVLD SDGSFFLYSR LTVDKSRWQE GNVFSCSVMH EALHNHYTQK SLSLSLGK |
| 57 | H0302-H2 heavy chain | QVQLVQSGAE VKKPGSSVKV SCKASGYTFS DFNIHWVRQA PGQGLEWIGY INPYTDVTVY NEKFKGRATL TSDKSTSTAY MELSSLRSED TAVYYCASYF DGTFDYALDY WGQGTLVTVS SASTKGPSVF PLAPCSRSTS ESTAALGCLV KDYFPEPVTV SWNSGALTSG VHTFPAVLQS SGLYSLSSVV TVPSSSLGTK TYTCNVDHKP SNTKVDKRVE SKYGPPCPPC PAPEFLGGPS VFLFPPKPKD TLMISRTPEV TCVVVDVSQE DPEVQFNWYV DGVEVHNAKT KPREEQFNST YRVVSVLTVL HQDWLNGKEY KCKVSNKGLP SSIEKTISKA KGQPREPQVY TLPPSQEEMT KNQVSLTCLV KGFYPSDIAV EWESNGQPEN NYKTTPPVLD SDGSFFLYSR LTVDKSRWQE GNVFSCSVMH EALHNHYTQK SLSLSLGK |
| 58 | E03114-11 heavy chain | QVQLVQSGAE VKKPGSSVKV SCKASGYIFT DYNMHWVRQA PGQGLEWMGE INPNNGVVVY NQKFKGRVTI TVDKSTSTAY MELSSLRSED TAVYYCTRAL YHSNFGWYFD SWGQGTLVTV SSASTKGPSV FPLAPCSRST SESTAALGCL VKDYFPEPVT VSWNSGALTS GVHTFPAVLQ SSGLYSLSSV VTVPSSSLGT KTYTCNVDHK PSNTKVDKRV ESKYGPPCPP CPAPEFLGGP SVFLFPPKPK DTLMISRTPE VTCVVVDVSQ EDPEVQFNWY VDGVEVHNAK TKPREEQFNS TYRVVSVLTV LHQDWLNGKE YKCKVSNKGL PSSIEKTISK AKGQPREPQV YTLPPSQEEM TKNQVSLTCL VKGFYPSDIA VEWESNGQPE NNYKTTPPVL DSDGSFFLYS RLTVDKSRWQ EGNVFSCSVM HEALHNHYTQ KSLSLSLGK |
| 59 | H0311-142 heavy chain | QVQLVQSGAE VKKPGSSVKV SCKASGYIFT DYNMHWVRQA PGQGLEWMGE INPNNGVVVY NQKFKGTTTL TVDKSTSTAY MELSSLRSED TAVYYCTRAL YHSNFGWYFD SWGQGTLVTV SSASTKGPSV FPLAPCSRST SESTAALGCL VKDYFPEPVT VSWNSGALTS GVHTFPAVLQ SSGLYSLSSV VTVPSSSLGT KTYTCNVDHK PSNTKVDKRV ESKYGPPCPP CPAPEFLGGP SVFLFPPKPK DTLMISRTPE VTCVVVDVSQ EDPEVQFNWY VDGVEVHNAK TKPREEQFNS TYRVVSVLTV LHQDWLNGKE YKCKVSNKGL PSSIEKTISK AKGQPREPQV YTLPPSQEEM TKNQVSLTCL VKGFYPSDIA VEWESNGQPE NNYKTTPPVL DSDGSFFLYS RLTVDKSRWQ EGNVFSCSVM HEALHNHYTQ KSLSLSLGK |
| 60 | h0301-L0 light chain | EIVLTQSPAT LSLSPGERAT LSCKASQSVD YDGDNYMNWY QQKPGQAPRL LIYAASNLES GIPARFSGSG SGTDFTLTIS SLEPEDFAVY YCHLSNEDLS TFGGGTKVEI KRTVAAPSVF IFPPSDEQLK SGTASVVCLL NNFYPREAKV QWKVDNALQS GNSQESVTEQ DSKDSTYSLS STLTLSKADY EKHKVYACEV THQGLSSPVT KSFNRGEC |
| 61 | h0301-L1 light chain | NIVLTQSPAT LSLSPGERAT LSCKASQSVD YDGDNYMNWY QQKPGQAPRL LIYAASNLES GIPARFSGSG SGTDFTLTIS SLEPEDFAVY YCHLSNEDLS |

TABLE 5-continued

Sequences and Descriptions

| SEQ ID NO | Description | Sequence |
|---|---|---|
| | | TFGGGTKVEI KRTVAAPSVF IFPPSDEQLK SGTASVVCLL NNFYPREAKV QWKVDNALQS GNSQESVTEQ DSKDSTYSLS STLTLSKADY EKHKVYACEV THQGLSSPVT KSFNRGEC |
| 62 | H0302-L0 light chain | EIVLTQSPAT LSLSPGERAT LSCRASESVD NYGLSFMNWY QQKPGQAPRL LIYTASNLES GIPARFSGSG SGTDFTLTIS SLEPEDFAVY YCQQSKELPW TFGQGTKVEI KRTVAAPSVF IFPPSDEQLK SGTASVVCLL NNFYPREAKV QWKVDNALQS GNSQESVTEQ DSKDSTYSLS STLTLSKADY EKHKVYACEV THQGLSSPVT KSFNRGEC |
| 63 | H0302-L1 light chain | EIVLTQSPAT LSLSPGERAT LSCRASESVD NYGLSFMNWY QQKPGQAPRL LIYTASNLES GIPARFSGSG SRTDFTLTIS SLEPEDFAVY YCQQSKELPW TFGQGTKVEI KRTVAAPSVF IFPPSDEQLK SGTASVVCLL NNFYPREAKV QWKVDNALQS GNSQESVTEQ DSKDSTYSLS STLTLSKADY EKHKVYACEV THQGLSSPVT KSFNRGEC |
| 64 | H0302-L2 light chain | EIVLTQSPAT LSLSPGERAT LSCRASESVD NYGLSFMNWF QQKPGQAPRL LIYTASNLES GIPARFSGSG SRTDFTLTIS SLEPEDFAVY YCQQSKELPW TFGQGTKVEI KRTVAAPSVF IFPPSDEQLK SGTASVVCLL NNFYPREAKV QWKVDNALQS GNSQESVTEQ DSKDSTYSLS STLTLSKADY EKHKVYACEV THQGLSSPVT KSFNRGEC |
| 65 | H0311-L0 light chain | EIVLTQSPAT LSLSPGERAT LSCKASQSVD YDGDSHMNWY QQKPGQAPRL LIYTASNLES GIPARFSGSG SGTDFTLTIS SLEPEDFAVY YCQQGNEDPW TFGQGTKVEI KRTVAAPSVF IFPPSDEQLK SGTASVVCLL NNFYPREAKV QWKVDNALQS GNSQESVTEQ DSKDSTYSLS STLTLSKADY EKHKVYACEV THQGLSSPVT KSFNRGEC |
| 66 | H0311-L1 light chain | DIVLTQSPAT LSLSPGERAT LSCKASQSVD YDGDSHMNWY QQKPGQAPRL LIYTASNLES GIPARFSGSG SGADFTLTIS SLEPEDFAVY YCQQGNEDPW TFGQGTKVEI KRTVAAPSVF IFPPSDEQLK SGTASVVCLL NNFYPREAKV QWKVDNALQS GNSQESVTEQ DSKDSTYSLS STLTLSKADY EKHKVYACEV THQGLSSPVT KSFNRGEC |
| 67 | Human CSF1 | EEVSEYCSHM IGSGHLQSLQ RLIDSQMETS CQITFEFVDQ EQLKDPVCYL KKAFLLVQDI MEDTMRFRDN TPNAIAIVQL QELSLRLKSC FTKDYEEHDK ACVRTFYETP LQLLEKVKNV FNETKNLLDK DWNIFSKNCN NSFAECSSQG HERQSEGS |
| 68 | Human IL-34 | NEPLEMWPLT QNEECTVTGF LRDKLQYRSR LQYMKHYFPI NYKISVPYEG VFRIANVTRL QRAQVSEREL RYLWVLVSLS ATESVQDVLL EGHPSWKYLQ EVQTLLLNVQ QGLTDVEVSP KVESVLSLLN APGPNLKLVR PKALLDNCFR VMELLYCSCC KQSSVLNWQD CEVPSPQSCS PEPSLQYAAT QLYPPPPWSP SSPPHSTGSV RPVRAQGEGL LP |
| 69 | Human A acceptor FR1 | QVQLVQSGAE VKKPGSSVKV SCKAS |
| 70 | Human acceptor A FR2 | WVRQAPGQGL EWMG |
| 71 | Human acceptor A FR3 | RVTITADKST STAYMELSSL RSEDTAVYYC AR |
| 72 | Human acceptor A FR4 | WGQGTLVTVS S |
| 73 | Human acceptor B FR1 | QVQLVQSGAE VKKPGSSVKV SCKAS |
| 74 | Human acceptor B FR2 | WVRQAPGQGL EWMG |
| 75 | Human acceptor B FR3 | RVTITADKST STAYMELSSL RSEDTAVYYC AR |

TABLE 5-continued

Sequences and Descriptions

| SEQ ID NO | Description | Sequence |
|---|---|---|
| 76 | Human acceptor B FR4 | WGQGTLVTVSS |
| 77 | Human acceptor C FR1 | QVQLVQSGAE VKKPGSSVKV SCKAS |
| 78 | Human acceptor C FR2 | WVRQAPGQGL EWMG |
| 79 | Human acceptor C FR3 | RVTITADKST STAYMELSSL RSEDTAVYYC AR |
| 80 | Human acceptor C FR4 | WGQGTLVTVS S |
| 81 | Human acceptor D FR1 | EIVLTQSPAT LSLSPGERAT LSC |
| 82 | Human acceptor D FR2 | WYQQKPGQAP RLLIY |
| 83 | Human acceptor D FR3 | GIPARFSGSG SGTDFTLTIS SLEPEDFAVY YC |
| 84 | Human acceptor D FR4 | FGGGTKVEIK |
| 85 | Human acceptor E FR1 | EIVLTQSPAT LSLSPGERAT LSC |
| 86 | Human acceptor E FR2 | WYQQKPGQAP RLLIY |
| 87 | Human acceptor E FR3 | GIPARFSGSG SGTDFTLTIS SLEPEDFAVY YC |
| 88 | Human acceptor E FR4 | FGQGTKVEIK |
| 89 | Human acceptor F FR1 | EIVLTQSPAT LSLSPGERAT LSC |
| 90 | Human acceptor F FR2 | WYQQKPGQAP RLLIY |
| 91 | Human acceptor F FR3 | GIPARFSGSG SGTDFTLTIS SLEPEDFAVY YC |
| 92 | Human acceptor F FR4 | FGQGTKVEIK |
| 93 | mCSF1R ECD-Fc | APVIEPSGPE LVVEPGETVT LRCVSNGSVE WDGPISPYWT LDPESPGSTL TTRNATFKNT GTYRCTELED PMAGSTTIHL YVKDPAHSWN LLAQEVTVVE GQEAVLPCLI TDPALKDSVS LMREGGRQVL RKTVYFFSPW RGFIIRKAKV LDSNTYVCKT MVNGRESTST GIWLKVNRVH PEPPQIKLEP SKLVRIRGEA AQIVCSATNA EVGFNVILKR GDTKLEIPLN SDFQDNYYKK VRALSLNAVD |

TABLE 5-continued

Sequences and Descriptions

| SEQ ID NO | Description | Sequence |
|---|---|---|
| | | FQDAGIYSCV ASNDVGTRTA TMNFQVVESA YLNLTSEQSL LQEVSVGDSL ILTVHADAYP SIQHYNWTYL GPFFEDQRKL EFITQRAIYR YTFKLFLNRV KASEAGQYFL MAQNKAGWNN LTFELTLRYP PEVSVTWMPV NGSDVLFCDV SGYPQPSVTW MECRGHTDRC DEAQALQVWN DTHPEVLSQK PFDKVIIQSQ LPIGTLKHNM TYFCKTHNSV GNSSQYFRAV SLGQSKQEPK SSDKTHTCPP CPAPELLGGP SVFLFPPKPK DTLMISRTPE VTCVVVDVSH EDPEVKFNWY VDGVEVHNAK TKPREEQYNS TYRVVSVLTV LHQDWLNGKE YKCKVSNKAL PAPIEKTISK AKGQPREPQV YTLPPSRDEL TKNQVSLTCL VKGFYPSDIA VEWESNGQPE NNYKTTPPVL DSDGSFFLYS KLTVDKSRWQ QGNVFSCSVM HEALHNHYTQ KSLSLSPGK |
| 94 | Human IgG4 S241P | ASTKGPSVFP LAPCSRSTSE STAALGCLVK DYFPEPVTVS WNSGALTSGV HTFPAVLQSS GLYSLSSVVT VPSSSLGTKT YTCNVDHKPS NTKVDKRVES KYGPPCPPCP APEFLGGPSV FLFPPKPKDT LMISRTPEVT CVVVDVSQED PEVQFNWYVD GVEVHNAKTK PREEQFNSTY RVVSVLTVLH QDWLNGKEYK CKVSNKGLPS SIEKTISKAK GQPREPQVYT LPPSQEEMTK NQVSLTCLVK GFYPSDIAVE WESNGQPENN YKTTPPVLDS DGSFFLYSRL TVDKSRWQEG NVFSCSVMHE ALHNHYTQKS LSLSLGK |
| 95 | Human Igκ | RTVAAPSVFI FPPSDEQLKS GTASVVCLLN NFYPREAKVQ WKVDNALQSG NSQESVTEQD SKDSTYSLSS TLTLSKADYE KHKVYACEVT HQGLSSPVTK SFNRGEC |

---

The invention claimed is:

1. A method of reducing pain in a subject with pigmented villonodular synovitis (PVNS), comprising administering to the subject a dose of 1-4 mg/kg of an antibody that binds CSF1R once per two weeks, wherein the dose of the antibody is capable of reducing pain in PVNS subjects independently of tumor response, and wherein the antibody is selected from:
   a) an antibody comprising a heavy chain comprising the sequence of SEQ ID NO: 39 and a light chain comprising the sequence of SEQ ID NO: 46;
   b) an antibody comprising a heavy chain comprising a heavy chain (HC) CDR1 having the sequence of SEQ ID NO: 15, an HC CDR2 having the sequence of SEQ ID NO: 16, and an HC CDR3 having the sequence of SEQ ID NO: 17, and a light chain comprising a light chain (LC) CDR1 having the sequence of SEQ ID NO: 18, a LC CDR2 having the sequence of SEQ ID NO: 19, and a LC CDR3 having the sequence of SEQ ID NO: 20; and
   c) an antibody comprising a heavy chain comprising the sequence of SEQ ID NO: 53 and a light chain comprising the sequence of SEQ ID NO: 60.

2. The method of claim 1, wherein PVNS tumor volume is reduced in the subject by at least 30% after administration of at least two, at least three, at least four, at least five, at least six, at least seven, at least eight, at least nine, or at least ten doses of the antibody that binds CSF1R.

3. The method of claim 2, wherein the tumor volume is tumor volume in a single joint.

4. The method of claim 3, wherein the single joint is selected from a hip joint and a knee joint.

5. The method of claim 2, wherein the tumor volume is total tumor volume in all joints affected by PVNS.

6. The method of claim 1, wherein, prior to administering the first dose of the antibody, the subject received a prior therapy selected from surgical synovectomy, radiation beam therapy, radio isotope synovectomy, and joint replacement.

7. The method of claim 6, wherein the PVNS recurred or progressed after the prior therapy.

8. The method of claim 1, wherein the antibody is administered prior to a therapy selected from surgical synovectomy, radiation beam therapy, radio isotope synovectomy, and joint replacement, or wherein the subject has a tumor that is unresectable.

9. The method of claim 1, wherein the subject has not received prior treatment with a CSF1R inhibitor.

10. The method of claim 1, wherein the anti-CSF1R antibody blocks binding of CSF1 and/or IL-34 to CSF1R.

11. The method of claim 1, wherein the anti-CSF1R antibody inhibits ligand-induced CSF1R phosphorylation in vitro.

12. The method of claim 1, wherein the antibody is a humanized antibody.

13. The method of claim 12, wherein the antibody is huAb1.

14. The method of claim 1, wherein the antibody is selected from a Fab, an Fv, an scFv, a Fab', and a (Fab')$_2$.

15. The method of claim 1, wherein the subject experiences (a) an increased range of motion in a joint, (b) an increase in functional capacity of a joint, or (c) both an increased range of motion in a joint and an increase in functional capacity of a joint, following at least one dose of the antibody.

16. The method of claim 1, wherein the antibody is administered at a dose of 1 mg/kg.

17. The method of claim 1, wherein the antibody is administered at a dose of 2 mg/kg.

18. The method of claim 1, wherein the antibody is administered at a dose of 3 mg/kg.

19. The method of claim 1, wherein the antibody is administered at a dose of 4 mg/kg.

20. The method of claim 1, wherein the subject has received prior treatment with a CSF1R inhibitor.

21. The method of claim 20, wherein the CSF1R inhibitor is a CSF1R kinase inhibitor.

22. The method of claim 21, wherein the CSF1R kinase inhibitor is PLX3397.

23. The method of claim 21, wherein the CSF1R kinase inhibitor is imatinib or nilotinib.

24. A method of reducing pain in a subject with PVNS, comprising administering to the subject a dose of 4 mg/kg of an antibody that binds CSF1R once per two weeks, wherein the dose of the antibody is capable of reducing pain in PVNS subjects independently of tumor response, and wherein the antibody comprises (a) a heavy chain comprising the sequence of SEQ ID NO: 39 and (b) a light chain comprising the sequence of SEQ ID NO: 46.

25. The method of claim 24, wherein, prior to administering the first dose of the antibody, the subject received a prior therapy selected from surgical synovectomy, radiation beam therapy, radio isotope synovectomy, and joint replacement.

26. The method of claim 25, wherein the PVNS recurred or progressed after the prior therapy.

27. The method of claim 24, wherein the antibody is administered prior to a therapy selected from surgical synovectomy, radiation beam therapy, radio isotope synovectomy, and joint replacement, or wherein the subject has a tumor that is unresectable.

28. The method of claim 24, wherein the subject has not received prior treatment with a CSF1R inhibitor.

29. The method of claim 24, wherein the subject has received prior treatment with a CSF1R inhibitor.

30. The method of claim 29, wherein the CSF1R inhibitor is a CSF1R kinase inhibitor.

31. The method of claim 30, wherein the CSF1R kinase inhibitor is PLX3397.

32. The method of claim 30, wherein the CSF1R kinase inhibitor is imatinib or nilotinib.

33. A method of reducing pain in a subject with PVNS, comprising administering to the subject a dose of 4 mg/kg of an antibody that binds CSF1R once per two weeks, wherein the dose of the antibody is capable of reducing pain in PVNS subjects independently of tumor response, and wherein the antibody comprises a heavy chain comprising a heavy chain (HC) CDR1 having the sequence of SEQ ID NO: 15, an HC CDR2 having the sequence of SEQ ID NO: 16, and an HC CDR3 having the sequence of SEQ ID NO: 17, and a light chain comprising a light chain (LC) CDR1 having the sequence of SEQ ID NO: 18, a LC CDR2 having the sequence of SEQ ID NO: 19, and a LC CDR3 having the sequence of SEQ ID NO: 20.

34. The method of claim 33, wherein, prior to administering the first dose of the antibody, the subject received a prior therapy selected from surgical synovectomy, radiation beam therapy, radio isotope synovectomy, and joint replacement.

35. The method of claim 34, wherein the PVNS recurred or progressed after the prior therapy.

36. The method of claim 33, wherein the antibody is administered prior to a therapy selected from surgical synovectomy, radiation beam therapy, radio isotope synovectomy, and joint replacement, or wherein the subject has a tumor that is unresectable.

37. The method of claim 33, wherein the subject has not received prior treatment with a CSF1R inhibitor.

38. The method of claim 33, wherein the subject has received prior treatment with a CSF1R inhibitor.

39. The method of claim 38, wherein the CSF1R inhibitor is a CSF1R kinase inhibitor.

40. The method of claim 39, wherein the CSF1R kinase inhibitor is PLX3397.

41. The method of claim 39, wherein the CSF1R kinase inhibitor is imatinib or nilotinib.

42. A method of reducing pain in a subject with PVNS, comprising administering to the subject a dose of 4 mg/kg of an antibody that binds CSF1R once per two weeks, wherein the dose of the antibody is capable of reducing pain in PVNS subjects independently of tumor response, and wherein the antibody comprises a heavy chain comprising the sequence of SEQ ID NO: 53 and a light chain comprising the sequence of SEQ ID NO: 60.

43. The method of claim 42, wherein, prior to administering the first dose of the antibody, the subject received a prior therapy selected from surgical synovectomy, radiation beam therapy, radio isotope synovectomy, and joint replacement.

44. The method of claim 43, wherein the PVNS recurred or progressed after the prior therapy.

45. The method of claim 42, wherein the antibody is administered prior to a therapy selected from surgical synovectomy, radiation beam therapy, radio isotope synovectomy, and joint replacement, or wherein the subject has a tumor that is unresectable.

46. The method of claim 42, wherein the subject has not received prior treatment with a CSF1R inhibitor.

47. The method of claim 42, wherein the subject has received prior treatment with a CSF1R inhibitor.

48. The method of claim 47, wherein the CSF1R inhibitor is a CSF1R kinase inhibitor.

49. The method of claim 48, wherein the CSF1R kinase inhibitor is PLX3397.

50. The method of claim 48, wherein the CSF1R kinase inhibitor is imatinib or nilotinib.

51. The method of claim 1, wherein the dose of the antibody is capable of reducing pain in PVNS subjects from severe (0 points) to none (3 points) according to Ogilvie-Harris scores for PVNS.

52. The method of claim 24, wherein the dose of the antibody is capable of reducing pain in PVNS subjects from severe (0 points) to none (3 points) according to Ogilvie-Harris scores for PVNS.

53. The method of claim 33, wherein the dose of the antibody is capable of reducing pain in PVNS subjects from severe (0 points) to none (3 points) according to Ogilvie-Harris scores for PVNS.

54. The method of claim 42, wherein the dose of the antibody is capable of reducing pain in PVNS subjects from severe (0 points) to none (3 points) according to Ogilvie-Harris scores for PVNS.

55. The method of claim 1, wherein PVNS tumor volume is reduced in the subject by at least 50% after administration of at least two, at least three, at least four, at least five, at least six, at least seven, at least eight, at least nine, or at least ten doses of the antibody that binds CSF1R.

56. The method of claim 1, wherein PVNS tumor volume is reduced in the subject by at least 70% after administration of at least two, at least three, at least four, at least five, at least six, at least seven, at least eight, at least nine, or at least ten doses of the antibody that binds CSF1R.

* * * * *